United States Patent
Altintas et al.

(10) Patent No.: US 10,968,280 B2
(45) Date of Patent: Apr. 6, 2021

(54) BINDING AGENTS BINDING TO PD-L1 AND CD137 AND USE THEREOF

(71) Applicants: GENMAB A/S, Copenhagen (DK); BIONTECH SE, Mainz (DE)

(72) Inventors: Isil Altintas, Utrecht (NL); David Satijn, Utrecht (NL); Rik Rademaker, Utrecht (NL); Paul Parren, Odijk (NL); Ugur Sahin, Mainz (DE); Friederike Gieseke, Mainz (DE); Alexander Muik, Mainz (DE); Christian Grunwitz, Mainz (DE)

(73) Assignees: GENMAB A/S, Copenhagen V (DK); BioNTech SE, Mainz (DE)

( * ) Notice: Subject to any disclaimer, the term of this patent is extended or adjusted under 35 U.S.C. 154(b) by 0 days.

(21) Appl. No.: 16/779,011

(22) Filed: Jan. 31, 2020

(65) Prior Publication Data
US 2020/0165349 A1   May 28, 2020

Related U.S. Application Data

(63) Continuation of application No. PCT/EP2018/071002, filed on Aug. 2, 2018.

(51) Int. Cl.
*C07K 16/28* (2006.01)

(52) U.S. Cl.
CPC ...... *C07K 16/2878* (2013.01); *C07K 16/2827* (2013.01); *C07K 2317/24* (2013.01); *C07K 2317/31* (2013.01); *C07K 2317/33* (2013.01); *C07K 2317/565* (2013.01); *C07K 2317/76* (2013.01)

(58) Field of Classification Search
None
See application file for complete search history.

(56) References Cited

U.S. PATENT DOCUMENTS

| | | |
|---|---|---|
| 8,779,108 B2 | 7/2014 | Queva |
| 2011/0223188 A1 | 9/2011 | Langermann |
| 2013/0039911 A1 | 2/2013 | Bedi |

FOREIGN PATENT DOCUMENTS

| | | |
|---|---|---|
| WO | WO 2008119353 A1 | 10/2008 |
| WO | WO 2009034172 A1 | 3/2009 |
| WO | WO 2011131746 A2 | 10/2011 |
| WO | WO 2013060867 A2 | 5/2013 |
| WO | WO 2015156268 A1 | 10/2015 |
| WO | WO 2016100882 A1 | 6/2016 |
| WO | WO 2016/110576 A1 | 7/2016 |
| WO | WO 2016/110584 A1 | 7/2016 |
| WO | WO 2017060144 A1 | 4/2017 |
| WO | WO 2017/123650 A2 | 7/2017 |
| WO | WO 2017182672 A1 | 10/2017 |
| WO | WO 2017201281 A1 | 11/2017 |
| WO | WO 2017205738 A1 | 11/2017 |
| WO | WO 2017214092 A1 | 12/2017 |
| WO | WO 2017218707 A2 | 12/2017 |
| WO | WO-2018011421 A1 * | 1/2018 ............ A61P 31/04 |
| WO | WO 2018014260 A1 | 1/2018 |
| WO | WO 2018017761 A1 | 1/2018 |
| WO | WO 2018056821 A1 | 3/2018 |
| WO | WO 2018/162749 A1 | 9/2018 |
| WO | WO 2018213747 A1 | 11/2018 |

OTHER PUBLICATIONS

Mariuzza et al. (Annu. Rev. Biophys. Biophys. Chem., 16: 139-159, 1987).*
Winkler et al (J. Imm., 265:4505-4514, 2000).*
Giusti et al (PNAS, 9: 2926-2930, 1987).*
Rudikoff et al (PNAS, 79:1979-1983, 1982).*
Fischer et al (CII, 61:1721-1733, 2012).*
Luan et al (II, 32:248-256, 2016).*
Lloyd et al (Protein Engineering, Design & Selection, 22:159-168, 2009).*
Edwards et al (J Mol Biol, 14;334(1):103-118, 2003).*
International Search Report and Written Opinion in related PCT Application No. PCT/EP2018/071002, dated Jan. 4, 2019 (18 pages).
Ramelet et al., "Beneficial outcome of combination therapy with 4-1 BB targeting antibody", European Journal of Cancer, vol. 69, Nov. 29, 2016.
Shindo et al., "Combination immunotherapy with 4-1 BB activation and PD-1 blockade enhances antitumor efficacy in a mouse model of subcutaneous tumor", Anticancer Research—International Journal of Cancer Research and Treatment, vol. 35, No. 1, Jan. 1, 2015, pp. 129-136.
Canfield et al., "The Binding Affinity of Human IgG for its High Affinity Fc Receptor Is Determined by Multiple Amino Acids in the $C_H2$ Domain and Is Modulated by the Hinge Region", J. Exp. Med., 1991, (173): 1483-1491.
Chen et al., Phase 1b/3 study of avelumab-based combination regimens in patients with relapsed or refractory diffuse large B-cell lymphoma (R/R DLBCL), J Clin Oncol, 2017, 35(15 suppl): abstr TPS7575.
ClinicalTrials.gov, Clinical Trial NCT02554812, "A Study of Avelumab in Combination With Other Cancer Immunotherapies in Advanced Malignancies (JAVELIN Medley)", Sep. 18, 2015.

(Continued)

*Primary Examiner* — Brad Duffy
(74) *Attorney, Agent, or Firm* — Lathrop GPM LLP; James H. Velema, Esq.; James V. DeGiulio, Esq.

(57) ABSTRACT

The present invention relates to novel binding agents and their use in medicine. In particular, the invention relates to binding agents such as bispecific antibodies binding human PD-L1 and binding human CD137. The invention furthermore relates to uses of the antibodies of the invention and to methods, nucleic acid constructs and host cells for producing antibodies of the invention.

12 Claims, 22 Drawing Sheets
Specification includes a Sequence Listing.

(56) References Cited

OTHER PUBLICATIONS

Colman et al., "Effects of amino acid sequence changes on antibody-antigen interactions", Research in Immunology, 1994, 145: 33-36.
Dall'Acqua et al., "Modulation of the Effector Functions of a Human IgG1 through Engineering of Its Hinge Region", J Immunol., 2006, 177(2): 1129-1138.
Duncan et al., "The Binding Site for C1q on IgG", Nature, 1988 (332): 738-740.
Hezareh et al., "Effector Function Activities of a Panel of Mutant of a Broadly Neutralizing Antibody against Human Immunodeficiency Virus Type 1", J Virol., 2001, 75(24): 12161-12168.
Horton et al., "Agonist anti-4-1BB plus neutralizing anti-CTLA-4 or -PD-L1 synergize to promote tumor regression by rescuing dying dysfunctional CD8+ T cells within the tumor microenvironment", J Immunother Cancer, 2015, 3(Suppl 2): O10.
Idusogie et al., "Mapping of the C1q Binding Site on Rituxan, a Chimeric Antibody with a Human IgG1 Fc", J Immunol., 2000, 164: 4178-4184.
Leabman et al., "Effects of Altered FcγR binding on antibody pharmacokinetics in cynomolgus monkeys", MAbs, 2013, 5(6): 896-903.
Oganesyan et al., "Structural characterization of a human Fc fragment engineered for lack of effector functions", Acta Cryst., 2008, (D64): 700-704.
Paul et al., Fundamental Immunology, Third Edition, 1993, Chapter 9, pp. 292-295.
Rudikoff et al., "Single amino acid substitution altering antigen-binding specificity", Proc. Natl Acad. Sci. USA, 1982, 79: 1979-1983, Immunology.
Shields et al., "High Resolution Mapping of the Binding Site on Human OgG1 for FcγRI, FcγRII, FcγRIII, and FcRn and Design of IgG1 Variants with Improved Binding to the FcγR", J. Biol. Chem., 2001, 276(9): 6591-6604.
Storz, "Intellectual property issues of immune checkpoint inhibitors", mAbs, 2016, 8(1): 10-26.
Xu et al., "In Vitro Characterization of Five Humanized OKT3 Effector Function Variant Antibodies", Cell Immunol., 2000, 200: 16-26.

* cited by examiner

Figure 1

```
                                   1                                                50
    Human (TNR9_HUMAN)       (1)   -----MGNSCYNIVATLLLVLNFERTRSLQDPCSNCPAGTFCDNNRNQIC
 Elephant (XP_003413533)     (1)   MQDFIMGNYYNIVATLLVNFERTGQOLSCRCLAGTCVNESQIC
Wild Boar (XP_005665023)     (1)   MQDFIMGNYYNIVATLLVNFERTRSPDPCSNCAGTFCKNIQEIC 51                                               100
    Human (TNR9_HUMAN)      (46)   SPCPPNSFSSAGGQRTCDICRQCKGVFRTRKECSSTSNAECDCTPGFHCL
 Elephant (XP_003413533)    (51)   SPCPLNSFSSGGQMCFCRGVETACSTREAECGFHCL
Wild Boar (XP_005665023)    (51)   MPCPNSFSSGQCRGVFRTKECSSTSNAVQCPGFCL 101                                              150
    Human (TNR9_HUMAN)      (96)   GAGCSMCEQDCKQGQELTKKGCKDCCFGTFNDQKRGICRPWTNCSLDGKS
 Elephant (XP_003413533)   (101)   GAGCMCQDCKQGQELTKGCKDCCGTFNDQKGICRPWTNCSLGKS
Wild Boar (XP_005665023)   (101)   GAGCMCEYCQGQELTGCKDCFGTFNDGCRPWTCSLAGR 151                                              200
    Human (TNR9_HUMAN)     (146)   VLVNGTKERDVVCGPSPADLSPGASSVTPPAPAREPGHSPQIISFFLALT
 Elephant (XP_003413533)   (151)   VLNGTKRDVVCGPAADSFESSVTVPAPERDHHPQITFFLALI
Wild Boar (XP_005665023)   (151)   VLNGTKARDVVCGFRESFCSTMEPGEPGHIIEFFLALM 201                                              250
    Human (TNR9_HUMAN)     (196)   STALLFLLFFLTLRFSVVKRGRKKLLYIFKQPFMRPVQTTQEEDGCSCRF
 Elephant (XP_003413533)   (201)   SALLFIFFIRPSVKWGRKKLLYIFKQPFPVQTQEEDGCSCRF
Wild Boar (XP_005665023)   (201)   STAVILSLRFSVVGRKKLLYIVKQPFQIQEEDCSCRF
                                   251
    Human (TNR9_HUMAN)     (246)   PEEEEGGCEL
 Elephant (XP_003413533)   (251)   PEEEEGCEL
Wild Boar (XP_005665023)   (251)   PEEEEGECEL
```

Figure 6A
Figure 6B
A. PD1-mediated T cell inhibition
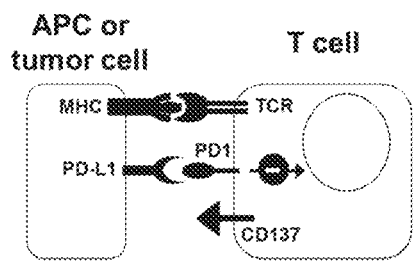
B. PD-L1-blockade + T cell co-stimulation
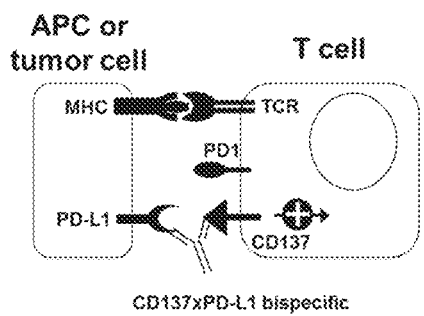

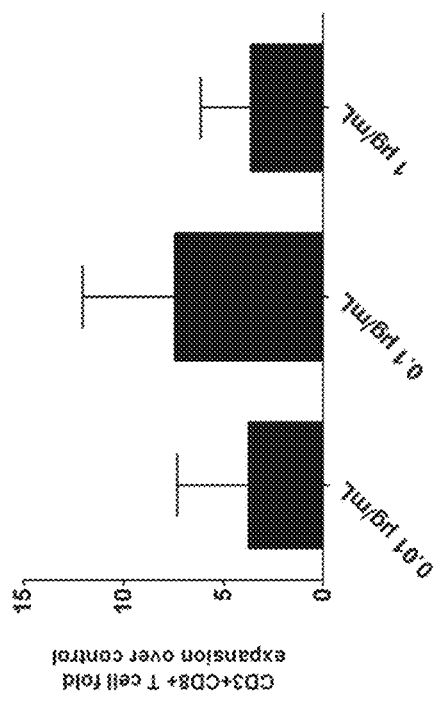
Figure 10A
Figure 10B
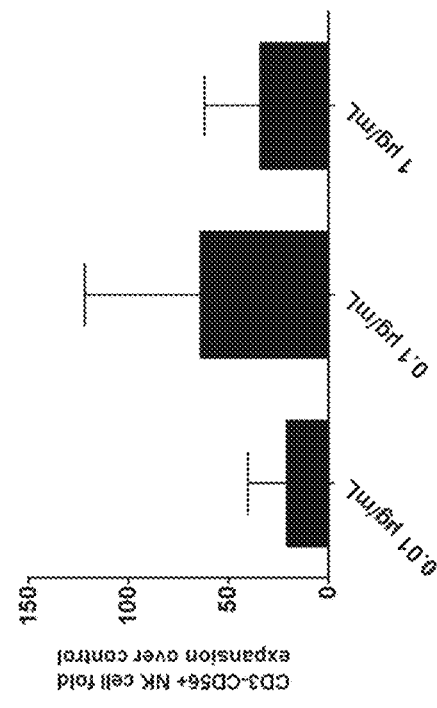
Figure 10C
Figure 10D
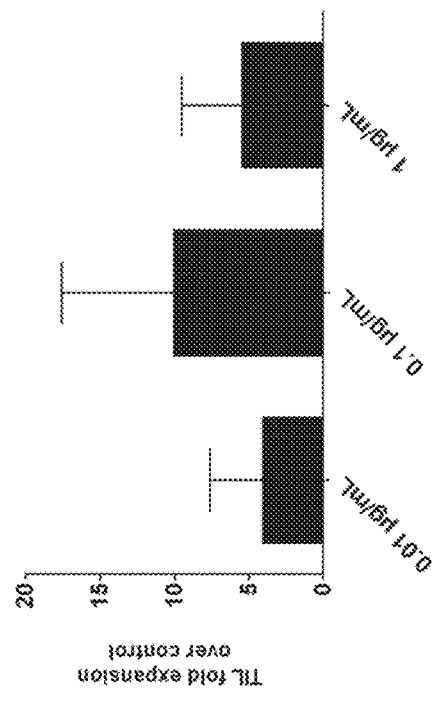

Figure 11A
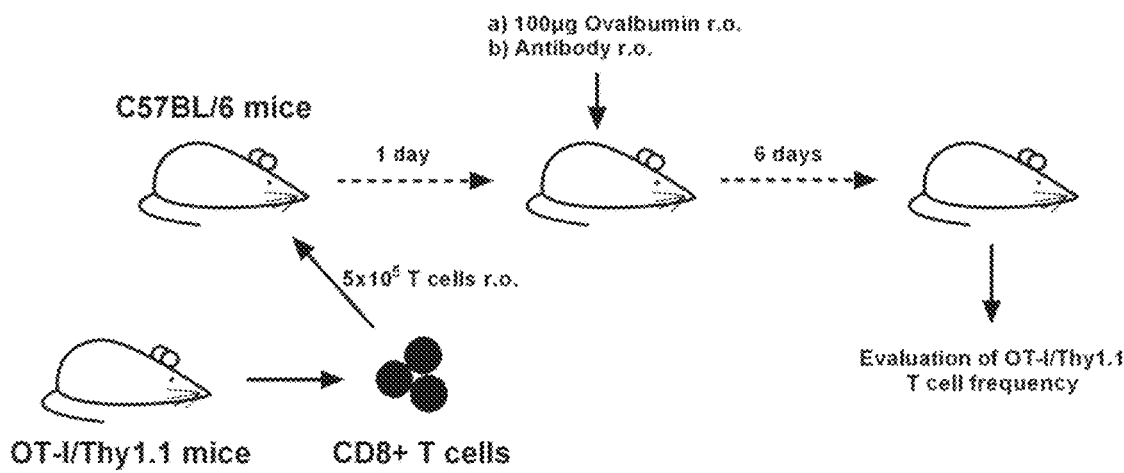
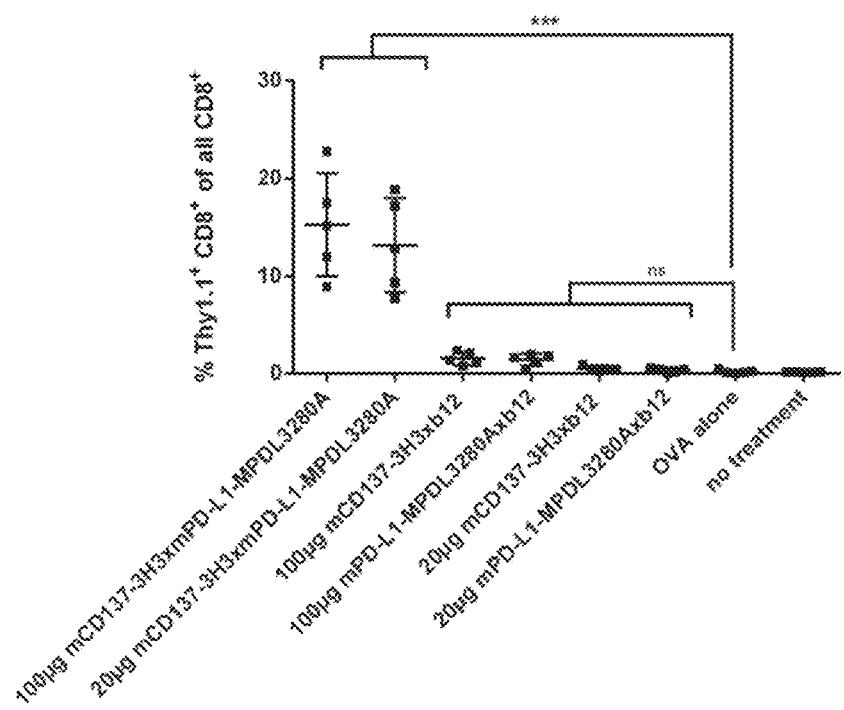
Figure 11B

Figure 12A
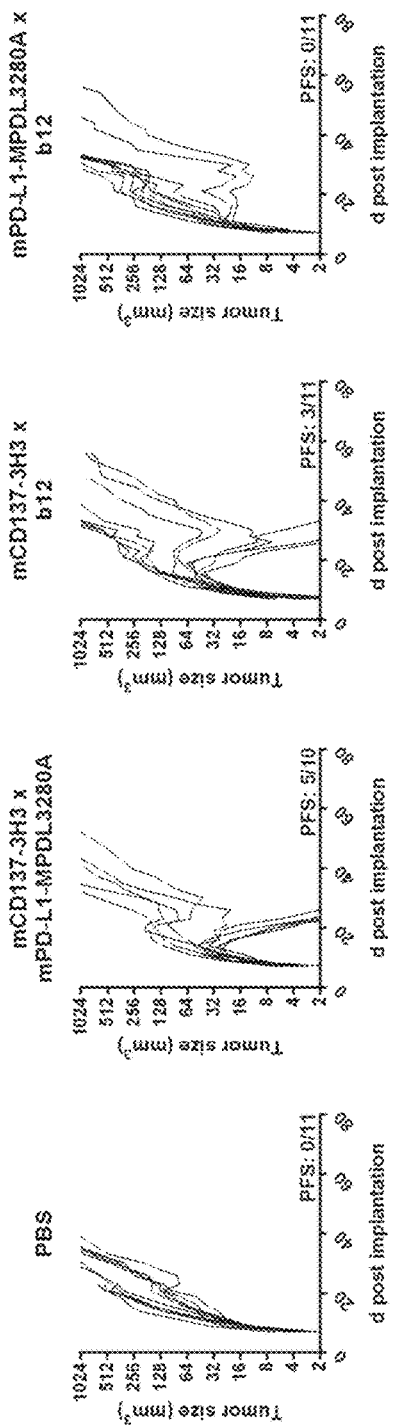
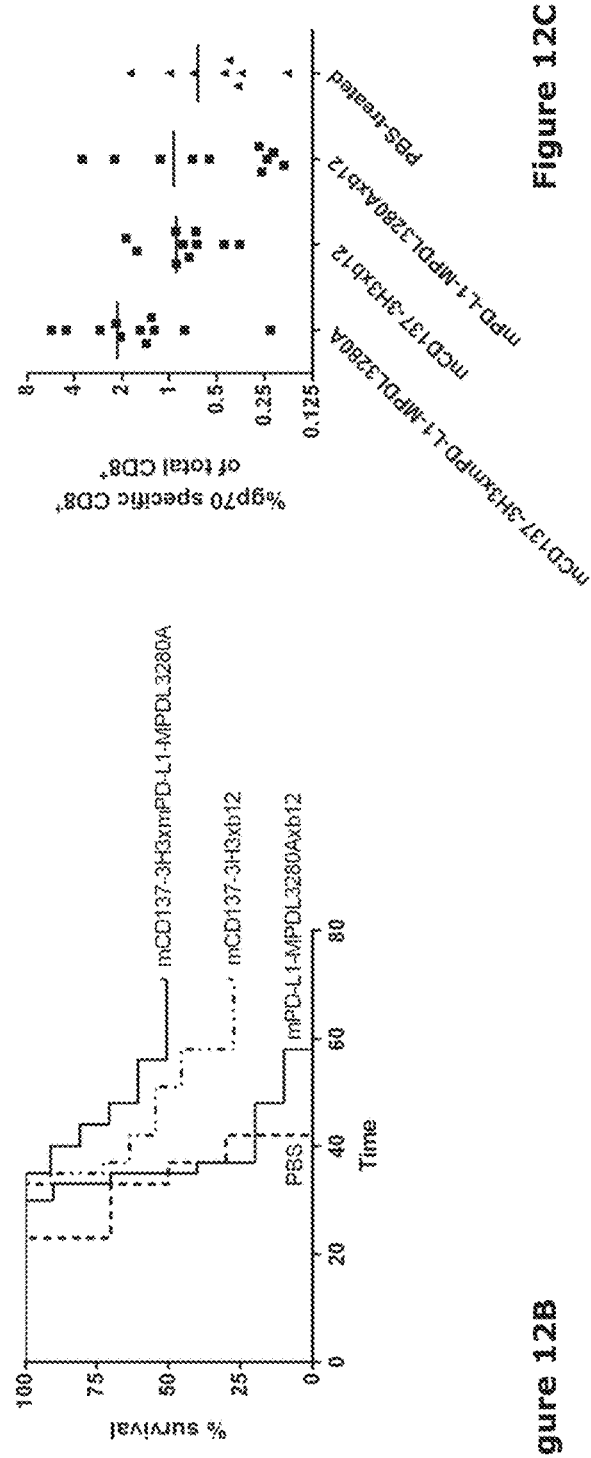
Figure 12B
Figure 12C

SEQUENCE LISTING

```
<160> NUMBER OF SEQ ID NOS: 58

<210> SEQ ID NO 1
<211> LENGTH: 127
<212> TYPE: PRT
<213> ORGANISM: Homo Sapiens

<400> SEQUENCE: 1

Gln Val Gln Leu Val Gln Ser Gly Ala Glu Val Lys Lys Pro Gly Ala
1               5                   10                  15

Ser Val Lys Val Ser Cys Gln Ala Ser Gly Tyr Arg Phe Ser Asn Phe
            20                  25                  30

Val Ile His Trp Val Arg Gln Ala Pro Gly Gln Arg Phe Glu Trp Met
        35                  40                  45

Gly Trp Ile Asn Pro Tyr Asn Gly Asn Lys Glu Phe Ser Ala Lys Phe
    50                  55                  60

Gln Asp Arg Val Thr Phe Thr Ala Asp Thr Ser Ala Asn Thr Ala Tyr
65                  70                  75                  80
```

```
Met Glu Leu Arg Ser Leu Arg Ser Ala Asp Thr Ala Val Tyr Tyr Cys
                85                  90                  95

Ala Arg Val Gly Pro Tyr Ser Trp Asp Ser Pro Gln Asp Asn Tyr
            100                 105                 110

Tyr Met Asp Val Trp Gly Lys Gly Thr Thr Val Ile Val Ser Ser
        115                 120                 125

<210> SEQ ID NO 2
<211> LENGTH: 8
<212> TYPE: PRT
<213> ORGANISM: Homo Sapiens

<400> SEQUENCE: 2

Gly Tyr Arg Phe Ser Asn Phe Val
1               5

<210> SEQ ID NO 3
<211> LENGTH: 8
<212> TYPE: PRT
<213> ORGANISM: Homo Sapiens

<400> SEQUENCE: 3

Ile Asn Pro Tyr Asn Gly Asn Lys
1               5

<210> SEQ ID NO 4
<211> LENGTH: 20
<212> TYPE: PRT
<213> ORGANISM: Homo Sapiens

<400> SEQUENCE: 4

Ala Arg Val Gly Pro Tyr Ser Trp Asp Ser Pro Gln Asp Asn Tyr
1               5                   10                  15

Tyr Met Asp Val
            20

<210> SEQ ID NO 5
<211> LENGTH: 108
<212> TYPE: PRT
<213> ORGANISM: Homo Sapiens

<400> SEQUENCE: 5

Glu Ile Val Leu Thr Gln Ser Pro Gly Thr Leu Ser Leu Ser Pro Gly
1               5                   10                  15

Glu Arg Ala Thr Phe Ser Cys Arg Ser Ser His Ser Ile Arg Ser Arg
            20                  25                  30

Arg Val Ala Trp Tyr Gln His Lys Pro Gly Gln Ala Pro Arg Leu Val
        35                  40                  45

Ile His Gly Val Ser Asn Arg Ala Ser Gly Ile Ser Asp Arg Phe Ser
    50                  55                  60

Gly Ser Gly Ser Gly Thr Asp Phe Thr Leu Thr Ile Thr Arg Val Glu
65                  70                  75                  80

Pro Glu Asp Phe Ala Leu Tyr Tyr Cys Gln Val Tyr Gly Ala Ser Ser
                85                  90                  95

Tyr Thr Phe Gly Gln Gly Thr Lys Leu Glu Arg Lys
            100                 105

<210> SEQ ID NO 6
<211> LENGTH: 7
<212> TYPE: PRT
```

```
<213> ORGANISM: Homo Sapiens

<400> SEQUENCE: 6

His Ser Ile Arg Ser Arg Arg
1               5

<210> SEQ ID NO 7
<211> LENGTH: 9
<212> TYPE: PRT
<213> ORGANISM: Homo Sapiens

<400> SEQUENCE: 7

Gln Val Tyr Gly Ala Ser Ser Tyr Thr
1               5

<210> SEQ ID NO 8
<211> LENGTH: 114
<212> TYPE: PRT
<213> ORGANISM: Homo Sapiens

<400> SEQUENCE: 8

Gln Ser Leu Glu Glu Ser Gly Gly Arg Leu Val Thr Pro Gly Thr Pro
1               5                   10                  15

Leu Thr Leu Thr Cys Thr Val Ser Gly Phe Ser Leu Asn Asp Tyr Trp
            20                  25                  30

Met Ser Trp Val Arg Gln Ala Pro Gly Lys Gly Leu Glu Trp Ile Gly
        35                  40                  45

Tyr Ile Asp Val Gly Gly Ser Leu Tyr Tyr Ala Ser Trp Ala Lys Gly
    50                  55                  60

Arg Phe Thr Ile Ser Arg Thr Ser Thr Thr Val Asp Leu Lys Met Thr
65                  70                  75                  80

Ser Leu Thr Thr Glu Asp Thr Ala Thr Tyr Phe Cys Ala Arg Gly Gly
                85                  90                  95

Leu Thr Tyr Gly Phe Asp Leu Trp Gly Pro Gly Thr Leu Val Thr Val
            100                 105                 110

Ser Ser

<210> SEQ ID NO 9
<211> LENGTH: 8
<212> TYPE: PRT
<213> ORGANISM: Homo Sapiens

<400> SEQUENCE: 9

Gly Phe Ser Leu Asn Asp Tyr Trp
1               5

<210> SEQ ID NO 10
<211> LENGTH: 7
<212> TYPE: PRT
<213> ORGANISM: Homo Sapiens

<400> SEQUENCE: 10

Ile Asp Val Gly Gly Ser Leu
1               5

<210> SEQ ID NO 11
<211> LENGTH: 11
<212> TYPE: PRT
<213> ORGANISM: Homo Sapiens

<400> SEQUENCE: 11
```

```
Ala Arg Gly Gly Leu Thr Tyr Gly Phe Asp Leu
1               5                   10
```

<210> SEQ ID NO 12
<211> LENGTH: 110
<212> TYPE: PRT
<213> ORGANISM: Homo Sapiens

<400> SEQUENCE: 12

```
Asp Ile Val Met Thr Gln Thr Pro Ala Ser Val Ser Glu Pro Val Gly
1               5                   10                  15

Gly Thr Val Thr Ile Asn Cys Gln Ala Ser Glu Asp Ile Ser Ser Tyr
                20                  25                  30

Leu Ala Trp Tyr Gln Gln Lys Pro Gly Gln Arg Pro Lys Arg Leu Ile
            35                  40                  45

Tyr Gly Ala Ser Asp Leu Ala Ser Gly Val Pro Ser Arg Phe Ser Ala
        50                  55                  60

Ser Gly Ser Gly Thr Glu Tyr Ala Leu Thr Ile Ser Asp Leu Glu Ser
65                  70                  75                  80

Ala Asp Ala Ala Thr Tyr Tyr Cys His Tyr Tyr Ala Thr Ile Ser Gly
                85                  90                  95

Leu Gly Val Ala Phe Gly Gly Gly Thr Glu Val Val Val Lys
            100                 105                 110
```

<210> SEQ ID NO 13
<211> LENGTH: 6
<212> TYPE: PRT
<213> ORGANISM: Homo Sapiens

<400> SEQUENCE: 13

```
Glu Asp Ile Ser Ser Tyr
1               5
```

<210> SEQ ID NO 14
<211> LENGTH: 12
<212> TYPE: PRT
<213> ORGANISM: Homo Sapiens

<400> SEQUENCE: 14

```
His Tyr Tyr Ala Thr Ile Ser Gly Leu Gly Val Ala
1               5                   10
```

<210> SEQ ID NO 15
<211> LENGTH: 117
<212> TYPE: PRT
<213> ORGANISM: Homo Sapiens

<400> SEQUENCE: 15

```
Glu Val Gln Leu Val Glu Ser Gly Gly Gly Leu Val Gln Pro Gly Arg
1               5                   10                  15

Ser Leu Arg Leu Ser Cys Thr Ala Ser Gly Phe Ser Leu Asn Asp Tyr
                20                  25                  30

Trp Met Ser Trp Val Arg Gln Ala Pro Gly Lys Gly Leu Glu Trp Val
            35                  40                  45

Gly Tyr Ile Asp Val Gly Gly Ser Leu Tyr Tyr Ala Ala Ser Val Lys
        50                  55                  60

Gly Arg Phe Thr Ile Ser Arg Asp Asp Ser Lys Ser Ile Ala Tyr Leu
65                  70                  75                  80

Gln Met Asn Ser Leu Lys Thr Glu Asp Thr Ala Val Tyr Tyr Cys Ala
                85                  90                  95
```

-continued

```
Arg Gly Gly Leu Thr Tyr Gly Phe Asp Leu Trp Gly Gln Gly Thr Leu
            100                 105                 110

Val Thr Val Ser Ser
        115
```

<210> SEQ ID NO 16
<211> LENGTH: 110
<212> TYPE: PRT
<213> ORGANISM: Homo Sapiens

<400> SEQUENCE: 16

```
Asp Ile Val Met Thr Gln Ser Pro Ser Ser Leu Ser Ala Ser Val Gly
1               5                   10                  15

Asp Arg Val Thr Ile Thr Cys Gln Ala Ser Glu Asp Ile Ser Ser Tyr
            20                  25                  30

Leu Ala Trp Tyr Gln Gln Lys Pro Gly Lys Ala Pro Lys Arg Leu Ile
        35                  40                  45

Tyr Gly Ala Ser Asp Leu Ala Ser Gly Val Pro Ser Arg Phe Ser Ala
    50                  55                  60

Ser Gly Ser Gly Thr Asp Tyr Thr Phe Thr Ile Ser Ser Leu Gln Pro
65                  70                  75                  80

Glu Asp Ile Ala Thr Tyr Tyr Cys His Tyr Tyr Ala Thr Ile Ser Gly
                85                  90                  95

Leu Gly Val Ala Phe Gly Gly Thr Lys Val Glu Ile Lys
            100                 105                 110
```

<210> SEQ ID NO 17
<211> LENGTH: 121
<212> TYPE: PRT
<213> ORGANISM: Homo Sapiens

<400> SEQUENCE: 17

```
Glu Val Gln Leu Leu Glu Pro Gly Gly Gly Leu Val Gln Pro Gly Gly
1               5                   10                  15

Ser Leu Arg Leu Ser Cys Glu Ala Ser Gly Ser Thr Phe Ser Thr Tyr
            20                  25                  30

Ala Met Ser Trp Val Arg Gln Ala Pro Gly Lys Gly Leu Glu Trp Val
        35                  40                  45

Ser Gly Phe Ser Gly Ser Gly Phe Thr Phe Tyr Ala Asp Ser Val
    50                  55                  60

Arg Gly Arg Phe Thr Ile Ser Arg Asp Ser Ser Lys Asn Thr Leu Phe
65                  70                  75                  80

Leu Gln Met Ser Ser Leu Arg Ala Glu Asp Thr Ala Val Tyr Tyr Cys
                85                  90                  95

Ala Ile Pro Ala Arg Gly Tyr Asn Tyr Gly Ser Phe Gln His Trp Gly
            100                 105                 110

Gln Gly Thr Leu Val Thr Val Ser Ser
        115                 120
```

<210> SEQ ID NO 18
<211> LENGTH: 8
<212> TYPE: PRT
<213> ORGANISM: Homo Sapiens

<400> SEQUENCE: 18

```
Gly Ser Thr Phe Ser Thr Tyr Ala
1               5
```

<210> SEQ ID NO 19
<211> LENGTH: 8
<212> TYPE: PRT
<213> ORGANISM: Homo Sapiens

<400> SEQUENCE: 19

Phe Ser Gly Ser Gly Gly Phe Thr
1               5

<210> SEQ ID NO 20
<211> LENGTH: 14
<212> TYPE: PRT
<213> ORGANISM: Homo Sapiens

<400> SEQUENCE: 20

Ala Ile Pro Ala Arg Gly Tyr Asn Tyr Gly Ser Phe Gln His
1               5                   10

<210> SEQ ID NO 21
<211> LENGTH: 108
<212> TYPE: PRT
<213> ORGANISM: Homo Sapiens

<400> SEQUENCE: 21

Ser Tyr Val Leu Thr Gln Pro Pro Ser Val Ser Val Ala Pro Gly Gln
1               5                   10                  15

Thr Ala Arg Ile Thr Cys Gly Gly Asn Asn Ile Gly Ser Lys Ser Val
            20                  25                  30

His Trp Tyr Gln Gln Lys Pro Gly Gln Ala Pro Val Leu Val Val Tyr
        35                  40                  45

Asp Asp Asn Asp Arg Pro Ser Gly Leu Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp His
                85                  90                  95

Val Val Phe Gly Gly Gly Thr Lys Leu Thr Val Leu
            100                 105

<210> SEQ ID NO 22
<211> LENGTH: 6
<212> TYPE: PRT
<213> ORGANISM: Homo Sapiens

<400> SEQUENCE: 22

Asn Ile Gly Ser Lys Ser
1               5

<210> SEQ ID NO 23
<211> LENGTH: 11
<212> TYPE: PRT
<213> ORGANISM: Homo Sapiens

<400> SEQUENCE: 23

Gln Val Trp Asp Ser Ser Ser Asp His Val Val
1               5                   10

<210> SEQ ID NO 24
<211> LENGTH: 330
<212> TYPE: PRT
<213> ORGANISM: Artificial Sequence
<220> FEATURE:

<223> OTHER INFORMATION: IgG1 with FEAR substitutions

<400> SEQUENCE: 24

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Phe Glu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Ala Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Arg Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 25
<211> LENGTH: 330
<212> TYPE: PRT
<213> ORGANISM: Artificial Sequence
<220> FEATURE:
<223> OTHER INFORMATION: IgG1 with FEAL substitutions

<400> SEQUENCE: 25

Ala Ser Thr Lys Gly Pro Ser Val Phe Pro Leu Ala Pro Ser Ser Lys
1               5                   10                  15

```
Ser Thr Ser Gly Gly Thr Ala Ala Leu Gly Cys Leu Val Lys Asp Tyr
             20                  25                  30

Phe Pro Glu Pro Val Thr Val Ser Trp Asn Ser Gly Ala Leu Thr Ser
         35                  40                  45

Gly Val His Thr Phe Pro Ala Val Leu Gln Ser Ser Gly Leu Tyr Ser
     50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                 85                  90                  95

Arg Val Glu Pro Lys Ser Cys Asp Lys Thr His Thr Cys Pro Pro Cys
            100                 105                 110

Pro Ala Pro Glu Phe Glu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Ala Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Leu
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 26
<211> LENGTH: 107
<212> TYPE: PRT
<213> ORGANISM: Homo Sapiens

<400> SEQUENCE: 26

Arg Thr Val Ala Ala Pro Ser Val Phe Ile Phe Pro Pro Ser Asp Glu
1               5                  10                  15

Gln Leu Lys Ser Gly Thr Ala Ser Val Val Cys Leu Leu Asn Asn Phe
             20                  25                  30

Tyr Pro Arg Glu Ala Lys Val Gln Trp Lys Val Asp Asn Ala Leu Gln
         35                  40                  45

Ser Gly Asn Ser Gln Glu Ser Val Thr Glu Gln Asp Ser Lys Asp Ser
```

-continued

```
                50                  55                  60
Thr Tyr Ser Leu Ser Ser Thr Leu Thr Leu Ser Lys Ala Asp Tyr Glu
 65                  70                  75                  80

Lys His Lys Val Tyr Ala Cys Glu Val Thr His Gln Gly Leu Ser Ser
                 85                  90                  95

Pro Val Thr Lys Ser Phe Asn Arg Gly Glu Cys
                100                 105

<210> SEQ ID NO 27
<211> LENGTH: 106
<212> TYPE: PRT
<213> ORGANISM: Homo Sapiens

<400> SEQUENCE: 27

Gly Gln Pro Lys Ala Ala Pro Ser Val Thr Leu Phe Pro Pro Ser Ser
  1               5                  10                  15

Glu Glu Leu Gln Ala Asn Lys Ala Thr Leu Val Cys Leu Ile Ser Asp
                 20                  25                  30

Phe Tyr Pro Gly Ala Val Thr Val Ala Trp Lys Ala Asp Ser Ser Pro
                 35                  40                  45

Val Lys Ala Gly Val Glu Thr Thr Thr Pro Ser Lys Gln Ser Asn Asn
 50                  55                  60

Lys Tyr Ala Ala Ser Ser Tyr Leu Ser Leu Thr Pro Glu Gln Trp Lys
 65                  70                  75                  80

Ser His Arg Ser Tyr Ser Cys Gln Val Thr His Glu Gly Ser Thr Val
                 85                  90                  95

Glu Lys Thr Val Ala Pro Thr Glu Cys Ser
                100                 105

<210> SEQ ID NO 28
<211> LENGTH: 290
<212> TYPE: PRT
<213> ORGANISM: Homo Sapiens
<220> FEATURE:
<221> NAME/KEY: SIGNAL
<222> LOCATION: (1)..(18)

<400> SEQUENCE: 28

Met Arg Ile Phe Ala Val Phe Ile Phe Met Thr Tyr Trp His Leu Leu
  1               5                  10                  15

Asn Ala Phe Thr Val Thr Val Pro Lys Asp Leu Tyr Val Val Glu Tyr
                 20                  25                  30

Gly Ser Asn Met Thr Ile Glu Cys Lys Phe Pro Val Glu Lys Gln Leu
                 35                  40                  45

Asp Leu Ala Ala Leu Ile Val Tyr Trp Glu Met Glu Asp Lys Asn Ile
 50                  55                  60

Ile Gln Phe Val His Gly Glu Glu Asp Leu Lys Val Gln His Ser Ser
 65                  70                  75                  80

Tyr Arg Gln Arg Ala Arg Leu Leu Lys Asp Gln Leu Ser Leu Gly Asn
                 85                  90                  95

Ala Ala Leu Gln Ile Thr Asp Val Lys Leu Gln Asp Ala Gly Val Tyr
                100                 105                 110

Arg Cys Met Ile Ser Tyr Gly Gly Ala Asp Tyr Lys Arg Ile Thr Val
                115                 120                 125

Lys Val Asn Ala Pro Tyr Asn Lys Ile Asn Gln Arg Ile Leu Val Val
                130                 135                 140

Asp Pro Val Thr Ser Glu His Glu Leu Thr Cys Gln Ala Glu Gly Tyr
```

```
                145                 150                 155                 160
        Pro Lys Ala Glu Val Ile Trp Thr Ser Ser Asp His Gln Val Leu Ser
                        165                 170                 175

Gly Lys Thr Thr Thr Thr Asn Ser Lys Arg Glu Glu Lys Leu Phe Asn
                        180                 185                 190

Val Thr Ser Thr Leu Arg Ile Asn Thr Thr Asn Glu Ile Phe Tyr
                    195                 200                 205

Cys Thr Phe Arg Arg Leu Asp Pro Glu Glu Asn His Thr Ala Glu Leu
                        210                 215                 220

Val Ile Pro Glu Leu Pro Leu Ala His Pro Pro Asn Glu Arg Thr His
        225                 230                 235                 240

Leu Val Ile Leu Gly Ala Ile Leu Leu Cys Leu Gly Val Ala Leu Thr
                            245                 250                 255

Phe Ile Phe Arg Leu Arg Lys Gly Arg Met Met Asp Val Lys Lys Cys
                        260                 265                 270

Gly Ile Gln Asp Thr Asn Ser Lys Lys Gln Ser Asp Thr His Leu Glu
                        275                 280                 285

Glu Thr
            290

<210> SEQ ID NO 29
<211> LENGTH: 290
<212> TYPE: PRT
<213> ORGANISM: Macaca Fascicularis
<220> FEATURE:
<221> NAME/KEY: SIGNAL
<222> LOCATION: (1)..(18)

<400> SEQUENCE: 29

Met Arg Ile Phe Ala Val Phe Ile Phe Thr Ile Tyr Trp His Leu Leu
        1               5                   10                  15

Asn Ala Phe Thr Val Thr Val Pro Lys Asp Leu Tyr Val Val Glu Tyr
                        20                  25                  30

Gly Ser Asn Met Thr Ile Glu Cys Lys Phe Pro Val Glu Lys Gln Leu
                    35                  40                  45

Asp Leu Thr Ser Leu Ile Val Tyr Trp Glu Met Glu Asp Lys Asn Ile
            50                  55                  60

Ile Gln Phe Val His Gly Glu Glu Asp Leu Lys Val Gln His Ser Asn
        65                  70                  75                  80

Tyr Arg Gln Arg Ala Gln Leu Leu Lys Asp Gln Leu Ser Leu Gly Asn
                        85                  90                  95

Ala Ala Leu Arg Ile Thr Asp Val Lys Leu Gln Asp Ala Gly Val Tyr
                    100                 105                 110

Arg Cys Met Ile Ser Tyr Gly Gly Ala Asp Tyr Lys Arg Ile Thr Val
                    115                 120                 125

Lys Val Asn Ala Pro Tyr Asn Lys Ile Asn Gln Arg Ile Leu Val Val
            130                 135                 140

Asp Pro Val Thr Ser Glu His Glu Leu Thr Cys Gln Ala Glu Gly Tyr
        145                 150                 155                 160

Pro Lys Ala Glu Val Ile Trp Thr Ser Ser Asp His Gln Val Leu Ser
                        165                 170                 175

Gly Lys Thr Thr Thr Thr Asn Ser Lys Arg Glu Glu Lys Leu Leu Asn
                        180                 185                 190

Val Thr Ser Thr Leu Arg Ile Asn Thr Thr Ala Asn Glu Ile Phe Tyr
                    195                 200                 205
```

```
Cys Ile Phe Arg Arg Leu Asp Pro Glu Glu Asn His Thr Ala Glu Leu
    210                 215                 220
Val Ile Pro Glu Leu Pro Leu Ala Leu Pro Pro Asn Glu Arg Thr His
225                 230                 235                 240
Leu Val Ile Leu Gly Ala Ile Phe Leu Leu Gly Val Ala Leu Thr
                    245                 250                 255
Phe Ile Phe Tyr Leu Arg Lys Gly Arg Met Met Asp Met Lys Lys Cys
                260                 265                 270
Gly Ile Arg Val Thr Asn Ser Lys Lys Gln Arg Asp Thr Gln Leu Glu
                275                 280                 285
Glu Thr
    290

<210> SEQ ID NO 30
<211> LENGTH: 255
<212> TYPE: PRT
<213> ORGANISM: Homo Sapiens
<220> FEATURE:
<221> NAME/KEY: SIGNAL
<222> LOCATION: (1)..(23)

<400> SEQUENCE: 30

Met Gly Asn Ser Cys Tyr Asn Ile Val Ala Thr Leu Leu Leu Val Leu
1               5                   10                  15
Asn Phe Glu Arg Thr Arg Ser Leu Gln Asp Pro Cys Ser Asn Cys Pro
                20                  25                  30
Ala Gly Thr Phe Cys Asp Asn Asn Arg Asn Gln Ile Cys Ser Pro Cys
                35                  40                  45
Pro Pro Asn Ser Phe Ser Ser Ala Gly Gly Gln Arg Thr Cys Asp Ile
    50                  55                  60
Cys Arg Gln Cys Lys Gly Val Phe Arg Thr Arg Lys Glu Cys Ser Ser
65                  70                  75                  80
Thr Ser Asn Ala Glu Cys Asp Cys Thr Pro Gly Phe His Cys Leu Gly
                85                  90                  95
Ala Gly Cys Ser Met Cys Glu Gln Asp Cys Lys Gln Gly Gln Glu Leu
                100                 105                 110
Thr Lys Lys Gly Cys Lys Asp Cys Cys Phe Gly Thr Phe Asn Asp Gln
            115                 120                 125
Lys Arg Gly Ile Cys Arg Pro Trp Thr Asn Cys Ser Leu Asp Gly Lys
    130                 135                 140
Ser Val Leu Val Asn Gly Thr Lys Glu Arg Asp Val Val Cys Gly Pro
145                 150                 155                 160
Ser Pro Ala Asp Leu Ser Pro Gly Ala Ser Ser Val Thr Pro Pro Ala
                165                 170                 175
Pro Ala Arg Glu Pro Gly His Ser Pro Gln Ile Ile Ser Phe Phe Leu
                180                 185                 190
Ala Leu Thr Ser Thr Ala Leu Leu Phe Leu Leu Phe Phe Leu Thr Leu
            195                 200                 205
Arg Phe Ser Val Val Lys Arg Gly Arg Lys Lys Leu Leu Tyr Ile Phe
    210                 215                 220
Lys Gln Pro Phe Met Arg Pro Val Gln Thr Thr Gln Glu Glu Asp Gly
225                 230                 235                 240
Cys Ser Cys Arg Phe Pro Glu Glu Glu Glu Gly Gly Cys Glu Leu
                245                 250                 255

<210> SEQ ID NO 31
```

<211> LENGTH: 253
<212> TYPE: PRT
<213> ORGANISM: Macaca Fascicularis
<220> FEATURE:
<221> NAME/KEY: SIGNAL
<222> LOCATION: (1)..(23)

<400> SEQUENCE: 31

Met Gly Asn Ser Cys Tyr Asn Ile Val Ala Thr Leu Leu Leu Val Leu
1               5                   10                  15

Asn Phe Glu Arg Thr Arg Ser Leu Gln Asp Leu Cys Ser Asn Cys Pro
            20                  25                  30

Ala Gly Thr Phe Cys Asp Asn Asn Arg Ser Gln Ile Cys Ser Pro Cys
        35                  40                  45

Pro Pro Asn Ser Phe Ser Ser Ala Gly Gly Gln Arg Thr Cys Asp Ile
50                  55                  60

Cys Arg Gln Cys Lys Gly Val Phe Lys Thr Arg Lys Glu Cys Ser Ser
65                  70                  75                  80

Thr Ser Asn Ala Glu Cys Asp Cys Ile Ser Gly Tyr His Cys Leu Gly
                85                  90                  95

Ala Glu Cys Ser Met Cys Glu Gln Asp Cys Lys Gln Gly Gln Glu Leu
            100                 105                 110

Thr Lys Lys Gly Cys Lys Asp Cys Cys Phe Gly Thr Phe Asn Asp Gln
        115                 120                 125

Lys Arg Gly Ile Cys Arg Pro Trp Thr Asn Cys Ser Leu Asp Gly Lys
130                 135                 140

Ser Val Leu Val Asn Gly Thr Lys Glu Arg Asp Val Val Cys Gly Pro
145                 150                 155                 160

Ser Pro Ala Asp Leu Ser Pro Gly Ala Ser Ala Thr Pro Pro Ala
                165                 170                 175

Pro Ala Arg Glu Pro Gly His Ser Pro Gln Ile Ile Phe Phe Leu Ala
            180                 185                 190

Leu Thr Ser Thr Val Val Leu Phe Leu Leu Phe Phe Leu Val Leu Arg
        195                 200                 205

Phe Ser Val Val Lys Arg Ser Arg Lys Lys Leu Leu Tyr Ile Phe Lys
210                 215                 220

Gln Pro Phe Met Arg Pro Val Gln Thr Thr Gln Glu Glu Asp Gly Cys
225                 230                 235                 240

Ser Cys Arg Phe Pro Glu Glu Glu Gly Gly Cys Glu
                245                 250

<210> SEQ ID NO 32
<211> LENGTH: 205
<212> TYPE: PRT
<213> ORGANISM: Artificial Sequence
<220> FEATURE:
<223> OTHER INFORMATION: Human-Wild boar chimeric CD137
<220> FEATURE:
<221> NAME/KEY: SIGNAL
<222> LOCATION: (1)..(23)

<400> SEQUENCE: 32

Met Gly Asn Ser Cys Tyr Asn Ile Val Ala Thr Leu Leu Leu Val Leu
1               5                   10                  15

Asn Phe Glu Arg Thr Arg Ser Val Pro Asp Pro Cys Ser Asn Cys Ser
            20                  25                  30

Ala Gly Thr Phe Cys Gly Lys Asn Ile Gln Glu Leu Cys Met Pro Cys
        35                  40                  45

```
Pro Pro Asn Ser Phe Ser Ser Ala Gly Gly Gln Arg Thr Cys Asp Ile
    50                  55                  60

Cys Arg Gln Cys Lys Gly Val Phe Arg Thr Arg Lys Glu Cys Ser Ser
65                  70                  75                  80

Thr Ser Asn Ala Glu Cys Asp Cys Thr Pro Gly Phe His Cys Leu Gly
                85                  90                  95

Ala Gly Cys Ser Met Cys Glu Gln Asp Cys Lys Gln Gly Gln Glu Leu
            100                 105                 110

Thr Lys Lys Gly Cys Lys Asp Cys Cys Phe Gly Thr Phe Asn Asp Gln
            115                 120                 125

Lys Arg Gly Ile Cys Arg Pro Trp Thr Asn Cys Ser Leu Asp Gly Lys
            130                 135                 140

Ser Val Leu Val Asn Gly Thr Lys Glu Arg Asp Val Val Cys Gly Pro
145                 150                 155                 160

Ser Pro Ala Asp Leu Ser Pro Gly Ala Ser Ser Val Thr Pro Pro Ala
                165                 170                 175

Pro Ala Arg Glu Pro Gly His Ser Pro Gln Ile Ile Ser Phe Phe Leu
            180                 185                 190

Ala Leu Thr Ser Thr Ala Leu Leu Gly Gly Cys Glu Leu
            195                 200                 205

<210> SEQ ID NO 33
<211> LENGTH: 255
<212> TYPE: PRT
<213> ORGANISM: Artificial Sequence
<220> FEATURE:
<223> OTHER INFORMATION: Human-Wild boar chimeric CD137
<220> FEATURE:
<221> NAME/KEY: SIGNAL
<222> LOCATION: (1)..(23)

<400> SEQUENCE: 33

Met Gly Asn Ser Cys Tyr Asn Ile Val Ala Thr Leu Leu Leu Val Leu
1               5                   10                  15

Asn Phe Glu Arg Thr Arg Ser Leu Gln Asp Pro Cys Ser Asn Cys Pro
            20                  25                  30

Ala Gly Thr Phe Cys Asp Asn Asn Arg Asn Gln Ile Cys Ser Pro Cys
            35                  40                  45

Pro Leu Asn Ser Phe Ser Ser Thr Gly Gly Gln Met Asn Cys Asp Met
    50                  55                  60

Cys Arg Lys Cys Glu Gly Val Phe Lys Thr Lys Arg Ala Cys Ser Pro
65                  70                  75                  80

Thr Arg Asp Ala Glu Cys Glu Cys Thr Pro Gly Phe His Cys Leu Gly
                85                  90                  95

Ala Gly Cys Ser Met Cys Glu Gln Asp Cys Lys Gln Gly Gln Glu Leu
            100                 105                 110

Thr Lys Lys Gly Cys Lys Asp Cys Cys Phe Gly Thr Phe Asn Asp Gln
            115                 120                 125

Lys Arg Gly Ile Cys Arg Pro Trp Thr Asn Cys Ser Leu Asp Gly Lys
            130                 135                 140

Ser Val Leu Val Asn Gly Thr Lys Glu Arg Asp Val Val Cys Gly Pro
145                 150                 155                 160

Ser Pro Ala Asp Leu Ser Pro Gly Ala Ser Ser Val Thr Pro Pro Ala
                165                 170                 175

Pro Ala Arg Glu Pro Gly His Ser Pro Gln Ile Ile Ser Phe Phe Leu
            180                 185                 190
```

```
Ala Leu Thr Ser Thr Ala Leu Leu Phe Leu Leu Phe Phe Leu Thr Leu
            195                 200                 205

Arg Phe Ser Val Val Lys Arg Gly Arg Lys Lys Leu Leu Tyr Ile Phe
    210                 215                 220

Lys Gln Pro Phe Met Arg Pro Val Gln Thr Thr Gln Glu Glu Asp Gly
225                 230                 235                 240

Cys Ser Cys Arg Phe Pro Glu Glu Glu Glu Gly Gly Cys Glu Leu
                245                 250                 255

<210> SEQ ID NO 34
<211> LENGTH: 255
<212> TYPE: PRT
<213> ORGANISM: Artificial Sequence
<220> FEATURE:
<223> OTHER INFORMATION: Human-Wild boar chimeric CD137
<220> FEATURE:
<221> NAME/KEY: SIGNAL
<222> LOCATION: (1)..(23)

<400> SEQUENCE: 34

Met Gly Asn Ser Cys Tyr Asn Ile Val Ala Thr Leu Leu Leu Val Leu
1               5                   10                  15

Asn Phe Glu Arg Thr Arg Ser Leu Gln Asp Pro Cys Ser Asn Cys Pro
            20                  25                  30

Ala Gly Thr Phe Cys Asp Asn Asn Arg Asn Gln Ile Cys Ser Pro Cys
        35                  40                  45

Pro Pro Asn Ser Phe Ser Ser Ala Gly Gly Gln Arg Thr Cys Asp Ile
    50                  55                  60

Cys Arg Gln Cys Lys Gly Val Phe Arg Thr Arg Lys Glu Cys Ser Ser
65                  70                  75                  80

Thr Ser Asn Ala Glu Cys Asp Cys Val Pro Gly Phe Arg Cys Leu Gly
                85                  90                  95

Ala Gly Cys Ala Met Cys Glu Glu Tyr Cys Gln Gln Gly Gln Glu Leu
            100                 105                 110

Thr Gln Lys Gly Cys Lys Asp Cys Cys Phe Gly Thr Phe Asn Asp Gln
        115                 120                 125

Lys Arg Gly Ile Cys Arg Pro Trp Thr Asn Cys Ser Leu Asp Gly Lys
    130                 135                 140

Ser Val Leu Val Asn Gly Thr Lys Glu Arg Asp Val Val Cys Gly Pro
145                 150                 155                 160

Ser Pro Ala Asp Leu Ser Pro Gly Ala Ser Ser Val Thr Pro Pro Ala
                165                 170                 175

Pro Ala Arg Glu Pro Gly His Ser Pro Gln Ile Ile Ser Phe Phe Leu
            180                 185                 190

Ala Leu Thr Ser Thr Ala Leu Leu Phe Leu Leu Phe Phe Leu Thr Leu
        195                 200                 205

Arg Phe Ser Val Val Lys Arg Gly Arg Lys Lys Leu Leu Tyr Ile Phe
    210                 215                 220

Lys Gln Pro Phe Met Arg Pro Val Gln Thr Thr Gln Glu Glu Asp Gly
225                 230                 235                 240

Cys Ser Cys Arg Phe Pro Glu Glu Glu Glu Gly Gly Cys Glu Leu
                245                 250                 255

<210> SEQ ID NO 35
<211> LENGTH: 255
<212> TYPE: PRT
<213> ORGANISM: Artificial Sequence
<220> FEATURE:
```

<223> OTHER INFORMATION: Human-Wild boar chimeric CD137
<220> FEATURE:
<221> NAME/KEY: SIGNAL
<222> LOCATION: (1)..(23)

<400> SEQUENCE: 35

```
Met Gly Asn Ser Cys Tyr Asn Ile Val Ala Thr Leu Leu Val Leu
1               5                   10                  15

Asn Phe Glu Arg Thr Arg Ser Leu Gln Asp Pro Cys Ser Asn Cys Pro
            20                  25                  30

Ala Gly Thr Phe Cys Asp Asn Asn Arg Asn Gln Ile Cys Ser Pro Cys
        35                  40                  45

Pro Pro Asn Ser Phe Ser Ser Ala Gly Gly Gln Arg Thr Cys Asp Ile
50                  55                  60

Cys Arg Gln Cys Lys Gly Val Phe Arg Thr Arg Lys Glu Cys Ser Ser
65                  70                  75                  80

Thr Ser Asn Ala Glu Cys Asp Cys Thr Pro Gly Phe His Cys Leu Gly
                85                  90                  95

Ala Gly Cys Ser Met Cys Glu Gln Asp Cys Lys Gln Gly Gln Glu Leu
            100                 105                 110

Thr Lys Glu Gly Cys Lys Asp Cys Ser Phe Gly Thr Phe Asn Asp Glu
        115                 120                 125

Glu His Gly Val Cys Arg Pro Trp Thr Asp Cys Ser Leu Asp Gly Lys
130                 135                 140

Ser Val Leu Val Asn Gly Thr Lys Glu Arg Asp Val Val Cys Gly Pro
145                 150                 155                 160

Ser Pro Ala Asp Leu Ser Pro Gly Ala Ser Ser Val Thr Pro Pro Ala
                165                 170                 175

Pro Ala Arg Glu Pro Gly His Ser Pro Gln Ile Ile Ser Phe Phe Leu
            180                 185                 190

Ala Leu Thr Ser Thr Ala Leu Leu Phe Leu Leu Phe Phe Leu Thr Leu
        195                 200                 205

Arg Phe Ser Val Val Lys Arg Gly Arg Lys Lys Leu Leu Tyr Ile Phe
210                 215                 220

Lys Gln Pro Phe Met Arg Pro Val Gln Thr Thr Gln Glu Glu Asp Gly
225                 230                 235                 240

Cys Ser Cys Arg Phe Pro Glu Glu Glu Glu Gly Gly Cys Glu Leu
                245                 250                 255
```

<210> SEQ ID NO 36
<211> LENGTH: 255
<212> TYPE: PRT
<213> ORGANISM: Artificial Sequence
<220> FEATURE:
<223> OTHER INFORMATION: Human-Wild boar chimeric CD137
<220> FEATURE:
<221> NAME/KEY: SIGNAL
<222> LOCATION: (1)..(23)

<400> SEQUENCE: 36

```
Met Gly Asn Ser Cys Tyr Asn Ile Val Ala Thr Leu Leu Val Leu
1               5                   10                  15

Asn Phe Glu Arg Thr Arg Ser Leu Gln Asp Pro Cys Ser Asn Cys Pro
            20                  25                  30

Ala Gly Thr Phe Cys Asp Asn Asn Arg Asn Gln Ile Cys Ser Pro Cys
        35                  40                  45

Pro Pro Asn Ser Phe Ser Ser Ala Gly Gly Gln Arg Thr Cys Asp Ile
50                  55                  60
```

```
Cys Arg Gln Cys Lys Gly Val Phe Arg Thr Arg Lys Glu Cys Ser Ser
 65                  70                  75                  80

Thr Ser Asn Ala Glu Cys Asp Cys Thr Pro Gly Phe His Cys Leu Gly
                 85                  90                  95

Ala Gly Cys Ser Met Cys Glu Gln Asp Cys Lys Gln Gly Gln Glu Leu
            100                 105                 110

Thr Lys Lys Gly Cys Lys Asp Cys Cys Phe Gly Thr Phe Asn Asp Gln
            115                 120                 125

Lys Arg Gly Ile Cys Arg Pro Trp Thr Asn Cys Ser Leu Ala Gly Lys
130                 135                 140

Pro Val Leu Met Asn Gly Thr Lys Ala Arg Asp Val Val Cys Gly Pro
145                 150                 155                 160

Arg Pro Ala Asp Leu Ser Pro Gly Ala Ser Ser Val Thr Pro Pro Ala
                165                 170                 175

Pro Ala Arg Glu Pro Gly His Ser Pro Gln Ile Ile Ser Phe Phe Leu
            180                 185                 190

Ala Leu Thr Ser Thr Ala Leu Leu Phe Leu Leu Phe Phe Leu Thr Leu
            195                 200                 205

Arg Phe Ser Val Val Lys Arg Gly Arg Lys Lys Leu Leu Tyr Ile Phe
210                 215                 220

Lys Gln Pro Phe Met Arg Pro Val Gln Thr Thr Gln Glu Glu Asp Gly
225                 230                 235                 240

Cys Ser Cys Arg Phe Pro Glu Glu Glu Glu Gly Gly Cys Glu Leu
                245                 250                 255
```

<210> SEQ ID NO 37
<211> LENGTH: 255
<212> TYPE: PRT
<213> ORGANISM: Artificial Sequence
<220> FEATURE:
<223> OTHER INFORMATION: Human-Wild boar chimeric CD137
<220> FEATURE:
<221> NAME/KEY: SIGNAL
<222> LOCATION: (1)..(23)

<400> SEQUENCE: 37

```
Met Gly Asn Ser Cys Tyr Asn Ile Val Ala Thr Leu Leu Leu Val Leu
 1               5                  10                  15

Asn Phe Glu Arg Thr Arg Ser Leu Gln Asp Pro Cys Ser Asn Cys Pro
                 20                  25                  30

Ala Gly Thr Phe Cys Asp Asn Asn Arg Asn Gln Ile Cys Ser Pro Cys
             35                  40                  45

Pro Pro Asn Ser Phe Ser Ser Ala Gly Gly Gln Arg Thr Cys Asp Ile
 50                  55                  60

Cys Arg Gln Cys Lys Gly Val Phe Arg Thr Arg Lys Glu Cys Ser Ser
 65                  70                  75                  80

Thr Ser Asn Ala Glu Cys Asp Cys Thr Pro Gly Phe His Cys Leu Gly
                 85                  90                  95

Ala Gly Cys Ser Met Cys Glu Gln Asp Cys Lys Gln Gly Gln Glu Leu
            100                 105                 110

Thr Lys Lys Gly Cys Lys Asp Cys Cys Phe Gly Thr Phe Asn Asp Gln
            115                 120                 125

Lys Arg Gly Ile Cys Arg Pro Trp Thr Asn Cys Ser Leu Asp Gly Lys
130                 135                 140

Ser Val Leu Val Asn Gly Thr Lys Glu Arg Asp Val Val Cys Gly Pro
145                 150                 155                 160
```

```
Ser Pro Thr Asp Phe Ser Pro Gly Thr Pro Ser Thr Met Pro Val
            165                 170                 175

Pro Gly Gly Glu Pro Gly His Thr Ser His Ile Ile Ser Phe Leu
            180                 185                 190

Ala Leu Thr Ser Thr Ala Leu Leu Phe Leu Leu Phe Leu Thr Leu
            195                 200                 205

Arg Phe Ser Val Val Lys Arg Gly Arg Lys Lys Leu Leu Tyr Ile Phe
            210                 215                 220

Lys Gln Pro Phe Met Arg Pro Val Gln Thr Thr Gln Glu Glu Asp Gly
225                 230                 235                 240

Cys Ser Cys Arg Phe Pro Glu Glu Glu Glu Gly Gly Cys Glu Leu
            245                 250                 255

<210> SEQ ID NO 38
<211> LENGTH: 255
<212> TYPE: PRT
<213> ORGANISM: Sus Scrofa
<220> FEATURE:
<221> NAME/KEY: SIGNAL
<222> LOCATION: (1)..(23)

<400> SEQUENCE: 38

Met Gly Asn Gly Tyr Tyr Asn Ile Val Ala Thr Val Leu Leu Val Met
1               5                   10                  15

Asn Phe Glu Arg Thr Arg Ser Val Pro Asp Pro Cys Ser Asn Cys Ser
            20                  25                  30

Ala Gly Thr Phe Cys Gly Lys Asn Ile Gln Glu Leu Cys Met Pro Cys
            35                  40                  45

Pro Ser Asn Ser Phe Ser Ser Thr Ser Gly Gln Lys Ala Cys Asn Val
50                  55                  60

Cys Arg Lys Cys Glu Gly Val Phe Arg Thr Lys Lys Glu Cys Ser Ser
65                  70                  75                  80

Thr Ser Asn Ala Val Cys Glu Cys Val Pro Gly Phe Arg Cys Leu Gly
            85                  90                  95

Ala Gly Cys Ala Met Cys Glu Glu Tyr Cys Gln Gln Gly Gln Glu Leu
            100                 105                 110

Thr Gln Glu Gly Cys Lys Asp Cys Ser Phe Gly Thr Phe Asn Asp Glu
            115                 120                 125

Glu His Gly Val Cys Arg Pro Trp Thr Asp Cys Ser Leu Ala Gly Lys
            130                 135                 140

Pro Val Leu Met Asn Gly Thr Lys Ala Arg Asp Val Val Cys Gly Pro
145                 150                 155                 160

Arg Pro Thr Asp Phe Ser Pro Gly Thr Pro Ser Thr Thr Met Pro Val
            165                 170                 175

Pro Gly Gly Glu Pro Gly His Thr Ser His Val Ile Ile Phe Phe Leu
            180                 185                 190

Ala Leu Met Ser Thr Ala Val Phe Val Leu Val Ser Tyr Leu Ala Leu
            195                 200                 205

Arg Phe Ser Val Val Gln Gln Gly Arg Lys Lys Leu Leu Tyr Ile Val
            210                 215                 220

Lys Gln Pro Phe Leu Lys Pro Ala Gln Thr Val Gln Glu Glu Asp Ala
225                 230                 235                 240

Cys Ser Cys Arg Phe Pro Glu Glu Glu Glu Gly Glu Cys Glu Leu
            245                 250                 255
```

```
<210> SEQ ID NO 39
<211> LENGTH: 255
<212> TYPE: PRT
<213> ORGANISM: Loxodonta Africana
<220> FEATURE:
<221> NAME/KEY: SIGNAL
<222> LOCATION: (1)..(23)

<400> SEQUENCE: 39
```

Met Gly Asn Gly Tyr Tyr Asn Met Val Ala Thr Val Leu Leu Val Met
1               5                   10                  15

Asn Phe Glu Arg Thr Gly Ala Val Gln Asp Ser Cys Arg Asp Cys Leu
            20                  25                  30

Ala Gly Thr Tyr Cys Val Lys Asn Glu Ser Gln Ile Cys Ser Pro Cys
        35                  40                  45

Pro Leu Asn Ser Phe Ser Ser Thr Gly Gln Met Asn Cys Asp Met
    50                  55                  60

Cys Arg Lys Cys Glu Gly Val Phe Lys Thr Lys Arg Ala Cys Ser Pro
65              70                  75                  80

Thr Arg Asp Ala Glu Cys Glu Cys Val Ser Gly Phe His Cys Leu Gly
                85                  90                  95

Ala Gly Cys Thr Met Cys Gln Gln Asp Cys Lys Gln Gly Gln Glu Leu
            100                 105                 110

Thr Lys Glu Gly Cys Lys Asp Cys Cys Leu Gly Thr Phe Asn Asp Gln
        115                 120                 125

Lys Asn Gly Ile Cys Arg Pro Trp Thr Asn Cys Ser Leu Glu Gly Lys
130                 135                 140

Ser Val Leu Ala Asn Gly Thr Lys Lys Arg Asp Val Val Cys Gly Pro
145                 150                 155                 160

Pro Ala Ala Asp Ser Phe Pro Asp Thr Ser Ser Val Thr Val Pro Ala
                165                 170                 175

Pro Glu Arg Lys Pro Asp His His Pro Gln Ile Ile Thr Phe Phe Leu
            180                 185                 190

Ala Leu Ile Ser Ala Ala Leu Leu Phe Leu Val Phe Phe Leu Val Val
        195                 200                 205

Arg Phe Ser Val Ala Lys Trp Gly Arg Lys Lys Leu Leu Tyr Ile Phe
210                 215                 220

Lys Gln Pro Phe Ile Lys Pro Val Gln Thr Ala Gln Glu Glu Asp Gly
225                 230                 235                 240

Cys Ser Cys Arg Phe Pro Glu Glu Glu Gly Asp Cys Glu Leu
                245                 250                 255

```
<210> SEQ ID NO 40
<211> LENGTH: 41
<212> TYPE: PRT
<213> ORGANISM: Homo Sapiens

<400> SEQUENCE: 40
```

Cys Pro Pro Asn Ser Phe Ser Ser Ala Gly Gly Gln Arg Thr Cys Asp
1               5                   10                  15

Ile Cys Arg Gln Cys Lys Gly Val Phe Arg Thr Arg Lys Glu Cys Ser
            20                  25                  30

Ser Thr Ser Asn Ala Glu Cys Asp Cys
        35                  40

```
<210> SEQ ID NO 41
<211> LENGTH: 232
<212> TYPE: PRT
```

<213> ORGANISM: Homo Sapiens

<400> SEQUENCE: 41

Leu Gln Asp Pro Cys Ser Asn Cys Pro Ala Gly Thr Phe Cys Asp Asn
1               5                   10                  15

Asn Arg Asn Gln Ile Cys Ser Pro Cys Pro Pro Asn Ser Phe Ser Ser
            20                  25                  30

Ala Gly Gly Gln Arg Thr Cys Asp Ile Cys Arg Gln Cys Lys Gly Val
        35                  40                  45

Phe Arg Thr Arg Lys Glu Cys Ser Ser Thr Ser Asn Ala Glu Cys Asp
50                  55                  60

Cys Thr Pro Gly Phe His Cys Leu Gly Ala Gly Cys Ser Met Cys Glu
65                  70                  75                  80

Gln Asp Cys Lys Gln Gly Gln Glu Leu Thr Lys Lys Gly Cys Lys Asp
            85                  90                  95

Cys Cys Phe Gly Thr Phe Asn Asp Gln Lys Arg Gly Ile Cys Arg Pro
        100                 105                 110

Trp Thr Asn Cys Ser Leu Asp Gly Lys Ser Val Leu Val Asn Gly Thr
            115                 120                 125

Lys Glu Arg Asp Val Val Cys Gly Pro Ser Pro Ala Asp Leu Ser Pro
130                 135                 140

Gly Ala Ser Ser Val Thr Pro Pro Ala Pro Ala Arg Glu Pro Gly His
145                 150                 155                 160

Ser Pro Gln Ile Ile Ser Phe Phe Leu Ala Leu Thr Ser Thr Ala Leu
            165                 170                 175

Leu Phe Leu Leu Phe Phe Leu Thr Leu Arg Phe Ser Val Val Lys Arg
            180                 185                 190

Gly Arg Lys Lys Leu Leu Tyr Ile Phe Lys Gln Pro Phe Met Arg Pro
            195                 200                 205

Val Gln Thr Thr Gln Glu Glu Asp Gly Cys Ser Cys Arg Phe Pro Glu
210                 215                 220

Glu Glu Glu Gly Gly Cys Glu Leu
225                 230

<210> SEQ ID NO 42
<211> LENGTH: 116
<212> TYPE: PRT
<213> ORGANISM: Artificial Sequence
<220> FEATURE:
<223> OTHER INFORMATION: VH-CD137 with FEAR substitutions

<400> SEQUENCE: 42

Glu Val Gln Leu Val Gln Ser Gly Ala Glu Val Lys Lys Pro Gly Glu
1               5                   10                  15

Ser Leu Arg Ile Ser Cys Lys Gly Ser Gly Tyr Ser Phe Ser Thr Tyr
            20                  25                  30

Trp Ile Ser Trp Val Arg Gln Met Pro Gly Lys Gly Leu Glu Trp Met
        35                  40                  45

Gly Lys Ile Tyr Pro Gly Asp Ser Tyr Thr Asn Tyr Ser Pro Ser Phe
50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
            85                  90                  95

Ala Arg Gly Tyr Gly Ile Phe Asp Tyr Trp Gly Gln Gly Thr Leu Val
        100                 105                 110

Thr Val Ser Ser
        115

<210> SEQ ID NO 43
<211> LENGTH: 8
<212> TYPE: PRT
<213> ORGANISM: Homo Sapiens

<400> SEQUENCE: 43

Gly Tyr Ser Phe Ser Thr Tyr Trp
1               5

<210> SEQ ID NO 44
<211> LENGTH: 8
<212> TYPE: PRT
<213> ORGANISM: Homo Sapiens

<400> SEQUENCE: 44

Ile Tyr Pro Gly Asp Ser Tyr Thr
1               5

<210> SEQ ID NO 45
<211> LENGTH: 9
<212> TYPE: PRT
<213> ORGANISM: Homo Sapiens

<400> SEQUENCE: 45

Ala Arg Gly Tyr Gly Ile Phe Asp Tyr
1               5

<210> SEQ ID NO 46
<211> LENGTH: 108
<212> TYPE: PRT
<213> ORGANISM: Homo Sapiens

<400> SEQUENCE: 46

Ser Tyr Glu Leu Thr Gln Pro Pro Ser Val Ser Val Ser Pro Gly Gln
1               5                   10                  15

Thr Ala Ser Ile Thr Cys Ser Gly Asp Asn Ile Gly Asp Gln Tyr Ala
            20                  25                  30

His Trp Tyr Gln Gln Lys Pro Gly Gln Ser Pro Val Leu Val Ile Tyr
        35                  40                  45

Gln Asp Lys Asn Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys Ala Thr Tyr Thr Gly Phe Gly Ser Leu
                85                  90                  95

Ala Val Phe Gly Gly Gly Thr Lys Leu Thr Val Leu
            100                 105

<210> SEQ ID NO 47
<211> LENGTH: 6
<212> TYPE: PRT
<213> ORGANISM: Homo Sapiens

<400> SEQUENCE: 47

Asn Ile Gly Asp Gln Tyr
1               5

<210> SEQ ID NO 48

```
<211> LENGTH: 11
<212> TYPE: PRT
<213> ORGANISM: Homo Sapiens

<400> SEQUENCE: 48

Ala Thr Tyr Thr Gly Phe Gly Ser Leu Ala Val
1               5                   10

<210> SEQ ID NO 49
<211> LENGTH: 119
<212> TYPE: PRT
<213> ORGANISM: Homo Sapiens

<400> SEQUENCE: 49

Gln Ser Val Glu Glu Ser Gly Gly Arg Leu Val Thr Pro Gly Thr Pro
1               5                   10                  15

Leu Thr Leu Thr Cys Thr Ala Ser Gly Phe Thr Ile Ser Asp Phe His
            20                  25                  30

Val Thr Trp Val Arg Gln Ala Pro Gly Lys Gly Leu Glu Trp Ile Gly
        35                  40                  45

Thr Ile Ile Thr Ser Ala Ser Thr Thr Ala Tyr Ala Thr Trp Ala Arg
    50                  55                  60

Gly Arg Phe Thr Ile Ser Lys Ser Ser Thr Thr Val Asn Leu Lys Ile
65                  70                  75                  80

Val Ser Pro Thr Thr Glu Asp Thr Ala Thr Tyr Phe Cys Ala Arg Ser
                85                  90                  95

Thr Tyr Thr Asp Thr Ser Gly Tyr Tyr Phe Asp Phe Trp Gly Gln Gly
            100                 105                 110

Thr Leu Val Thr Val Ser Ser
        115

<210> SEQ ID NO 50
<211> LENGTH: 8
<212> TYPE: PRT
<213> ORGANISM: Homo Sapiens

<400> SEQUENCE: 50

Gly Phe Thr Ile Ser Asp Phe His
1               5

<210> SEQ ID NO 51
<211> LENGTH: 8
<212> TYPE: PRT
<213> ORGANISM: Homo Sapiens

<400> SEQUENCE: 51

Ile Ile Thr Ser Ala Ser Thr Thr
1               5

<210> SEQ ID NO 52
<211> LENGTH: 15
<212> TYPE: PRT
<213> ORGANISM: Homo Sapiens

<400> SEQUENCE: 52

Ala Arg Ser Thr Tyr Thr Asp Thr Ser Gly Tyr Tyr Phe Asp Phe
1               5                   10                  15

<210> SEQ ID NO 53
<211> LENGTH: 113
<212> TYPE: PRT
<213> ORGANISM: Homo Sapiens
```

<400> SEQUENCE: 53

Ala Gln Val Leu Thr Gln Thr Ala Ser Pro Val Ser Ala Val Gly
1               5                   10                  15

Gly Thr Val Ile Ile Asn Cys Gln Ser Ser Gln Ser Ile Tyr Asn Gly
                20                  25                  30

Asn Arg Leu Ser Trp Tyr Gln Gln Lys Pro Gly Gln Pro Pro Lys Leu
            35                  40                  45

Leu Ile Tyr Ser Ala Ser Thr Leu Ala Ser Gly Val Ser Ser Arg Phe
        50                  55                  60

Lys Gly Ser Gly Ser Gly Thr Gln Phe Thr Leu Ala Ile Ser Asp Val
65                  70                  75                  80

Gln Ser Asp Asp Ala Ala Thr Tyr Tyr Cys Leu Gly Ser Tyr Asp Cys
                85                  90                  95

Asp Ser Ala Asp Cys Phe Ala Phe Gly Gly Thr Glu Val Val Val
                100                 105                 110

Glu

<210> SEQ ID NO 54
<211> LENGTH: 8
<212> TYPE: PRT
<213> ORGANISM: Homo Sapiens

<400> SEQUENCE: 54

Gln Ser Ile Tyr Asn Gly Asn Arg
1               5

<210> SEQ ID NO 55
<211> LENGTH: 13
<212> TYPE: PRT
<213> ORGANISM: Homo Sapiens

<400> SEQUENCE: 55

Leu Gly Ser Tyr Asp Cys Asp Ser Ala Asp Cys Phe Ala
1               5                   10

<210> SEQ ID NO 56
<211> LENGTH: 153
<212> TYPE: PRT
<213> ORGANISM: Artificial sequence
<220> FEATURE:
<223> OTHER INFORMATION: Recombinant human interleukin analog
<220> FEATURE:
<221> NAME/KEY: SIGNAL
<222> LOCATION: (1)..(20)

<400> SEQUENCE: 56

Met Tyr Arg Met Gln Leu Leu Ser Cys Ile Ala Leu Ser Leu Ala Leu
1               5                   10                  15

Val Thr Asn Ser Ala Pro Thr Ser Ser Ser Thr Lys Lys Thr Gln Leu
                20                  25                  30

Gln Leu Glu His Leu Leu Leu Asp Leu Gln Met Ile Leu Asn Gly Ile
            35                  40                  45

Asn Asn Tyr Lys Asn Pro Lys Leu Thr Arg Met Leu Thr Phe Lys Phe
        50                  55                  60

Tyr Met Pro Lys Lys Ala Thr Glu Leu Lys His Leu Gln Cys Leu Glu
65                  70                  75                  80

Glu Glu Leu Lys Pro Leu Glu Glu Val Leu Asn Leu Ala Gln Ser Lys
                85                  90                  95

```
Asn Phe His Leu Arg Pro Arg Asp Leu Ile Ser Asn Ile Asn Val Ile
            100                 105                 110

Val Leu Glu Leu Lys Gly Ser Glu Thr Thr Phe Met Ser Glu Tyr Ala
            115                 120                 125

Asp Glu Thr Ala Thr Ile Val Glu Phe Leu Asn Arg Trp Ile Thr Phe
            130                 135                 140

Cys Gln Ser Ile Ile Ser Thr Leu Thr
145                 150

<210> SEQ ID NO 57
<211> LENGTH: 118
<212> TYPE: PRT
<213> ORGANISM: Homo sapiens

<400> SEQUENCE: 57

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Ser
            20                  25                  30

Trp Ile His Trp Tyr Arg Gln Ala Pro Gly Lys Gly Leu Glu Trp Tyr
        35                  40                  45

Ala Trp Ile Ser Pro Tyr Gly Gly Ser Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Arg His Trp Pro Gly Gly Phe Asp Tyr Trp Gly Gln Gly Thr
            100                 105                 110

Leu Val Thr Val Ser Ser
            115

<210> SEQ ID NO 58
<211> LENGTH: 107
<212> TYPE: PRT
<213> ORGANISM: Homo sapiens

<400> SEQUENCE: 58

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Leu Tyr His Pro Ala
                85                  90                  95

Thr Phe Gly Gln Gly Thr Lys Val Glu Ile Lys
            100                 105
```

BINDING AGENTS BINDING TO PD-L1 AND CD137 AND USE THEREOF

RELATED APPLICATIONS

This application is a continuation of International Patent Application No. PCT/EP2018/071002, filed Aug. 2, 2018, which claims priority to International Patent Application Nos. PCT/EP2018/052946, filed Feb. 6, 2018; and PCT/EP2017/069839, filed Aug. 4, 2017, the entire disclosures of which are hereby incorporated herein by reference.

FIELD OF THE INVENTION

The present invention relates to novel binding agents and their use in medicine. In particular, the invention relates to binding agents, such as bispecific antibodies, binding human PD-L1 and binding human CD137. The invention furthermore relates to uses of the binding agents of the invention and to methods, nucleic acid constructs and host cells for producing antibodies of the invention.

BACKGROUND OF THE INVENTION

CD137 (4-1BB, TNFRSF9) is a member of the tumor necrosis factor (TNF) receptor (TNFR) family. CD137 is a co-stimulatory molecule on $CD8^+$ and $CD4^+$ T cells, regulatory T cells (Tregs), natural killer (NK) and NKT cells, B cells and neutrophils. On T cells, CD137 is not constitutively expressed, but induced upon T-cell receptor (TCR)-activation. Stimulation via its natural ligand 4-1BBL or agonist antibodies leads to signaling using TNFR-associated factor (TRAF)-2 and TRAF-1 as adaptors. Early signaling by CD137 involves K-63 poly-ubiquitination reactions that ultimately result in activation of the nuclear factor (NF)— KB and mitogen-activated protein (MAP)-kinase pathways. Signaling leads to increased T cell co-stimulation, proliferation, cytokine production, maturation and prolonged $CD8^+$ T-cell survival. Agonistic antibodies against CD137 have been shown to promote anti-tumor control by T cells in various pre-clinical models (Murillo et al. 2008 Clin. Cancer Res. 14(21): 6895-6906). Antibodies stimulating CD137 can induce survival and proliferation of T cells, thereby enhancing the anti-tumor immune response. Antibodies stimulating CD137 have been disclosed in the prior art, and include urelumab, a human IgG4 antibody (WO2005035584) and utomilumab, a human IgG2 antibody (Fisher et al. 2012 Cancer Immunol. Immunother. 61: 1721-1733).

Programmed death ligand 1 (PD-L1, PDL1, CD274, B7H1) is a 33 kDa, single-pass type I membrane protein. Three isoforms of PD-L1 have been described, based on alternative splicing. PD-L1 belongs to the immunoglobulin (Ig) superfamily and contains one Ig-like C2-type domain and one Ig-like V-type domain. Freshly isolated T and B cells express negligble amounts of PD-L1 and a fraction (about 16%) of $CD14^+$ monocytes constitutively express PD-L1. However, interferon-γ (IFNγ) is known to upregulate PD-L1 on tumor cells.

PD-L1 obstructs anti-tumor immunity by 1) tolerizing tumor-reactive T cells by binding to its receptor, programmed cell death protein 1 (PD-1) (CD279) on activated T cells; 2) rendering tumor cells resistant to $CD8^+$ T cell and Fas ligand-mediated lysis by PD-1 signaling through tumor cell-expressed PD-L1; 3) tolerizing T cells by reverse signaling through T cell-expressed CD80 (B7.1); and 4) promoting the development and maintenance of induced T regulatory cells. PD-L1 is expressed in many human cancers, including melanoma, ovarian, lung and colon cancer (Latchman et al., 2004 Proc Natl Acad Sci USA 101, 10691-6).

PD-L1 blocking antibodies have shown clinical activity in several cancers known to overexpress PD-L1 (incl. melanoma, NSCLC). For example, atezolizumab is a humanized IgG1 monoclonal antibody against PD-L1. It is currently in clinical trials as an immunotherapy for several indications including various types of solid tumors (see e.g. Rittmeyer et al., 2017 Lancet 389:255-265) and is approved for non-small-cell lung cancer and bladder cancer indications. Avelumab, a PD-L1 antibody, (Kaufman et al Lancet Oncol. 2016; 17(10):1374-1385) has been approved by the FDA for the treatment of adults and pediatric patients 12 years and older with metastatic Merkel cell carcinoma, and is currently in clinical trials in several cancer indiciations, including bladder cancer, gastric cancer, head and neck cancer, mesothelioma, NSCLC, ovarian cancer and renal cancer. Durvalumab, a PD-L1 antibody, is approved for locally advanced or metastatic urothelial carcinoma indications, and is in clinical development in multiple solid tumors and blood cancers (see e.g. Massard et al., 2016 J Clin Oncol. 34(26): 3119-25). Further anti-PD-L1 antibodies have been described in WO2004004771, WO2007005874, WO2010036959, WO2010077634, WO2013079174, WO2013164694, WO2013173223 and WO2014022758.

Horton et al (J Immunother Cancer. 2015; 3 (Suppl 2): 010) discloses combination of an agonistic 4-1BB antibody with a neutralizing PD-L1 antibody.

Combination therapy of utomilumab and avelumab is currently being tested in the clinic (Chen et al., J Clin Oncol 35, 2017 suppl; abstr TPS7575, and clinical trial NCT02554812).

However, despite advances in the art, there is a need for multispecific antibodies that can bind both PD-L1 and CD137. These will give simultaneous binding to PD-L1-expressing antigen-presenting cells (APCs) or tumor cells and CD137-expressing T cells, resulting in conditional activation of (cytotoxic) T cells. PD-L1 binding to PD1 expressed on activated T cells will result in T cell inhibition. Accordingly, it is an object of the present invention to provide PD-L1×CD137 bispecific binding agents such as bispecific antibodies which block the PD1-(PD-L1) inhibitory signaling and at the same time co-stimulate T cells via trans binding to the CD137 molecule expressed on activated T cells, with the activation occurring through the trans binding. This can lead to efficient induction of anti-tumor immunity. It is a further object of the present invention to provide a PD-L1×CD137 bispecific binding agent with an inert Fc region or alternatively without an Fc binding region, thereby providing a bispecific binding agent which does not induce complement-dependent cytotoxicity (CDC) or other Fc-mediated effector functions on the T cells when binding to CD137. It is a further object of the present invention to provide a PD-L1×CD137 bispecific binding agent suitable for activating T cells. It is a further object of the present invention to provide a PD-L1×CD137 bispecific binding agent suitable for activating tumor-specific T cells such as tumor infiltrating T cells. It is a further object of the present invention to provide a bispecific binding agent with an improved toxicology profile compared to current treatment options in the field. It is yet a further object of the present invention to provide a binding agent with improved efficacy profile compared to current treatment options in the field.

SUMMARY OF THE INVENTION

In a first aspect, the invention provides for binding agents comprising a first antigen-binding region binding to human CD137 and a second antigen-binding region binding to human PD-L1, wherein the second antigen-binding region inhibits the binding of human PD-L1 to human PD-1. Such binding agents comprising a first and a second antigen-binding region have a dual effect:

Firstly, through its PD-L1 binding region, the binding agent binds PD-L1-expressing tumor cells or antigen-presenting cells (APCs), while through its CD137-binding region, the binding agent binds and activates T cells, resulting in conditional activation of the T cells. Thus, without being bound by theory, the binding agent according to the invention may mediate clustering of CD137 when the binding agent simultaneously binds to PD-L1 and CD137. Clustering of CD137 by the binding agent is needed for sufficient activation of this receptor and CD137-mediated co-stimulation of T cells. Secondly, the binding agent thus brings T cells in close proximity to tumor cells, thereby facilitating tumor cell killing by T cells. Furthermore, without being limited by any specific theory, it is hypothesized that bringing PD-L1-expressing tumor cells and effector T cells, such as $CD8^+$ T cells in close proximity to each other might initiate the release of interferon-0 which in turn could upregulate PD-L1 on tumor cells, thus facilitating recruitment of more binding agent to the tumor and further enhance its killing.

Lastly, the binding agent of the invention inhibits the binding of human PD-L1 to human PD-1 thus preventing PD-L1 from obstructing anti-tumor immunity through PD-1. Thus, the binding agent prevents that the T cells receives an inhibitory signal through PD-1/PD-L1 interaction, while receiving an activation signal through binding to the CD137 molecule resulting in signaling that strengthens T cell proliferation, activation, effector and memory functions.

The PD-L1×CD137 binding agents of the present invention are particularly useful in therapeutic settings where stimulation of an activation receptor such as CD137 and blocking of an inhibition signal such as PD-1/PD-L1 on T cells can be achieved simultaneously. This can result in a higher magnitude of T cell proliferation, activation and survival than stimulating CD137 and blocking PD-1/PD-L1 via PD-L1 separately.

In one embodiment of the invention, the PD-L1×CD137 binding agent is a bispecific antibody.

In another embodiment of the invention, the binding agent is a bispecific antibody having a first antigen-binding region binding to human CD137 and a second antigen-binding region binding to human PD-L1, wherein the second antigen-binding region inhibits the binding of human PD-L1 to human PD-1.

In a further embodiment of the invention, the binding agent comprises a first antigen-binding region binding to human CD137 and a second antigen-binding region binding to human PD-L1, wherein a) the first antigen-binding region comprises a heavy chain variable region (VH) comprising a HCDR1, HCDR2, and HCDR3 sequence, as set forth in: SEQ ID NO:9, 10, 11, respectively, and a light chain variable region (VL) comprising a LCDR1, LCDR2, and LCDR3 sequence, as set forth in: SEQ ID NO: 13, GAS, 14, respectively, and b) the second antigen-binding region comprises a heavy chain variable region (VH) comprising a HCDR1, HCDR2, and HCDR3 sequence, as set forth in: SEQ ID NO:18, 19, 20 respectively, and a light chain variable region (VL) comprising a LCDR1, LCDR2, and LCDR3 sequence, as set forth in: SEQ ID NO:22, DDN, 23, respectively.

Alternatively, the binding agent comprises a first antigen-binding region binding to human CD137 and a second antigen-binding region binding to human PD-L1, wherein a) the first antigen-binding region comprises a heavy chain variable region (VH) comprising a HCDR1, HCDR2, and HCDR3 sequence, as set forth in: SEQ ID NO: 50, 51, 52, respectively, and a light chain variable region (VL) comprising a LCDR1, LCDR2, and LCDR3 sequence, as set forth in: SEQ ID NO: 54, SAS, 55, respectively, and b) the second antigen-binding region comprises a heavy chain variable region (VH) comprising a HCDR1, HCDR2, and HCDR3 sequence, as set forth in: SEQ ID NO:18, 19, 20 respectively, and a light chain variable region (VL) comprising a LCDR1, LCDR2, and LCDR3 sequence, as set forth in: SEQ ID NO:22, DDN, 23, respectively.

In another embodiment of the invention, the binding agent comprises a first antigen-binding region binding to human CD137, which is derived from a humanized antibody, and/or a second antigen-binding region binding to human PD-L1, which is derived from a human antibody.

In a further aspect, the invention relates to the use of the binding agents of the invention in medicine, in particular for the treatment of cancer.

These and other aspects and embodiments of the invention, including nucleic acids encoding the amino acid sequences of such binding agents e.g. antibodies; expression vectors comprising such nucleic acids; cells comprising such nucleic acids or expression vectors; compositions comprising such binding agents, nucleic acids, expression vectors or cells; such binding agents, nucleic acids, expression vectors, cells or compositions for use in treating cancer or other diseases; methods for producing such binding agents e.g. bispecific antibodies; and diagnostic methods and kits based on such binding agents e.g. multispecific in particular bispecific antibodies, are described in further detail below.

BRIEF DESCRIPTION OF THE DRAWINGS

FIG. 1: Sequence alignments for human, African elephant and wild boar CD137. Amino acids in African elephant and wild boar CD137 that differ from those in the human sequence are highlighted in black.

FIGS. 6A-6B: Schematic representation of the anticipated mode of action of CD137×PD-L1 bispecific antibodies. (FIG. 6A) PD-L1 is expressed on antigen-presenting cells (APCs) as well as on tumor cells. PD-L1 binding to T cells expressing the negative regulatory molecule PD-1 effectively overrides T cell activation signals and eventually leads to T cell inhibition. (FIG. 6B) Upon addition of a CD137×PD-L1 bispecific antibody, the inhibitory PD-1:PD-L1 interaction is blocked via the PD-L1-specific arm and at the same time, the bispecific antibody, through the cell-cell interaction provides agonistic signaling to CD137 expressed on the T cells resulting in strong T cell costimulation.

(FIG. 7B) shows analysis of data from donor 1 representatively shown in (FIG. 7A). (FIG. 7D) shows analysis of data from donor 2 representatively shown in (FIG. 7C). Error bars (SD) indicate variation within the experiment (three replicates, using cells from one donor).

FIGS. 10A-10D: Ex vivo expansion of tumor infiltrating lymphocytes (TIL) from a human non-small-cell lung cancer tissue resection by CD137-009-FEAL×PD-L1-547-FEAR. Tumor pieces from the resected tissue were cultured with 10 U/mL IL-2 and the indicated concentration of CD137-009-FEAL×PD-L1-547-FEAR. After 10 days of culture, cells were harvested and analyzed by flow cytometry. (FIG. 10A) TIL count as fold expansion compared to untreated controls, (FIG. 10B) CD3$^+$CD8$^+$ T cell count as fold expansion compared to untreated controls, (FIG. 10C) CD3$^+$CD4$^+$ T cell count as fold expansion compared to untreated controls, (FIG. 10D) CD3$^+$-CD56$^+$ NK cell count as fold expansion compared to untreated controls. Bars represent the mean±SD of n=5 individual wells, with two tumor pieces per well as starting material.

FIGS. 11A-11B: Effect of mCD137-3H3×mPD-L1-MPDL3280A mouse surrogate antibody on antigen-specific T cell proliferation in an OT-I adoptive cell transfer set up. Ovalbumin (OVA) specific OT1$^+$Thy1.1$^+$ double positive cytotoxic T cells isolated from donor mice were retro-orbitally (r.o.) injected into naïve C57BL/6 recipient mice. The day after adoptive cell transfer, recipient mice were injected r.o. with 100 μg OVA as antigenic stimulus followed by a r.o. injection of 100 μg or 20 μg mCD137-3H3×mPD-L1-MPDL3280A, mCD137-3H3×b12 or mPD-L1-MPDL3280A×b12 antibody per mouse. Injection of PBS (indicated as OVA alone in the figure) was used as baseline reference and untreated animals were used as negative control. After 6 days, 100 μL blood was drawn via the r.o. route and analyzed for Thy1.1$^+$CD8$^+$ T cells. Data shown are (FIG. 11A) a schematic representation of the OT-I adoptive cell transfer experimental outline, and (FIG. 11B) the Thy1.1$^+$CD8$^+$ T cell frequency for each treatment group at day 6. Squares represent individual animals and error bars (SD) indicate the variation within the experiment (n=5 mice per group). Statistical analysis was performed using One-way Anova with Tukey's multiple comparisons test; ns=no significant difference between groups, ***=P<0.001.

FIGS. 12A-12C: Anti-tumor efficacy of the mCD137-3H3×mPD-L1-MPDL3280A mouse surrogate antibody in a subcutaneous, syngeneic CT26 mouse tumor model. Female BALB/c mice bearing subcutaneous CT26 tumors were treated with intraperitoneal injections of 20 μg (i) mCD137-3H3×mPD-L1-MPDL3280A, (ii) mCD137-3H3×b12 or (iii) mPD-L1-MPDL3280A×b12 antibody per mouse, or (iv) PBS, after tumors reached a volume ≥30 mm$^3$. Dosing schedule was: every 2-3 days for the first eight injections, followed by an injection every 7 days until the end of the experiment. At day 29, 100 μL blood was drawn via the r.o. route and analyzed for gp70-specific CD8$^+$ T cells. Data shown are (FIG. 12A) tumor growth curves with each line representing a single mouse, (FIG. 12B) the resulting Kaplan-Meier survival analysis, and (FIG. 12C) the gp70-specific CD8$^+$ T-cell frequencies for each treatment group at day 29 post implantation. PFS=progression free survival.

(FIG. 14A) Zscores for binding of b12-FEAL×CD137-009-FEAR-A488 to CD137 variants with alanine or glycine mutations at position 1 to 163, using CD137-005-FEAR-A488 as non-cross blocking CD137-specific control antibody for normalization. (FIG. 14B) Zscores for binding of CD137-005-FEAR-A488 to CD137 variants with alanine or glycine mutations at position 1 to 163, using CD137-MOR7480-FEAR-A488 as non-cross blocking CD137 specific control antibody for normalization. (FIG. 14C) Zscores for binding of CD137-MOR7480-FEAR-A488 to CD137 variants with alanine or glycine mutations at position 1 to 163, using CD137-005-FEAR-A488 as non-cross blocking CD137 specific control antibody for normalization.

DETAILED DESCRIPTION OF THE INVENTION

Definitions

Figure 2:
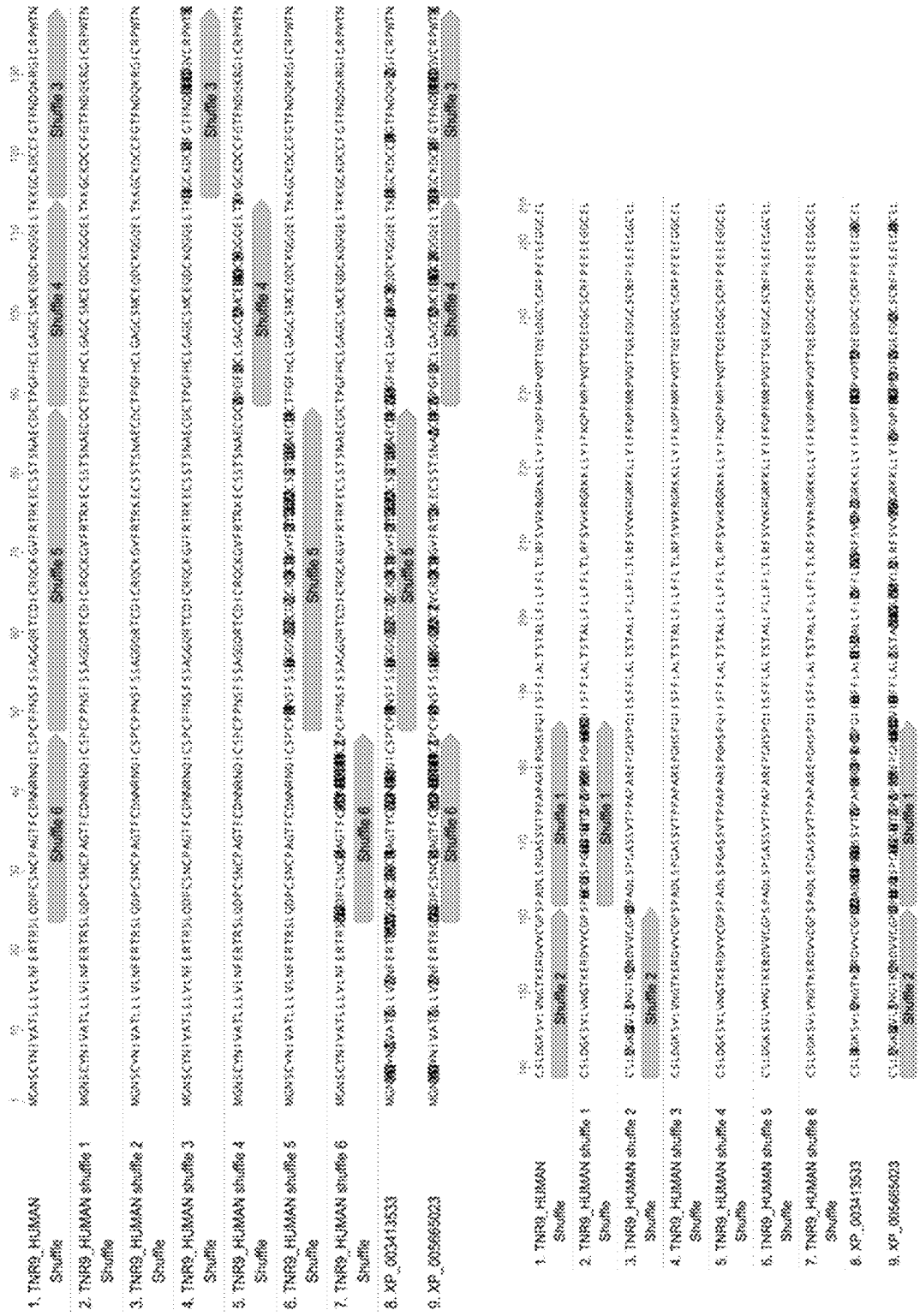
FIG. 2: CD137 shuffle constructs, containing African elephant (shuffle 5) or wild boar (shuffle 1-4, 6) CD137 domains.
Figure 3:
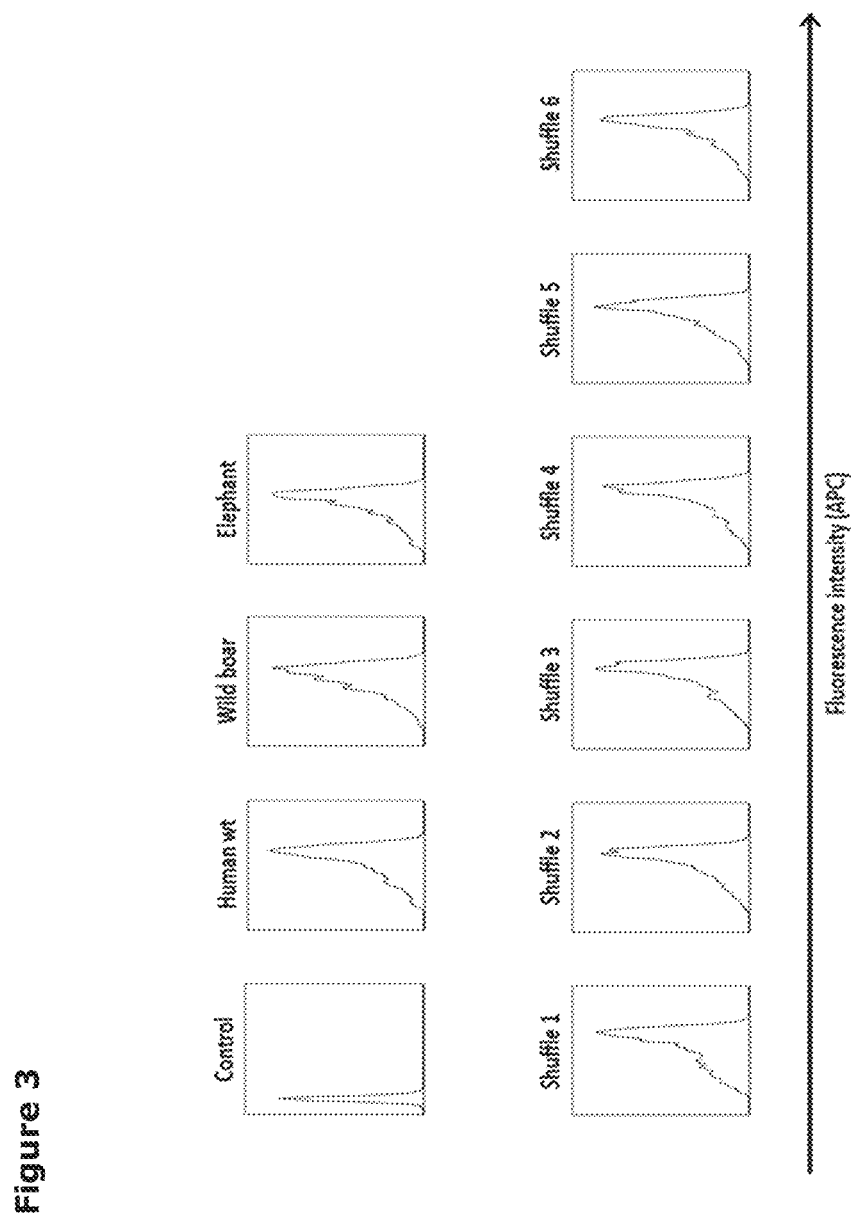
FIG. 3: Expression of CD137 shuffle constructs on HEK293-T17 cells. HEK293-T17 cells were transfected with the CD137 shuffle constructs. Cell surface expression of the constructs was measured by flow cytometry, using a polyclonal anti-CD137 antibody that recognizes human, wild boar and African elephant CD137.
Figure 4:
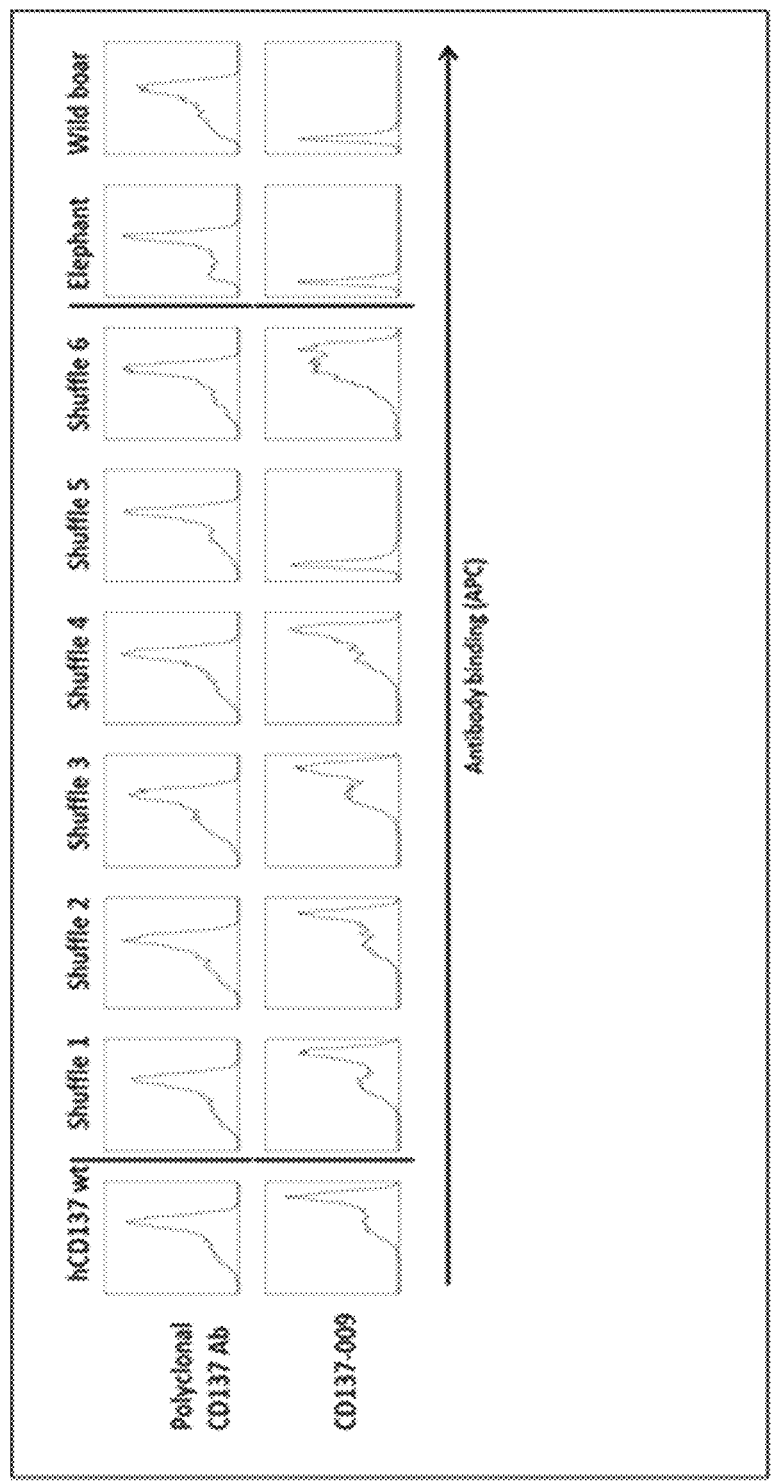
FIG. 4: Binding of antibody CD137-009 to CD137 shuffle constructs expressed on HEK293-T17 cells. HEK293-T17 cells were transfected with the CD137 shuffle constructs, and with human CD137 (hCD137 wt), African elephant of wild boar CD137. Binding of antibody CD137-009 to these constructs expressed on HEK293-T17 cells was measured by flow cytometry. Staining with polyclonal anti-CD137 antibody is shown as a control.

The term "immunoglobulin" refers to a class of structurally related glycoproteins consisting of two pairs of polypeptide chains, one pair of light (L) low molecular weight chains and one pair of heavy (H) chains, all four interconnected by disulfide bonds. The structure of immunoglobulins has been well characterized. See for instance Fundamental Immunology Ch. 7 (Paul, W., ed., 2nd ed. Raven Press, N.Y. (1989)). Briefly, each heavy chain typically is comprised of a heavy chain variable region (abbreviated herein as $V_H$ or VH) and a heavy chain constant region (abbreviated herein as CH or CH). The heavy chain constant region typically is comprised of three domains, CH1, CH2, and CH3. The hinge region is the region between the CH1 and CH2 domains of the heavy chain and is highly flexible. Disulphide bonds in the hinge region are part of the interactions between two heavy chains in an IgG molecule. Each light chain typically is comprised of a light chain variable region (abbreviated herein as $V_L$ or VL) and a light chain constant region (abbreviated herein as $C_L$ or CL). The light chain constant region typically is comprised of one domain, CL. The VH and VL regions may be further subdivided into regions of hypervariability (or hypervariable regions which may be hypervariable in sequence and/or form of structurally defined loops), also termed complementarity determining regions (CDRs), interspersed with regions that are more conserved, termed framework regions (FRs). Each VH and VL is typically composed of three CDRs and four FRs, arranged from amino-terminus to carboxy-terminus in the following order: FR1, CDR1, FR2, CDR2, FR3, CDR3, FR4 (see also Chothia and Lesk 3. Mol. Biol. 196, 901-917 (1987)). Unless otherwise stated or contradicted by context, CDR sequences herein are identified according to IMGT rules using DomainGapAlign (Lefranc M P., Nucleic Acids Research 1999; 27:209-212 and Ehrenmann F., Kaas Q. and Lefranc M.-P. Nucleic Acids Res., 38, D301-307 (2010); see also internet http address www.imgt.org/). Unless otherwise stated or contradicted by context, reference to amino acid positions in the constant regions in the present invention is according to the EU-numbering (Edelman et al., Proc Natl Acad Sci USA. 1969 May; 63(1):78-85;

Kabat et al., Sequences of Proteins of Immunological Interest, Fifth Edition. 1991 NIH Publication No. 91-3242). For example, SEQ ID NO:93 herein sets forth amino acids positions 118-447 according to EU numbering, of the IgG1m(f) heavy chain constant region.

The term "amino acid corresponding to position . . . " as used herein refers to an amino acid position number in a human IgG1 heavy chain. Corresponding amino acid positions in other immunoglobulins may be found by alignment with human IgG1. Thus, an amino acid or segment in one sequence that "corresponds to" an amino acid or segment in another sequence is one that aligns with the other amino acid or segment using a standard sequence alignment program such as ALIGN, ClustalW or similar, typically at default settings and has at least 50%, at least 80%, at least 90%, or at least 95% identity to a human IgG1 heavy chain. It is considered well-known in the art how to align a sequence or segment in a sequence and thereby determine the corresponding position in a sequence to an amino acid position according to the present invention.

The term "binding agent" in the context of the present invention refers to any agent capable of binding to desired antigens. In certain embodiments of the invention, the binding agent is an antibody, antibody fragment, or construct thereof. The binding agent may also comprise synthetic, modified or non-naturally occurring moieties, in particular non-peptide moieties. Such moieties may, for example, link desired antigen-binding functionalities or regions such as antibodies or antibody fragments. In one embodiment, the binding agent is a synthetic construct comprising antigen-binding CDRs or variable regions.

The term "antibody" (Ab) in the context of the present invention refers to an immunoglobulin molecule, a fragment of an immunoglobulin molecule, or a derivative of either thereof, which has the ability to specifically bind to an antigen under typical physiological conditions with a half-life of significant periods of time, such as at least about 30 minutes, at least about 45 minutes, at least about one hour, at least about two hours, at least about four hours, at least about 8 hours, at least about 12 hours, about 24 hours or more, about 48 hours or more, about 3, 4, 5, 6, 7 or more days, etc., or any other relevant functionally-defined period (such as a time sufficient to induce, promote, enhance, and/or modulate a physiological response associated with antibody binding to the antigen and/or time sufficient for the antibody to recruit an effector activity). The variable regions of the heavy and light chains of the immunoglobulin molecule contain a binding domain that interacts with an antigen. The term "antigen-binding region", wherein used herein, refers to the region which interacts with the antigen and comprises both a VH region and a VL region. The term antibody when used herein comprises not only monospecific antibodies, but also multispecific antibodies which comprise multiple, such as two or more, e.g. three or more, different antigen-binding regions. The constant regions of the antibodies (Abs) may mediate the binding of the immunoglobulin to host tissues or factors, including various cells of the immune system (such as effector cells) and components of the complement system such as C1q, the first component in the classical pathway of complement activation. As indicated above, the term antibody herein, unless otherwise stated or clearly contradicted by context, includes fragments of an antibody that are antigen-binding fragments, i.e., retain the ability to specifically bind to the antigen. It has been shown that the antigen-binding function of an antibody may be performed by fragments of a full-length antibody. Examples of antigen-binding fragments encompassed within the term "antibody" include (i) a Fab' or Fab fragment, a monovalent fragment consisting of the VL, VH, CL and CH1 domains, or a monovalent antibody as described in WO2007059782 (Genmab); (ii) F(ab')$_2$ fragments, bivalent fragments comprising two Fab fragments linked by a disulfide bridge at the hinge region; (iii) a Fd fragment consisting essentially of the VH and CH1 domains; (iv) a Fv fragment consisting essentially of the VL and VH domains of a single arm of an antibody, (v) a dAb fragment (Ward et al., Nature 341, 544-546 (1989)), which consists essentially of a VH domain and also called domain antibodies (Holt et al; Trends Biotechnol. 2003 November; 21(11):484-90); (vi) camelid or Nanobody molecules (Revets et al; Expert Opin Biol Ther. 2005 January; 5(1):111-24) and (vii) an isolated complementarity determining region (CDR). Furthermore, although the two domains of the Fv fragment, VL and VH, are coded for by separate genes, they may be joined, using recombinant methods, by a synthetic linker that enables them to be made as a single protein chain in which the VL and VH regions pair to form monovalent molecules (known as single chain antibodies or single chain Fv (scFv), see for instance Bird et al., Science 242, 423-426 (1988) and Huston et al., PNAS USA 85, 5879-5883 (1988)). Such single chain antibodies are encompassed within the term antibody unless otherwise noted or clearly indicated by context. Although such fragments are generally included within the meaning of antibody, they collectively and each independently are unique features of the present invention, exhibiting different biological properties and utility. These and other useful antibody fragments in the context of the present invention, as well as bispecific formats of such fragments, are discussed further herein. It also should be understood that the term antibody, unless specified otherwise, also includes polyclonal antibodies, monoclonal antibodies (mAbs), antibody-like polypeptides, such as chimeric antibodies and humanized antibodies, and antibody fragments retaining the ability to specifically bind to the antigen (antigen-binding fragments) provided by any known technique, such as enzymatic cleavage, peptide synthesis, and recombinant techniques. An antibody as generated can possess any isotype. As used herein, the term "isotype" refers to the immunoglobulin class (for instance IgG1, IgG2, IgG3, IgG4, IgD, IgA, IgE, or IgM) that is encoded by heavy chain constant region genes. When a particular isotype, e.g. IgG1, is mentioned herein, the term is not limited to a specific isotype sequence, e.g. a particular IgG1 sequence, but is used to indicate that the antibody is closer in sequence to that isotype, e.g. IgG1, than to other isotypes. Thus, e.g. an IgG1 antibody of the invention may be a sequence variant of a naturally-occurring IgG1 antibody, including variations in the constant regions.

The term "monoclonal antibody" as used herein refers to a preparation of antibody molecules of single molecular composition. A monoclonal antibody composition displays a single binding specificity and affinity for a particular epitope. Accordingly, the term "human monoclonal antibody" refers to antibodies displaying a single binding specificity which have variable and constant regions derived from human germline immunoglobulin sequences. The human monoclonal antibodies may be generated by a hybridoma which includes a B cell obtained from a transgenic or transchromosomal non-human animal, such as a transgenic mouse, having a genome comprising a human heavy chain transgene and a light chain transgene, fused to an immortalized cell.

The term "bispecific antibody" or "bs" in the context of the present invention refers to an antibody having two different antigen-binding regions defined by different antibody sequences. In some embodiments, said different antigen-binding regions bind different epitopes on the same antigen. However, in preferred embodiments, said different antigen-binding regions bind different target antigens. A bispecific antibody can be of any format, including any of the bispecific antibody formats described herein below.

When used herein, unless contradicted by context, the term "Fab-arm" or "arm" includes one heavy chain-light chain pair and is used interchangeably with "half-molecule" herein.

When a bispecific antibody is described to comprise a half-molecule antibody "derived from" a first antibody, and a half-molecule antibody "derived from" a second antibody, the term "derived from" indicates that the bispecific antibody was generated by recombining, by any known method, said half-molecules from each of said first and second antibodies into the resulting bispecific antibody. In this context, "recombining" is not intended to be limited by any particular method of recombining and thus includes all of the methods for producing bispecific antibodies described herein below, including for example recombining by half-molecule exchange, as well as recombining at nucleic acid level and/or through co-expression of two half-molecules in the same cells.

The term "monovalent antibody" means in the context of the present invention that an antibody molecule is capable of binding a single molecule of an antigen, and thus is not capable of crosslinking antigens or cells.

The term "full-length" when used in the context of an antibody indicates that the antibody is not a fragment, but contains all of the domains of the particular isotype normally found for that isotype in nature, e.g. the VH, CH1, CH2, CH3, hinge, VL and CL domains for an IgG1 antibody.

When used herein, unless contradicted by context, the term "Fc region" refers to an antibody region consisting of the two Fc sequences of the heavy chains of an immunoglobulin, wherein said Fc sequences comprise at least a hinge region, a CH2 domain, and a CH3 domain.

When used herein, the term "heterodimeric interaction between the first and second CH3 regions" refers to the interaction between the first CH3 region and the second CH3 region in a first-CH3/second-CH3 heterodimeric protein.

When used herein, the term "homodimeric interactions of the first and second CH3 regions" refers to the interaction between a first CH3 region and another first CH3 region in a first-CH3/first-CH3 homodimeric protein and the interaction between a second CH3 region and another second CH3 region in a second-CH3/second-CH3 homodimeric protein.

As used herein, the terms "binding" or "capable of binding" in the context of the binding of an antibody to a predetermined antigen or epitope typically is a binding with an affinity corresponding to a $K_D$ of about $10^{-7}$ M or less, such as about $10^{-8}$ M or less, such as about $10^{-9}$ M or less, about $10^{-10}$ M or less, or about $10^{-11}$ M or even less, when determined using Bio-Layer Interferometry (BLI) or, for instance, when determined using surface plasmon resonance (SPR) technology in a BIAcore 3000 instrument using the antigen as the ligand and the antibody as the analyte. The antibody binds to the predetermined antigen with an affinity corresponding to a $K_D$ that is at least ten-fold lower, such as at least 100-fold lower, for instance at least 1,000-fold lower, such as at least 10,000-fold lower, for instance at least 100,000-fold lower than its $K_D$ for binding to a non-specific antigen (e.g., BSA, casein) other than the predetermined antigen or a closely-related antigen. The amount with which the affinity is higher is dependent on the $K_D$ of the antibody, so that when the $K_D$ of the antibody is very low (that is, the antibody is highly specific), then the degree to which the affinity for the antigen is lower than the affinity for a non-specific antigen may be at least 10,000-fold.

The term "$k_d$" (sec$^{-1}$), as used herein, refers to the dissociation rate constant of a particular antibody-antigen interaction. Said value is also referred to as the $k_{off}$ value.

The term "$K_D$" (M), as used herein, refers to the dissociation equilibrium constant of a particular antibody-antigen interaction.

In a preferred embodiment, the antibody of the invention is isolated. An "isolated antibody" as used herein, is intended to refer to an antibody which is substantially free of other antibodies having different antigenic specificities. In a preferred embodiment, an isolated bispecific antibody that specifically binds to PD-L1 and CD137 is substantially free of monospecific antibodies that specifically bind to PD-L1 or CD137. In another preferred embodiment, the antibody, or a pharmaceutical composition comprising the antibody, is substantially free of naturally-arising antibodies that are not capable of binding to PD-L1. In a further preferred embodiment, the antibody of the invention possesses a structural change in its amino acid sequence, relative to the structure of a naturally-occurring anti-PD-L1 antibody, wherein said structural change causes said antibody to exhibit an altered functionality relative to the functionality exhibited by said naturally-occurring anti-PD-L1 antibody, said functionality being selected from the group consisting of: (i) PD-L1 binding affinity, (ii) ability to inhibit binding of PD-L1 to PD-1, (iii) ability to induce Fc-mediated effector functions and (iv) ability to not induce Fc-mediated effector functions.

The term "PD-L1" when used herein, refers to the Programmed Death-Ligand 1 protein. PD-L1 is found in humans and other species, and thus, the term "PD-L1" is not limited to human PD-L1 unless contradicted by context. Human, macaque (cynomolgus monkey), African elephant, wild boar and mouse PD-L1 sequences can be found through Genbank accession no. NP_054862.1, XP_005581836, XP_003413533, XP_005665023 and NP_068693, respectively. The sequence of human PD-L1 is also shown in SEQ ID NO: 28, wherein amino acids 1-18 are predicted to be a signal peptide. The sequence of macaque (cynomolgus monkey) PD-L1 is also shown in SEQ ID NO: 29, wherein amino acids 1-18 are predicted to be a signal peptide.

The term "PD-L2" when used herein, refers to the human Programmed Death 1-Ligand 2 protein (Genbank accession no. NP_079515).

The term "PD-1" when used herein, refers to the human Programmed Death-1 protein, also known as CD279.

The term "CD137" as used herein, refers to the human Cluster of Differentiation 137 protein. CD137 (4-1BB), also referred to as TNFRSF9, is the receptor for the ligand TNFSF9/4-1BBL. CD137 is believed to be involved in T cell activation. In one embodiment, CD137 is human CD137, having UniProt accession number Q07011. The sequence of human CD137 is also shown in SEQ ID NO: 30, wherein amino acids 1-23 are predicted to be a signal peptide. In one embodiment CD137 is cynomolgus monkey (*Macaca fascicularis*) CD137, having UniProt accession number A9YYE7-1. The sequence of cynomolgus monkey CD137 is shown in SEQ ID NO: 31, wherein amino acids 1-23 are predicted to be aa signal peptide. Wild boar (*Sus scrofa*) CD137 is shown in SEQ ID NO: 38, wherein amino acids 1-23 are predicted to be aa signal peptide. African elephant (*Loxodonta africana*) CD137 is shown in SEQ ID NO: 39, wherein amino acids 1-23 are predicted to be aa signal peptide.

A "PD-L1 antibody" or "anti-PD-L1 antibody" is an antibody as described above, which binds specifically to the antigen PD-L1, in particular human PD-L1.

A "CD137 antibody" or "anti-CD137 antibody" is an antibody as described above, which binds specifically to the antigen CD137.

A "CD137×PD-L1 antibody", "anti-CD137×PD-L1 antibody", "PD-L1×CD137 antibody" or "anti-PD-L1×CD137 antibody" is a bispecific antibody, which comprises two different antigen-binding regions, one of which binds specifically to the antigen PD-L1 and one of which binds specifically to CD137.

The present invention also provides antibodies comprising functional variants of the VL regions, VH regions, or one or more CDRs of the antibodies of the examples. A functional variant of a VL, VH, or CDR used in the context of an antibody still allows the antibody to retain at least a substantial proportion (at least about 50%, 60%, 70%, 80%, 90%, 95% or more) of the affinity and/or the specificity/selectivity of the "reference" or "parent" antibody and in some cases, such an antibody may be associated with greater affinity, selectivity and/or specificity than the parent antibody.

Such functional variants typically retain significant sequence identity to the parent antibody. The percent identity between two sequences is a function of the number of identical positions shared by the sequences (i.e., % homology=# of identical positions/total # of positions×100), taking into account the number of gaps, and the length of each gap, which need to be introduced for optimal alignment of the two sequences. The percent identity between two nucleotide or amino acid sequences may e.g. be determined using the algorithm of E. Meyers and W. Miller, Comput. Appl. Biosci 4, 11-17 (1988) which has been incorporated into the ALIGN program (version 2.0), using a PAM120 weight residue table, a gap length penalty of 12 and a gap penalty of 4. In addition, the percent identity between two amino acid sequences may be determined using the Needleman and Wunsch, 3. Mol. Biol. 48, 444-453 (1970) algorithm.

Exemplary variants include those which differ from VH and/or VL and/or CDR regions of the parent antibody sequences mainly by conservative substitutions; for instance, 10, such as 9, 8, 7, 6, 5, 4, 3, 2 or 1 of the substitutions in the variant are conservative amino acid residue replacements.

In the context of the present invention, conservative substitutions may be defined by substitutions within the classes of amino acids reflected in the following table:

| Amino acid residue classes for conservative substitutions | |
| --- | --- |
| Acidic Residues | Asp (D) and Glu (E) |
| Basic Residues | Lys (K), Arg (R), and His (H) |
| Hydrophilic Uncharged Residues | Ser (S), Thr (T), Asn (N), and Gln (Q) |
| Aliphatic Uncharged Residues | Gly (G), Ala (A), Val (V), Leu (L), and Ile (I) |
| Non-polar Uncharged Residues | Cys (C), Met (M), and Pro (P) |
| Aromatic Residues | Phe (F), Tyr (Y), and Trp (W) |

In the context of the present invention, the following notations are, unless otherwise indicated, used to describe a mutation: i) substitution of an amino acid in a given position is written as e.g. K409R which means a substitution of a lysine in position 409 of the protein with an arginine; and ii) for specific variants the specific three or one letter codes are used, including the codes Xaa and X to indicate any amino acid residue. Thus, the substitution of lysine with arginine in position 409 is designated as: K409R, and the substitution of lysine with any amino acid residue in position 409 is designated as K409X. In case of deletion of lysine in position 409 it is indicated by K409*.

In the context of the present invention, "inhibition of PD-L1 binding to PD-1" refers to any detectably significant reduction in the binding of PD-L1 to PD-1 in the presence of an antibody capable of binding PD-L1. Typically, inhibition means an at least about 10% reduction, such as an at least about 15%, e.g. an at least about 20%, such as an at least 40% reduction in binding between PD-L1 and PD-1, caused by the presence of an anti-PD-L1 antibody. Inhibition of PD-L1 binding to PD-1 may be determined by any suitable technique. In one embodiment, inhibition is determined as described in Example 6 herein.

The term "specificity" as used herein is intended to have the following meaning unless contradicted by context. Two antibodies have the "same specificity" if they bind to the same antigen and the same epitope.

The term "epitope" means a protein determinant capable of specific binding to an antibody. Epitopes usually consist of surface groupings of molecules such as amino acids or sugar side chains and usually have specific three-dimensional structural characteristics, as well as specific charge characteristics. Conformational and non-conformational epitopes are distinguished in that the binding to the former but not the latter is lost in the presence of denaturing solvents. The epitope may comprise amino acid residues directly involved in the binding and other amino acid residues, which are not directly involved in the binding, such as amino acid residues which are effectively blocked or covered by the specifically antigen binding peptide (in other words, the amino acid residue is within the footprint of the specifically antigen binding peptide).

The term "chimeric antibody" as used herein, refers to an antibody wherein the variable region is derived from a non-human species (e.g. derived from rodents) and the constant region is derived from a different species, such as human. Chimeric monoclonal antibodies for therapeutic applications are developed to reduce antibody immunogenicity. The terms "variable region" or "variable domain" as used in the context of chimeric antibodies, refer to a region which comprises the CDRs and framework regions of both the heavy and light chains of the immunoglobulin. Chimeric antibodies may be generated by using standard DNA techniques as described in Sambrook et al., 1989, Molecular Cloning: A laboratory Manual, New York: Cold Spring Harbor Laboratory Press, Ch. 15. The chimeric antibody may be a genetically or an enzymatically engineered recombinant antibody. It is within the knowledge of the skilled person to generate a chimeric antibody, and thus, generation of the chimeric antibody according to the present invention may be performed by other methods than described herein.

The term "humanized antibody" as used herein, refers to a genetically engineered non-human antibody, which contains human antibody constant domains and non-human variable domains modified to contain a high level of sequence homology to human variable domains. This can be achieved by grafting of the six non-human antibody complementarity-determining regions (CDRs), which together form the antigen binding site, onto a homologous human acceptor framework region (FR) (see WO92/22653 and EP0629240). In order to fully reconstitute the binding affinity and specificity of the parental antibody, the substitution of framework residues from the parental antibody (i.e. the non-human antibody) into the human framework regions (back-mutations) may be required. Structural homology modeling may help to identify the amino acid residues in the framework regions that are important for the binding properties of the antibody. Thus, a humanized antibody may comprise non-human CDR sequences, primarily human framework regions optionally comprising one or more amino acid back-mutations to the non-human amino acid sequence, and fully human constant regions. Optionally, additional amino acid modifications, which are not necessarily back-mutations, may be applied to obtain a humanized antibody with preferred characteristics, such as affinity and biochemical properties.

The term "human antibody" as used herein, refers to antibodies having variable and constant regions derived from human germline immunoglobulin sequences. Human antibodies may include amino acid residues not encoded by human germline immunoglobulin sequences (e.g., mutations introduced by random or site-specific mutagenesis in vitro or by somatic mutation in vivo). However, the term "human antibody", as used herein, is not intended to include antibodies in which CDR sequences derived from the germline of another mammalian species, such as a mouse or rat, have been grafted onto human framework sequences. Human monoclonal antibodies can be produced by a variety of techniques, including conventional monoclonal antibody methodology, e.g., the standard somatic cell hybridization technique of Kohler and Milstein, Nature 256: 495 (1975). Although somatic cell hybridization procedures are preferred, in principle, other techniques for producing monoclonal antibody can be employed, e.g., viral or oncogenic transformation of B-lymphocytes or phage display techniques using libraries of human antibody genes. A suitable animal system for preparing hybridomas that secrete human monoclonal antibodies is the murine system. Hybridoma production in the mouse is a very well established procedure. Immunization protocols and techniques for isolation of immunized splenocytes for fusion are known in the art. Fusion partners (e.g., murine myeloma cells) and fusion procedures are also known. Human monoclonal antibodies can thus e.g. be generated using transgenic or transchromosomal mice or rats carrying parts of the human immune system rather than the mouse or rat system. Accordingly, in one embodiment, a human antibody is obtained from a transgenic animal, such as a mouse or a rat, carrying human germline immunoglobulin sequences instead of animal immunoglobulin sequences. In such embodiments, the antibody originates from human germline immunoglobulin sequences introduced in the animal, but the final antibody sequence is the result of said human germline immunoglobulin sequences being further modified by somatic hypermutations and affinity maturation by the endogeneous animal antibody machinery, see e.g. Mendez et al. 1997 Nat Genet. 15(2):146-56. The term "reducing conditions" or "reducing environment" refers to a condition or an environment in which a substrate, here a cysteine residue in the hinge region of an antibody, is more likely to become reduced than oxidized.

The term "recombinant host cell" (or simply "host cell"), as used herein, is intended to refer to a cell into which an expression vector has been introduced, e.g. an expression vector encoding an antibody of the invention. Recombinant host cells include, for example, transfectomas, such as CHO, CHO—S, HEK, HEK293, HEK-293F, Expi293F, PER.C6 or NS0 cells, and lymphocytic cells.

The term "treatment" refers to the administration of an effective amount of a therapeutically active antibody of the present invention with the purpose of easing, ameliorating, arresting or eradicating (curing) symptoms or disease states.

The term "effective amount" or "therapeutically effective amount" refers to an amount effective, at dosages and for periods of time necessary, to achieve a desired therapeutic result. A therapeutically effective amount of an antibody may vary according to factors such as the disease state, age, sex, and weight of the individual, and the ability of the antibody to elicit a desired response in the individual. A therapeutically effective amount is also one in which any toxic or detrimental effects of the antibody or antibody portion are outweighed by the therapeutically beneficial effects.

The term "anti-idiotypic antibody" refers to an antibody which recognizes unique determinants generally associated with the antigen-binding site of an antibody.

The term "competes" and "competition" refers to the competition between a first antibody and a second antibody to the same antigen. Alternatively "competes" and "competition" may also refer to the competition between an antibody and an endogenous ligand for binding to the corresponding receptor of the endogenous ligand. If an antibody prevents the binding of the endogenous ligand to its receptor, such an antibody is said to block the endogenous interaction of the ligand with its receptor and therefore is competing with the endogenous ligand. It is well known to a person skilled in the art how to test for competition of antibodies for binding to a target antigen. An example of such a method is a so-called cross-competition assay, which may e.g. be performed as an ELISA or by flow-cytometry. Alternatively, competition may be determined using biolayer interferometry.

FURTHER ASPECTS AND EMBODIMENTS OF THE INVENTION

As described above, in a first aspect, the invention relates to a binding agent comprising a first antigen-binding region binding to human CD137 and a second antigen-binding region binding to human PD-L1, wherein the second antigen-binding region inhibits the binding of human PD-L1 to human PD-1.

Such a binding agent thus comprises two different antigen-binding regions, one which is capable of binding PD-L1 and one which is capable of binding CD137.

As shown by the inventor of the present invention, a binding agent according to the present invention may activate and/or induce proliferation in one cell by binding to CD137, while simultaneously binding to PD-L1 on another cell. In humans, CD137 is expressed on activated T cells, such as CD8$^+$ T cells and CD4$^+$ T cells, whereas PD-L1 is predominantly expressed on antigen-presenting cells (APCs) such as dendritic cells or tumor cells. Thus, binding agents, such as bispecific antibodies, according to the present invention capable of binding both CD137 and PD-L1 are able to simultaneously bind to T cells and APCs or T cells and tumor cells. Thus, binding agents, such as bispecific antibodies, according to the invention may mediate cell-to-cell interaction between APCs and T cells by simultaneous binding of PD-L1 and CD137 on the cells. Thus, this may lead to proliferation of antigen-specific T cells. Further, binding agents, such as bispecific antibodies, according to the invention may mediate cell-to-cell interaction between tumor cells and T cells by simultaneous binding of PD-L1 on tumor cells and CD137 on T cells. Thus, this may lead to further activation of T cells in the presence of tumor cells by binding of CD137 on the T cell, while binding of PD-L1 on tumor cells brings the T cell and tumor cell into close proximity. Thus, activation of T cells in the presence of tumor cells may lead to enhanced killing of tumor cells by the T cells. Further, the ability of the PD-L1 antigen-binding region, of the binding agent according to the invention, to inhibit binding of PD-L1 on tumor cells with PD-1 on T cells prevents that the tumor cell is able to induce T cell inhibition, and thereby escaping the anti-tumor effect of the activated T cell.

Thus, a binding agent, such as a bispecific antibody, of the present invention may be used for treatment of a disease which can benefit from re-activation of T cells, such as cancer.

In one embodiment of the invention, the second antigen-binding region binds to human PD-L1 as set forth in SEQ ID NO: 28 or the mature polypeptide thereof.

In one embodiment of the invention, the second antigen-binding region binds to cynomolgus monkey (*Macaca fascicularis*) PD-L1 as set forth in SEQ ID NO: 29 or the mature polypeptide thereof. Thus, binding agents having an antigen-binding region which is cross-specific for both human and cynomolgus monkey PD-L1 are suitable for preclinical testing in the cynomolgus monkey.

Different binding agents, such as antibodies, capable of binding to the same antigen, such as PD-L1, may bind different regions of said antigen. In some cases, binding of one PD-L1 antibody to PD-L1 may still permit binding of a different PD-L1 antibody to PD-L1. In other cases, however, binding of one PD-L1 antibody to PD-L1 may compete with (block) binding of a different PD-L1 antibody to PD-L1. Thus, competition experiments provide information on where on the target antigen an antibody binds, which may impact the functional effects of antibody binding.

In one embodiment of the invention, the second antigen-binding region binding to human PD-L1 does not bind to human PD-L2.

In one embodiment of the invention, said second antigen-binding region binding to human PD-L1 comprises heavy and light chain variable regions of an antibody which competes for human PD-L1 binding with an antibody comprising:

a. a heavy chain variable region comprising a heavy chain complementarity determining region 3 (HCDR3) having the sequence set forth in SEQ ID NO: 20 or a sequence wherein up to one amino acid, such as one amino acid, is modified in SEQ ID NO: 20 and
b. a light chain variable region comprising a light chain complementarity determining region 3 (LCDR3) having the sequence set forth in SEQ ID NO: 23 or a sequence wherein up to two amino acids, such as two amino acids, such as one amino acid, are modified in SEQ ID NO: 23.

In one embodiment of the invention, said modified amino acids may be an amino acid substitution, such as a conservative amino acid substitution. In one embodiment of the invention, up to one amino acid is modified in SEQ ID NO: 20, such as up to one conservative amino acid substitution in SEQ ID NO:20. In one embodiment of the invention, up to two amino acid are modified in SEQ ID NO: 23, such as one, such as two conservative amino acid substitution in SEQ ID NO:23.

In one embodiment of the invention, said second antigen-binding region binding to human PD-L1 comprises heavy and light chain variable regions of an antibody which competes for human PD-L1 binding with an antibody comprising:

a. a heavy chain variable region comprising a heavy chain complementarity determining region 1, 2 and 3 (HCDR1, HCDR2 and HCDR3) having the sequence set forth in SEQ ID NO: 18, 19 and 20 respectively, and
b. a light chain variable region comprising a light chain complementarity determining region 1, 2 and 3 (LCDR1, LCDR2 and LCDR3) having the sequence set forth in SEQ ID NO: 22, DDN and 23 respectively.

In one embodiment of the invention, said second antigen-binding region binding to human PD-L1 comprises heavy and light chain variable regions of an antibody, which competes for binding to human PD-L1 with an antigen-binding region comprising a heavy chain variable region (VH) and a light chain variable region (VL), wherein the VH comprises a sequence as set forth in: SEQ ID NO: 17 and the VL comprises a sequence as set forth in: SEQ ID NO: 21. Antibodies which compete for binding to a target antigen binding may bind different epitopes on the antigen, wherein the epitopes are so close to each other that a first antibody binding to one epitope prevents binding of a second antibody to the other epitope. In other situations, however, two different antibodies may bind the same epitope on the antigen and would compete for binding in a competition binding assay.

In one embodiment of the invention, said second antigen-binding region binding to human PD-L1 comprises heavy and light chain variable regions of an antibody which has the specificity for PD-L1 of an antibody comprising a heavy chain variable region comprising a HCDR3 having the sequence set forth in SEQ ID NO: 20 or a sequence wherein up to one amino acid is modified in SEQ ID NO: 20 and a light chain variable region comprising a LCDR3 having the sequence set forth in SEQ ID NO: 23 or a sequence wherein up to two amino acids are modified in SEQ ID NO: 23.

In one embodiment of the invention, said second antigen-binding region binding to human PD-L1 comprises heavy and light chain variable regions of an antibody which binds the same epitope on PD-L1 as an antibody comprising a heavy chain variable region comprising a HCDR1, HCDR2 and HCDR3, having the sequence set forth in SEQ ID NO: 18, 19 and 20 respectively or a sequence wherein up to one amino acid is modified in total across the HCDR sequences set forth in SEQ ID NO: 18, 19 and 20 and a light chain variable region comprising a LCDR1, LCDR2 and LCDR3 having the sequences set forth in SEQ ID NO:22, DDN and 23 respectively or a sequence wherein up to two amino acids are modified in total across the LCDR sequences set forth in SEQ ID NO: 22, DDN and 23. Hereby, embodiments are described that allow for the modification of up to one amino acid across the three HCDR sequences of the VH and up to two amino acid modifications across the three LCDR sequences of the VL.

In one embodiment of the invention, said second antigen-binding region binding to human PD-L1 binds to the same epitope of human PD-L1 as an antibody comprising a VH comprising a sequence as set forth in SEQ ID NO: 17 and a VL comprising a sequence as set forth in SEQ ID NO: 21. Thus, in one embodiment the antigen-binding region binding to human PD-L1 binds to the same epitope as an antibody comprising a specific VH and VL sequences is to be understood as that the binding agent of the invention and the antibody bind to the same amino acids on the PD-L1 molecule. That a binding agent and an antibody or antibodies bind to the same epitope on a target antigen may be determined by standard alanine scanning experiments or antibody-antigen crystallization experiments known to a person skilled in the art.

In one embodiment of the invention, said second antigen-binding region binding to human PD-L1 comprises a heavy chain variable region (VH) comprising a HCDR3 having the sequence set forth in SEQ ID NO: 20 or a sequence wherein up to one amino acid is modified in SEQ ID NO: 20.

In one embodiment of the invention, said second antigen-binding region binding to human PD-L1 comprises a heavy chain variable region (VH) comprising a HCDR2 having the sequence set forth in SEQ ID NO: 19 or a sequence wherein up to one amino acid is modified in SEQ ID NO: 19.

In one embodiment of the invention, said second antigen-binding region binding to human PD-L1 comprises a heavy chain variable region (VH) comprising a HCDR1 having the sequence set forth in SEQ ID NO: 18 or a sequence wherein up to one amino acid is modified in SEQ ID NO: 18.

In one embodiment of the invention, said second antigen-binding region binding to human PD-L1 comprises a heavy chain variable region (VH) comprising an HCDR1, HCDR2, and HCDR3 sequence, wherein the HCDR1, HCDR2 and HCDR3 sequence comprises the sequence as set forth in: SEQ ID NO: 18, 19 and 20, respectively, wherein up to three amino acids, such as two amino acids, such as one amino acid, are modified in total across the three HCDR sequences. In one embodiment of the invention, up to one amino acid is modified in total across the three HCDR sequences. In one embodiment of the invention, up to two amino acids are modified in total across the three HCDR sequences. In one embodiment, the up to two amino acids are modified in the same HCDR sequence. In one embodiment, the up to two amino acids are modified in different HCDR sequences. In one embodiment, up to three amino acids, such as three amino acids, such as two amino acids, such as one amino acid, are modified in total across the three HCDR sequences. In one embodiment, the up to three amino acids, such as three amino acids, such as two amino acids, such as one amino acid, are modified in the same HCDR sequence. In one embodiment, the up to three amino acids, such as three amino acids, such as two amino acids, such as one amino acid, are modified in different HCDR sequences.

In one embodiment of the invention, said second antigen-binding region binding to human PD-L1 comprises a heavy chain variable region (VH) comprising an HCDR1, HCDR2, and HCDR3 sequence, wherein the HCDR1, HCDR2 and HCDR3 sequence comprises the sequence as set forth in: SEQ ID NO: 18, 19 and 20, respectively.

In one embodiment of the invention, said second antigen-binding region binding to human PD-L1 comprises a light chain variable region (VL) comprising a LCDR3 having the sequence set forth in SEQ ID NO: 23 or a sequence wherein up to two amino acids, such as two amino acids, such as one amino acid, are modified in SEQ ID NO: 23.

In one embodiment of the invention, said second antigen-binding region binding to human PD-L1 comprises a light chain variable region (VL) comprising a LCDR2 having the sequence of DDN or a sequence wherein up to one amino acid, such as one amino acid, is modified in DDN.

In one embodiment of the invention, said second antigen-binding region binding to human PD-L1 comprises a heavy chain variable region (VL) comprising a LCDR1 having the sequence set forth in SEQ ID NO: 22 or a sequence wherein up to two amino acids, such as two amino acids, such as one amino acid, are modified in SEQ ID NO: 22.

In one embodiment of the invention, said second antigen-binding region binding to human PD-L1 comprises a light chain variable region (VL) comprising a LCDR1, LCDR2, and LCDR3 sequence, wherein the LCDR1, LCDR2 and LCDR3 sequence comprises the sequence as set forth in: SEQ ID NO: 22, DDN, 23, respectively wherein up to two amino acids, such as two amino acids, such as one amino acid, are modified in total across the three LCDR sequences.

In one embodiment of the invention, said second antigen-binding region binding to human PD-L1 comprises a light chain variable region (VL) comprising a LCDR1, LCDR2, and LCDR3 sequence, wherein the LCDR1, LCDR2 and LCDR3 sequence comprises the sequence as set forth in: SEQ ID NO: 22, DDN, 23, respectively.

In one embodiment of the invention, said second antigen-binding region binding to human PD-L1 comprises a heavy chain variable region (VH) comprising a HCDR1, HCDR2, and HCDR3 sequence and a light chain variable region (VL) comprising a LCDR1, LCDR2, and LCDR3 sequence, wherein the HCDR1, HCDR2 and HCDR3 sequences are the sequences as set forth in: SEQ ID NO: 18, 19, and 20 respectively and the LCDR1, LCDR2 and LCDR3 sequences are the sequences as set forth in: SEQ ID NO: 22, DDN, 23 respectively.

In one embodiment of the invention, said second antigen-binding region binding to human PD-L1 comprises a heavy chain variable region (VH) comprising a sequence having at least 70%, at least 75%, at least 80%, at least 85%, at least 90%, at least 95%, at least 97%, at least 99%, or 100% identity to the amino acid sequence of the VH sequence as set forth in: SEQ ID NO: 17.

In one embodiment of the invention, said second antigen-binding region binding to human PD-L1 comprises a light chain variable region (VL) comprising a sequence having at least 70%, at least 75%, at least 80%, at least 85%, at least 90%, at least 95%, at least 97%, at least 99%, or 100% identity to the amino acid sequence of the VL sequence as set forth in: SEQ ID NO: 21.

Thus, for example, said antigen-binding region capable of binding to human PD-L1 comprises:
a VH sequence which has at least 70% amino acid sequence identity to the VH sequence set forth in: SEQ ID NO:17 and a VL sequence which has at least 70% amino acid sequence identity to the VL sequence set forth in: SEQ ID NO:21, or
a VH sequence which has at least 75% amino acid sequence identity to the VH sequence set forth in: SEQ ID NO:17 and a VL sequence which has at least 75% amino acid sequence identity to the VL sequence set forth in: SEQ ID NO:21, or
a VH sequence which has at least 80% amino acid sequence identity to the VH sequence set forth in: SEQ ID NO:17 and a VL sequence which has at least 80% amino acid sequence identity to the VL sequence set forth in: SEQ ID NO:21, or
a VH sequence which has at least 85% amino acid sequence identity to the VH sequence set forth in: SEQ ID NO:17 and a VL sequence which has at least 85% amino acid sequence identity to the VL sequence set forth in: SEQ ID NO:21, or
a VH sequence which has at least 90% amino acid sequence identity to the VH sequence set forth in: SEQ ID NO:17 and a VL sequence which has at least 90% amino acid sequence identity to the VL sequence set forth in: SEQ ID NO:21, or
a VH sequence which has at least 95% amino acid sequence identity to the VH sequence set forth in: SEQ ID NO:17 and a VL sequence which has at least 95% amino acid sequence identity to the VL sequence set forth in: SEQ ID NO:21, or
a VH sequence which has at least 97% amino acid sequence identity to the VH sequence set forth in: SEQ ID NO:17 and a VL sequence which has at least 97% amino acid sequence identity to the VL sequence set forth in: SEQ ID NO:21, or
a VH sequence which has at least 99% amino acid sequence identity to the VH sequence set forth in: SEQ ID NO:17 and a VL sequence which has at least 99% amino acid sequence identity to the VL sequence set forth in: SEQ ID NO:21, or a VH sequence which has at least 100% amino acid sequence identity to the VH sequence set forth in: SEQ ID NO:17 and a VL sequence which has at least 100% amino acid sequence identity to the VL sequence set forth in: SEQ ID NO:21.

In one embodiment of the invention, said second antigen-binding region binding to human PD-L1 comprises a heavy chain variable region (VH), wherein the VH comprises the sequence as set forth in: SEQ ID NO: 17.

In one embodiment of the invention, said second antigen-binding region binding to human PD-L1 comprises a light chain variable region (VL), wherein the VL comprises the sequence as set forth in: SEQ ID NO: 21.

In a preferred embodiment of the invention, said second antigen-binding region binding to human PD-L1 comprises a heavy chain variable region (VH) and a variable region (VL), wherein the VH comprises the sequence as set forth in: SEQ ID NO: 17 and the VL comprises the sequence as set forth in: SEQ ID NO: 21.

In a further embodiment, said VH and VL sequences each comprise three CDR sequences, CDR1, CDR2 and CDR3, respectively, and four framework sequences, FR1, FR2, FR3 and FR4, respectively, and the respective combined FR1, FR2, FR3 and FR4 framework sequences of the VH have at least 90%, at least 95%, at least 97%, or at least 99% amino acid sequence identity to the respective combined FR1, FR2, FR3 and FR4 framework sequences of said VH sequences and wherein the VH CDR sequences are not mutated and wherein the respective combined FR1, FR2, FR3 and FR4 framework sequences of the VL have at least 90%, at least 95%, at least 97%, or at least 99% amino acid sequence identity to the respective combined FR1, FR2, FR3 and FR4 framework sequences of said VL sequences and wherein the VL CDR sequences are not mutated. In the context of this embodiment, the % identity refers to the percentage identity obtained when the framework sequences are taken together as one consecutive sequence without the intermediate CDR sequences.

CD137

As described above, the above-mentioned binding agents of the invention comprise a first antigen-binding binding to human CD137. Thus, the binding agent according to the invention may be a bispecific antibody having a first antigen-binding region binding to human CD137 and a second antigen-binding region binding to human PD-L1, wherein the second antigen-binding region inhibits the binding of human PD-L1 to human PD-1.

In one embodiment of the invention, the first antigen-binding region binds to human CD137, as set forth in SEQ ID NO: 30 or a mature polypeptide thereof.

In one embodiment of the invention, the first antigen-binding region binds to cynomolgus monkey (*Macaca fascicularis*) CD137, as set forth in SEQ ID NO: 31 or a mature polypeptide thereof. Thus, binding agents having an antigen-binding region which is cross-specific for both human and cynomolgus monkey CD137 are suitable for preclinical testing in the cynomolgus monkey.

In one embodiment of the invention, the first antigen-binding region binds to human CD137 as set forth in SEQ ID NO: 30 or a mature polypeptide thereof to a higher degree measured by cellular binding to transfected cells with the following constructs than it binds to a mutant human CD137 as set forth in SEQ ID NO: 33 or a mature polypeptide thereof. Mutant human CD137 as set forth in SEQ ID NO: 33 (Shuffle 5/elephant) corresponds to the amino acid sequence of human CD137 wherein amino acids 48-88 were replaced by the corresponding amino acids from elephant CD137. In one embodiment of the invention the first antigen-binding region has reduced binding to a mutant human CD137 as set forth in SEQ ID NO: 33 (shuffle 5/elephant) or a mature polypeptide thereof, compared to human CD137 as set forth in SEQ ID NO: 30 or a mature polypeptide thereof. In one embodiment of the invention the first antigen-binding region does not bind to a mutant human CD137 as set for in SEQ ID NO: 33 or a mature polypeptide thereof (shuffle 5/elephant). Thus, in one embodiment of the invention, the first antigen-binding region binding to human CD137 binds to an epitope of human CD137, which is located within the amino acid sequence defined by positions 48-88 of SEQ ID NO: 30, corresponding to positions 25-65 of SEQ ID NO: 41, such as an epitope, which comprises or requires one or more of the amino acids C, P, P, N, S, F, S, S, A, G, G, Q, R, T, C, D, I, C, R, Q, C, K, G, V, F, R, T, R, K, E, C, S, S, T, S, N, A, E, C, D, C, at positions 48-88 of SEQ ID NO:30, corresponding to positions 25-65 of SEQ ID NO: 41. The binding of the first antigen-binding region to human CD137 may depend on any of the amino acid residues within the sequence of amino acids defined by positions 48-88 of SEQ ID NO: 30, corresponding to positions 25-65 of SEQ ID NO: 41, such as one or more of the amino acids C, P, P, N, S, F, S, S, A, G, G, Q, R, T, C, D, I, C, R, Q, C, K, G, V, F, R, T, R, K, E, C, S, S, T, S, N, A, E, C, D, C, at positions 48-88 of SEQ ID NO:30, corresponding to positions 25-65 of SEQ ID NO: 41.

In one embodiment of the invention, said first antigen-binding region binding to human CD137 binds to at least one, such as at least 2, at least 3, at least 4, or at least 5 of the amino acids in the amino acid sequence as set forth in SEQ ID NO:40. In particular, and such as when determined by alanine scanning; e.g. as described in the following and in example 13, the binding of the antibody according to the invention to human CD137 may be dependent on one or more of the following amino acid residues: Phe (F) at position 13, Phe (F) at position 30, Thr (T) at position 38, Asp (D) at position 40, and Asn (N) at position 60 in SEQ ID NO: 41, corresponding to F36, F53, T61, D63 and N83, respectively, in SEQ ID NO: 30.

According to this embodiment, binding of the antibody to a mutant CD137 in which any one or more of the amino acid residues at positions corresponding to positions 13, 30, 38, 40 and 60 in SEQ ID NO: 41 has/have been substituted with alanines, is reduced as compared to wild type CD137 having the amino acid sequence set forth in SEQ ID NO: 41. Preferably, reduced binding is determined as zscore (fold change) of said antibody being less than −1.5, wherein zscore (fold change) for binding of the antibody to the mutant CD137 is calculated as set forth in Example 13.

Phe (F) at position 13 and/or Phe (F) at position 30 may have structural impact on the epitope, without being directly involved in binding of the antibody. Hence the antibody according to the invention may bind to an epitope on human CD137, wherein Thr (T) at position 38, Asp (D) at position 40, and/or Asn (N) at position 60 in SEQ ID NO: 41 is/are directly involved in binding of the antibody.

In another embodiment, binding of the antibody according to the invention to human CD137 may be dependent on one or more of the following amino acid residues: Leu (L) at position 1, Gln (Q) at position 2, Pro (P) at position 4, Gly (G) at position 11, Thr (T) at position 12, Asp (D) at position 15, Gln (Q) and at position 20 in SEQ ID NO: 41, corresponding to positions of SEQ ID NO:30, corresponding to L24, Q25, P27, G34, T35, D38 and Q43 of SEQ ID NO: 30, respectively.

According to this embodiment, binding of the antibody to a mutant CD137 in which any one or more of the amino acid residues at positions corresponding to positions 1, 2, 4, 11, 12, 15, and 20 in SEQ ID NO: 41 has/have been substituted with alanines, is reduced as compared to wild type CD137 having the amino acid sequence set forth in SEQ ID NO: 41. Preferably, reduced binding is determined as zscore (fold change) of said antibody being less than −1.5, wherein zscore (fold change) for binding of the antibody to the mutant CD137 is calculated as set forth in Example 13.

The procedure for comparing binding to wild type and alanine substituted CD137 may comprise the steps of:
  i) expressing wild type and alanine substituted CD137 in a suitable cell line, such as HEK293 cells;
  ii) harvesting the cells one day post transfection and incubating, for each data point, a sample of 100.000 cells with antibody according to the invention, labeled, such as with a compound according to formula I (A488), at room temperature for 30 minutes in FACS buffer (Phosphate-buffered saline (PBS), 1% Bovine Serum Albumin, 0.02% sodium azide),
  iii) washing each sample with FACS buffer and subjecting the sample to analysis by flow cytometry and determining the geometric mean of the fluorescence intensity (gMFI) for binding of the antibody; and
  iv) Normalizing the data to the binding intensity of a non-crossblocking CD137-specific antibody and calculating the zscore (fold change) as described in Example 13.

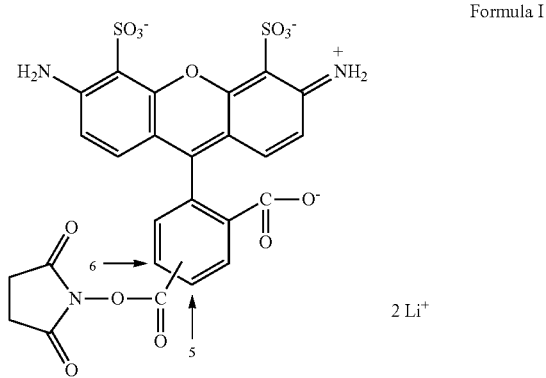

Formula I

As described in Example 13, data may be normalized against the binding intensity of a non-cross blocking CD137 specific control antibody, using the following equation:

$$\text{Normalized } gMFI_{aa\ position} = \text{Log}_{10}\left(\frac{gMFI_{Test\ Ab}}{gMFI_{Control\ Ab}}\right)$$

in which 'aa position' refers to the position that was mutated into an alanine or a glycine.

The zscore may be calculated according to the following calculation:

$$zscore(\text{fold change}) = \frac{\text{Normalized } gMFI_{aa\ position} - \mu}{\sigma}$$

where $\mu$ and $\sigma$ are the mean and standard deviation of the Normalized gMFI calculated from all mutants.

In one embodiment of the invention, the first antigen-binding region binds to mutant human CD137 as set forth in SEQ ID NO:34 (shuffle 4/wild boar), or a mature polypeptide thereof, to the same degree as it binds to a human CD137 as set forth in SEQ ID: NO 30, or a mature polypeptide thereof, when measured by cellular binding to transfected cells with the constructs set forth in SEQ ID NO:34 and SEQ ID NO:30. Mutant human CD137 as set forth in SEQ ID NO:34 (Shuffle 4/wild boar) corresponds to the amino acid sequence of human CD137 wherein amino acids 89-114 were replaced by the corresponding amino acids from wild boar CD137. Thus, in one embodiment of the invention first antigen-binding region binding to human CD137 does not bind to an epitope of human CD137 which comprises or requires one or more of the amino acids at positions 89-114 of SEQ ID:30.

In one embodiment of the invention, said first antigen-binding region binding to human CD137 competes for binding to human CD137 with an antigen-binding region comprising a heavy chain variable region (VH) and a light chain variable region (VL), wherein the VH comprises a sequence as set forth in: SEQ ID NO: 8 and the VL comprises a sequence as set forth in: SEQ ID NO: 12.

In one embodiment of the invention, said first antigen-binding region binding to human CD137 competes for binding to human CD137 with an antigen-binding region comprising a heavy chain variable region (VH) and a light chain variable region (VL), wherein the VH comprises a sequence as set forth in: SEQ ID NO: 15 and the VL comprises a sequence as set forth in: SEQ ID NO: 16.

In one embodiment of the invention, said first antigen-binding region binding to human CD137 competes for binding to human CD137 with an antigen-binding region comprising a heavy chain variable region (VH) and a light chain variable region (VL), wherein the VH comprises a sequence as set forth in: SEQ ID NO: 49 and the VL comprises a sequence as set forth in: SEQ ID NO: 53.

In one embodiment of the invention, said first antigen-binding region binding to human CD137 comprises heavy and light chain variable regions of an antibody which competes for human CD137 binding with an antibody comprising:
  a. a heavy chain variable region comprising a heavy chain complementarity determining region 3 (HCDR3) having the sequence set forth in SEQ ID NO: 11 or a sequence wherein up to three amino acids, such as three amino acids, such as two amino acids, such as one amino acid, are modified in SEQ ID NO: 11 and
  b. a light chain variable region comprising a light chain complementarity determining region 3 (LCDR3) having the sequence set forth in SEQ ID NO: 14 or a sequence wherein up to four amino acids, such as four amino acids, such as three amino acids, such as two amino acids, such as one amino acid, are modified in SEQ ID NO: 14.

In one embodiment of the invention, said first antigen-binding region binding to human CD137 comprises heavy and light chain variable regions of an antibody which competes for human CD137 binding with an antibody comprising:
  a. a heavy chain variable region comprising a heavy chain complementarity determining region 3 (HCDR3) having the sequence set forth in SEQ ID NO: 52 or a sequence wherein up to three amino acids, such as three amino acids, such as two amino acids, such as one amino acid, are modified in SEQ ID NO: 52 and
  b. a light chain variable region comprising a light chain complementarity determining region 3 (LCDR3) having the sequence set forth in SEQ ID NO: 55 or a sequence wherein up to four amino acids, such as four amino acids, such as three amino acids, such as two amino acids, such as one amino acid, are modified in SEQ ID NO: 55.

In one embodiment of the invention, up to one amino acid, such as one amino acid, is modified in the HCDR3 sequence. In one embodiment of the invention, up to two amino acids, such as two amino acids, such as one amino acid, are modified in the HCDR3 sequence. In one embodiment, the up to three amino acids, such as three amino acids, such as two amino acids, such as one amino acid, are modified in the HCDR3 sequence. In one embodiment of the invention, up to one amino acid, such as one amino acid, is modified in the LCDR3 sequence. In one embodiment of the invention, up to two amino acids, such as two amino acids, such as one amino acid, are modified in the LCDR3 sequence. In one embodiment, the up to three amino acids, such as three amino acids, such as two amino acids, such as one amino acid, are modified in the LCDR3 sequence. In one embodiment, the up to four amino acids, such as four amino acids, such as three amino acids, such as two amino acids, such as one amino acid, are modified in the LCDR3 sequence.

In one embodiment of the invention, said first antigen-binding region binding to human CD137 comprises heavy and light chain variable regions of an antibody which competes for human CD137 binding with an antibody comprising:
a. a heavy chain variable region comprising a heavy chain complementarity determining region 1, 2, and 3 (HCDR1, HCDR2, and HCDR3) having the sequence set forth in SEQ ID NO: 9, 10, and 11 respectively and
b. a light chain variable region comprising a light chain complementarity determining region 1, 2, and 3 (LCDR1, LCDR2, and LCDR3) having the sequence set forth in SEQ ID NO: 13, GAS, and 14 respectively.

In one embodiment of the invention, said first antigen-binding region binding to human CD137 comprises heavy and light chain variable regions of an antibody which competes for human CD137 binding with an antibody comprising:
a. a heavy chain variable region comprising a heavy chain complementarity determining region 1, 2, and 3 (HCDR1, HCDR2, and HCDR3) having the sequence set forth in SEQ ID NO: 50, 51, and 52 respectively and
b. a light chain variable region comprising a light chain complementarity determining region 1, 2, and 3 (LCDR1, LCDR2, and LCDR3) having the sequence set forth in SEQ ID NO: 54, SAS, and 55 respectively.

In one embodiment of the invention, said first antigen-binding region binding to human CD137 binds to the same epitope of human CD137 as an antibody comprising a VH sequence as set forth in SEQ ID NO: 15 and a VL sequence as set forth in SEQ ID NO: 16.

In one embodiment of the invention, said first antigen-binding region binding to human CD137 binds to the same epitope of human CD137 as an antibody comprising a VH sequence as set forth in SEQ ID NO: 49 and a VL sequence as set forth in SEQ ID NO: 53.

In one embodiment of the invention, said first antigen-binding region binding to human CD137 comprises heavy and light chain variable regions of an antibody which has the specificity for CD137 of an antibody comprising a heavy chain variable region comprising a HCDR3 having the sequence set forth in SEQ ID NO: 11 or a sequence wherein up to three amino acids, such as three amino acids, such as two amino acids, such as one amino acid are modified in SEQ ID NO: 11 and a light chain variable region comprising a LCDR3 having the sequence set forth in SEQ ID NO: 14 or a sequence wherein up to four amino acids, such as three amino acids, such as two amino acids, such as one amino acid, are modified in SEQ ID NO: 14.

In one embodiment of the invention, said first antigen-binding region binding to human CD137 comprises heavy and light chain variable regions of an antibody which has the specificity for CD137 of an antibody comprising a heavy chain variable region comprising a HCDR3 having the sequence set forth in SEQ ID NO: 52 or a sequence wherein up to three amino acids, such as three amino acids, such as two amino acids, such as one amino acid are modified in SEQ ID NO: 52 and a light chain variable region comprising a LCDR3 having the sequence set forth in SEQ ID NO: 55 or a sequence wherein up to four amino acids, such as three amino acids, such as two amino acids, such as one amino acid, are modified in SEQ ID NO: 55.

In one embodiment of the invention, said first antigen-binding region binding to human CD137 comprises a heavy chain variable region (VH) comprising a HCDR3 having the sequence set forth in SEQ ID NO: 11 or a sequence wherein up to three amino acid, such as three amino acids, such as two amino acids, such as one amino acid, are modified in SEQ ID NO: 11. In one embodiment of the invention, up to one amino acid is modified in the HCDR3 sequence. In one embodiment of the invention, up to two amino acids are modified in the HCDR3 sequence. In one embodiment, the up to three amino acids are modified in the HCDR3 sequence.

In one embodiment of the invention, said first antigen-binding region binding to human CD137 comprises a heavy chain variable region (VH) comprising a HCDR3 having the sequence set forth in SEQ ID NO: 52 or a sequence wherein up to three amino acid, such as three amino acids, such as two amino acids, such as one amino acid, are modified in SEQ ID NO: 52. In one embodiment of the invention, up to one amino acid is modified in the HCDR3 sequence. In one embodiment of the invention, up to two amino acids are modified in the HCDR3 sequence. In one embodiment, the up to three amino acids are modified in the HCDR3 sequence.

In one embodiment of the invention, said first antigen-binding region binding to human CD137 comprises a heavy chain variable region (VH) comprising a HCDR2 having the sequence set forth in SEQ ID NO: 10 or a sequence wherein up to three, such as three amino acids, such as two amino acids, such as one amino acid, amino acids are modified in SEQ ID NO: 10. In one embodiment of the invention, up to one amino acid is modified in the HCDR2 sequence. In one embodiment of the invention, up to two amino acids are modified in the HCDR2 sequence. In one embodiment, the up to three amino acids are modified in the HCDR2 sequence.

In one embodiment of the invention, said first antigen-binding region binding to human CD137 comprises a heavy chain variable region (VH) comprising a HCDR2 having the sequence set forth in SEQ ID NO: 51 or a sequence wherein up to three, such as three amino acids, such as two amino acids, such as one amino acid, amino acids are modified in SEQ ID NO: 51. In one embodiment of the invention, up to one amino acid is modified in the HCDR2 sequence. In one embodiment of the invention, up to two amino acids are modified in the HCDR2 sequence. In one embodiment, the up to three amino acids are modified in the HCDR2 sequence.

In one embodiment of the invention, said first antigen-binding region binding to human CD137 comprises a heavy chain variable region (VH) comprising a HCDR1 having the sequence set forth in SEQ ID NO: 9 or a sequence wherein up to three, such as three amino acids, such as two amino acids, such as one amino acid amino acids are modified in SEQ ID NO: 9. In one embodiment of the invention, up to one amino acid is modified in the HCDR1 sequence. In one embodiment of the invention, up to two amino acids are modified in the HCDR1 sequence. In one embodiment, the up to three amino acids are modified in the HCDR1 sequence.

In one embodiment of the invention, said first antigen-binding region binding to human CD137 comprises a heavy chain variable region (VH) comprising a HCDR1 having the sequence set forth in SEQ ID NO: 50 or a sequence wherein up to three, such as three amino acids, such as two amino acids, such as one amino acid amino acids are modified in SEQ ID NO: 50. In one embodiment of the invention, up to one amino acid is modified in the HCDR1 sequence. In one embodiment of the invention, up to two amino acids are modified in the HCDR1 sequence. In one embodiment, the up to three amino acids are modified in the HCDR1 sequence.

In one embodiment of the invention, said first antigen-binding region binding to human CD137 comprises a heavy chain variable region (VH) comprising HCDR1, HCDR2, and HCDR3 sequences, wherein the HCDR1, HCDR2, and HCDR3 sequence comprises the sequence as set forth in: SEQ ID NO: 9, 10, and 11 respectively, wherein up to three amino acids are modified in total across the three HCDR sequences.

In one embodiment of the invention, said first antigen-binding region binding to human CD137 comprises a heavy chain variable region (VH) comprising HCDR1, HCDR2, and HCDR3 sequences, wherein the HCDR1, HCDR2, and HCDR3 sequence comprises the sequence as set forth in: SEQ ID NO: 50, 51, and 52 respectively, wherein up to three amino acids are modified in total across the three HCDR sequences.

In one embodiment of the invention, said first antigen-binding region binding to human CD137 comprises a heavy chain variable region (VH) comprising HCDR1, HCDR2, and HCDR3 sequences, wherein the HCDR1, HCDR2, and HCDR3 sequence comprises the sequence as set forth in: SEQ ID NO: 9, 10, and 11 respectively.

In one embodiment of the invention, said first antigen-binding region binding to human CD137 comprises a heavy chain variable region (VH) comprising HCDR1, HCDR2, and HCDR3 sequences, wherein the HCDR1, HCDR2, and HCDR3 sequence comprises the sequence as set forth in: SEQ ID NO: 50, 51, and 52 respectively.

In one embodiment of the invention, said first antigen-binding region binding to human CD137 comprises a light chain variable region (VL) comprising a LCDR3 having the sequence set forth in SEQ ID NO: 14 or a sequence wherein up to four amino acids, such as four amino acids, such as three amino acids, such as two amino acids, such as one amino acid are modified in SEQ ID NO: 14.

In one embodiment of the invention, said first antigen-binding region binding to human CD137 comprises a light chain variable region (VL) comprising a LCDR3 having the sequence set forth in SEQ ID NO: 55 or a sequence wherein up to four amino acids, such as four amino acids, such as three amino acids, such as two amino acids, such as one amino acid are modified in SEQ ID NO: 55.

In one embodiment of the invention, said first antigen-binding region binding to human CD137 comprises a light chain variable region (VL) comprising a LCDR2 having the sequence GAS or a sequence wherein up to two amino acids are modified in the GAS sequence. In one embodiment of the invention, up to one amino acid is modified in the GAS sequence.

In one embodiment of the invention, said first antigen-binding region binding to human CD137 comprises a light chain variable region (VL) comprising a LCDR2 having the sequence SAS or a sequence wherein up to two amino acids are modified in the SAS sequence. In one embodiment of the invention, up to one amino acid is modified in the SAS sequence.

In one embodiment of the invention, said first antigen-binding region binding to human CD137 comprises a light chain variable region (VL) comprising a LCDR1 having the sequence set forth in SEQ ID NO: 13 or a sequence wherein up to four amino acids, such as four amino acids, such as three amino acids, such as two amino acids, such as one amino acid, are modified in SEQ ID NO: 13.

In one embodiment of the invention, said first antigen-binding region binding to human CD137 comprises a light chain variable region (VL) comprising a LCDR1 having the sequence set forth in SEQ ID NO: 54 or a sequence wherein up to four amino acids, such as four amino acids, such as three amino acids, such as two amino acids, such as one amino acid, are modified in SEQ ID NO: 54.

In one embodiment of the invention, said first antigen-binding region binding to human CD137 comprises a light chain variable region (VL) comprising LCDR1, LCDR2, and LCDR3 sequences, wherein the LCDR1, LCDR2, and LCDR3 sequence comprises the sequence as set forth in: SEQ ID NO: 13, GAS, 14 respectively, wherein up to four amino acids, such as four amino acids, such as three amino acids, such as two amino acids, such as one amino acid, are modified in total across the three LCDR sequences.

In one embodiment of the invention, said first antigen-binding region binding to human CD137 comprises a light chain variable region (VL) comprising LCDR1, LCDR2, and LCDR3 sequences, wherein the LCDR1, LCDR2, and LCDR3 sequence comprises the sequence as set forth in: SEQ ID NO: 54, SAS, 55 respectively, wherein up to four amino acids, such as four amino acids, such as three amino acids, such as two amino acids, such as one amino acid, are modified in total across the three LCDR sequences.

In one embodiment of the invention, said first antigen-binding region binding to human CD137 comprises a light chain variable region (VL) comprising LCDR1, LCDR2, and LCDR3 sequences, wherein the LCDR1, LCDR2, and LCDR3 sequence comprises the sequence as set forth in: SEQ ID NO: 13, GAS, 14, respectively.

In one embodiment of the invention, said first antigen-binding region binding to human CD137 comprises a light chain variable region (VL) comprising LCDR1, LCDR2, and LCDR3 sequences, wherein the LCDR1, LCDR2, and LCDR3 sequence comprises the sequence as set forth in: SEQ ID NO: 54, SAS, 55, respectively.

In a preferred embodiment of the invention, said first antigen-binding region binding to human CD137 comprises a heavy chain variable region (VH) comprising a HCDR1, HCDR2, and HCDR3 sequence and a light chain variable region (VL) comprising a LCDR1, LCDR2, and LCDR3 sequence, wherein the HCDR1, HCDR2, and HCDR3 sequences are the sequences as set forth in: SEQ ID NO: 9, 10, 11 respectively and the LCDR1, LCDR2, and LCDR3 sequences are the sequences as set forth in: SEQ ID NO: 13, GAS, 14 respectively.

In a preferred embodiment of the invention, said first antigen-binding region binding to human CD137 comprises a heavy chain variable region (VH) comprising a HCDR1, HCDR2, and HCDR3 sequence and a light chain variable region (VL) comprising a LCDR1, LCDR2, and LCDR3 sequence, wherein the HCDR1, HCDR2, and HCDR3 sequences are the sequences as set forth in: SEQ ID NO: 50, 51 and 52 respectively, and the LCDR1, LCDR2, and LCDR3 sequences are the sequences as set forth in: SEQ ID NO: 54, SAS, 55 respectively.

In one embodiment of the invention, said first antigen-binding region binding to human CD137 comprises a heavy chain variable region (VH) comprising a sequence having at least 70%, at least 75%, at least 80%, at least 85%, at least 90%, at least 95%, at least 97%, at least 99%, or 100% identity to the amino acid sequence of the VH sequence as set forth in: SEQ ID NO: 15. In one embodiment of the invention, said first antigen-binding region binding to human CD137 comprises a heavy chain variable region (VH) comprising a sequence having at least 70%, at least 75%, at least 80%, at least 85%, at least 90%, at least 95%, at least 97%, at least 99%, or 100% identity to the amino acid sequence of the VH sequence as set forth in: SEQ ID NO: 8.

In one embodiment of the invention, said first antigen-binding region binding to human CD137 comprises a heavy chain variable region (VH) comprising a sequence having at least 70%, at least 75%, at least 80%, at least 85%, at least 90%, at least 95%, at least 97%, at least 99%, or 100% identity to the amino acid sequence of the VH sequence as set forth in: SEQ ID NO: 49.

In one embodiment of the invention, said first antigen-binding region binding to human CD137 comprises a light chain variable region (VL) comprising a sequence having at least 70%, at least 75%, at least 80%, at least 85%, at least 90%, at least 95%, at least 97%, at least 99%, or 100% identity to the amino acid sequence of the VL sequence as set forth in: SEQ ID NO: 16.

In one embodiment of the invention, said first antigen-binding region binding to human CD137 comprises a light chain variable region (VL) comprising a sequence having at least 70%, at least 75%, at least 80%, at least 85%, at least 90%, at least 95%, at least 97%, at least 99%, or 100% identity to the amino acid sequence of the VL sequence as set forth in: SEQ ID NO: 12.

In one embodiment of the invention, said first antigen-binding region binding to human CD137 comprises a light chain variable region (VL) comprising a sequence having at least 70%, at least 75%, at least 80%, at least 85%, at least 90%, at least 95%, at least 97%, at least 99%, or 100% identity to the amino acid sequence of the VL sequence as set forth in: SEQ ID NO: 53.

Thus, for example, said first antigen-binding region capable of binding to human CD137 comprises:
a VH sequence which has at least 70% amino acid sequence identity to the VH sequence set forth in: SEQ ID NO:15 and a VL sequence which has at least 70% amino acid sequence identity to the VL sequence set forth in: SEQ ID NO: 16, or
a VH sequence which has at least 75% amino acid sequence identity to the VH sequence set forth in: SEQ ID NO:15 and a VL sequence which has at least 75% amino acid sequence identity to the VL sequence set forth in: SEQ ID NO:16, or
a VH sequence which has at least 80% amino acid sequence identity to the VH sequence set forth in: SEQ ID NO:15 and a VL sequence which has at least 80% amino acid sequence identity to the VL sequence set forth in: SEQ ID NO:16, or
a VH sequence which has at least 85% amino acid sequence identity to the VH sequence set forth in: SEQ ID NO:15 and a VL sequence which has at least 85% amino acid sequence identity to the VL sequence set forth in: SEQ ID NO:16, or
a VH sequence which has at least 90% amino acid sequence identity to the VH sequence set forth in: SEQ ID NO:15 and a VL sequence which has at least 90% amino acid sequence identity to the VL sequence set forth in: SEQ ID NO:16, or
a VH sequence which has at least 95% amino acid sequence identity to the VH sequence set forth in: SEQ ID NO:15 and a VL sequence which has at least 95% amino acid sequence identity to the VL sequence set forth in: SEQ ID NO: 16, or
a VH sequence which has at least 97% amino acid sequence identity to the VH sequence set forth in: SEQ ID NO:15 and a VL sequence which has at least 97% amino acid sequence identity to the VL sequence set forth in: SEQ ID NO:16, or
a VH sequence which has at least 99% amino acid sequence identity to the VH sequence set forth in: SEQ ID NO:15 and a VL sequence which has at least 99% amino acid sequence identity to the VL sequence set forth in: SEQ ID NO:16, or
a VH sequence which has at least 100% amino acid sequence identity to the VH sequence set forth in: SEQ ID NO:15 and a VL sequence which has at least 100% amino acid sequence identity to the VL sequence set forth in: SEQ ID NO: 16.

In one embodiment of the invention, said first antigen-binding region binding to human CD137 comprises a heavy chain variable region (VH), wherein the VH comprises the sequence as set forth in: SEQ ID NO: 15.

In one embodiment of the invention, said first antigen-binding region binding to human CD137 comprises a light chain variable region (VL), wherein the VL comprises the sequence as set forth in: SEQ ID NO: 16.

In one embodiment of the invention, said first antigen-binding region binding to human CD137 comprises a heavy chain variable region (VH) and a variable region (VL), wherein the VH sequence comprises the sequence as set forth in: SEQ ID NO: 15 and the VL sequence comprises the sequence as set forth in: SEQ ID NO: 16.

In one embodiment of the invention, said first antigen-binding region binding to human CD137 comprises a heavy chain variable region (VH), wherein the VH comprises the sequence as set forth in: SEQ ID NO: 8.

In one embodiment of the invention, said first antigen-binding region binding to human CD137 comprises a light chain variable region (VL), wherein the VL comprises the sequence as set forth in: SEQ ID NO: 12.

In one embodiment of the invention, said first antigen-binding region binding to human CD137 comprises a heavy chain variable region (VH) and a variable region (VL), wherein the VH sequence comprises the sequence as set forth in: SEQ ID NO: 8 and the VL sequence comprises the sequence as set forth in: SEQ ID NO: 12.

In one embodiment of the invention, said first antigen-binding region binding to human CD137 comprises a heavy chain variable region (VH), wherein the VH comprises the sequence as set forth in: SEQ ID NO: 49.

In one embodiment of the invention, said first antigen-binding region binding to human CD137 comprises a light chain variable region (VL), wherein the VL comprises the sequence as set forth in: SEQ ID NO: 53.

In one embodiment of the invention, said first antigen-binding region binding to human CD137 comprises a heavy chain variable region (VH) and a variable region (VL), wherein the VH sequence comprises the sequence as set forth in: SEQ ID NO: 49 and the VL sequence comprises the sequence as set forth in: SEQ ID NO: 53.

Bispecific Binding Agents

As described above, the binding agent according to the invention comprise a first antigen-binding region binding to human CD137 and a second antigen-binding region binding to human PD-L1. Thus, the binding agent according to the invention may be a multispecific binding agent, e.g. a multispecific antibody or a bispecific antibody.

In one embodiment of the invention, the binding agent comprises a first antigen-binding region binding to human CD137 and a second antigen-binding region binding to human PD-L1, wherein
- a. the first antigen-binding region comprises a heavy chain variable region (VH) comprising an HCDR3 sequence, as set forth in: SEQ ID NO: 11, and
- b. the second antigen-binding region comprises a heavy chain variable region (VH) comprising the HCDR3 sequence, as set forth in: SEQ ID NO: 20.

In one embodiment of the invention, the binding agent comprises a first antigen-binding region binding to human CD137 and a second antigen-binding region binding to human PD-L1, wherein
- a. the first antigen-binding region comprises a heavy chain variable region (VH) comprising an HCDR2 sequence, as set forth in: SEQ ID NO:10, and
- b. the second antigen-binding region comprises a heavy chain variable region (VH) comprising an HCDR2 sequence, as set forth in: SEQ ID NO: 19.

In one embodiment of the invention, the binding agent comprises a first antigen-binding region binding to human CD137 and a second antigen-binding region binding to human PD-L1, wherein
- a. the first antigen-binding region comprises a heavy chain variable region (VH) comprising an HCDR1 sequence, as set forth in: SEQ ID NO:9, and
- b. the second antigen-binding region comprises a heavy chain variable region (VH) comprising an HCDR1 sequence, as set forth in: SEQ ID NO: 18.

In one embodiment of the invention, the binding agent comprises a first antigen-binding region binding to human CD137 and a second antigen-binding region binding to human PD-L1, wherein
- c. the first antigen-binding region comprises a heavy chain variable region (VH) comprising an HCDR3 sequence, as set forth in: SEQ ID NO: 52, and
- d. the second antigen-binding region comprises a heavy chain variable region (VH) comprising the HCDR3 sequence, as set forth in: SEQ ID NO: 20.

In one embodiment of the invention, the binding agent comprises a first antigen-binding region binding to human CD137 and a second antigen-binding region binding to human PD-L1, wherein
- c. the first antigen-binding region comprises a heavy chain variable region (VH) comprising an HCDR2 sequence, as set forth in: SEQ ID NO: 51, and
- d. the second antigen-binding region comprises a heavy chain variable region (VH) comprising an HCDR2 sequence, as set forth in: SEQ ID NO: 19.

In one embodiment of the invention, the binding agent comprises a first antigen-binding region binding to human CD137 and a second antigen-binding region binding to human PD-L1, wherein
- a. the first antigen-binding region comprises a heavy chain variable region (VH) comprising an HCDR1 sequence, as set forth in: SEQ ID NO: 50, and
- b. the second antigen-binding region comprises a heavy chain variable region (VH) comprising an HCDR1 sequence, as set forth in: SEQ ID NO: 18.

In one embodiment of the invention, the binding agent comprises a first antigen-binding region binding to human CD137 and a second antigen-binding region binding to human PD-L1, wherein
- a. the first antigen-binding region comprises a heavy chain variable region (VH) comprising the HCDR1, HCDR2, and HCDR3 sequences, as set forth in: SEQ ID NO:9, 10, 11 respectively, and
- b. the second antigen-binding region comprises a heavy chain variable region (VH) comprising the HCDR1, HCDR2, and HCDR3 sequences, as set forth in: SEQ ID NO: 18, 19, 20 respectively.

In one embodiment of the invention, the binding agent comprises a first antigen-binding region binding to human CD137 and a second antigen-binding region binding to human PD-L1, wherein
- a. the first antigen-binding region comprises a heavy chain variable region (VH) comprising the HCDR1, HCDR2, and HCDR3 sequences, as set forth in: SEQ ID NO:50, 51, 52 respectively, and
- b. the second antigen-binding region comprises a heavy chain variable region (VH) comprising the HCDR1, HCDR2, and HCDR3 sequences, as set forth in: SEQ ID NO: 18, 19, 20 respectively.

In one embodiment of the invention, the binding agent comprises a first antigen-binding region binding to human CD137 and a second antigen-binding region binding to human PD-L1, wherein
- a. the first antigen-binding region comprises a light chain variable region (VL) comprising a LCDR3 sequence, as set forth in: SEQ ID NO: 14, and
- b. the second antigen-binding region comprises a light chain variable region (VL) comprising a LCDR3 sequence, as set forth in: SEQ ID NO: 23.

In one embodiment of the invention, the binding agent comprises a first antigen-binding region binding to human CD137 and a second antigen-binding region binding to human PD-L1, wherein
- a. the first antigen-binding region comprises a light chain variable region (VL) comprising a LCDR2 having the sequence GAS, and
- b. the second antigen-binding region comprises a light chain variable region (VL) comprising a LCDR2 having the sequence DDN.

In one embodiment of the invention, the binding agent comprises a first antigen-binding region binding to human CD137 and a second antigen-binding region binding to human PD-L1, wherein
- a. the first antigen-binding region comprises a light chain variable region (VL) comprising a LCDR1 sequence, as set forth in: SEQ ID NO: 13, and
- b. the second antigen-binding region comprises a light chain variable region (VL) comprising a LCDR1 sequence, as set forth in: SEQ ID NO: 22.

In one embodiment of the invention, the binding agent comprises a first antigen-binding region binding to human CD137 and a second antigen-binding region binding to human PD-L1, wherein
- c. the first antigen-binding region comprises a light chain variable region (VL) comprising a LCDR3 sequence, as set forth in: SEQ ID NO: 55, and
- d. the second antigen-binding region comprises a light chain variable region (VL) comprising a LCDR3 sequence, as set forth in: SEQ ID NO: 23.

In one embodiment of the invention, the binding agent comprises a first antigen-binding region binding to human CD137 and a second antigen-binding region binding to human PD-L1, wherein
  c. the first antigen-binding region comprises a light chain variable region (VL) comprising a LCDR2 having the sequence SAS, and
  d. the second antigen-binding region comprises a light chain variable region (VL) comprising a LCDR2 having the sequence DDN.

In one embodiment of the invention, the binding agent comprises a first antigen-binding region binding to human CD137 and a second antigen-binding region binding to human PD-L1, wherein
  c. the first antigen-binding region comprises a light chain variable region (VL) comprising a LCDR1 sequence, as set forth in: SEQ ID NO: 54, and
  d. the second antigen-binding region comprises a light chain variable region (VL) comprising a LCDR1 sequence, as set forth in: SEQ ID NO: 22.

In one embodiment of the invention, the binding agent comprises a first antigen-binding region binding to human CD137 and a second antigen-binding region binding to human PD-L1, wherein
  a. the first antigen-binding region comprises a light chain variable region (VL) comprising the LCDR1, LCDR2, and LCDR3 sequences, as set forth in: SEQ ID NO:13, GAS and 14 respectively, and
  b. the second antigen-binding region comprises a light chain variable region (VL) comprising the LCDR1, LCDR2, and LCDR3 sequences, as set forth in: SEQ ID NO: 22, DDN, 23 respectively.

In one embodiment of the invention, the binding agent comprises a first antigen-binding region binding to human CD137 and a second antigen-binding region binding to human PD-L1, wherein
  a. the first antigen-binding region comprises a light chain variable region (VL) comprising the LCDR1, LCDR2, and LCDR3 sequences, as set forth in: SEQ ID NO:54, SAS and 55 respectively, and
  b. the second antigen-binding region comprises a light chain variable region (VL) comprising the LCDR1, LCDR2, and LCDR3 sequences, as set forth in: SEQ ID NO: 22, DDN, 23 respectively.

In one embodiment of the invention, the binding agent comprises a first antigen-binding region binding to human CD137 and a second antigen-binding region binding to human PD-L1, wherein
  a. the first antigen-binding region comprises a heavy chain variable region (VH) comprising a HCDR1, HCDR2, and HCDR3 sequence, as set forth in: SEQ ID NO: 9, 10 and 11, respectively, and a light chain variable region (VL) comprising a LCDR1, LCDR2, and LCDR3 sequence, as set forth in: SEQ ID NO: 13, GAS and 14, respectively, and
  b. the second antigen-binding region comprises a heavy chain variable region (VH) comprising a HCDR1, HCDR2, and HCDR3 sequence, as set forth in: SEQ ID NO:18, 19 and, 20 respectively, and a light chain variable region (VL) comprising a LCDR1, LCDR2, and LCDR3 sequence, as set forth in: SEQ ID NO: 22, DDN and 23, respectively.

In one embodiment of the invention, the binding agent comprises a first antigen-binding region binding to human CD137 and a second antigen-binding region binding to human PD-L1, wherein
  a. the first antigen-binding region comprises a heavy chain variable region (VH) comprising a HCDR1, HCDR2, and HCDR3 sequence, as set forth in: SEQ ID NO:50, 51 and 52, respectively, and a light chain variable region (VL) comprising a LCDR1, LCDR2, and LCDR3 sequence, as set forth in: SEQ ID NO: 54, SAS and 55, respectively, and
  b. the second antigen-binding region comprises a heavy chain variable region (VH) comprising a HCDR1, HCDR2, and HCDR3 sequence, as set forth in: SEQ ID NO:18, 19 and, 20 respectively, and a light chain variable region (VL) comprising a LCDR1, LCDR2, and LCDR3 sequence, as set forth in: SEQ ID NO: 22, DDN and 23, respectively.

In one embodiment of the invention, the binding agent comprises a first antigen-binding region binding to human CD137 and a second antigen-binding region binding to human PD-L1, wherein
  a. the first antigen-binding region comprises a heavy chain variable region (VH) comprising the sequence as set forth in: SEQ ID NO:8, and
  b. the second antigen-binding region comprises a heavy chain variable region (VH) comprising the sequence as set forth in: SEQ ID NO:17.

In one embodiment of the invention, the binding agent comprises a first antigen-binding region binding to human CD137 and a second antigen-binding region binding to human PD-L1, wherein
  a. the first antigen-binding region comprises a heavy chain variable region (VH) comprising the sequence as set forth in: SEQ ID NO:15, and
  b. the second antigen-binding region comprises a heavy chain variable region (VH) comprising the sequence as set forth in: SEQ ID NO:17.

In one embodiment of the invention, the binding agent comprises a first antigen-binding region binding to human CD137 and a second antigen-binding region binding to human PD-L1, wherein
  a. the first antigen-binding region comprises a heavy chain variable region (VH) comprising the sequence as set forth in: SEQ ID NO:49, and
  b. the second antigen-binding region comprises a heavy chain variable region (VH) comprising the sequence as set forth in: SEQ ID NO:17.

In one embodiment of the invention, the binding agent comprises a first antigen-binding region binding to human CD137 and a second antigen-binding region binding to human PD-L1, wherein
  a. the first antigen-binding region comprises a light chain variable region (VL) comprising the sequence as set forth in: SEQ ID NO:12, and
  b. the second antigen-binding region comprises a light chain variable region (VL) comprising the sequence as set forth in: SEQ ID NO:21.

In one embodiment of the invention, the binding agent, comprises a first antigen-binding region binding to human CD137 and a second antigen-binding region binding to human PD-L1, wherein
  a. the first antigen-binding region comprises a light chain variable region (VL) comprising the sequence as set forth in: SEQ ID NO:16, and
  b. the second antigen-binding region comprises a light chain variable region (VL) comprising the sequence as set forth in: SEQ ID NO:21.

In one embodiment of the invention, the binding agent, comprises a first antigen-binding region binding to human CD137 and a second antigen-binding region binding to human PD-L1, wherein
  a. the first antigen-binding region comprises a light chain variable region (VL) comprising the sequence as set forth in: SEQ ID NO:53, and
  b. the second antigen-binding region comprises a light chain variable region (VL) comprising the sequence as set forth in: SEQ ID NO:21.

In one embodiment of the invention, the binding agent comprises a first antigen-binding region binding to human CD137 and a second antigen-binding region binding to human PD-L1, wherein
  a. the first antigen-binding region comprises a heavy chain variable region (VH) comprising the sequence as set forth in: SEQ ID NO:8 and a light chain variable region (VL) comprising the sequence as set forth in: SEQ ID NO: 12, and
  b. the second antigen-binding region comprises a heavy chain variable region (VH) comprising the sequence as set forth in: SEQ ID NO:17 and a light chain variable region (VL) comprising the sequence as set forth in: SEQ ID NO:21.

In one embodiment of the invention, the binding agent comprises a first antigen-binding region binding to human CD137 and a second antigen-binding region binding to human PD-L1, wherein
  a. the first antigen-binding region comprises a heavy chain variable region (VH) comprising the sequence as set forth in: SEQ ID NO:15 and a light chain variable region (VL) comprising the sequence as set forth in: SEQ ID NO: 16, and
  b. the second antigen-binding region comprises a heavy chain variable region (VH) comprising the sequence as set forth in: SEQ ID NO:17 and a light chain variable region (VL) comprising the sequence as set forth in: SEQ ID NO:21.

In one embodiment of the invention, the binding agent comprises a first antigen-binding region binding to human CD137 and a second antigen-binding region binding to human PD-L1, wherein
  a. the first antigen-binding region comprises a heavy chain variable region (VH) comprising the sequence as set forth in: SEQ ID NO:49 and a light chain variable region (VL) comprising the sequence as set forth in: SEQ ID NO: 53, and
  b. the second antigen-binding region comprises a heavy chain variable region (VH) comprising the sequence as set forth in: SEQ ID NO:17 and a light chain variable region (VL) comprising the sequence as set forth in: SEQ ID NO:21.

In a further embodiment of the invention, the binding agent is a multispecific antibody such as a bispecific antibody.

In a preferred embodiment of the invention, the binding agent is a bispecific antibody.

In one embodiment of the invention, the binding agent is in the format of a full-length antibody or an antibody fragment.

In one embodiment of the invention, the binding agent, in particular in the form of a multispecific antibody such as a bispecific antibody, comprises a first and a second antigen-binding region, wherein each of the antigen-binding regions comprises a heavy chain variable region (VH) and a light chain variable region (VL), and wherein preferably said variable regions each comprise three CDR sequences, CDR1, CDR2 and CDR3, respectively, and four framework sequences, FR1, FR2, FR3 and FR4, respectively. Thus, the CDRs in the heavy chain variable regions may be denoted as HCDR1, HCDR2 and HCDR3 respectively and the CDRs in the light chain variable regions may be denoted as LCDR1, LCDR2 and LCDR3 respectively. Further, the framework sequences in the heavy chain variable regions may be denoted as HFR1, HFR2, HFR3 and HFR4 respectively and the framework sequences in the light chain variable regions may be denoted as LFR1, LFR2, LFR3 and LFR4 respectively.

Thus, in one embodiment of the multispecific, such as bispecific antibody of the invention, each of the antigen-binding regions comprises a heavy chain variable region (VH) and a light chain variable region (VL), wherein said variable regions each comprise three CDR sequences, CDR1, CDR2 and CDR3, respectively, and four framework sequences, FR1, FR2, FR3 and FR4, respectively. In further preferred embodiments of the bispecific antibody of the invention, the antibody comprises two heavy chain constant regions (CH)), and two light chain constant regions (CL).

In one embodiment of the invention, the binding agent, in particular in the form of a multispecific antibody, such as a bispecific antibody, comprises said first antigen-binding region comprising a first heavy chain variable region (VH) and a first light chain variable region (VL) and said second antigen-binding region comprises a second heavy chain variable region (VH) and a second light chain variable region (VL).

In one embodiment of the invention, the binding agent, in particular in the form of a multispecific antibody such as a bispecific antibody, comprises a heavy chain and a light chain variable region, wherein each variable region comprises three complementarity determining regions (CDR1, CDR2, and CDR3) and four framework regions (FR1, FR2, FR3, and FR4).

In one embodiment of the invention, the binding agent, in particular in the form of a multispecific antibody such as a bispecific antibody, comprises said complementarity determining regions and said framework regions which are arranged from amino-terminus to carboxy-terminus in the following order: FR1, CDR1, FR2, CDR2, FR3, CDR3, FR4.

In one embodiment of the invention, the binding agent, in particular in the form of a multispecific antibody such as a bispecific antibody, comprises a heavy chain variable region, wherein the complementary determining regions and the framework regions are arranged from the amino-terminus to the carboxy-terminus in the following order: HFR1, HCDR1, HFR2, HCDR2, HFR3, HCDR3, HFR4.

In one embodiment of the invention, the binding agent, in particular in the form of a multispecific antibody such as a bispecific antibody, comprises a light chain variable region, wherein the complementary determining regions and the framework regions are arranged from the amino-terminus to the carboxy-terminus in the following order: LFR1, LCDR1, LFR2, LCDR2, LFR3, LCDR3, LFR4.

In one embodiment of the invention, the binding agent, comprises a polypeptide wherein the polypeptide is a heavy chain (HC). In one embodiment of the invention the heavy chain (HC) comprises a variable heavy chain region (VH) and a heavy chain constant region (CH).

In one embodiment of the invention, the heavy chain constant region (CH) comprises a constant region domain 1 region (CH1), a hinge region, a constant region domain 2 region (CH2), and a constant region domain 3 region (CH3).

In one embodiment of the invention, the binding agent, in particular in the form of a multispecific antibody such as a bispecific antibody, comprises (i) a polypeptide comprising said first heavy chain variable region (VH) and further comprising a first heavy chain constant region (CH) and (ii) a polypeptide comprising said second heavy chain variable region (VH) and further comprising a second heavy chain constant region (CH).

In one embodiment of the invention, the binding agent, in particular in the form of a multispecific antibody such as a bispecific antibody, comprises (i) a polypeptide comprising said first light chain variable region (VL) and further comprising a first light chain constant region (CL) and (ii) a polypeptide comprising said second light chain variable region (VL) and further comprising a second light chain constant region (CL).

In one embodiment of the invention, the binding agent is an antibody, such as a multispecific, preferably bispecific antibody, comprising a first binding arm and a second binding arm, wherein
 a. the first binding arm comprises i) a polypeptide comprising said first heavy chain variable region (VH) and said first heavy chain constant region (CH) and ii) a polypeptide comprising said first light chain variable region (VL) and said first light chain constant region (CL) and;
 b. the second binding arm comprises iii) a polypeptide comprising said second heavy chain variable region (VH) and said second heavy chain constant region (CH) and iv) a polypeptide comprising said second light chain variable region (VL) and said second light chain constant region (CL).

In one embodiment of the invention, the binding agent, in particular in the form of a multispecific antibody such as a bispecific antibody, comprises a first and second heavy chain constant region (CH) comprising one or more of a constant region domain 1 region (CH1 region), a hinge region, a CH2 region and a CH3 region, preferably at least a hinge region, a CH2 region and a CH3 region.

In one embodiment of the invention, the binding agent, in particular in the form of a multispecific antibody such as a bispecific antibody, is of an isotype selected from the group consisting of IgG1, IgG2, IgG3, and IgG4. In one embodiment of the invention the isotype is selected from the group consisting of human IgG1, human IgG2, human IgG3 and human IgG4.

In one embodiment of the invention, the first antigen-binding region is derived from a rabbit antibody. In one embodiment of the invention, the first antigen-binding region is derived from a humanized antibody. In one embodiment of the invention, the first binding arm is derived from a full-length antibody. In one embodiment of the invention, the first binding arm is derived from a monoclonal antibody. In one embodiment of the invention, the first binding arm is derived from a full-length IgG1, λ (lambda) or IgG1, κ (kappa) antibody. In one embodiment of the invention, the second antigen-binding region is derived from a rat antibody. In one embodiment of the invention, the second antigen-binding region is human. In one embodiment of the invention, the second antigen-binding region is derived from a humanized antibody. In one embodiment of the invention, the second binding arm is derived from a full-length antibody. In one embodiment of the invention, the second binding arm is derived from a monoclonal antibody. In one embodiment of the invention, the second binding arm is derived from a full-length IgG1, A (lambda) or IgG1, K (kappa) antibody. In one embodiment of the invention, the first and second antigen-binding regions are derived from humanized antibodies. In one embodiment of the invention, the first and second antigen-binding regions are human antibodies. In one embodiment of the invention, the first and second binding arms are derived from full-length antibodies, such as from full-length IgG1, λ (lambda) or IgG1, κ (kappa) antibodies. In one embodiment of the invention, the first and second binding arms are derived from monoclonal antibodies.

In one embodiment of the invention, the first antigen binding region is derived from an IgG1 lambda and the second antigen binding region is derived from an IgG1 kappa.

Antibodies described herein include IgG1, IgG2, IgG3 and IgG4 antibodies and combinations thereof, wherein the heavy chains are of different isotypes and/or subclasses. In various embodiments, the antibody is an IgG1 antibody, more particularly an IgG1, kappa or IgG1, lambda isotype (i.e. IgG1, κ, λ), an IgG2a antibody (e.g. IgG2a, κ, Δ), an IgG2b antibody (e.g. IgG2b, κ, Δ), an IgG3 antibody (e.g. IgG3, κ, λ) or an IgG4 antibody (e.g. IgG4, κ, λ).

In one embodiment of the invention, the binding agent is a multispecific such as a bispecific binding agent. In one embodiment of the invention, the binding agent is an antibody (in particular a multispecific antibody, e.g., a bispecific antibody), such as a chimeric or humanized or human antibody. In one embodiment of the invention, the binding agent is in the format of a full-length antibody or an antibody fragment. In one embodiment of the invention, the first antigen-binding region is derived from a monoclonal antibody. In one embodiment of the invention, the second antigen-binding region is derived from a monoclonal antibody. In one embodiment of the invention, the first antigen-binding region is derived from a monoclonal antibody and the second antigen-binding region is derived from a monoclonal antibody.

In one embodiment of the invention, the binding agent is a full-length IgG1 antibody. In one embodiment of the invention, the binding agent is a full-length human IgG1 antibody. In one embodiment of the invention, the binding agent is a full-length human IgG1 antibody with one or more mutations in the constant region.

In one embodiment of the invention, the binding agent is chimeric, humanized or human antibody. In embodiments of the invention wherein the binding agent is a bispecific antibody, both half-molecules can be human, humanized or chimeric, or the half-molecules can differ in character with respect to sequence origin.

In one embodiment of the invention, the binding agent comprises a first and a second antigen-binding region, wherein
 a. the first antigen-binding region binding to CD137 is derived from a chimeric antibody, and/or
 b. the second antigen-binding region binding to human PD-L1 is derived from a chimeric antibody.

In one embodiment of the invention, the binding agent comprises a first and a second antigen-binding region, wherein
 a. the first antigen-binding region binding to CD137 is derived from a humanized antibody, and/or
 b. the second antigen-binding region binding to human PD-L1 is derived from a humanized antibody.

In one embodiment of the invention, the binding agent comprises a first and a second antigen-binding region, wherein
 a. the first antigen-binding region binding to human CD137 is derived from a human antibody, and/or b. the second antigen-binding region binding to human PD-L1 is derived from a human antibody.

In a preferred embodiment of the invention, the binding agent comprises a first and a second antigen-binding region, wherein a. the first antigen-binding region binding to human CD137 is derived from a humanized antibody, and/or
b. the second antigen-binding region binding to human PD-L1 is derived from a human antibody.

In one embodiment of the invention, the binding agent, in particular in the form of a multispecific antibody such as a bispecific antibody, comprises a first and second heavy chain constant region (CH) comprising a CH3 region and wherein the two CH3 regions comprise asymmetrical mutations.

In a preferred embodiment of the invention, the binding agent, in particular in the form of a multispecific antibody such as a bispecific antibody comprises a first and second heavy chain constant region (CH), wherein each of said first and second heavy chains comprises at least a hinge region, a CH2 and a CH3 region the, wherein in said first heavy chain constant region (CH) at least one of the amino acids in a position corresponding to a position selected from the group consisting of T366, L368, K370, D399, F405, Y407, and K409 in a human IgG1 heavy chain according to EU numbering has been substituted, and in said second heavy chain at least one of the amino acids in a position corresponding to a position selected from the group consisting of T366, L368, K370, D399, F405, Y407, and K409 in a human IgG1 heavy chain according to EU numbering has been substituted, and wherein said first and said second heavy chains are not substituted in the same positions.

Most preferably, (i) the amino acid in the position corresponding to F405 in a human IgG1 heavy chain according to EU numbering is L in said first heavy chain constant region (CH), and the amino acid in the position corresponding to K409 in a human IgG1 heavy chain according to EU numbering is R in said second heavy chain constant region (CH), or (ii) the amino acid in the position corresponding to K409 in a human IgG1 heavy chain according to EU numbering is R in said first heavy chain, and the amino acid in the position corresponding to F405 in a human IgG1 heavy chain according to EU numbering is L in said second heavy chain.

In one embodiment of the invention, the binding agent is an antibody, such as a multispecific, preferably bispecific antibody, wherein said antibody induces Fc-mediated effector function to a lesser extent compared to another antibody comprising the same first and second antigen binding regions and two heavy chain constant regions (CHs) comprising human IgG1 hinge, CH2 and CH3 regions. In one embodiment of the invention, said first and second heavy chain constant regions are modified so that the antibody induces Fc-mediated effector function to a lesser extent compared to an antibody which is identical except for comprising non-modified first and second heavy chains.

In one embodiment of the invention, said Fc-mediated effector function is measured by binding to IgG Fc (Fcγ) receptors, binding to C1q, or induction of Fc-mediated cross-linking of FcRs.

In a preferred embodiment of the invention, said Fc-mediated effector function is measured by binding to C1q.

In one embodiment of the invention, said first and second heavy chain constant regions have been modified so that binding of C1q to said antibody is reduced compared to a wild-type antibody, preferably reduced by at least 70%, at least 80%, at least 90%, at least 95%, at least 97%, or 100%, wherein C1q binding is preferably determined by ELISA.

In one embodiment of the invention, in at least one of said first and second heavy chain constant regions one or more amino acids in the positions corresponding to positions L234, L235, D265, N297, and P331 in a human IgG1 heavy chain according to EU numbering, are not L, L, D, N, and P, respectively. In one embodiment of the invention, the positions corresponding to positions L234 and L235 in a human IgG1 heavy chain according to EU numbering are F and E, respectively, in said first and second heavy chain constant regions. In one embodiment of the invention, the positions corresponding to positions L234, L235, and D265 in a human IgG1 heavy chain according to EU numbering are F, E, and A, respectively, in said first and second heavy chains.

In a further particularly preferred embodiment, the binding agent is a PD-L1×CD137 bispecific antibody comprising a first and second heavy chain constant region, wherein the positions corresponding to positions L234, L235, and D265 in a human IgG1 heavy chain according to EU numbering of both the first and second heavy chain constant regions are F, E, and A, respectively, and wherein (i) the position corresponding to F405 in a human IgG1 heavy chain according to EU numbering of the first heavy chain is L, and the position corresponding to K409 in a human IgG1 heavy chain according to EU numbering of the second heavy chain is R, or (ii) the position corresponding to K409 in a human IgG1 heavy chain according to EU numbering of the first heavy chain is R, and the position corresponding to F405 in a human IgG1 heavy chain according to EU numbering of the second heavy chain is L.

In one embodiment of the invention, the binding agent induces and/or enhances proliferation of T cells. In one embodiment of the invention, said T cells are $CD4^+$ and/or $CD8^+$ T cells.

In one embodiment of the invention, the binding agent activates CD137 signaling only when the second antigen-binding region binds to PD-L1.

In one embodiment of the invention, proliferation of T cells is measured by co-culturing T-cells expressing a specific T cell receptor (TCR) with dendritic cells (DCs) presenting the corresponding antigen on the major histocompatibility complex, which is recognized by the TCR.

In one embodiment, said induction or enhancement of proliferation of T cells is determined by an antigen-specific assay, where DCs are transfected with claudin-6 antigen and T cells are transfected with a TCR that recognizes a claudin-6-derived epitope presented in HLA-A2 on the DC. This assay is described in Example 7.

The bispecific binding agent of the invention may be able to mediate expansion of tumor-infiltrating lymphocytes (TILs) in an ex vivo culture of human tumor tissue. The expansion of TILs may be 1.5 fold or more, 2-fold or more, 3-fold or more, 4-fold or more, 5-fold or more, 6-fold or more, 7-fold or more, 8-fold or more, 9 fold or more or 10-fold or more. The expansion of $CD3^-CD56^+$ natural killer (NK) cells may be from at least 10-fold, such as at least 20-fold, at least 30-fold, at least 40-fold, or such as at least 50-fold. The expansion of $CD3^+CD8^+$ cytotoxic T-lymphocytes (CTLs) may be at least 2-fold, at least 3-fold, at least 4-fold, at least 5-fold, at least 6-fold or such as at least 7-fold. Preferably, the expansion of TILs is determined as TIL expansion from a human non-small-cell lung carcinoma tissue specimen in response to incubation with a concentration of bispecific binding agent corresponding to 0.01, 0.1 and 1 μg/mL, such as in response to incubation with a concentration of bispecific binding agent corresponding to 0.1 μg/mL.

The expansion of TILs may be determined in an assay comprising the steps of:
  i) providing a resection specimen, such as a fresh resection specimen, of tumor tissue and washing the specimen in hematopoietic cell medium,
  ii) cutting the tumor tissue in pieces having a diameter of 1-2 mm and providing a sample containing two pieces of tumor tissue,
  iii) incubating the sample with bispecific binding agent of the invention at a concentration of 0.1 µg/ml in hematopoietic cell medium, such as Lonza™ X-VIVO™ 15, with 10% Human Serum Albumin, antibiotics and Proleukin®S (recombinant human IL-2 analog; SEQ ID NO: 56) in a well of a tissue culture plate at 37° C., 5% $CO_2$ for 72 hours; wherein when more than 25 TIL microclusters are observed in a sample, then the cells in said sample are split and transferred into 6 samples, or 6 wells in a tissue culture plate,
  iv) harvesting TILs after a total incubation period of 10-14 days and subjecting them to staining with labelled antibodies against human CD3, human CD4, human CD56 and human CD8 and with a dye that stains non-viable cells, such as aminoactinomycin D; and
  v) analyzing each sample by flow cytometry.

The bispecific binding agent of the invention may in particular be able to induce expansion of $CD40^+$ and $CD8^+$ T-cells in a population of peripheral blood mononuclear cells (PBMCs), wherein T-cells are activated, such as suboptimally activated, by incubation with a an anti-CD3 antibody, such as clone UCHT1), preferably at a concentration between 0.03 and 0.1 µg/mL and are preferably incubated with bispecific binding agent according to the invention at a concentration corresponding to 0.2 µg/mL. In particular, the process for determining T-cell expansion may comprise the steps of:
  i) obtaining PBMCs from buffy coats of healthy donors, such as by isolation of a Ficoll gradient,
  ii) labelling the PBMCs with carboxyfluorescein succinimidyl ester (CFSE) in PBS,
  iii) providing a sample comprising 75000 CFSE-labelled PBMCs and incubating the sample with anti-CD3 antibody, preferably at a concentration between 0.03 and 0.1 µg/mL as predetermined for each donor to be a concentration inducing suboptimal T-cell proliferation, and with bispecific binding agent of the invention at a concentration of 0.2 µg/mL, at 37° C., 5% $CO_2$, for four days in Iscove's Modified Dulbecco's Medium with glutamine and supplemented with human AB serum,
  iv) subjecting the PBMCs to staining with labeled antibodies against human CD4, human CD8, human CD56 and with a dye that stains non-viable cells, such as 7-aminoactinomycin D; and
  v) analyzing CSFE in different subpopulations ($CD4^+$ and $CD8^+$ T-cells) in the samples by flow cytometry.

Antibody Formats

As described above, various formats of antibodies have been described in the art. The binding agent of the invention can in principle be an antibody of any isotype. The choice of isotype typically will be guided by the desired Fc-mediated effector functions, such as ADCC induction, or the requirement for an antibody devoid of Fc-mediated effector function ("inert" antibody). Exemplary isotypes are IgG1, IgG2, IgG3, and IgG4. Either of the human light chain constant regions, kappa or lambda, may be used. The effector function of the antibodies of the present invention may be changed by isotype switching to, e.g., an IgG1, IgG2, IgG3, IgG4, IgD, IgA, IgE, or IgM antibody for various therapeutic uses. In one embodiment, both heavy chains of an antibody of the present invention are of the IgG1 isotype, for instance an IgG1,κ. Optionally, the heavy chain may be modified in the hinge and/or CH3 region as described elsewhere herein.

Preferably, each of the antigen-binding regions comprises a heavy chain variable region (VH) and a light chain variable region (VL), and wherein said variable regions each comprise three CDR sequences, CDR1, CDR2 and CDR3, respectively, and four framework sequences, FR1, FR2, FR3 and FR4, respectively. Furthermore, preferably, the antibody comprises two heavy chain constant regions (CH), and two light chain constant regions (CL).

In one embodiment of the invention, the binding agent is a full-length antibody, such as a full-length IgG1 antibody. In another embodiment, the antibody is a full-length IgG4 antibody, preferably with a stabilized hinge region. Modifications that stabilize the IgG4 hinge region, such as the S228P mutation in the core hinge, have been described in the art, see e.g. Labrijn et al., 2009 Nat Biotechnol. 27(8):767-71.

In other embodiments of the invention, the binding agent of the invention comprises an antibody fragment, such as a Fab' or Fab fragment, a monovalent fragment consisting of the VL, VH, CL and CH1 domains, a monovalent antibody as described in WO2007059782 (Genmab), a $F(ab')_2$ fragment, an Fd fragment, an Fv fragment, a dAb fragment, camelid or nanobodies, or an isolated complementarity determining region (CDR).

Binding agents of the invention are preferably human, humanized or chimeric antibodies. In embodiments, wherein the antibody is a bispecific antibody, both half-molecules can be human, humanized or chimeric, or the half-molecules can differ in character with respect to sequence origin.

For example, in one embodiment, the binding agent, e.g. a bispecific antibody, comprises two half-molecules each comprising an antigen-binding region, wherein
(i) the half-molecule(s) comprising the antigen-binding region capable of binding to human PD-L1 is/are chimeric, and/or
(ii) the half-molecule comprising the antigen-binding region capable of binding to human CD137, if present, is chimeric.

For example, in another embodiment, the bispecific antibody comprises two half-molecules each comprising an antigen-binding region, wherein
(i) the half-molecule(s) comprising the antigen-binding region capable of binding to human PD-L1 is/are humanized, and/or
(ii) the half-molecule comprising the antigen-binding region capable of binding to human CD137, if present, is humanized.

For example, in a further embodiment, the bispecific antibody comprises two half-molecules each comprising an antigen-binding region, wherein
(i) the half-molecule(s) comprising the antigen-binding region capable of binding to human PD-L1 is/are human, and/or
(ii) the half-molecule comprising the antigen-binding region capable of binding to human CD137, if present, is human.

Thus, for example, in one embodiment, the antigen-binding region(s) capable of binding to human PD-L1 is/are humanized, and the antigen-binding region capable of binding to human CD137, if present, is humanized.

In a different embodiment of the invention, the antigen-binding region(s) capable of binding to human PD-L1 is/are human, and the antigen-binding region capable of binding to human CD137, if present, is human.

In a further embodiment, the binding agent is a bispecific antibody comprising an antigen-binding region capable of binding to human PD-L1 and an antigen-binding region capable of binding to human CD137, wherein the half-molecule comprising the antigen-binding region capable of binding to human PD-L1 is human, humanized or chimeric, and the half-molecule comprising the antigen-binding region capable of binding to human CD137 is humanized.

Preferably, the half-molecule comprising the antigen-binding region capable of binding to human PD-L1 is human and the half-molecule comprising the antigen-binding region capable of binding to human CD137 is humanized.

Bispecific Antibody Formats

Many different formats and uses of bispecific antibodies are known in the art, and were reviewed by Kontermann; Drug Discov Today, 2015 July; 20(7):838-47 and; MAbs, 2012 March-April; 4(2): 182-97.

A bispecific antibody according to the present invention is not limited to any particular bispecific format or method of producing it.

Examples of bispecific antibody molecules which may be used in the present invention comprise (i) a single antibody that has two arms comprising different antigen-binding regions; (ii) a single chain antibody that has specificity to two different epitopes, e.g., via two scFvs linked in tandem by an extra peptide linker; (iii) a dual-variable-domain antibody (DVD-Ig), where each light chain and heavy chain contains two variable domains in tandem through a short peptide linkage (Wu et al., Generation and Characterization of a Dual Variable Domain Immunoglobulin (DVD-Ig™) Molecule, In: Antibody Engineering, Springer Berlin Heidelberg (2010)); (iv) a chemically-linked bispecific (Fab')2 fragment; (v) a Tandab, which is a fusion of two single chain diabodies resulting in a tetravalent bispecific antibody that has two binding sites for each of the target antigens; (vi) a flexibody, which is a combination of scFvs with a diabody resulting in a multivalent molecule; (vii) a so-called "dock and lock" molecule, based on the "dimerization and docking domain" in Protein Kinase A, which, when applied to Fabs, can yield a trivalent bispecific binding protein consisting of two identical Fab fragments linked to a different Fab fragment; (viii) a so-called Scorpion molecule, comprising, e.g., two scFvs fused to both termini of a human Fab-arm; and (ix) a diabody.

In one embodiment of the invention, the binding agent of the present invention is a diabody or a cross-body. In one embodiment, the binding agent of the invention is a bispecific antibody obtained via a controlled Fab-arm exchange (such as described in WO2011131746 (Genmab)).

Examples of different classes of binding agents according to the present invention include but are not limited to (i) IgG-like molecules with complementary CH3 domains to force heterodimerization; (ii) recombinant IgG-like dual targeting molecules, wherein the two sides of the molecule each contain the Fab fragment or part of the Fab fragment of at least two different antibodies; (iii) IgG fusion molecules, wherein full length IgG antibodies are fused to extra Fab fragment or parts of Fab fragment; (iv) Fc fusion molecules, wherein single chain Fv molecules or stabilized diabodies are fused to heavy-chain constant-domains, Fc regions or parts thereof; (v) Fab fusion molecules, wherein different Fab-fragments are fused together, fused to heavy-chain constant-domains, Fc regions or parts thereof; and (vi) ScFv- and diabody-based and heavy chain antibodies (e.g., domain antibodies, nanobodies) wherein different single chain Fv molecules or different diabodies or different heavy-chain antibodies (e.g. domain antibodies, nanobodies) are fused to each other or to another protein or carrier molecule fused to heavy-chain constant-domains, Fc regions or parts thereof.

Examples of IgG-like molecules with complementary CH3 domain molecules include but are not limited to the Triomab/Quadroma molecules (Trion Pharma/Fresenius Biotech; Roche, WO2011069104), the so-called Knobs-into-Holes molecules (Genentech, WO9850431), CrossMAbs (Roche, WO2011117329) and the electrostatically-matched molecules (Amgen, EP1870459 and WO2009089004; Chugai, US201000155133; Oncomed, WO2010129304), the LUZ-Y molecules (Genentech, Wranik et al. 3. Biol. Chem. 2012, 287(52): 43331-9, doi: 10.1074/jbc.M112.397869. Epub 2012 Nov. 1), DIG-body and PIG-body molecules (Pharmabcine, WO2010134666, WO2014081202), the Strand Exchange Engineered Domain body (SEEDbody) molecules (EMD Serono, WO2007110205), the Biclonics molecules (Merus, WO2013157953), FcΔAdp molecules (Regeneron, WO201015792), bispecific IgG1 and IgG2 molecules (Pfizer/Rinat, WO11143545), Azymetric scaffold molecules (Zymeworks/Merck, WO2012058768), mAb-Fv molecules (Xencor, WO2011028952), bivalent bispecific antibodies (WO2009080254) and the DuoBody® molecules (Genmab, WO2011131746).

Examples of recombinant IgG-like dual targeting molecules include but are not limited to Dual Targeting (DT)-Ig molecules (WO2009058383), Two-in-one Antibody (Genentech; Bostrom, et al 2009. Science 323, 1610-1614.), Cross-linked Mabs (Karmanos Cancer Center), mAb2 (F-Star, WO2008003116), Zybody molecules (Zyngenia; LaFleur et al. MAbs. 2013 March-April; 5(2):208-18), approaches with common light chain (Crucell/Merus, U.S. Pat. No. 7,262,028), KλBodies (NovImmune, WO2012023053) and CovX-body (CovX/Pfizer; Doppalapudi, V. R., et al 2007. Bioorg. Med. Chem. Lett. 17,501-506.).

Examples of IgG fusion molecules include but are not limited to Dual Variable Domain (DVD)-Ig molecules (Abbott, U.S. Pat. No. 7,612,181), Dual domain double head antibodies (Unilever; Sanofi Aventis, WO20100226923), IgG-like Bispecific molecules (ImClone/Eli Lilly, Lewis et al. Nat Biotechnol. 2014 February; 32(2):191-8), Ts2Ab (MedImmune/AZ; Dimasi et al. J Mol Biol. 2009 Oct. 30; 393(3):672-92) and BsAb molecules (Zymogenetics, WO2010111625), HERCULES molecules (Biogen Idec, U.S. Ser. No. 00/795,1918), scFv fusion molecules (Novartis), scFv fusion molecules (Changzhou Adam Biotech Inc, CN 102250246) and TvAb molecules (Roche, WO2012025525, WO2012025530).

Examples of Fc fusion molecules include but are not limited to ScFv/Fc Fusions (Pearce et al., Biochem Mol Biol Int. 1997 September; 42(6):1179-88), SCORPION molecules (Emergent BioSolutions/Trubion, Blankenship J W, et al. AACR 100th Annual meeting 2009 (Abstract #5465); Zymogenetics/BMS, WO2010111625), Dual Affinity Retargeting Technology (Fc-DART) molecules (MacroGenics, WO2008157379, WO2010080538) and Dual (ScFv)2-Fab molecules (National Research Center for Antibody Medicine-China).

Examples of Fab fusion bispecific antibodies include but are not limited to F(ab)2 molecules (Medarex/AMGEN; Deo et al J Immunol. 1998 Feb. 15; 160(4):1677-86.), Dual-Action or Bis-Fab molecules (Genentech, Bostrom, et al 2009. Science 323, 1610-1614.), Dock-and-Lock (DNL) molecules (ImmunoMedics, WO2003074569, WO2005004809), Bivalent Bispecific molecules (Biotecnol, Schoonjans, J Immunol. 2000 Dec. 15; 165(12):7050-7.) and Fab-Fv molecules (UCB-Celltech, WO 2009040562 A1).

Examples of ScFv-, diabody-based and domain antibodies include but are not limited to Bispecific T Cell Engager (BiTE) molecules (Micromet, WO2005061547), Tandem Diabody molecules (TandAb) (Affimed) Le Gall et al., Protein Eng Des Sel. 2004 April; 17(4):357-66.), Dual Affinity Retargeting Technology (DART) molecules (MacroGenics, WO2008157379, WO2010080538), Single-chain Diabody molecules (Lawrence, FEBS Lett. 1998 Apr. 3; 425(3):479-84), TCR-like Antibodies (AIT, ReceptorLogics), Human Serum Albumin ScFv Fusion (Merrimack, WO2010059315) and COMBODY molecules (Epigen Biotech, Zhu et al. Immunol Cell Biol. 2010 August; 88(6):667-75.), dual targeting nanobodies (Ablynx, Hmila et al., FASEB J. 2010) and dual targeting heavy chain only domain antibodies.

In one aspect, the bispecific antibody of the invention comprises a first Fc sequence comprising a first CH3 region, and a second Fc sequence comprising a second CH3 region, wherein the sequences of the first and second CH3 regions are different and are such that the heterodimeric interaction between said first and second CH3 regions is stronger than each of the homodimeric interactions of said first and second CH3 regions. More details on these interactions and how they can be achieved are provided in WO2011131746 and WO2013060867 (Genmab), which are hereby incorporated by reference.

As described further herein, a stable bispecific PD-L1× CD137 antibody can be obtained at high yield using a particular method on the basis of one homodimeric starting PD-L1 antibody and one homodimeric starting CD137 antibody containing only a few, conservative, asymmetrical mutations in the CH3 regions. Asymmetrical mutations mean that the sequences of said first and second CH3 regions contain amino acid substitutions at non-identical positions.

In one embodiment, the bispecific antibody of the invention as defined in any of the embodiments disclosed herein, comprises a first CH3 region which has an amino acid substitution at a position selected from the group consisting of: 366, 368, 370, 399, 405, 407 and 409 in a human IgG1 heavy chain, and a second CH3 region which has an amino acid substitution at a position selected from the group consisting of: 366, 368, 370, 399, 405, 407 and 409 in a human IgG1 heavy chain, and wherein the first and second CH3 regions are not substituted in the same positions.

In one embodiment, the bispecific antibody of the invention as defined in any of the embodiments disclosed herein, comprises a first CH3 region which has an amino acid substitution at position 366 in a human IgG1 heavy chain, and a second CH3 region which has an amino acid substitution at a position selected from the group consisting of: 368, 370, 399, 405, 407 and 409 in a human IgG1 heavy chain. In one embodiment, the amino acid at position 366 in a human IgG1 heavy chain is selected from Ala, Asp, Glu, His, Asn, Val, or Gln.

In one embodiment, the bispecific antibody of the invention as defined in any of the embodiments disclosed herein, comprises a first CH3 region which has an amino acid substitution at position 368 in a human IgG1 heavy chain, and a second CH3 region which has an amino acid substitution at a position selected from the group consisting of: 366, 370, 399, 405, 407 and 409 in a human IgG1 heavy chain.

In one embodiment, the bispecific antibody of the invention as defined in any of the embodiments disclosed herein, comprises a first CH3 region which has an amino acid substitution at position 370 in a human IgG1 heavy chain, and a second CH3 region which has an amino acid substitution at a position selected from the group consisting of: 366, 368, 399, 405, 407 and 409 in a human IgG1 heavy chain.

In one embodiment, the bispecific antibody of the invention as defined in any of the embodiments disclosed herein, comprises a first CH3 region which has an amino acid substitution at position 399 in a human IgG1 heavy chain, and a second CH3 region which has an amino acid substitution at a position selected from the group consisting of: 366, 368, 370, 405, 407 and 409 in a human IgG1 heavy chain.

In one embodiment, the bispecific antibody of the invention as defined in any of the embodiments disclosed herein, comprises a first CH3 region which has an amino acid substitution at position 405 in a human IgG1 heavy chain, and a second CH3 region which has an amino acid substitution at a position selected from the group consisting of: 366, 368, 370, 399, 407 and 409 in a human IgG1 heavy chain.

In one embodiment, the bispecific antibody of the invention as defined in any of the embodiments disclosed herein, comprises a first CH3 region which has an amino acid substitution at position 407 in a human IgG1 heavy chain, and a second CH3 region which has an amino acid substitution at a position selected from the group consisting of: 366, 368, 370, 399, 405, and 409 in a human IgG1 heavy chain.

In one embodiment, the bispecific antibody of the invention as defined in any of the embodiments disclosed herein, comprises a first CH3 region which has an amino acid substitution at position 409 in a human IgG1 heavy chain, and a second CH3 region has an amino acid substitution at a position selected from the group consisting of: 366, 368, 370, 399, 405, and 407 in a human IgG1 heavy chain.

Accordingly, in one embodiment the bispecific antibody of the invention as defined in any of the embodiments disclosed herein, comprises the sequences of said first and second CH3 regions contain asymmetrical mutations, i.e. mutations at different positions in the two CH3 regions, e.g. a mutation at position 405 in one of the CH3 regions and a mutation at position 409 in the other CH3 region.

In one embodiment, the bispecific antibody of the invention as defined in any of the embodiments disclosed herein, the first CH3 region has an amino acid other than Lys, Leu or Met, e.g. Gly, Ala, Val, Ile, Ser, Thr, Phe, Arg, His, Asp, Asn, Glu, Gln, Pro, Trp, Tyr, or Cys, at position 409 and said second CH3 region has an amino-acid substitution at a position selected from the group consisting of: 366, 368, 370, 399, 405 and 407. In one such embodiment, said first CH3 region has an amino acid other than Lys, Leu or Met, e.g. Gly, Ala, Val, Ile, Ser, Thr, Phe, Arg, His, Asp, Asn, Glu, Gln, Pro, Trp, Tyr, or Cys, at position 409 and said second CH3 region has an amino acid other than Phe, e.g. Gly, Ala, Val, Ile, Ser, Thr, Lys, Arg, His, Asp, Asn, Glu, Gln, Pro, Trp, Tyr, Cys, Lys, or Leu, at position 405. In a further embodiment hereof, said first CH3 region has an amino acid other than Lys, Leu or Met, e.g. Gly, Ala, Val, Ile, Ser, Thr, Phe, Arg, His, Asp, Asn, Glu, Gln, Pro, Trp, Tyr, or Cys, at position 409 and said second CH3 region has an amino acid other than Phe, Arg or Gly, e.g. Leu, Ala, Val, Ile, Ser, Thr, Met, Lys, His, Asp, Asn, Glu, Gln, Pro, Trp, Tyr, or Cys, at position 405.

In another embodiment, the bispecific antibody of the invention as defined in any of the embodiments disclosed herein, said first CH3 region comprises a Phe at position 405 and an amino acid other than Lys, Leu or Met, e.g. Gly, Ala, Val, Ile, Ser, Thr, Phe, Arg, His, Asp, Asn, Glu, Gln, Pro, Trp, Tyr, or Cys, at position 409 and said second CH3 region comprises an amino acid other than Phe, e.g. Gly, Ala, Val, Ile, Ser, Thr, Lys, Arg, His, Asp, Asn, Glu, Gln, Pro, Trp, Tyr, Leu, Met, or Cys, at position 405 and a Lys at position 409. In a further embodiment hereof, said first CH3 region comprises a Phe at position 405 and an amino acid other than Lys, Leu or Met, e.g. Gly, Ala, Val, Ile, Ser, Thr, Phe, Arg, His, Asp, Asn, Glu, Gln, Pro, Trp, Tyr, or Cys, at position 409 and said second CH3 region comprises an amino acid other than Phe, Arg or Gly, e.g. Leu, Ala, Val, Ile, Ser, Thr, Met, Lys, His, Asp, Asn, Glu, Gln, Pro, Trp, Tyr, or Cys, at position 405 and a Lys at position 409.

In another embodiment, the bispecific antibody of the invention as defined in any of the embodiments disclosed herein, said first CH3 region comprises a Phe at position 405 and an amino acid other than Lys, Leu or Met, e.g. Gly, Ala, Val, Ile, Ser, Thr, Phe, Arg, His, Asp, Asn, Glu, Gln, Pro, Trp, Tyr, or Cys, at position 409 and said second CH3 region comprises a Leu at position 405 and a Lys at position 409. In a further embodiment hereof, said first CH3 region comprises a Phe at position 405 and an Arg at position 409 and said second CH3 region comprises an amino acid other than Phe, Arg or Gly, e.g. Leu, Ala, Val, Ile, Ser, Thr, Lys, Met, His, Asp, Asn, Glu, Gln, Pro, Trp, Tyr, or Cys, at position 405 and a Lys at position 409. In another embodiment, said first CH3 region comprises Phe at position 405 and an Arg at position 409 and said second CH3 region comprises a Leu at position 405 and a Lys at position 409.

In a further embodiment, the bispecific antibody of the invention as defined in any of the embodiments disclosed herein, said first CH3 region comprises an amino acid other than Lys, Leu or Met, e.g. Gly, Ala, Val, Ile, Ser, Thr, Phe, Arg, His, Asp, Asn, Glu, Gln, Pro, Trp, Tyr, or Cys, at position 409 and said second CH3 region comprises a Lys at position 409, a Thr at position 370 and a Leu at position 405. In a further embodiment, said first CH3 region comprises an Arg at position 409 and said second CH3 region comprises a Lys at position 409, a Thr at position 370 and a Leu at position 405.

In an even further embodiment, the bispecific antibody of the invention as defined in any of the embodiments disclosed herein, said first CH3 region comprises a Lys at position 370, a Phe at position 405 and an Arg at position 409 and said second CH3 region comprises a Lys at position 409, a Thr at position 370 and a Leu at position 405.

In another embodiment, the bispecific antibody of the invention as defined in any of the embodiments disclosed herein, said first CH3 region comprises an amino acid other than Lys, Leu or Met, e.g. Gly, Ala, Val, Ile, Ser, Thr, Phe, Arg, His, Asp, Asn, Glu, Gln, Pro, Trp, Tyr, or Cys, at position 409 and said second CH3 region comprises a Lys at position 409 and: a) an Ile at position 350 and a Leu at position 405, or b) a Thr at position 370 and a Leu at position 405.

In another embodiment, the bispecific antibody of the invention as defined in any of the embodiments disclosed herein, said first CH3 region comprises an Arg at position 409 and said second CH3 region comprises a Lys at position 409 and: a) an Ile at position 350 and a Leu at position 405, or b) a Thr at position 370 and a Leu at position 405.

In another embodiment, the bispecific antibody of the invention as defined in any of the embodiments disclosed herein, said first CH3 region comprises a Thr at position 350, a Lys at position 370, a Phe at position 405 and an Arg at position 409 and said second CH3 region comprises a Lys at position 409 and: a) an Ile at position 350 and a Leu at position 405, or b) a Thr at position 370 and a Leu at position 405.

In another embodiment, the bispecific antibody of the invention as defined in any of the embodiments disclosed herein, said first CH3 region comprises a Thr at position 350, a Lys at position 370, a Phe at position 405 and an Arg at position 409 and said second CH3 region comprises an Ile at position 350, a Thr at position 370, a Leu at position 405 and a Lys at position 409.

In one embodiment, the bispecific antibody of the invention as defined in any of the embodiments disclosed herein, said first CH3 region has an amino acid other than Lys, Leu or Met at position 409 and said second CH3 region has an amino acid other than Phe at position 405, such as other than Phe, Arg or Gly at position 405; or said first CH3 region has an amino acid other than Lys, Leu or Met at position 409 and said second CH3 region has an amino acid other than Tyr, Asp, Glu, Phe, Lys, Gln, Arg, Ser or Thr at position 407.

In one embodiment, the bispecific antibody of the invention as defined in any of the embodiments disclosed herein comprises a first CH3 region having an amino acid other than Lys, Leu or Met at position 409 and a second CH3 region having an amino acid other than Tyr, Asp, Glu, Phe, Lys, Gln, Arg, Ser or Thr at position 407.

In one embodiment, bispecific antibody of the invention as defined in any of the embodiments disclosed herein comprises a first CH3 region having a Tyr at position 407 and an amino acid other than Lys, Leu or Met at position 409 and a second CH3 region having an amino acid other than Tyr, Asp, Glu, Phe, Lys, Gln, Arg, Ser or Thr at position 407 and a Lys at position 409.

In one embodiment of invention, the bispecific antibody as defined in any of the embodiments disclosed herein comprises a first CH3 region having a Tyr at position 407 and an Arg at position 409 and a second CH3 region having an amino acid other than Tyr, Asp, Glu, Phe, Lys, Gln, Arg, Ser or Thr at position 407 and a Lys at position 409.

In another embodiment of invention, said first CH3 region has an amino acid other than Lys, Leu or Met, e.g. Gly, Ala, Val, Ile, Ser, Thr, Phe, Arg, His, Asp, Asn, Glu, Gln, Pro, Trp, Tyr, or Cys, at position 409 and said second CH3 region has an amino acid other than Tyr, Asp, Glu, Phe, Lys, Gln, Arg, Ser or Thr, e.g. Leu, Met, Gly, Ala, Val, Ile, His, Asn, Pro, Trp, or Cys, at position 407. In another embodiment of invention, said first CH3 region has an amino acid other than Lys, Leu or Met, e.g. Gly, Ala, Val, Ile, Ser, Thr, Phe, Arg, His, Asp, Asn, Glu, Gln, Pro, Trp, Tyr, or Cys, at position 409 and said second CH3 region has an Ala, Gly, His, Ile, Leu, Met, Asn, Val or Trp at position 407.

In another embodiment, the bispecific antibody of the invention as defined in any of the embodiments disclosed herein, said first CH3 region has an amino acid other than Lys, Leu or Met, e.g. Gly, Ala, Val, Ile, Ser, Thr, Phe, Arg, His, Asp, Asn, Glu, Gln, Pro, Trp, Tyr, or Cys, at position 409 and said second CH3 region has a Gly, Leu, Met, Asn or Trp at position 407.

In another embodiment, the bispecific antibody of the invention as defined in any of the embodiments disclosed herein, said first CH3 region has a Tyr at position 407 and an amino acid other than Lys, Leu or Met, e.g. Gly, Ala, Val, Ile, Ser, Thr, Phe, Arg, His, Asp, Asn, Glu, Gln, Pro, Trp, Tyr, or Cys, at position 409 and said second CH3 region has an amino acid other than Tyr, Asp, Glu, Phe, Lys, Gln, Arg, Ser or Thr, e.g. Leu, Met, Gly, Ala, Val, Ile, His, Asn, Pro, Trp, or Cys, at position 407 and a Lys at position 409.

In another embodiment, the bispecific antibody of the invention as defined in any of the embodiments disclosed herein, said first CH3 region has a Tyr at position 407 and an amino acid other than Lys, Leu or Met, e.g. Gly, Ala, Val, Ile, Ser, Thr, Phe, Arg, His, Asp, Asn, Glu, Gln, Pro, Trp, Tyr, or Cys, at position 409 and said second CH3 region has an Ala, Gly, His, Ile, Leu, Met, Asn, Val or Trp at position 407 and a Lys at position 409.

In another embodiment, the bispecific antibody of the invention as defined in any of the embodiments disclosed herein, said first CH3 region has a Tyr at position 407 and an amino acid other than Lys, Leu or Met, e.g. Gly, Ala, Val, Ile, Ser, Thr, Phe, Arg, His, Asp, Asn, Glu, Gln, Pro, Trp, Tyr, or Cys, at position 409 and said second CH3 region has a Gly, Leu, Met, Asn or Trp at position 407 and a Lys at position 409.

In another embodiment, the bispecific antibody of the invention as defined in any of the embodiments disclosed herein, said first CH3 region has a Tyr at position 407 and an Arg at position 409 and said second CH3 region has an amino acid other than Tyr, Asp, Glu, Phe, Lys, Gln, Arg, Ser or Thr, e.g. Leu, Met, Gly, Ala, Val, Ile, His, Asn, Pro, Trp, or Cys, at position 407 and a Lys at position 409.

In another embodiment, the bispecific antibody of the invention as defined in any of the embodiments disclosed herein, said first CH3 region has a Tyr at position 407 and an Arg at position 409 and said second CH3 region has an Ala, Gly, His, Ile, Leu, Met, Asn, Val or Trp at position 407 and a Lys at position 409.

In another embodiment, the bispecific antibody of the invention as defined in any of the embodiments disclosed herein, said first CH3 region has a Tyr at position 407 and an Arg at position 409 and said second CH3 region has a Gly, Leu, Met, Asn or Trp at position 407 and a Lys at position 409.

In another embodiment, the bispecific antibody of the invention as defined in any of the embodiments disclosed herein, the first CH3 region has an amino acid other than Lys, Leu or Met, e.g. Gly, Ala, Val, Ile, Ser, Thr, Phe, Arg, His, Asp, Asn, Glu, Gln, Pro, Trp, Tyr, or Cys, at position 409, and the second CH3 region has
(i) an amino acid other than Phe, Leu and Met, e.g. Gly, Ala, Val, Ile, Ser, Thr, Lys, Arg, His, Asp, Asn, Glu, Gln, Pro, Trp, Tyr, or Cys, at position 368, or
(ii) a Trp at position 370, or
(iii) an amino acid other than Asp, Cys, Pro, Glu or Gln, e.g. Phe, Leu, Met, Gly, Ala, Val, Ile, Ser, Thr, Lys, Arg, His, Asn, Trp, Tyr, or Cys, at position 399 or
(iv) an amino acid other than Lys, Arg, Ser, Thr, or Trp, e.g. Phe, Leu, Met, Ala, Val, Gly, Ile, Asn, His, Asp, Glu, Gln, Pro, Tyr, or Cys, at position 366.

In one embodiment, the first CH3 region has an Arg, Ala, His or Gly at position 409, and the second CH3 region has
(i) a Lys, Gln, Ala, Asp, Glu, Gly, His, Ile, Asn, Arg, Ser, Thr, Val, or Trp at position 368, or
(ii) a Trp at position 370, or
(iii) an Ala, Gly, Ile, Leu, Met, Asn, Ser, Thr, Trp, Phe, His, Lys, Arg or Tyr at position 399, or
(iv) an Ala, Asp, Glu, His, Asn, Val, Gln, Phe, Gly, Ile, Leu, Met, or Tyr at position 366.

In one embodiment, the first CH3 region has an Arg at position 409, and the second CH3 region has
(i) an Asp, Glu, Gly, Asn, Arg, Ser, Thr, Val, or Trp at position 368, or
(ii) a Trp at position 370, or
(iii) a Phe, His, Lys, Arg or Tyr at position 399, or
(iv) an Ala, Asp, Glu, His, Asn, Val, Gln at position 366.

In a preferred embodiment of the invention, the bispecific antibody comprises a first and second heavy chain, wherein each of said first and second heavy chains comprises at least a hinge region, a CH2 and a CH3 region, wherein (i) the amino acid in the position corresponding to F405 in human IgG1 heavy chain is L in said first heavy chain, and the amino acid in the position corresponding to K409 in human IgG1 heavy chain is R in said second heavy chain, or (ii) the amino acid in the position corresponding to K409 in human IgG1 heavy chain is R in said first heavy chain, and the amino acid in the position corresponding to F405 in human IgG1 heavy chain is L in said second heavy chain.

In addition to the above-specified amino-acid substitutions, said first and second heavy chains may contain further amino-acid substitutions, deletion or insertions relative to wild-type heavy chain sequences.

In one embodiment of the invention, neither said first nor said second Fc sequence comprises a Cys-Pro-Ser-Cys sequence in the (core) hinge region.

In a further embodiment of the invention, both said first and said second Fc sequence comprise a Cys-Pro-Pro-Cys sequence in the (core) hinge region.

Methods of Preparing Bispecific Antibodies

Traditional methods such as the hybrid hybridoma and chemical conjugation methods (Marvin and Zhu (2005) Acta Pharmacol Sin 26:649) can be used in the preparation of the bispecific antibodies of the invention. Co-expression in a host cell of two antibodies, consisting of different heavy and light chains, leads to a mixture of possible antibody products in addition to the desired bispecific antibody, which can then be isolated by, e.g., affinity chromatography or similar methods.

Strategies favoring the formation of a functional bispecific, product, upon co-expression of different antibody constructs can also be used, e.g., the method described by Lindhofer et al. (1995 J Immunol 155:219). Fusion of rat and mouse hybridomas producing different antibodies leads to a limited number of heterodimeric proteins because of preferential species-restricted heavy/light chain pairing. Another strategy to promote formation of heterodimers over homodimers is a "knob-into-hole" strategy in which a protuberance is introduced on a first heavy-chain polypeptide and a corresponding cavity in a second heavy-chain polypeptide, such that the protuberance can be positioned in the cavity at the interface of these two heavy chains so as to promote heterodimer formation and hinder homodimer formation. "Protuberances" are constructed by replacing small amino-acid side-chains from the interface of the first polypeptide with larger side chains. Compensatory "cavities" of identical or similar size to the protuberances are created in the interface of the second polypeptide by replacing large amino-acid side-chains with smaller ones (U.S. Pat. No. 5,731,168). EP1870459 (Chugai) and WO2009089004 (Amgen) describe other strategies for favoring heterodimer formation upon co-expression of different antibody domains in a host cell. In these methods, one or more residues that make up the CH3-CH3 interface in both CH3 domains are replaced with a charged amino acid such that homodimer formation is electrostatically unfavorable and heterodimerization is electrostatically favorable. WO2007110205 (Merck) describe yet another strategy, wherein differences between IgA and IgG CH3 domains are exploited to promote heterodimerization.

Another in vitro method for producing bispecific antibodies has been described in WO2008119353 (Genmab), wherein a bispecific antibody is formed by "Fab-arm" or "half-molecule" exchange (swapping of a heavy chain and attached light chain) between two monospecific IgG4- or IgG4-like antibodies upon incubation under reducing conditions. The resulting product is a bispecific antibody having two Fab arms which may comprise different sequences.

A preferred method for preparing bispecific PD-L1× CD137 antibodies of the present invention includes the methods described in WO2011131746 and WO2013060867 (Genmab) comprising the following steps:

a) providing a first antibody comprising an Fc region, said Fc region comprising a first CH3 region;
b) providing a second antibody comprising a second Fc region, said Fc region comprising a second CH3 region, wherein the first antibody is a CD137 antibody and the second antibody is a PD-L1 antibody, or vice versa; wherein the sequences of said first and second CH3 regions are different and are such that the heterodimeric interaction between said first and second CH3 regions is stronger than each of the homodimeric interactions of said first and second CH3 regions;
c) incubating said first antibody together with said second antibody under reducing conditions; and
d) obtaining said bispecific PD-L1×CD137 antibody.

Similarly, there is provided a method for producing an antibody according to the invention, comprising the steps of:
a) culturing a host cell producing a first antibody comprising an antigen-binding region capable of binding to human CD137 as defined herein and purifying said first antibody from the culture;
b) culturing a host cell producing a second antibody comprising an antigen-binding region capable of binding to human PD-L1 as defined herein purifying said second antibody from the culture;
c) incubating said first antibody together with said second antibody under reducing conditions sufficient to allow the cysteines in the hinge region to undergo disulfide-bond isomerization, and
d) obtaining said bispecific antibody.

In one embodiment of the invention, the said first antibody together with said second antibody are incubated under reducing conditions sufficient to allow the cysteines in the hinge region to undergo disulfide-bond isomerization, wherein the heterodimeric interaction between said first and second antibodies in the resulting heterodimeric antibody is such that no Fab-arm exchange occurs at 0.5 mM GSH after 24 hours at 37° C.

Without being limited to theory, in step c), the heavy-chain disulfide bonds in the hinge regions of the parent antibodies are reduced and the resulting cysteines are then able to form inter heavy-chain disulfide bonds with cysteine residues of another parent antibody molecule (originally with a different specificity). In one embodiment of this method, the reducing conditions in step c) comprise the addition of a reducing agent, e.g. a reducing agent selected from the group consisting of: 2-mercaptoethylamine (2-MEA), dithiothreitol (DTT), dithioerythritol (DTE), glutathione, tris(2-carboxyethyl)phosphine (TCEP), L-cysteine and beta-mercapto-ethanol, preferably a reducing agent selected from the group consisting of: 2-mercaptoethylamine, dithiothreitol and tris(2-carboxyethyl)phosphine. In a further embodiment, step c) comprises restoring the conditions to become non-reducing or less reducing, for example by removal of a reducing agent, e.g. by desalting.

For this method, any of the CD137 and PD-L1 antibodies described above may be used including first and second CD137 and PD-L1 antibodies, respectively, comprising a first and/or second Fc region. Examples of such first and second Fc regions, including combination of such first and second Fc regions may include any of those described above. In a particular embodiment, the first and second CD137 and PD-L1 antibodies, respectively, may be chosen so as to obtain a bispecific antibody as described herein.

In one embodiment of this method, said first and/or second antibodies are full-length antibodies.

The Fc regions of the first and second antibodies may be of any isotype, including, but not limited to, IgG1, IgG2, IgG3 or IgG4. In one embodiment of this method, the Fc regions of both said first and said second antibodies are of the IgG1 isotype. In another embodiment, one of the Fc regions of said antibodies is of the IgG1 isotype and the other of the IgG4 isotype. In the latter embodiment, the resulting bispecific antibody comprises an Fc sequence of an IgG1 and an Fc sequence of IgG4 and may thus have interesting intermediate properties with respect to activation of effector functions.

In a further embodiment, one of the antibody starting proteins has been engineered to not bind Protein A, thus allowing to separate the heterodimeric protein from said homodimeric starting protein by passing the product over a protein A column.

As described above, the sequences of the first and second CH3 regions of the homodimeric starting antibodies are different and are such that the heterodimeric interaction between said first and second CH3 regions is stronger than each of the homodimeric interactions of said first and second CH3 regions. More details on these interactions and how they can be achieved are provided in WO2011131746 and WO2013060867 (Genmab), which are hereby incorporated by reference in their entirety.

In particular, a stable bispecific PD-L1×CD137 antibody can be obtained at high yield using the above method of the invention on the basis of two homodimeric starting antibodies which bind CD137 and PD-L1, respectively, and contain only a few, conservative, asymmetrical mutations in the CH3 regions. Asymmetrical mutations mean that the sequences of said first and second CH3 regions contain amino acid substitutions at non-identical positions.

The bispecific antibodies of the invention may also be obtained by co-expression of constructs encoding the first and second polypeptides in a single cell. Thus, in a further aspect, the invention relates to a method for producing a bispecific antibody, said method comprising the following steps:

a) providing a first nucleic-acid construct encoding a first polypeptide comprising a first Fc sequence and a first antigen-binding region of a first antibody heavy chain, said first Fc sequence comprising a first CH3 region,
b) providing a second nucleic-acid construct encoding a second polypeptide comprising a second Fc sequence and a second antigen-binding region of a second antibody heavy chain, said second Fc sequence comprising a second CH3 region,
wherein the sequences of said first and second CH3 regions are different and are such that the heterodimeric interaction between said first and second CH3 regions is stronger than each of the homodimeric interactions of said first and second CH3 regions, and wherein said first homodimeric protein has an amino acid other than Lys, Leu or Met at position 409 and said second homodimeric protein has an amino-acid substitution at a position selected from the group consisting of: 366, 368, 370, 399, 405 and 407, optionally wherein said first and second nucleic acid constructs encode light chain sequences of said first and second antibodies c) co-expressing said first and second nucleic-acid constructs in a host cell, and d) obtaining said heterodimeric protein from the cell culture.

Materials and Methods for the Production of Antibodies of the Invention

In further aspects, the invention relates to materials and methods for the recombinant production of antibodies according to the invention. Suitable expression vectors, including promoters, enhancers, etc., and suitable host cells for the production of antibodies are well-known in the art.

Thus, in one aspect, there is provided a nucleic acid construct comprising:

(i) a nucleic acid sequence encoding a heavy chain sequence of an antibody comprising an antigen-binding region capable of binding to human PD-L1 as defined herein, and/or (ii) a nucleic acid sequence encoding a light chain sequence of an antibody comprising an antigen-binding region capable of binding to human PD-L1 as defined herein.

In one embodiment, the nucleic acid construct further comprises:

(i) a nucleic acid sequence encoding a heavy chain sequence of an antibody comprising an antigen-binding region capable of binding to human CD137 as defined herein, and (ii) a nucleic acid sequence encoding a light chain sequence of an antibody comprising an antigen-binding region capable of binding to human CD137 as defined herein.

In an even further aspect, the invention relates to an expression vector comprising nucleic acid constructs as defined herein above.

In another aspect, the invention relates to a nucleic acid encoding a binding agent according to any aspect or embodiment described herein or a polypeptide chain thereof. In another aspect, the invention relates to an expression vector comprising a nucleic acid.

An expression vector in the context of the present invention may be any suitable vector, including chromosomal, non-chromosomal, and synthetic nucleic acid vectors (a nucleic acid sequence comprising a suitable set of expression control elements). Examples of such vectors include derivatives of SV40, bacterial plasmids, phage DNA, baculovirus, yeast plasmids, vectors derived from combinations of plasmids and phage DNA, and viral nucleic acid (RNA or DNA) vectors. In one embodiment, a PD-L1 or a CD137 antibody-encoding nucleic acid is comprised in a naked DNA or RNA vector, including, for example, a linear expression element (as described in for instance Sykes and Johnston, Nat Biotech 17, 355-59 (1997)), a compacted nucleic acid vector (as described in for instance U.S. Pat. No. 6,077,835 and/or WO 00/70087), a plasmid vector such as pBR322, pUC 19/18, or pUC 118/119, a "midge" minimally-sized nucleic acid vector (as described in for instance Schakowski et al., Mol Ther 3, 793-800 (2001)), or as a precipitated nucleic acid vector construct, such as a $Ca_3(PO_4)_2$-precipitated construct (as described in for instance WO200046147, Benvenisty and Reshef, PNAS USA 83, 9551-55 (1986), Wigler et al., Cell 14, 725 (1978), and Coraro and Pearson, Somatic Cell Genetics 7, 603 (1981)). Such nucleic acid vectors and the usage thereof are well known in the art (see for instance U.S. Pat. Nos. 5,589,466 and 5,973,972).

In one embodiment, the vector is suitable for expression of the PD-L1 antibody and/or the CD137 antibody in a bacterial cell. Examples of such vectors include expression vectors such as BlueScript (Stratagene), pIN vectors (Van Heeke & Schuster, J Biol Chem 264, 5503-5509 (1989), pET vectors (Novagen, Madison Wis.) and the like).

An expression vector may also or alternatively be a vector suitable for expression in a yeast system. Any vector suitable for expression in a yeast system may be employed. Suitable vectors include, for example, vectors comprising constitutive or inducible promoters such as alpha factor, alcohol oxidase and PGH (reviewed in: F. Ausubel et al., ed. Current Protocols in Molecular Biology, Greene Publishing and Wiley InterScience New York (1987), and Grant et al., Methods in Enzymol 153, 516-544 (1987)).

An expression vector may also or alternatively be a vector suitable for expression in mammalian cells, e.g. a vector comprising glutamine synthetase as a selectable marker, such as the vectors described in Bebbington (1992) Biotechnology (NY) 10:169-175.

A nucleic acid and/or vector may also comprise a nucleic acid sequence encoding a secretion/localization sequence, which can target a polypeptide, such as a nascent polypeptide chain, to the periplasmic space or into cell culture media. Such sequences are known in the art, and include secretion leader or signal peptides.

The expression vector may comprise or be associated with any suitable promoter, enhancer, and other expression-facilitating elements. Examples of such elements include strong expression promoters (e.g., human CMV IE promoter/enhancer as well as RSV, SV40, SL3-3, MMTV, and HIV LTR promoters), effective poly (A) termination sequences, an origin of replication for plasmid product in *E. coli*, an antibiotic resistance gene as selectable marker, and/or a convenient cloning site (e.g., a polylinker). Nucleic acids may also comprise an inducible promoter as opposed to a constitutive promoter such as CMV IE.

In one embodiment, the PD-L1 and/or CD137 antibody-encoding expression vector may be positioned in and/or delivered to the host cell or host animal via a viral vector.

In an even further aspect, the invention relates to a host cell comprising one or more of the nucleic-acid constructs or the expression vector specified herein above.

Thus, the present invention also relates to a recombinant eukaryotic or prokaryotic host cell which produces an antibody of the present invention, such as a transfectoma.

Examples of host cells include yeast, bacterial, plant and mammalian cells, such as CHO, CHO—S, HEK, HEK293, HEK-293F, Expi293F, PER.C6 or NS0 cells or lymphocytic cells. A preferred host cell is a CHO-K1 cell.

In one embodiment of the invention, the cell is a mammalian cell, such as a Chinese hamster ovary cell.

For example, in one embodiment, the host cell may comprise a first and second nucleic acid construct stably integrated into the cellular genome. In another embodiment, the present invention provides a cell comprising a non-integrated nucleic acid, such as a plasmid, cosmid, phagemid, or linear expression element, which comprises a first and second nucleic acid construct as specified above.

In a further aspect, the invention relates to a hybridoma which produces a PD-L1 antibody as defined herein.

Fc Regions

In some embodiments of the invention, the binding agent according to the present invention comprises, in addition to the antigen-binding regions, an Fc region consisting of the Fc sequences of the two heavy chains.

The first and second Fc sequences may each be of any isotype, including, but not limited to, IgG1, IgG2, IgG3 and IgG4, and may comprise one or more mutations or modifications. In one embodiment, each of the first and second Fc sequences is of the IgG4 isotype or derived therefrom, optionally with one or more mutations or modifications. In another embodiment, each of the first and second Fc sequences is of the IgG1 isotype or derived therefrom, optionally with one or more mutations or modifications. In another embodiment, one of the Fc sequences is of the IgG1 isotype and the other of the IgG4 isotype, or is derived from such respective isotypes, optionally with one or more mutations or modifications.

In one embodiment of the invention, one or both Fc sequences are effector-function-deficient. For example, the Fc sequence(s) may be of an IgG4 isotype, or a non-IgG4 type, e.g. IgG1, IgG2 or IgG3, which has been mutated such that the ability to mediate effector functions, such as ADCC, has been reduced or even eliminated. Such mutations have e.g. been described in Dall'Acqua W F et al., J Immunol. 177(2):1129-1138 (2006) and Hezareh M, J Virol.; 75(24): 12161-12168 (2001). In another embodiment, one or both Fc sequences comprise an IgG1 wildtype sequence.

Antibodies according to the present invention may comprise modifications in the Fc region. When an antibody comprises such modifications, it may become an inert, or non-activating, antibody. The term "inertness", "inert" or "non-activating" as used herein, refers to an Fc region which is at least not able to bind any Fcγ receptors, induce Fc-mediated cross-linking of FcRs, or induce FcR-mediated cross-linking of target antigens via two Fc regions of individual antibodies, or is not able to bind C1q. The inertness of an Fc region of a humanized or chimeric CD137 or PD-L1 antibody is advantageously tested using the antibody in a monospecific format.

Several variants can be constructed to make the Fc region of an antibody inactive for interactions with Fcγ (gamma) receptors and C1q for therapeutic antibody development. Examples of such variants are described herein.

Thus, in one embodiment of the antibody of the invention, said antibody comprises a first and a second heavy chain, wherein one or both heavy chains are modified so that the antibody induces Fc-mediated effector function to a lesser extent relative to an antibody which is identical, except for comprising non-modified first and second heavy chains. Said Fc-mediated effector function may be measured by determining, by binding to Fcγ receptors, by binding to C1q, or by induction of Fc-mediated cross-linking of FcRs.

In another such embodiment, the heavy and light chain constant sequences have been modified so that binding of C1q to said antibody is reduced compared to an unmodified antibody by at least 70%, at least 80%, at least 90%, at least 95%, at least 97%, or 100%, wherein C1q binding is determined by ELISA.

Thus, amino acids in the Fc region that play a dominant role in the interactions with C1q and the Fcγ receptors may be modified.

Examples of amino acid positions that may be modified, e.g. in an IgG1 isotype antibody, include positions L234, L235 and P331. Combinations thereof, such as L234F/L235E/P331S, can cause a profound decrease in binding to human CD64, CD32, CD16 and C1q.

Hence, in one embodiment, the amino acid in at least one position corresponding to L234, L235 and P331, may be A, A and S, respectively (Xu et al., 2000, Cell Immunol. 200(1):16-26; Oganesyan et al., 2008, Acta Cryst. (D64): 700-4). Also, L234F and L235E amino acid substitutions can result in Fc regions with abrogated interactions with Fcγ receptors and C1q (Canfield et al., 1991, 3. Exp. Med. (173):1483-91; Duncan et al., 1988, Nature (332):738-40). Hence, in one embodiment, the amino acids in the positions corresponding to L234 and L235, may be F and E, respectively. A D265A amino acid substitution can decrease binding to all Fcγ receptors and prevent ADCC (Shields et al., 2001, 3. Biol. Chem. (276):6591-604). Hence, in one embodiment, the amino acid in the position corresponding to D265 may be A. Binding to C1q can be abrogated by mutating positions D270, K322, P329, and P331. Mutating these positions to either D270A or K322A or P329A or P331A can make the antibody deficient in CDC activity (Idusogie E E, et al., 2000, 3 Immunol. 164: 4178-84). Hence, in one embodiment, the amino acids in at least one position corresponding to D270, K322, P329 and P331, may be A, A, A, and A, respectively.

An alternative approach to minimize the interaction of the Fc region with Fcγ receptors and C1q is by removal of the glycosylation site of an antibody. Mutating position N297 to e.g. Q, A, or E removes a glycosylation site which is critical for IgG-Fc gamma Receptor interactions. Hence, in one embodiment, the amino acid in a position corresponding to N297 may be G, Q, A or E (Leabman et al., 2013, MAbs; 5(6):896-903). Another alternative approach to minimize interaction of the Fc region with Fcγ receptors may be obtained by the following mutations; P238A, A327Q, P329A or E233P/L234V/L235A/G236del (Shields et al., 2001, 3. Biol. Chem. (276):6591-604).

Alternatively, human IgG2 and IgG4 subclasses are considered naturally compromised in their interactions with C1q and Fc gamma Receptors although interactions with Fcγ receptors were reported (Parren et al., 1992, 3. Clin Invest. 90: 1537-1546; Bruhns et al., 2009, Blood 113: 3716-3725). Mutations abrogating these residual interactions can be made in both isotypes, resulting in reduction of unwanted side-effects associated with FcR binding. For IgG2, these include L234A and G237A, and for IgG4, L235E. Hence, in one embodiment, the amino acid in a position corresponding to L234 and G237 in a human IgG2 heavy chain, may be A and A, respectively. In one embodiment, the amino acid in a position corresponding to L235 in a human IgG4 heavy chain, may be E.

Other approaches to further minimize the interaction with Fcγ receptors and C1q in IgG2 antibodies include those described in WO2011066501 and Lightle, S., et al., 2010, Protein Science (19):753-62.

The hinge region of the antibody can also be of importance with respect to interactions with Fcγ receptors and complement (Brekke et al., 2006, 3 Immunol 177:1129-1138; Dall'Acqua W F, et al., 2006, 3 Immunol 177:1129-1138). Accordingly, mutations in or deletion of the hinge region can influence effector functions of an antibody.

Thus, in one embodiment, the antibody comprises a first and a second immunoglobulin heavy chain, wherein in at least one of said first and second immunoglobulin heavy chains one or more amino acids in the positions corresponding to positions L234, L235, D265, N297, and P331 in a human IgG1 heavy chain, are not L, L, D, N, and P, respectively.

In one embodiment, in both the first and second heavy chains one or more amino acids in the position corresponding to positions L234, L235, D265, N297, and P331 in a human IgG1 heavy chain, are not L, L, D, N, and P, respectively.

In one embodiment of the invention, in both said first and second heavy chains the amino acid in the position corresponding to position D265 in a human IgG1 heavy chain, is not D.

Thus, in one embodiment of the invention, in both said first and second heavy chains the amino acid in the position corresponding to position D265 in a human IgG1 heavy chain are selected from the group consisting of: A and E.

In a further embodiment of the invention, in at least one of said first and second heavy chains the amino acids in the positions corresponding to positions L234 and L235 in a human IgG1 heavy chain, are not L and L, respectively.

In a particular embodiment of the invention, in at least one of said first and second heavy chains the amino acids in the positions corresponding to positions L234 and L235 in a human IgG1 heavy chain, are F and E, respectively.

In one embodiment of the invention, in both said first and second heavy chains the amino acids in the positions corresponding to positions L234 and L235 in a human IgG1 heavy chain, are F and E, respectively.

In a particular embodiment of the invention, in at least one of said first and second heavy chains the amino acids in the positions corresponding to positions L234, L235, and D265 in a human IgG1 heavy chain, are F, E, and A, respectively.

In a particularly preferred embodiment of the invention, in both said first and second heavy chains the amino acids in the positions corresponding to positions L234, L235, and D265 in a human IgG1 heavy chain, are F, E, and A, respectively.

In a further particularly preferred embodiment of the invention, the binding agent is a bispecific antibody comprising a first and second heavy chain, wherein the positions corresponding to positions L234 and L235 in a human IgG1 heavy chain according to EU numbering of both the first heavy chain and the second heavy chain are F and E, respectively, and wherein (i) the position corresponding to F405 in a human IgG1 heavy chain according to EU numbering of the first heavy chain is L, and the position corresponding to K409 in a human IgG1 heavy chain according to EU numbering of the second heavy chain is R, or (ii) the position corresponding to K409 in a human IgG1 heavy chain according to EU numbering of the first heavy chain is R, and the position corresponding to F405 in a human IgG1 heavy chain according to EU numbering of the second heavy chain is L.

In a further particularly preferred embodiment of the invention, the binding agent is a bispecific antibody comprising a first and second heavy chain, wherein the positions corresponding to positions L234, L235, and D265 in a human IgG1 heavy chain according to EU numbering of both the first heavy chain and the second heavy chain are F, E, and A, respectively, and wherein (i) the position corresponding to F405 in a human IgG1 heavy chain according to EU numbering of the first heavy chain is L, and the position corresponding to K409 in a human IgG1 heavy chain according to EU numbering of the second heavy chain is R, or (ii) the position corresponding to K409 in a human IgG1 heavy chain according to EU numbering of the first heavy chain is R, and the position corresponding to F405 in a human IgG1 heavy chain according to EU numbering of the second heavy chain is L.

Antibody variants having the combination of three amino acid substitutions L234F, L235E and D265A and in addition the K409R or the F405L mutation are herein termed with the suffix "FEAR" or "FEAL", respectively.

In a preferred embodiment, the bispecific antibody of the invention comprises:
(i) a half-molecule antibody derived from IgG1-CD137-FEAR, and a half-molecule antibody derived from IgG1-PDL1-547-FEAR, or (ii) a half-molecule antibody derived from IgG1-CD137-FEAR, and a half-molecule antibody derived from and a half-molecule antibody derived from IgG1-PD-L1-547-FEAL.

In a further embodiment of the invention, one or both antibodies forming part of the bispecific antibody have been engineered to reduce or increase the binding to the neonatal Fc receptor (FcRn) in order to manipulate the serum half-life of the bispecific antibody. Techniques for increasing or reducing the serum half-life are well-known in the art. See for example Dall'Acqua et al. 2006, 3. Biol. Chem., 281: 23514-24; Hinton et al. 2006, J. Immunol., 176:346-56; and Zalevsky et al. 2010 Nat. Biotechnol., 28: 157-9.

Conjugates

In a further aspect, the present invention provides antibodies that are linked or conjugated to one or more therapeutic moieties, such as a cytokine, an immune-suppressant, an immune-stimulatory molecule and/or a radioisotope. Such conjugates are referred to herein as "immunoconjugates" or "drug conjugates". Immunoconjugates which include one or more cytotoxins are referred to as "immunotoxins".

In one embodiment, the first and/or second Fc sequence is conjugated to a drug or a prodrug or contains an acceptor group for the same. Such acceptor group may e.g. be an unnatural amino acid.

Compositions

In one aspect, the invention relates to a composition comprising a binding agent (such as a bispecific antibody), a nucleic acid, an expression vector, or a cell according to any one of the embodiments or aspects disclosed herein. In one embodiment of the invention, the composition is a pharmaceutical composition. In one embodiment of the invention the composition further comprises a pharmaceutical acceptable carrier and/or excipient.

In a further aspect, the invention relates to a pharmaceutical composition comprising a binding agent (such as a multispecific antibody, such as bispecific antibody), a nucleic acid, an expression vector, or a host cell according to any one of the embodiments disclosed herein and a pharmaceutically-acceptable carrier.

The pharmaceutical composition of the present invention may contain one binding agent (such as one multispecific, preferably a bispecific antibody) of the present invention or a combination of different binding agents (such as multispecific such as bispecific antibodies) of the present invention.

The pharmaceutical compositions may be formulated in accordance with conventional techniques such as those disclosed in Remington: The Science and Practice of Pharmacy, 19th Edition, Gennaro, Ed., Mack Publishing Co., Easton, Pa., 1995. A pharmaceutical composition of the present invention may e.g. include diluents, fillers, salts, buffers, detergents (e.g., a nonionic detergent, such as Tween-20 or Tween-80), stabilizers (e.g., sugars or protein-free amino acids), preservatives, tissue fixatives, solubilizers, and/or other materials suitable for inclusion in a pharmaceutical composition.

Pharmaceutically acceptable carriers include any and all suitable solvents, dispersion media, coatings, antibacterial and antifungal agents, isotonicity agents, antioxidants and absorption delaying agents, and the like that are physiologically compatible with a binding agent (e.g. a multispecific such as bispecific antibody), a nucleic acid, an expression vector, or a host cell of the present invention. Examples of suitable aqueous and nonaqueous carriers which may be employed in the pharmaceutical compositions of the present invention include water, saline, phosphate buffered saline, ethanol, dextrose, polyols (such as glycerol, propylene glycol, polyethylene glycol, and the like), and suitable mixtures thereof, vegetable oils, carboxymethyl cellulose colloidal solutions, tragacanth gum and injectable organic esters, such as ethyl oleate, and/or various buffers. Pharmaceutically acceptable carriers include sterile aqueous solutions or dispersions and sterile powders for the extemporaneous preparation of sterile injectable solutions or dispersion. Proper fluidity may be maintained, for example, using coating materials, such as lecithin, by the maintenance of the required particle size in the case of dispersions, and using surfactants.

Pharmaceutical compositions of the present invention may also comprise pharmaceutically acceptable antioxidants for instance (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole, butylated hydroxytoluene, lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Pharmaceutical compositions of the present invention may also comprise isotonicity agents, such as sugars, polyalcohols, such as mannitol, sorbitol, glycerol or sodium chloride in the compositions.

The pharmaceutical compositions of the present invention may also contain one or more adjuvants appropriate for the chosen route of administration such as preservatives, wetting agents, emulsifying agents, dispersing agents, preservatives or buffers, which may enhance the shelf life or effectiveness of the pharmaceutical composition. The binding agents (such as multispecific such as bispecific antibodies) of the present invention may be prepared with carriers that will protect the binding agent against rapid release, such as a controlled release formulation, including implants, transdermal patches, and microencapsulated delivery systems. Such carriers may include gelatin, glyceryl monostearate, glyceryl distearate, biodegradable, biocompatible polymers such as ethylene vinyl acetate, polyanhydrides, polyglycolic acid, collagen, polyorthoesters, and polylactic acid alone or with a wax, or other materials well known in the art. Methods for the preparation of such formulations are generally known to those skilled in the art.

Sterile injectable solutions may be prepared by incorporating the active compound in the required amount in an appropriate solvent with one or a combination of ingredients e.g. as enumerated above, as required, followed by sterilization microfiltration. Generally, dispersions are prepared by incorporating the active compound into a sterile vehicle that contains a basic dispersion medium and the required other ingredients e.g. from those enumerated above. In the case of sterile powders for the preparation of sterile injectable solutions, examples of methods of preparation are vacuum drying and freeze-drying (lyophilization) that yield a powder of the active ingredient plus any additional desired ingredient from a previously sterile-filtered solution thereof.

The actual dosage levels of the active ingredients in the pharmaceutical compositions may be varied so as to obtain an amount of the active ingredient which is effective to achieve the desired therapeutic response for a particular patient, composition, and mode of administration, without being toxic to the patient. The selected dosage level will depend upon a variety of pharmacokinetic factors including the activity of the particular compositions of the present invention employed, or the amide thereof, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts.

The pharmaceutical composition may be administered by any suitable route and mode. In one embodiment, a pharmaceutical composition of the present invention is administered parenterally. "Administered parenterally" as used herein means modes of administration other than enteral and topical administration, usually by injection, and include epidermal, intravenous, intramuscular, intraarterial, intrathecal, intracapsular, intraorbital, intracardiac, intradermal, intraperitoneal, intratendinous, transtracheal, subcutaneous, subcuticular, intraarticular, subcapsular, subarachnoid, intraspinal, intracranial, intrathoracic, epidural and intrasternal injection and infusion.

In one embodiment, that pharmaceutical composition is administered by intravenous or subcutaneous injection or infusion.

Uses

In one aspect, the invention relates to the binding agent according to any one of the embodiments disclosed herein, or the nucleic acid, expression vector, host cell or pharmaceutical composition as disclosed herein, for use as a medicament.

In a further aspect, the invention relates to the binding agent according to any one of the embodiments disclosed herein, or the nucleic acid, expression vector, host cell or pharmaceutical composition as disclosed herein for use in the treatment of a disease, such as cancer.

In a further aspect, the invention relates to a method of treatment of a disease comprising administering an effective amount of a binding agent according to any one of the embodiments disclosed herein, or the nucleic acid, expression vector, host cell or pharmaceutical composition as disclosed herein to a subject in need thereof.

In particular, the binding agents according to the invention may be useful in therapeutic settings in which specific targeting and T cell-mediated killing of cells that express PD-L1 is desired, and they may be more efficient compared to a regular anti-PD-L1 antibody in certain such indications and settings.

The binding agents of the invention also have additional utility in therapy and diagnosis of a variety of PD-L1-related diseases. For example, the binding agents (in particular antibodies) can be used to elicit in vivo or in vitro one or more of the following biological activities: to inhibit the growth of and/or differentiation of a cell expressing PD-L1; to kill a cell expressing PD-L1; to mediate phagocytosis or ADCC of a cell expressing PD-L1 in the presence of human effector cells; to mediate CDC of a cell expressing PD-L1 in the presence of complement; to mediate apoptosis of a cell expressing PD-L1; and/or to induce translocation into lipid rafts upon binding PD-L1. In another aspect the invention relates to a method of treatment of a disease comprising administering a binding agent, a nucleic acid, an expression vector, a cell, or a composition according to any embodiment disclosed herein to a subject in need thereof. In one embodiment of the invention the method relates to treatment of a disease, wherein the disease is cancer.

In one aspect, the invention relates to the binding agent according to any one of the embodiments disclosed herein, or the nucleic acid, expression vector, host cell or pharmaceutical composition as disclosed herein for use in the treatment of cancer.

In a further aspect, the invention relates to the binding agent according to any one of the embodiments disclosed herein, or the nucleic acid, expression vector, host cell or pharmaceutical composition as disclosed herein for use in the treatment of cancer disease characterized by the presence of solid tumors.

In one embodiment of the invention, the binding agent, nucleic acid, expression vector, cell, or composition as disclosed herein is for use in treatment of cancer or a method of treatment of cancer, wherein the cancer is characterized by the presence of solid tumors, or is selected form the group consisting of: melanoma, ovarian cancer, lung cancer, colon cancer, and head and neck cancer.

In a further aspect, the invention relates to the binding agent according to any one of the embodiments disclosed herein, or the nucleic acid, expression vector, host cell or pharmaceutical composition as disclosed herein for use in the treatment of cancer disease selected from the group consisting of: melanoma, ovarian cancer, lung cancer, colorectal cancer, head and neck cancer, gastric cancer, breast cancer, renal cancer, bladder cancer, esophageal cancer, pancreatic cancer, hepatic cancer, thymoma and thymic carcinoma, brain cancer, glioma, adrenocortical carcinoma, thyroid cancer, other skin cancers, sarcoma, multiple myeloma, leukemia, lymphoma, myelodysplastic syndromes, ovarian cancer, endometriosis cancer, prostate cancer, penile cancer, Hodgkin's lymphoma, non-Hodgkin's lymphoma, Merkel cell carcinoma and mesothelioma.

In a particular embodiment, the lung cancer is non-small-cell lung cancer (NSCLC).

In a further aspect, the invention relates to the use of a binding agent according to any one of the embodiments disclosed herein or the nucleic acid, expression vector, host cell or pharmaceutical composition as disclosed herein for the manufacture of a medicament, such as a medicament for the treatment of cancer, e.g. a cancer disease characterized by the presence of solid tumors or a cancer disease selected from the group consisting of: melanoma, ovarian cancer, lung cancer, colon cancer and head and neck cancer.

In one embodiment of the invention, the method or use according to any embodiment disclosed herein comprises combination with one or more further therapeutic agents, such as a chemotherapeutic agent.

In one aspect, the present invention relates to a method for producing a bispecific antibody according to any embodiment disclosed herein, comprising the steps of:
  a. culturing a host cell producing a first antibody comprising an antigen-binding region binding to human CD137 and optionally purifying said first antibody from the culture;
  b. culturing a host cell producing a second antibody comprising an antigen-binding region binding to human PD-L1 and optionally purifying said second antibody from the culture;
  c. incubating said first antibody together with said second antibody under reducing conditions sufficient to allow the cysteines in the hinge region to undergo disulfide-bond isomerization, and
  d. obtaining said CD137×PD-L1 bispecific antibody.

The present invention also relates to a method for inhibiting growth and/or proliferation of one or more tumor cells expressing PD-L1, and/or inducing killing and/or elimination of one or more tumor cells expressing PD-L1, comprising administration, to an individual in need thereof, of a binding agent (e.g. a bispecific antibody) of the present invention or a composition of the present invention.

The present invention also relates to a method for treating cancer, comprising
  a) selecting a subject suffering from a cancer comprising tumor cells expressing PD-L1, and
  b) administering to the subject the binding agent (e.g. a bispecific antibody) of the present invention or a pharmaceutical composition of the present invention.

Dosage regimens in the above methods of treatment and uses are adjusted to provide the optimum desired response (e.g., a therapeutic response). For example, a single bolus may be administered, several divided doses may be administered over time or the dose may be proportionally reduced or increased as indicated by the exigencies of the therapeutic situation. Parenteral compositions may be formulated in dosage unit form for ease of administration and uniformity of dosage.

The efficient dosages and the dosage regimens for the binding agent depend on the disease or condition to be treated and may be determined by the persons skilled in the art. An exemplary, non-limiting range for a therapeutically effective amount of a compound of the present invention is about 0.001-10 mg/kg, such as about 0.001-5 mg/kg, for example about 0.001-2 mg/kg, such as about 0.001-1 mg/kg, for instance about 0.001, about 0.01, about 0.1, about 1 or about 10 mg/kg. Another exemplary, non-limiting range for a therapeutically effective amount of a binding agent (e.g. a bispecific antibody) of the present invention is about 0.1-100 mg/kg, such as about 0.1-50 mg/kg, for example about 0.1-20 mg/kg, such as about 0.1-10 mg/kg, for instance about 0.5, about such as 0.3, about 1, about 3, about 5, or about 8 mg/kg.

A physician or veterinarian having ordinary skill in the art may readily determine and prescribe the effective amount of the pharmaceutical composition required. For example, the physician or veterinarian could start doses of the binding agent (e.g. a bispecific antibody) employed in the pharmaceutical composition at levels lower than that required to achieve the desired therapeutic effect and gradually increase the dosage until the desired effect is achieved. In general, a suitable daily dose of a binding agent (e.g. a bispecific antibody) of the present invention will be that amount of the compound which is the lowest dose effective to produce a therapeutic effect. Administration may e.g. be parenteral, such as intravenous, intramuscular or subcutaneous. In one embodiment, the binding agents (e.g. bispecific antibodies) may be administered by infusion in a weekly dosage of calculated by mg/m$^2$. Such dosages can, for example, be based on the mg/kg dosages provided above according to the following: dose (mg/kg)×70:1.8. Such administration may be repeated, e.g., 1 to 8 times, such as 3 to 5 times. The administration may be performed by continuous infusion over a period of from 2 to 24 hours, such as from 2 to 12 hours. In one embodiment, the binding agents (e.g. bispecific antibodies) may be administered by slow continuous infusion over a long period, such as more than 24 hours, to reduce toxic side effects.

In one embodiment, the binding agent may be administered in a weekly dosage of calculated as a fixed dose for up to 8 times, such as from 4 to 6 times when given once a week. Such regimen may be repeated one or more times as necessary, for example, after 6 months or 12 months. Such fixed dosages can, for example, be based on the mg/kg dosages provided above, with a body weight estimate of 70 kg. The dosage may be determined or adjusted by measuring the amount of binding agent (e.g. bispecific antibody) of the present invention in the blood upon administration by for instance taking out a biological sample and using anti-idiotypic antibodies which target the PD-L1 antigen antigen-binding region of the antibodies of the present invention.

In one embodiment, the binding agent may be administered as maintenance therapy, such as, e.g., once a week for a period of 6 months or more.

A binding agent may also be administered prophylactically to reduce the risk of developing cancer, delay the onset of the occurrence of an event in cancer progression, and/or reduce the risk of recurrence when a cancer is in remission.

The binding agents of the invention may also be administered in combination therapy, i.e., combined with other therapeutic agents relevant for the disease or condition to be treated. Accordingly, in one embodiment, the binding agent (e.g. bispecific antibody)-containing medicament is for combination with one or more further therapeutic agents, such as a cytotoxic, chemotherapeutic or anti-angiogenic agent.

In one aspect, the invention relates to an anti-idiotypic antibody which binds to the first and/or second antigen-binding region as defined in any one of the embodiments disclosed herein.

In a further aspect, the invention relates to an anti-idiotypic antibody which binds to the CD137-binding region as defined in any one of the embodiments disclosed herein. In a further aspect, the invention relates to an anti-idiotypic antibody which binds to the PD-L1-binding region as defined in any one of the embodiments disclosed herein.

The present invention is further illustrated by the following examples, which should not be construed as limiting the scope of the invention.

Sequences

TABLE 1

| SEQ ID | NAME | SEQUENCE |
|---|---|---|
| 1 | VH_b12 | QVQLVQSGAEVKKPGASVKVSCQAS<u>GYRFSNFV</u>IHWVRQAPGQ RFEWMGW<u>INPYNGNK</u>EFSAKFQDRVTFTADTSANTAYMELRSL RSADTAVYYC<u>ARVGPYSWDDSPQDNYYMDV</u>WGKGTTVIVSS |
| 2 | VH_b12-CDR1 | GYRFSNFV |
| 3 | VH_b12-CDR2 | INPYNGNK |
| 4 | VH_b12-CDR3 | ARVGPYSWDDSPQDNYYMDV |
| 5 | VL_b12 | EIVLTQSPGTLSLSPGERATFSCRSS<u>HSIRSRR</u>VAWYQHKPGQA PRLVIH<u>GVS</u>NRASGISDRFSGSGSGTDFTLTITRVEPEDFALYYC <u>QVYGASSYT</u>FGQGTKLERK |
| 6 | VL_b12-CDR1 VL_b12-CDR2 | HSIRSRR GVS |
| 7 | VL_b12-CDR3 | QVYGASSYT |
| 8 | VH_CD137-009 | QSLEESGGRLVTPGTPLTLTCTVS<u>GFSLNDYW</u>MSWVRQAPGKG LEWIGY<u>IDVGGSL</u>YYASWAKGRFTISRTSTTVDLKMTSLTTEDTA TYFC<u>ARGGLTYGFDL</u>WGPGTLVTVSS |
| 9 | VH_CD137-009_CDR1 | GFSLNDYW |
| 10 | VH_CD137-009_CDR2 | IDVGGSL |
| 11 | VH_CD137-009_CDR3 | ARGGLTYGFDL |
| 12 | VL_CD137-009 | DIVMTQTPASVSEPVGGTVTINCQAS<u>EDISSY</u>LAWYQQKPGQRP KRLIY<u>GAS</u>DLASGVPSRFSASGSGTEYALTISDLESADAATYYC<u>H YYATISGLGVA</u>FGGGTEVVVK |
| 13 | VL_CD137-009_CDR1 VL_CD137-009_CDR2 | EDISSY GAS |
| 14 | VL_CD137-009_CDR3 | HYYATISGLGVA |
| 15 | VH_CD137-009-H7 | EVQLVESGGGLVQPGRSLRLSCTAS<u>GFSLNDYW</u>MSWVRQAPG KGLEWVGY<u>IDVGGSL</u>YYAASVKGRFTISRDDSKSIAYLQMNSLK TEDTAVYYC<u>ARGGLTYGFDL</u>WGQGTLVTVSS |
| 9 | VH_CD137-009-H7_CDR1 | GFSLNDYW |
| 10 | VH_CD137-009-H7_CDR2 | IDVGGSL |
| 11 | VH_CD137-009-H7_CDR3 | ARGGLTYGFDL |
| 16 | VL_CD137-009-L2 | DIVMTQSPSSLSASVGDRVTITCQAS<u>EDISSY</u>LAWYQQKPGKAP KRLIY<u>GAS</u>DLASGVPSRFSASGSGTDYTFTISSLQPEDIATYYC<u>H YYATISGLGVA</u>FGGGTKVEIK |

TABLE 1-continued

| SEQ ID | NAME | SEQUENCE |
|---|---|---|
| 13 | VL_CD137-009-L2_CDR1 | EDISSY |
|  | VL_CD137-009-L2_CDR2 | GAS |
| 14 | VL_CD137-009-L2_CDR3 | HYYATISGLGVA |
| 17 | VH-PD-L1-547 | EVQLLEPGGGLVQPGGSLRLSCEAS<u>GSTFSTYA</u>MSWVRQAPGK GLEWVSG<u>FSGSGGFT</u>FYADSVRGRFTISRDSSKNTLFLQMSSLR AEDTAVYYC<u>AIPARGYNYGSFQH</u>WGQGTLVTVSS |
| 18 | VH-PD-L1-547-CDR1 | GSTFSTYA |
| 19 | VH-PD-L1-547-CDR2 | FSGSGGFT |
| 20 | VH-PD-L1-547-CDR3 | AIPARGYNYGSFQH |
| 21 | VL-PD-L1-547 | SYVLTQPPSVSVAPGQTARITCGG<u>NNIGSKS</u>VHWYQQKPGQAP VLVVY<u>DDN</u>DRPSGLPERFSGSNSGNTATLTISRVEAGDEADYYC <u>QVWDSSSDHVV</u>FGGGTKLTVL |
| 22 | VL-PD-L1-547-CDR1 VL-PD-L1-547-CDR2 | NIGSKS DDN |
| 23 | VL-PD-L1-547-CDR3 | QVWDSSSDHVV |
| 24 | IgG1-FEAR-Fc | ASTKGPSVFPLAPSSKSTSGGTAALGCLVKDYFPEPVTVSWNSG ALTSGVHTFPAVLQSSGLYSLSSVVTVPSSSLGTQTYICNVNHKP SNTKVDKRVEPKSCDKTHTCPPCPAPEFEGGPSVFLFPPKPKDTL MISRTPEVTCVVVAVSHEDPEVKFNWYVDGVEVHNAKTKPREE QYNSTYRVVSVLTVLHQDWLNGKEYKCKVSNKALPAPIEKTISK AKGQPREPQVYTLPPSREEMTKNQVSLTCLVKGFYPSDIAVEWE SNGQPENNYKTTPPVLDSDGSFFLYSRLTVDKSRWQQGNVFSC SVMHEALHNHYTQKSLSLSPGK |
| 25 | IgG1-FEAL-Fc | ASTKGPSVFPLAPSSKSTSGGTAALGCLVKDYFPEPVTVSWNSG ALTSGVHTFPAVLQSSGLYSLSSVVTVPSSSLGTQTYICNVNHKP SNTKVDKRVEPKSCDKTHTCPPCPAPEFEGGPSVFLFPPKPKDTL MISRTPEVTCVVVAVSHEDPEVKFNWYVDGVEVHNAKTKPREE QYNSTYRVVSVLTVLHQDWLNGKEYKCKVSNKALPAPIEKTISK AKGQPREPQVYTLPPSREEMTKNQVSLTCLVKGFYPSDIAVEWE SNGQPENNYKTTPPVLDSDGSFLLYSKLTVDKSRWQQGNVFSC SVMHEALHNHYTQKSLSLSPGK |
| 26 | Kappa-C | RTVAAPSVFIFPPSDEQLKSGTASVVCLLNNFYPREAKVQWKVD NALQSGNSQESVTEQDSKDSTYSLSSTLTLSKADYEKHKVYACE VTHQGLSSPVTKSFNRGEC |
| 27 | Lambda-C | GQPKAAPSVTLFPPSSEELQANKATLVCLISDFYPGAVTVAWKAD SSPVKAGVETTTPSKQSNNKYAASSYLSLTPEQWKSHRSYSCQV THEGSTVEKTVAPTECS |
| 28 | Human PD-L1 | MRIFAVFIFMTYWHLLNAFTVTVPKDLYVVEYGSNMTIECKFPVE KQLDLAALIVYWEMEDKNIIQFVHGEEDLKVQHSSYRQRARLLK DQLSLGNAALQITDVKLQDAGVYRCMISYGGADYKRITVKVNAP YNKINQRILVVDPVTSEHELTCQAEGYPKAEVIWTSSDHQVLSG KTTTTNSKREEKLFNVTSTLRINTTTNEIFYCTFRRLDPEENHTAE LVIPELPLAHPPNERTHLVILGAILLCLGVALTFIFRLRKGRMMDVK KCGIQDTNSKKQSDTHLEET |
| 29 | Cynomolgus monkey PD-L1 | MRIFAVFIFTIYWHLLNAFTVTVPKDLYVVEYGSNMTIECKFPVEK QLDLTSLIVYWEMEDKNIIQFVHGEEDLKVQHSNYRQRAQLLKD QLSLGNAALRITDVKLQDAGVYRCMISYGGADYKRITVKVNAPY NKINQRILVVDPVTSEHELTCQAEGYPKAEVIWTSSDHQVLSGK TTTTNSKREEKLLNVTSTLRINTTANEIFYCIFRRLDPEENHTAELV IPELPLALPPNERTHLVILGAIFLLLGVALTFIFYLRKGRMMDMKKC GIRVTNSKKQRDTQLEET |
| 30 | Human CD137 | MGNSCYNIVATLLLVLNFERTRSLQDPCSNCPAGTFCDNNRNQI CSPCPPNSFSSAGGQRTCDICRQCKGVFRTRKECSSTSNAECDC TPGFHCLGAGCSMCEQDCKQGQELTKKGCKDCCFGTFNDQKR GICRPWTNCSLDGKSVLVNGTKERDVVCGPSPADLSPGASSVTP PAPAREPGHSPQIISFFLALTSTALLFLLFFLTLRFSVVKRGRKKLL YIFKQPFMRPVQTTQEEDGCSCRFPEEEEGGCEL |

TABLE 1-continued

| SEQ ID | NAME | SEQUENCE |
|---|---|---|
| 31 | Cynomolgus monkey CD137 | MGNSCYNIVATLLLVLNFERTRSLQDLCSNCPAGTFCDNNRSQI CSPCPPNSFSSAGGQRTCDICRQCKGVFKTRKECSSTSNAECDC ISGYHCLGAECSMCEQDCKQGQELTKKGCKDCCFGTFNDQKRG ICRPWTNCSLDGKSVLVNGTKERDVVCGPSPADLSPGASSATPK APAREPGHSPQIIFFLALTSTVVLFLLFFLVLRFSVVKRSRKKLLYIF KQPFMRPVQTTQEEDGCSCRFPEEEEGGCEL |
| 32 | Human CD137 shuffle 6 (amino acids 24-47 of wild boar CD137) | MGNSCYNIVATLLLVLNFERTRSVPDPCSNCSAGTFCGKNIQELC MPCPPNSFSSAGGQRTCDICRQCKGVFRTRKECSSTSNAECDC TPGFHCLGAGCSMCEQDCKQGQELTKKGCKDCCFGTFNDQKR GICRPWTNCSLDGKSVLVNGTKERDVVCGPSPADLSPGASSVTP PAPAREPGHSPQIISFFLALTSTALLGGCEL |
| 33 | Human CD137 shuffle 5 (amino acids 48-88 of African elephant CD137) | MGNSCYNIVATLLLVLNFERTRSLQDPCSNCPAGTFCDNNRNQI CSPCPLNSFSSTGGQMNCDMCRKCEGVFKTKRACSPTRDAECE CTPGFHCLGAGCSMCEQDCKQGQELTKKGCKDCCFGTFNDQK RGICRPWTNCSLDGKSVLVNGTKERDVVCGPSPADLSPGASSV TPPAPAREPGHSPQIISFFLALTSTALLFLLFFLTLRFSVVKRGRKK LLYIFKQPFMRPVQTTQEEDGCSCRFPEEEEGGCEL |
| 34 | Human CD137 shuffle 4 (amino acids 89-114 of wild boar CD137) | MGNSCYNIVATLLLVLNFERTRSLQDPCSNCPAGTFCDNNRNQI CSPCPPNSFSSAGGQRTCDICRQCKGVFRTRKECSSTSNAECDC VPGFRCLGAGCAMCEEYCQQGQELTQKGCKDCCFGTFNDQKR GICRPWTNCSLDGKSVLVNGTKERDVVCGPSPADLSPGASSVTP PAPAREPGHSPQIISFFLALTSTALLFLLFFLTLRFSVVKRGRKKLL YIFKQPFMRPVQTTQEEDGCSCRFPEEEEGGCEL |
| 35 | Human CD137 shuffle 3 (amino acids 115-138 of wild boar CD137) | MGNSCYNIVATLLLVLNFERTRSLQDPCSNCPAGTFCDNNRNQI CSPCPPNSFSSAGGQRTCDICRQCKGVFRTRKECSSTSNAECDC TPGFHCLGAGCSMCEQDCKQGQELTKEGCKDCSFGTFNDEEHG VCRPWTDCSLDGKSVLVNGTKERDVVCGPSPADLSPGASSVTP PAPAREPGHSPQIISFFLALTSTALLFLLFFLTLRFSVVKRGRKKLL YIFKQPFMRPVQTTQEEDGCSCRFPEEEEGGCEL |
| 36 | Human CD137 shuffle 2 (amino acids 139-161 of wild boar CD137) | MGNSCYNIVATLLLVLNFERTRSLQDPCSNCPAGTFCDNNRNQI CSPCPPNSFSSAGGQRTCDICRQCKGVFRTRKECSSTSNAECDC TPGFHCLGAGCSMCEQDCKQGQELTKKGCKDCCFGTFNDQKR GICRPWTNCSLAGKPVLMNGTKARDVVCGPRPADLSPGASSVT PPAPAREPGHSPQIISFFLALTSTALLFLLFFLTLRFSVVKRGRKKL LYIFKQPFMRPVQTTQEEDGCSCRFPEEEEGGCEL |
| 37 | Human CD137 shuffle 1 (amino acids 162-186 of wild boarCD137) | MGNSCYNIVATLLLVLNFERTRSLQDPCSNCPAGTFCDNNRNQI CSPCPPNSFSSAGGQRTCDICRQCKGVFRTRKECSSTSNAECDC TPGFHCLGAGCSMCEQDCKQGQELTKKGCKDCCFGTFNDQKR GICRPWTNCSLDGKSVLVNGTKERDVVCGPSPTDFSPGTPSSTTM PVPGGEPGHTSHIISFFLALTSTALLFLLFFLTLRFSVVKRGRKKLL YIFKQPFMRPVQTTQEEDGCSCRFPEEEE GGCEL |
| 38 | Wild Boar CD137 | MGNGYYNIVATVLLVMNFERTRSVPDPCSNCSAGTFCGKNIQEL CMPCPSNSFSSTSGQKACNVCRKCEGVFRTKKECSSTSNAVCE CVPGFRCLGAGCAMCEEYCQQGQELTQEGCKDCSFGTFNDEEH GVCRPWTDCSLAGKPVLMNGTKARDVVCGPRPTDFSPGTPSTT MPVPGGEPGHTSHVIIFFLALMSTAVFVLVSYLALRFSVVQQGRK KLLYIVKQPFLKPAQTVQEEDACSCRFPEEEGECEL |
| 39 | African Elephant CD137 | MGNGYYNMVATVLLVMNFERTGAVQDSCRDCLAGTYCVKNESQ ICSPCPLNSFSSTGGQMNCDMCRKCEGVFKTKRACSPTRDAECE CVSGFHCLGAGCTMCQQDCKQGQELTKEGCKDCCLGTFNDQK NGICRPWTNCSLEGKSVLANGTKKRDVVCGPPAADSFPDTSSVT VPAPERKPDHHPQIITFFLALISAALLFLVFFLVVRFSVAKWGRKK LLYIFKQPPIKPVQTAQEEDGCSCRFPEEEEGDCEL |
| 40 | Human CD137 amino acids 48-88 | CPPNSFSSAGGQRTCDICRQCKGVFRTRKECSSTSNAECDC |
| 41 | Human CD137 (mature protein) | LQDPCSNCPAGTFCDNNRNQICSPCPPNSFSSAGGQRTCDICR QCKGVFRTRKECSSTSNAECDCTPGFHCLGAGCSMCEQDCKQG QELTKKGCKDCCFGTFNDQKRGICRPWTNCSLDGKSVLVNGTK ERDVVCGPSPADLSPGASSVTPPAPAREPGHSPQIISFFLALTSTA LLFLLFFLTLRFSVVKRGRKKLLYIFKQPFMRPVQTTQEEDGCSCR FPEEEEGGCEL |
| 42 | VH-CD137-MOR7480-FEAR | EVQLVQSGAEVKKPGESLRISCKGSGYSFSTYWISWVRQMPGK GLEWMGKIYPGDSYTNYSPSFQGQVTISADKSISTAYLQWSSLK ASDTAMYYCARGYGIFDYWGQGTLVTVSS |

TABLE 1-continued

| SEQ ID | NAME | SEQUENCE |
|---|---|---|
| 43 | VH-CD137-MOR7480-FEAR_CDR1 | GYSFSTYW |
| 44 | VH-CD137-MOR7480-FEAR_CDR2 | IYPGDSYT |
| 45 | VH-CD137-MOR7480-FEAR_CDR3 | ARGYGIFDY |
| 46 | VL-CD137-MOR7480 (Lambda) | SYELTQPPSVSVSPGQTASITCSGDNIGDQYAHWYQQKPGQSP VLVIYQDKNRPSGIPERFSGSNSGNTATLTISGTQAMDEADYYC ATYTGFGSLAVFGGGTKLTVL |
| 47 | VL-CD137-MOR7480_CDR1 | NIGDQY |
|  | VL-CD137-MOR7480_CDR2 | QDK |
| 48 | VL-CD137-MOR7480_CDR3 | ATYTGFGSLAV |
| 49 | VH-CD137-005-FEAR | QSVEESGGRLVTPGTPLTLTCTASGFTISDFHVTWVRQAPGKGL EWIGTIITSASTTAYATWARGRFTISKSSTTVNLKIVSPTTEDTAT YFCARSTYTDTSGYYFDFWGQGTLVTVSS |
| 50 | VH-CD137-005-FEAR_CDR1 | GFTISDFH |
| 51 | VH-CD137-005-FEAR_CDR2 | IITSASTT |
| 52 | VH-CD137-005-FEAR_CDR3 | ARSTYTDTSGYYFDF |
| 53 | VL-CD137-005 (Kappa) | AQVLTQTASPVSAAVGGTVIINCQSSQSIYNGNRLSWYQQKPG QPPKLLIYSASTLASGVSSRFKGSGSGTQFTLAISDVQSDDAATY YCLGSYDCDSADCFAFGGGTEVVVE |
| 54 | VL-CD137-005_CDR1 | QSIYNGNR |
|  | VL-CD137-005_CDR2 | SAS |
| 55 | VL-CD137-005_CDR3 | LGSYDCDSADCFA |
| 56 | Recombinant human interleukin analog (Proleukin ® (aldesleukin)) | MYRMQLLSCIALSLALVTNSAPTSSSTKKTQLQLEHLLLDLQMIL NGINNYKNPKLTRMLTFKFYMPKKATELKHLQCLEEELKPLEEVLN LAQSKNFHLRPRDLISNINVIVLELKGSETTFMSEYADETATIVEF LNRWITFCQSIISTLT |
| 57 | MPDL3280A VH | EVQLVESGGGLVQPGGSLRLSCAASGFTFSDSWIHWYRQAPGK GLEWYAWISPYGGSTYYADSVKGRFTISADTSKNTAYLQMNSLR AEDTAVYYCARRHWPGGFDYWGQGTLVTVSS |
| 58 | MPDL3280A VL | DIQMTQSPSSLSASVGDRVTITCRASQDVSTAVAWYQQKPGKA PKLLIYSASFLYSGVPSRFSGSGSGTDFTLTISSLQPEDFATYYCQ QYLYHPATFGQGTKVEIK |

EXAMPLES

Example 1: Generation of CD137 Antibody

The antibodies CD137-005 and CD137-009 were generated as described in example 1 of WO2016/110584. In short, rabbits were immunized with a mixture of proteins containing a human CD137-Fc fusion protein. Single B cells from blood were sorted and screened for production of CD137 specific antibody by ELISA and flow cytometry. From screening-positive B cells, RNA was extracted and sequencing was performed. The variable regions of heavy and light chain were gene synthesized and cloned into a human IgG1 kappa expression vector or human IgG1 lambda expression vector including a human IgG1 heavy chain containing the following amino acid mutations: L234F, L235E, D265A and F405L (FEAL) or F405L (FEAL) wherein the amino acid position number is according to EU numbering (correspond to SEQ ID NO: 25). The variable region sequences of the chimeric CD137 antibody (CD137-009) are shown in the Sequence Listing SEQ ID NO: 8 and SEQ ID NO: 12 herein.

Example 2: Humanization of the Rabbit (Chimeric) CD137 Antibody

Humanized antibody sequences from the rabbit anti-CD137-009 were generated at Antitope (Cambridge, UK). Humanized antibody sequences were generated using germline humanization (CDR-grafting) technology. Humanized V region genes were designed based on human germline sequences with closest homology to the VH and Vκ amino acid sequences of the rabbit antibody. A series of seven VH and three Vκ (VL) germline humanized V-region genes were designed. Structural models of the non-human parental antibody V regions were produced using Swiss PDB and analyzed in order to identify amino acids in the V region frameworks that may be important for the binding properties of the antibody. These amino acids were noted for incorporation into one or more variant CDR-grafted antibodies. The germline sequences used as the basis for the humanized designs are shown in Table 2.

TABLE 2

Closest matching human germline V segment and J segment sequences.

| | Heavy chain | | Light chain (κ) | |
| --- | --- | --- | --- | --- |
| Antibody | Human V region germline segment | Human J region germline segment | Human V region germline segment | Human J region germline segment |
| Rabbit anti-CD137-009 | hIGHV3-49*04 | hIGHJ4 | hIGKV1-33*01 | IGKJ4 |

Variant sequences with the lowest incidence of potential T cell epitopes were then selected using Antitope's proprietary in silico technologies, iTope™ and TCED™ (T Cell Epitope Database) (Perry, L. C. A, Jones, T. D. and Baker, M. P. New Approaches to Prediction of Immune Responses to Therapeutic Proteins during Preclinical Development (2008). Drugs in R&D 9 (6): 385-396; 20 Bryson, C. J., Jones, T. D. and Baker, M. P. Prediction of Immunogenicity of Therapeutic Proteins (2010). Biodrugs 24 (1):1-8). Finally, the nucleotide sequences of the designed variants have been codon-optimized.

The variable region sequences of the humanized CD137 antibody (CD137-009-HC7LC2) are shown in the Sequence Listing SEQ ID NO: 15 and SEQ ID NO: 16 herein.

Example 3: DNA Shuffling Between Wild Boar CD137 or Elephant CD137 and Human CD137 to Determine Domains Important for Binding of CD137 Antibody To determine domains important for binding of the CD137 antibody to human CD137, DNA shuffling was performed between human and wild boar CD137 (*Sus scrofa*; XP_005665023) or between human and African elephant CD137 (*Loxodonta africana*; XP_003413533). Shuffle constructs were prepared from DNA encoding human CD137, by replacing human domains with wild boar (shuffle construct 1-4, 6) or elephant (shuffle construct 5) domains. The amino acid sequence of the shuffle constructs are show in table 1.

If a domain in human CD137 is important for binding of an anti-CD137 antibody, binding will be lost upon replacement of that domain with the wild boar or African elephant domain. Homology between human and wild boar and between human and African elephant CD137 is 70.2 and 74.5%, respectively. Requirement for the selection of these two species was that the domain of interest in African elephant and wild boar was sufficiently different compared to human, resulting in loss of binding, while remaining critical structural interactions which is necessary to minimize the risk of misfolding or loss of expression. FIG. 1 shows sequence alignments of human, wild boar and African elephant CD137. FIG. 2 shows the constructs for human CD137 containing wild boar CD137 or African elephant CD137 domains, as indicated.

$3\times10^6$ HEK293T-17 cells were seeded in T75 culture flasks (Greiner Bio-One, cat. no. 658175) in 20 mL RPMI 1640 GlutaMAX medium containing 10% FCS (Biochrom, cat. no. S 0115). After O/N incubation, cells were transiently transduced with expression vectors encoding the shuffle constructs or the wild boar, African elephant or human CD137 downstream of a constitutively active human elongation factor-1 alpha (EF-1 alpha) promotor using TransIT®-LT1 Transfection Reagent, Mirus Bio (VWR International, cat. no. 731-0029), according to the manufacturer's instructions. The next day, cells were harvested using 1.5 mL Accutase (Sigma Aldrich, cat. no. A6964) (incubation at 37° C. for 5 min.) and flow cytometry was performed, essentially as described supra, to measure surface expression of the shuffle constructs and the human, African elephant and wild boar CD137 and to measure binding of the antibody clones to the different shuffle constructs. To measure cell surface expression of the constructs, transduced cells were incubated with 1 μg/mL goat polyclonal anti-human CD137 (R&D Systems, cat. no. AF838) in FACS buffer (4° C., 20 min.), followed by incubation with APC-labeled anti-goat IgG (H+L) (R&D Systems, cat. no. F0108) (4° C., 20 min.). Binding of the different CD137 antibody clones to cells expressing the shuffle constructs was measured by incubation of the transduced cells with 1 μg/mL of the antibody clones, followed by APC-labeled AffiniPure $F(ab')_2$ Fragment (1:50 final dilution; Jackson, cat. no. 109-136-127).

All CD137 shuffle constructs, as well as human, African elephant and wild boar CD137, were expressed on the cell surface with similar expression levels (FIG. 3).

FIG. 4 shows that CD137-009 showed loss of binding to African elephant and wild boar CD137. CD137-009 also showed loss of binding to shuffle construct 5, as compared to binding to human CD137.

Example 4: Generation of PD-L1 Antibody

Immunization and hybridoma generation was performed at Aldevron GmbH (Freiburg, Germany). A cDNA encoding amino acid 19-238 of human PD-L1 was cloned into Aldevron proprietary expression plasmids. Antibody PD-L1-547 was generated by immunization of OmniRat animals (transgenic rats expressing a diversified repertoire of antibodies with fully human idiotypes; Ligand Pharmaceuticals Inc., San Diego, USA) using intradermal application of human PD-L1 cDNA-coated gold-particles using a hand-held device for particle-bombardment ("gene gun"). Serum samples were collected after a series of immunizations and tested in flow cytometry on HEK cells transiently transfected with the aforementioned expression plasmids to express human PD-L1. Antibody-producing cells were isolated and fused with mouse myeloma cells (Ag8) according to standard procedures. RNA from hybridomas producing PD-L1 specific antibody was extracted and sequencing was performed. The variable regions of heavy and light chain (SEQ ID NO: 17 and 21) were gene synthesized and cloned into a human IgG1 lambda expression vector including a human IgG1 heavy chain containing the following amino acid mutations: L234F, L235E, D265A and K409R (FEAR)

wherein the amino acid position number is according to EU numbering (correspond to SEQ ID NOs:24).

Example 5: Generation of Bispecific Antibodies by 2-MEA-Induced Fab-Arm Exchange Bispecific IgG1 antibodies were generated by Fab-arm-exchange under controlled reducing conditions. The basis for this method is the use of complementary CH3 domains, which promote the formation of heterodimers under specific assay conditions as described in WO2011/131746. The F405L and K409R (EU numbering) mutations were introduced into the relevant antibodies to create antibody pairs with complementary CH3 domains.

To generate bispecific antibodies, the two parental complementary antibodies, each antibody at a final concentration of 0.5 mg/mL, were incubated with 75 mM 2-mercaptoethylamine-HCl (2-MEA) in a total volume of 100 µL PBS at 31° C. for 5 hours. The reduction reaction was stopped by removing the reducing agent 2-MEA using spin columns (Microcon centrifugal filters, 30 k, Millipore) according to the manufacturer's protocol. Bispecific antibodies were generated by combining the following antibodies from Example 1 and 4:

CD137-009-FEAL antibody combined with the PD-L1-547-FEAR antibody

PD-L1-547-FEAL antibody combined with the CD137-009-FEAR

PD-L1-547-FEAL antibody combined with CD137-009-HC7LC2-FEAR antibody, b12-FEAL antibody combined with the PD-L1-547-FEAR antibody, with CD137-009-FEAR or with CD137-009-HC7LC2-FEAR antibody, using as the first arm the antibody b12 which is a gp120 specific antibody (Barbas, C F. J Mol Biol. 1993 Apr. 5; 230(3):812-23)

PD-L1-547-FEAL or CD137-009-FEAL with b12-FEAR antibody.

Example 6: Effect of PD-L1 Antibody on the PD-1/PD-L1 Interaction

The effect of monovalent PD-L1 antibody b12-FEAL× PD-L1-547-FEAR on the interaction of PD-1 and PD-L1 was determined in a PD-1/PD-L1 inhibition bioassay as developed by Promega (Madison, USA). This is a bioluminescent cell-based assay consisting of two genetically engineered cell lines: PD-1 effector cells, which are Jurkat T cells expressing human PD-1 and a luciferase reporter driven by an NFAT response element (NFAT-RE), and PD-L1 aAPC/CHO-K1 cells, which are CHO-K1 cells expressing human PD-L1 and an engineered cell surface protein designed to activate cognate TCRs in an antigen-independent manner. When the two cell types are co-cultured, the PD-1/PD-L1 interaction inhibits TCR signaling and NFAT-RE-mediated luminescence. Addition of an antibody that blocks the PD-1/PD-L1 interaction releases the inhibitory signal and results in TCR activation and NFAT-RE-mediated luminescence.

Figure 5:
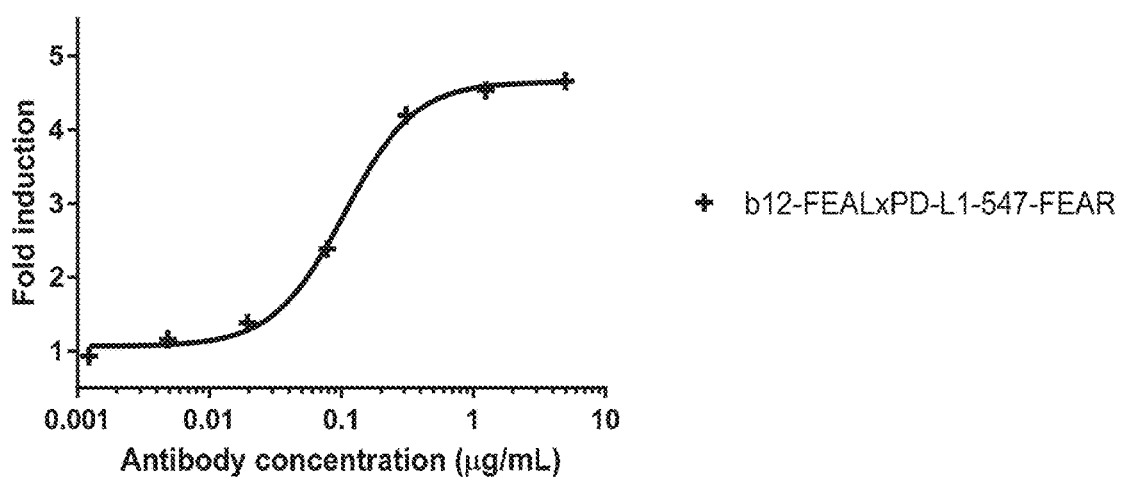
FIG. 5: Effect of monovalent antibody b12-FEAL×PD-L1-547-FEAR on the PD-1/PD-L1 interaction. The effect of b12-FEAL×PD-L1-547-FEAR was determined in a PD-1/PD-L1 inhibition bioassay. Data shown are fold induction relative to control (without antibody added), for one representative experiment.

PD-L1 aAPC/CHO-K1 cells (Promega, cat. no. J109A) were thawed according to the manufacturer's protocol, resuspended Ham's F12 medium (Promega, cat. no. J123A) containing 10% Fetal Bovine Serum (FBS; Promega, cat. no. J121A), and plated in 96 well flat bottom culture plates (CulturPlate-96, Perkin Elmer, cat. no. 6005680). Plates were incubated for 16 hours at 37° C., 5% $CO_2$. Supernatant was removed and serial dilutions of antibody (final concentration ranging from 5 to 0.001 µg/mL; 4-fold dilutions in RPMI 1640 [Lonza, cat. no. BE12-115F] containing 1% Fetal Bovine Serum [FBS; Promega, cat. no. J121A]) were added. PD-1 effector cells (Promega, cat. no. J115A; thawed according to the manufacturer's protocol and resuspended in RPMI/1% FBS) were added. Plates were incubated for 6 h at 37° C., 5% $CO_2$. After equilibration to room temperature, 40 µl Bio-Glo reagent (Bio-Glo luciferase assay substrate [Promega cat. no. G720B] reconstituted in Bio-Glo luciferase assay buffer [Promega, cat. no. G7198] according to the manufacturer's protocol) was added to each well. Plates were incubated at room temperature for 5-10 minutes and luminescence was measured using an EnVision Multilabel Reader (PerkinElmer). The effect on PD1-PD-L1 interaction, relative to control (without antibody added), was calculated as follows:

Fold induction=RLU (induced-background)/RLU (no antibody control-background), RLU is relative light units FIG. 5 shows that monovalent antibody b12-FEAL×PD-L1-547-FEAR efficiently inhibited PD1-PD-L1 interaction.

Example 7: Antigen-Specific CD8$^+$ T Cell Proliferation Assay to Measure Effects by Bispecific Antibodies Binding to PD-L1 and CD137

A schematic representation of the anticipated mode of action of CD137×PD-L1 bispecific antibodies is shown in FIGS. 6A-6B.

To measure induction of T cell proliferation by the bispecific antibody targeting PD-L1 and CD137 in an antigen-specific assay, dendritic cells (DCs) were transfected with claudin-6 in vitro-transcribed RNA (IVT-RNA) to express the claudin-6 antigen. T cells were transfected with PD-1 IVT-RNA and with the claudin-6-specific, HLA-A2-restricted T cell receptor (TCR). This TCR can recognize the claudin-6-derived epitope presented in HLA-A2 on the DC. The CD137×PD-L1 bispecific antibody can cross-link PD-L1 endogenously expressed on monocyte-derived dendritic cells or on tumor cells and CD137 on the T cells, leading to inhibition of the inhibitory PD-1/PD-L1 interaction and at the same time clustering of CD137, resulting in T cell proliferation. Clustering of the CD137 receptor expressed on T cells leads to activation of the CD137 receptor which thereby delivers a co-stimulatory signal to the T cell.

HLA-A$^2$ peripheral blood mononuclear cells (PBMCs) were obtained from healthy donors (Transfusionszentrale, University Hospital, Mainz, Germany). Monocytes were isolated from PBMCs by magnetic-activated cell sorting (MACS) technology using anti-CD14 MicroBeads (Miltenyi; cat. no. 130-050-201), according to the manufacturer's instructions. The peripheral blood lymphocytes (PBLs, CD14-negative fraction) were frozen for future T-cell isolation. For differentiation into immature DCs (iDCs), 1×10$^6$ monocytes/ml were cultured for five days in RPMI GlutaMAX (Life technologies GmbH, cat. no. 61870-044) containing 5% human AB serum (Sigma-Aldrich Chemie GmbH, cat. no. H4522-100 ML), sodium pyruvate (Life technologies GmbH, cat. no. 11360-039), non-essential amino acids (Life technologies GmbH, cat. no. 11140-035), 100 IU/mL penicillin-streptomycin (Life technologies GmbH, cat. no.15140-122), 1000 IU/mL granulocyte-macrophage colony-stimulating factor (GM-CSF; Miltenyi, cat. no. 130-093-868) and 1,000 IU/mL interleukin-4 (IL-4; Miltenyi, cat. no. 130-093-924). Once during these five days, half of the medium was replaced with fresh medium.

iDCs were harvested by collecting non-adherent cells and adherent cells were detached by incubation with PBS containing 2 mM EDTA for 10 min at 370. After washing, iDCs were frozen in RPMI GlutaMAX containing 10% v/v DMSO (AppliChem GmbH, cat. no A3672,0050)+50% v/v human AB serum for future antigen-specific T cell assays.

One day prior to the start of an antigen-specific $CD8^+$ T cell proliferation assay, frozen PBLs and iDCs, from the same donor, were thawed. $CD8^+$ T cells were isolated from PBLs by MACS technology using anti-CD8 MicroBeads (Miltenyi, cat. no. 130-045-201), according to the manufacturer's instructions. About $10\text{-}15\times10^6$ $CD8^+$ T cells were electroporated with 10 μg of in vitro translated (IVT)-RNA encoding the alpha-chain plus 10 μg of IVT-RNA encoding the beta-chain of a claudin-6-specific murine TCR (HLA-A2-restricted; described in WO 2015150327 A1) plus 10 μg IVT-RNA encoding PD-1 in 250 μL X-Vivo15 (Biozym Scientific GmbH, cat. no.881026) in a 4-mm electroporation cuvette (VWR International GmbH, cat. no. 732-0023) using the BTX ECM® 830 Electroporation System device (BTX; 500 V, 1×3 ms pulse). Immediately after electroporation, cells were transferred into fresh IMDM medium (Life Technologies GmbH, cat. no. 12440-061) supplemented with 5% human AB serum and rested at 37° C., 5% $CO_2$ for at least 1 hour. T cells were labeled using 1.6 μM carboxyfluorescein succinimidyl ester (CFSE; Invitrogen, cat. no. C34564) in PBS according to the manufacturer's instructions, and incubated in IMDM medium supplemented with 5% human AB serum, O/N.

Up to $5\times10^6$ thawed iDCs were electroporated with 5 μg IVT-RNA encoding full length claudin-6, in 250 μL X-Vivol5 medium, using the electroporation system as described above (300 V, 1×12 ms pulse) and incubated in IMDM medium supplemented with 5% human AB serum, O/N.

Figure 7A:
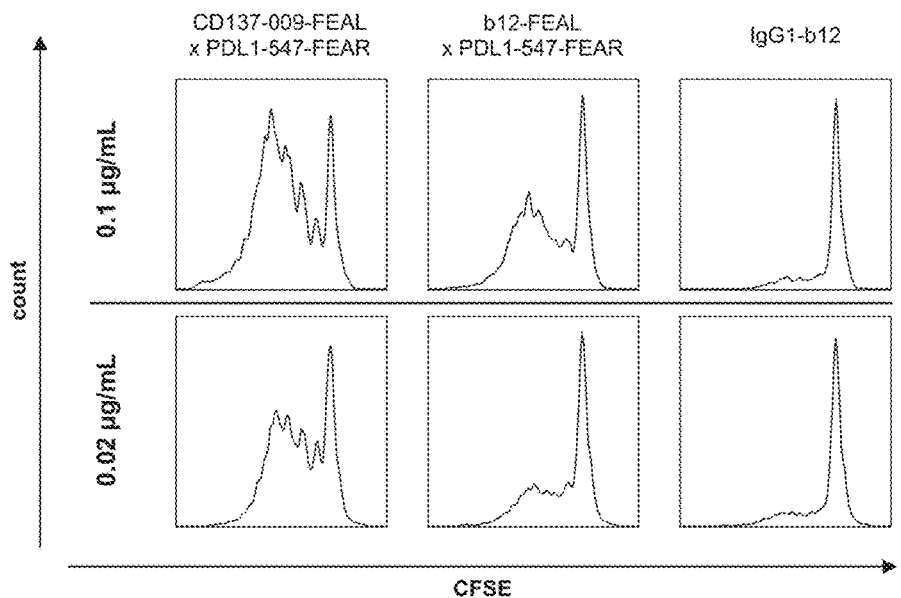
FIGS. 7A-7D: Release of the PD-1/PD-L1-mediated T cell inhibition and additional co-stimulation of CD8$^+$ T cell proliferation by CD137-009-FEAL×PD-L1-547-FEAR in an antigen-specific T cell assay with active PD-1/PD-L1 axis. CFSE-labelled T cells electroporated with a claudin-6-specific TCR- and PD-1-in vitro translated (IVT)-RNA were incubated with claudin-6-IVT-RNA-electroporated immature dendritic cells in the presence of 0.1 μg/mL and 0.02 μg/mL CD137-009-FEAL×PD-L1-547-FEAR, b12-FEAL×PD-L1-547-FEAR or b12 control antibody for five days. CD8$^+$ T cell proliferation was measured by flow cytometry. Data shown are (FIGS. 7A and 7C) representative CFSE histogram from two different donors and (FIGS. 7B and 7D) the corresponding percentages of divided cells and proliferation index as calculated using FlowJo software.
Figure 7B:
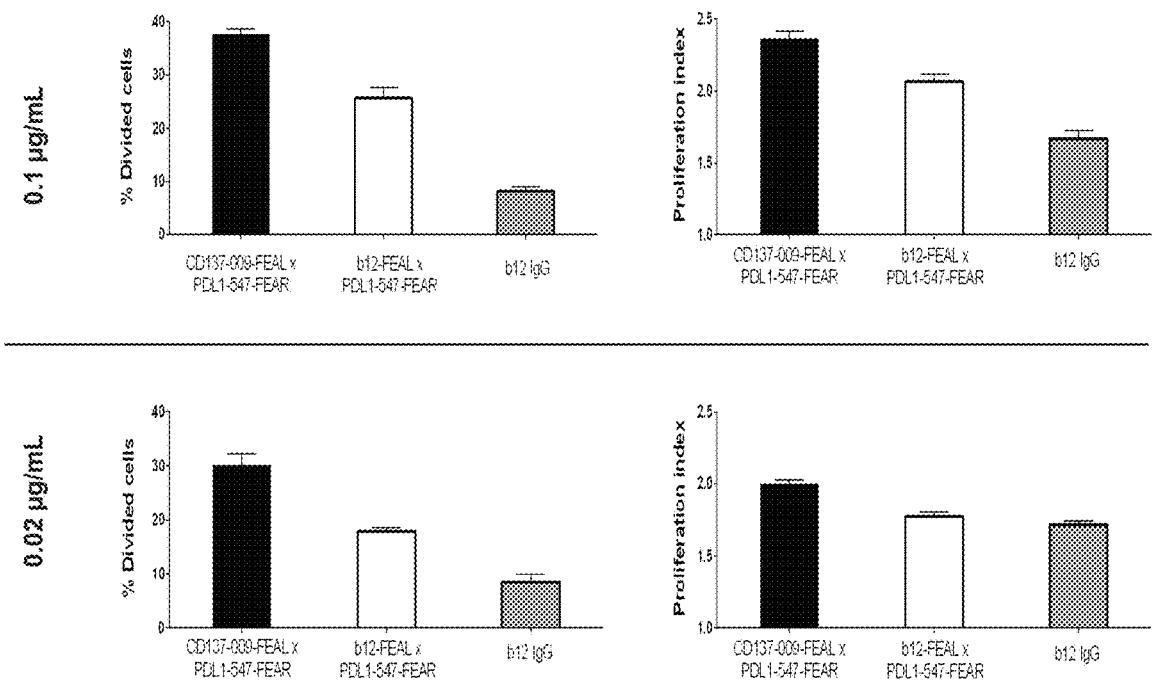
Figure 7C:
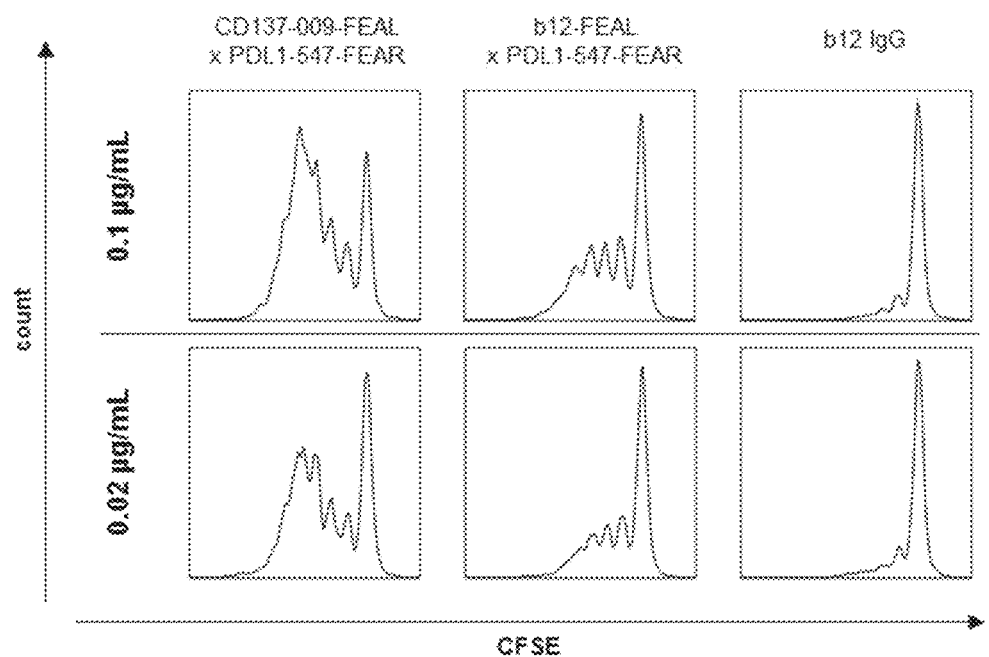
Figure 7D:
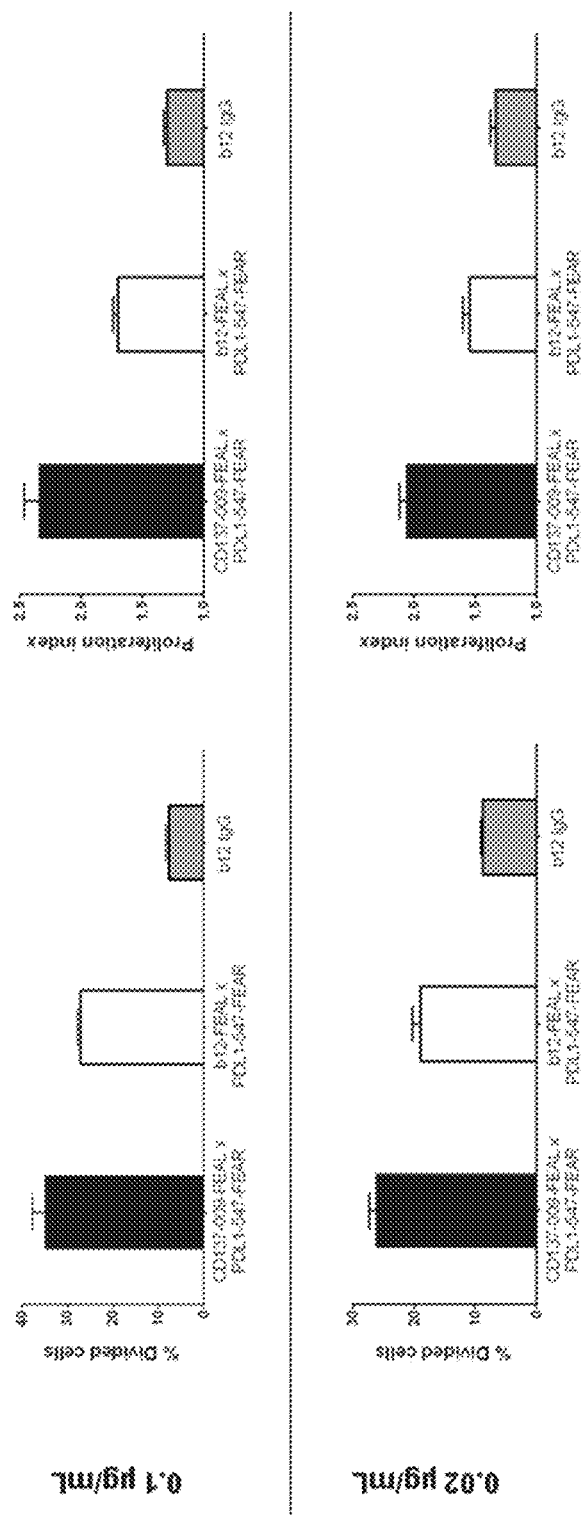

The next day, cells were harvested. Cell surface expression of claudin-6 and PD-L1 on DCs and TCR and PD-1 on T cells was checked by flow cytometry. DCs were stained with an Alexa647-conjugated CLDN6-specific antibody (non-commercially available; in-house production) and with anti-human CD274 antibody (PD-L1, eBioscienes, cat. no.12-5983) and T cells were stained with an anti-Mouse TCR β Chain antibody (Becton Dickinson GmbH, cat. no. 553174) and with anti-human CD279 antibody (PD-1, eBioscienes, cat. no. 17-2799). 5,000 electroporated DCs were incubated with 50,000 electroporated, CFSE-labeled T cells in the presence of bispecific or control antibodies in IMDM GlutaMAX supplemented with 5% human AB serum in a 96-well round-bottom plate. T cell proliferation was measured after 5 days by flow cytometry. Detailed analyses of T cell proliferation based on CFSE-peaks indicating cell divisions were made by FlowJo software. In the results, '% divided cells' indicates percentage of cells that went into division and 'proliferation index' indicates average number of divisions of cells that went into division The monovalent PD-L1-control antibody having one irrelevant binding-arm, b12-FEAL×PD-L1-547-FEAR, enhanced T cell proliferation to a certain extent compared to incubation with b12 (as regular IgG1), and the bispecific antibody CD137-009-FEAL×PD-L1-547-FEAR induced strong proliferation of $CD8^+$ T cells (FIGS. 7A-7D). This was reflected by both an increase in the percentage of divided cells (FIGS. 7B and 7D left panels) as well as an increase of the proliferation index (FIGS. 7B and 7D right panels).

Figure 8:
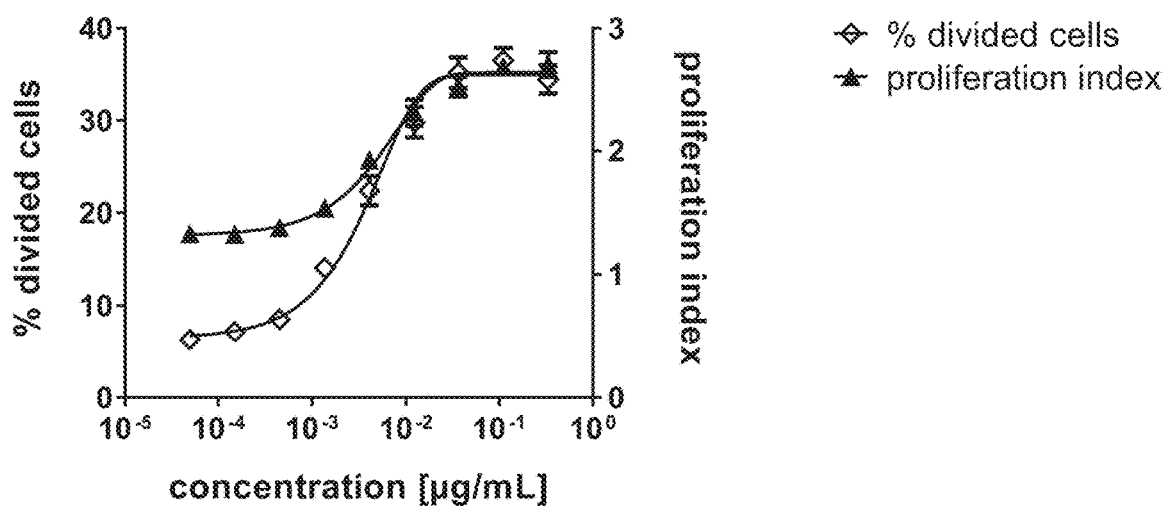
FIG. 8: Analysis of the EC$_{50}$ value of the bispecific antibody CD137-009-FEAL×PD-L1-547-FEAR in an antigen-specific T cell assay with active PD1/PD-L1 axis. CFSE-labeled T cells electroporated with a claudin-6-specific TCR- and PD-1-IVT-RNA were incubated with claudin-6-IVT-RNA-electroporated immature dendritic cells in the presence of CD137-009-FEAL×PD-L1-547-FEAR (at 3-fold serial dilutions from 1 to 0.00015 μg/mL) for five days. CD8$^+$ T cell proliferation was measured by flow cytometry. Data shown are percentages of divided cells (open diamonds) and proliferation indices (filled triangles) as a function of the antibody concentration. Error bars (SD) indicate variation within the experiment (six replicates, using cells from one donor). Curves were fitted by nonlinear regression and EC$_{50}$ values were determined using GraphPad Prism software.

In addition, the $EC_{50}$ value in this assay was determined for CD137-009-FEAL×PD-L1-547-FEAR. To this end, the bispecific antibody was analyzed at 3-fold serial dilutions from 1 to 0.00015 μg/mL (FIG. 8). Percentage of divided cells and proliferation index were determined by FlowJo software. Curves were analyzed by non-linear regression (sigmoidal dose-response with variable slope) using GraphPad Prism 5 software (GraphPad Software, San Diego, Calif., USA). The $EC_{50}$ values of the induction of antigen-specific T cell proliferation of CD137-009-FEAL×PD-L1-547-FEAR was 0.003492 μg/mL for '% divided cells' and 0.005388 μg/mL for 'proliferation index'.

Example 8: Comparison of the Bispecific Antibody Targeting PD-L1 and CD137 with a Combination of Two Monovalently Binding CD137 and PD-L1 Antibodies or the Two Parental Antibodies (PD-L1-547+CD137-009) in an Antigen-Specific T-Cell Assay with Active PD1/PD-L1 Axis To measure induction of T cell proliferation by the bispecific antibody targeting PD-L1 and CD137, an antigen-specific T cell proliferation assay with active PD1/PD-L1 axis was performed (general assay set-up analogous to example 7). In short, 5,000 claudin-6-IVT-RNA electroporated DCs were incubated with 50,000 claudin-6-specific TCR- and PD1-IVT-RNA electroporated, CFSE-labeled T cells in the presence of bispecific or control antibodies in IMDM GlutaMAX supplemented with 5% human AB serum in a 96-well round-bottom plate. T cell proliferation was measured after 5 days by flow cytometry. Detailed analyses of T cell proliferation based on CFSE-peaks indicating cell divisions were performed using FlowJo software. In the results, '% divided cells' indicates percentage of cells that went into division and 'proliferation index' indicates average number of divisions of cells that went into division.

Figure 9A:
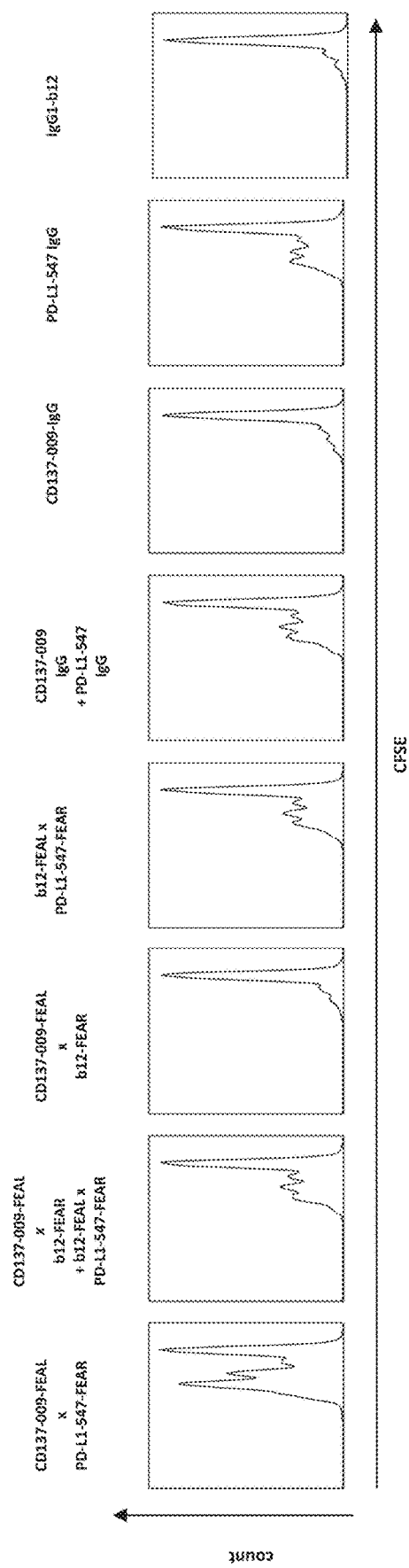
FIGS. 9A-9C: Comparison of CD137-009-FEAL×PD-L1-547-FEAR with a combination of the two monovalently binding CD137 antibodies (CD137-009-FEAL×b12-FEAR+b12-FEAL×PD-L1-547-FEAR) or the two parental antibodies (CD137-009+PD-L1-547) in an antigen-specific T cell assay with active PD1/PD-L1 axis. CFSE-labelled T cells electroporated with a claudin-6-specific TCR- and PD1-IVT-RNA were incubated with claudin-6-IVT-RNA electroporated immature dendritic cells in the presence of 0.25 μg/mL (i) CD137-009-FEAL×PD-L1-547-FEAR, (ii) CD137-009-FEAL×b12+b12-FEAL×PD-L1-547-FEAR, (iii) CD137-009-FEAL×b12, (iv) b12-FEAL×PD-L1-547-FEAR, (v) CD137-009+PD-L1-547, (vi) CD137-009, (vii) PD-L1-547, or (viii) b12 control antibody for five days. CD8$^+$ T cell proliferation was measured by flow cytometry. Data shown are (FIG. 9A) representative CFSE histograms and (FIGS. 9B and 9C) the corresponding mean values of percent divided cells and proliferation index as calculated using FlowJo software. Error bars (SD) indicate the variation within the experiment (three replicates, using cells from one donor)
Figure 9B:
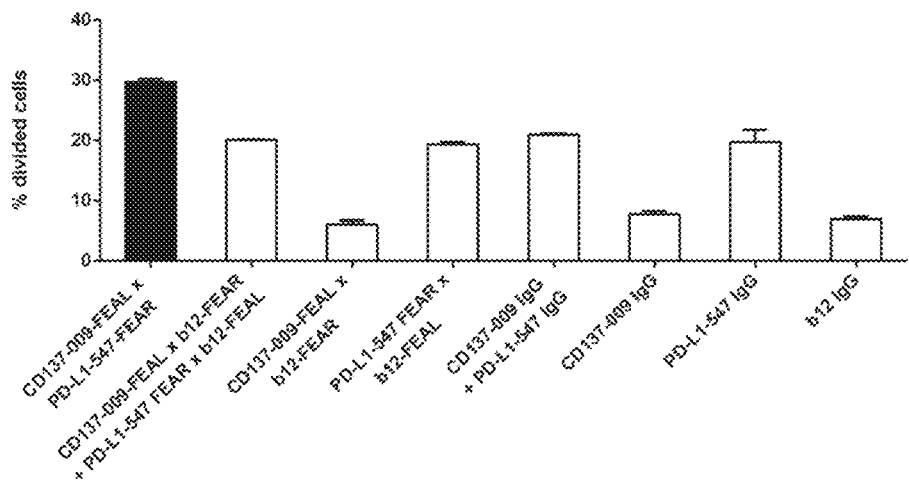
Figure 9C:
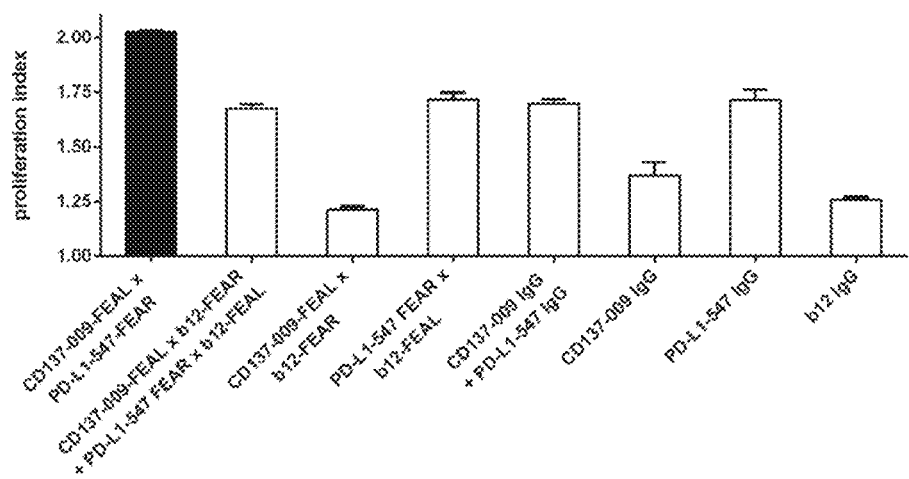

Neither the monovalent CD137-control antibody, CD137-009-FEAL×b12-FEAR, having one irrelevant binding-arm nor the corresponding bivalent parental antibody CD137-009 had an effect on T cell proliferation when compared IgG1-b12. In contrast, incubation with the monovalent PD-L1-control antibody as well as the bivalent parental antibody (b12-FEAL×PD-L1-547-FEAR and PD-L1-547, respectively) led to a moderately enhanced T-cell proliferation compared to incubation with IgG1-b12 control antibody. A comparable level of T-cell proliferation was detectable upon incubation with the combined monovalent control antibodies (CD137-009-FEAL×b12-FEAR+b12-FEAL×PD-L1-547-FEAR) and the combined corresponding parental antibodies (CD137-009+PD-L1-547). In contrast, the bispecific antibody CD137-009-FEAL×PD-L1-547-FEAR induced strong proliferation of $CD8^+$ T cells, which was superior to both combined controls (monovalent and bivalent) (FIGS. 9A-9C). This was reflected by both an increase in the percentage of divided cells (FIG. 9B) as well as an increase in the proliferation index (FIG. 9C).

Example 9: Ex Vivo TIL Expansion Assay to Evaluate the Effects of the CD137×PD-L1 Bispecific Antibody on Tumor Infiltrating Lymphocytes To evaluate the effects of CD137-009-FEAL×PD-L1-547-FEAR on tumor infiltrating lymphocytes (TIL), an ex vivo culture of human tumor tissue was performed as follows. Fresh human tumor tissue resection specimens were washed three times by transferring the isolated tumor chunks from one well in a 6-well plate (Fisher Scientific cat. no. 10110151) containing wash medium to the next using a spatula or serological pipette. Wash medium was composed of X-VIVO 15 (Biozym, cat. no. 881024) supplemented with 1% Pen/Strep (Thermo Fisher, cat. no. 15140-122) and 1% Fungizone (Thermo Fisher, cat. no. 15290-026). Next, the tumor was dissected with a surgical knife (Braun/Roth, cat. no. 5518091 BA223) and cut into pieces with a diameter of about 1-2 mm. Two pieces each were put into one well of a 24-well plate (VWR international, cat. no. 701605) containing 1 mL TIL medium (X-VIVO 15, 10% Human Serum Albumin (HSA, CSL Behring, cat. no. PZN-6446518) 1% Pen/Strep, 1% Fungizone and supplemented with 10 U/mL IL-2 (Proleukin®S, Novartis Pharma, cat. no. 02238131)). CD137-009-FEAL×PD-L1-547-FEAR was added at the indicated final concentrations. Culture plates were incubated at 37° C. and 5% $CO_2$. After 72 hours, 1 mL of fresh TIL medium containing the indicated concentration of the bispecific antibody was added to each well. Wells were monitored via a microscope for the occurrence of TIL clusters every other day. Wells were transferred individually when more than 25 TIL microclusters were detected in the respective well. To split TIL cultures, the cells in the wells of a 24-well plate were re-suspended in the 2 mL medium and transferred into a well of a 6-well plate. Each well was in addition supplemented with another 2 mL of TIL medium.

After a total culture period of 10-14 days, TILs were harvested and analyzed by flow cytometry. Cells were stained with the following reagents, all diluted 1:50 in staining-buffer, (D-PBS containing 5% FCS and 5 mM EDTA), anti-human CD4-FITC (Miltenyi Biotec, cat. no. 130-080-501), anti-human CD3-PE-Cy7 (BD Pharmingen, cat. no. 563423), 7-aminoactinomycin D (7-AAD, Beckman Coulter, cat. no. A07704), anti-human CD56-APC (eBioscience, cat. no. 17-0567-42), and anti-human CD8-PE (TONBO, cat. 50-0088). To allow for quantitative comparison of the acquired cells between different treatment groups, cell pellets were re-suspended after the last washing step in FACS-buffer supplemented with BD™ CompBeads (BD biosciences, cat. no. 51-90-9001291). Flow cytometric analysis was performed on a BD FACSCanto™ II flow cytometer (Becton Dickinson) and acquired data was analyzed using FlowJo 7.6.5 software. The relative viable TIL count, $CD3^+CD8^+$ T cell count, $CD3^+ CD4^+$ T cell count and $CD3^-CD56^+$ NK cell count per 1,000 beads correlating to the corresponding well in a 6-well plate was calculated by normalization of the acquired 7AAD-negative cell fraction to the acquired bead counts.

FIGS. 10A-10D show the analysis of a TIL expansion from a human non-small-cell lung carcinoma tissue specimen. Here, the following concentrations of CD137-009-FEAL×PD-L1-547-FEAR were added: 0.01, 0.1 and 1 µg/mL; a tissue specimen from the same patient without antibody addition served as negative control. After 10 days of culture, the TILs were harvested and analyzed by flow cytometry. Five samples (from 5 original wells) for each antibody concentration derived from different wells of the 24-well plate were measured. In all samples cultured with the bispecific antibody the viable count of TILs was significantly increased in comparison to the without antibody control samples. Overall, an up to 10-fold expansion of viable TILs was observed, when 0.1 µg/mL CD137-009-FEAL×PD-L1-547-FEAR was added to cultures (FIG. 10A). $CD3^+CD4^+$ T helper cells were only slightly expanded (FIG. 10C; 2.8-fold expansion), whereas in contrast, the most prominent TIL expansion was seen for $CD3^-CD56^+$ NK cells (FIG. 10D; up to 64-fold expansion over control). Also a strong effect on $CD3^+ CD8^+$ cytotoxic T lymphocytes (CTLs) was observed (FIG. 10B; 7.4-fold expansion over control).

Example 10: Effect of a Surrogate Bispecific Mouse Antibody Binding to mPD-L1 and mCD137 on Ovalbumin Specific T Cell Proliferation in C57BL/6 Mice after OT-I $CD8^+$ Adoptive T Cell Transfer Surrogate mouse bispecific antibodies mCD137-3H3× mPD-L1-MPDL3280A, mCD137-3H3×b12 and mPD-L1-MPDL3280A×b12 were generated using a method to generate murine bispecific antibodies based on controlled Fab-arm exchange (Labrijn et al, 2017 Sci Rep. 7(1): 2476 and WO2016097300).

The monoclonal antibody 3H3, which binds to mouse 4-1BB, was obtained from BioXcell (cat. No. BE0239) and protein sequenced at ProtTech. The inferred cDNA sequence was deducted using proprietary methods. The variable regions of heavy and light chain were gene synthesized and cloned into a mouse IgG2a expression vector including a murine IgG2a constant region containing the following amino acid mutations: L234A, L235A, F405L and R411T. Similarly, the variable regions of b12 were cloned into this expression vector.

The antibody MPDL3280A (heavy and light chain variable sequences set forth in SEQ ID NOs: 57 and 58, respectively) has been described to bind both human and mouse PD-L1. The variable regions of heavy and light chains of this antibody were cloned into a mouse IgG2a expression vector including a murine IgG2a constant region containing the following amino acid mutations: L234A, L235A, T370K and K409R.

Bispecific mouse (in essence rat-human-mouse chimeric) antibodies were generated by Fab-arm-exchange under controlled reducing conditions as described supra.

Female C57BL/6JOIaHsd mice (Envigo RMS GmbH, Rossdorf, Germany), 6-8 weeks of age, with a weight between 17 and 24 g, were acclimated to the animal facility for at least six days prior to study enrollment. These mice were used as recipients. Female or male C57BL/6 Thy1.1× C57BL/6J OT-1 mice homozygous for both the OT-1 and Thy1.1 allele were bred in-house (cross-bred from C57BL/6-Tg(TcraTcrb)1100Mjb/Crl and B6.PL-Thy1a/CyJ mice) and were used as donors. Mice had free access to food (ssniff M-Z autoclavable Soest, Germany) and sterile water and were housed on 12 hours light/dark cycle at 22° C.±2° C. with a relative humidity of 55%±15%.

At the day of study start, C57BL/6 Thy1.1×C57BL/6J OT-1 donor mice were sacrificed and spleens were isolated. Spleens were mechanically dissociated and erythrocytes were lysed by re-suspending the splenocyte pellet with erythrocyte-lysis buffer (8.25 g/L $NH_4Cl$, 1 g/L $KHCO_3$, 0.1 mM EDTA, pH7). Subsequently, splenocytes were washed with Dulbecco's PBS (DPBS) and $CD8^+$ T cells were isolated using the CD8a (Ly-2) MicroBeads, mouse in combination with the autoMACS Pro Separator (both Miltenyi Biotec GmbH, Bergisch Gladbach, Germany). $CD8^+$/ OT-$1^+$/Thy$1.1^+$ T cells ($2.5-5\times10^5$ cells) were injected retro-orbitally in a total volume of 200 µL per C57BL/6JOIaHsd recipient mouse. The day after adoptive cell transfer, recipient mice were 'vaccinated' retro-orbitally with 100 µg ovalbumin/200 µL PBS as antigenic stimulus. After 6 hours, the mice were treated retro-orbitally with the respective bispecific antibody. In detail, 100 µg or 20 µg mCD137-3H3×mPD-L1-MPDL3280A, mCD137-3H3×b12 or mPD-L1-MPDL3280A×b12 antibody was injected per mouse. Injection of plain PBS was used as baseline reference and untreated animals (mice that received donor cells only) were used as negative control. After 6 days, 100 µL blood was drawn via the retro-orbital route and analyzed for Thy1.1$^+$ CD8$^+$ T cells on a BD FACSCanto II cytometer (Becton Dickinson GmbH) using V500 rat anti-mouse CD45 (Becton Dickinson GmbH, Cat No. 561487), FITC rat anti-mouse CD8a (Life technologies, Cat No. MCDO801) and Alexa Fluor 647 anti-rat CD90/mouse CD90.1 (BioLegend Europe, Cat No. 202508) antibodies. Thy1.1 (CD90.1) positivity was used as surrogate for OT-1 specific T cells.

FIG. 11A is a schematic representation of the OT-1 adoptive T-cell transfer assay outline. FIG. 11B shows the analysis of the Thy1.1$^+$CD8$^+$ T-cell frequencies as determined by flow cytometry. For each bispecific antibody treatment modality, n=5 mice were used. The ovalbumin antigenic stimulus alone led to detectable increase in Thy1.1+CD8+ T-cell frequency compared to untreated animals. Interestingly, both monovalent control antibodies having one irrelevant b12 binding-arm, mCD137-3H3-×b12 and mPD-L1-MPDL3280A×b12, were not able to boost ovalbumin-specific OT-1 T-cell expansion compared to animals that had been treated with ovalbumin only. In contrast, the bispecific antibody mCD137-3H3×mPD-L1-MPDL3280A was able to induce a strong proliferation of OT-1 T cells leading to T-cell frequencies of 10-20% CD8$^+$/OT-1$^+$/Thy1.1$^+$ T-cells (% of total T cell population) at both dose levels tested (20 and 100 μg antibody).

Example 11: Effect of a Surrogate Bispecific Mouse Antibody Binding to mPD-L1 and mCD137 on Tumor Growth in a Subcutaneous, Syngeneic CT26 Mouse Tumor Model Female BALB/c Rj mice (Janvier, Genest-St.-Îsle, France), 6-8 weeks of age, with a weight between 17 and 24 g, were acclimated for at least six days prior to study enrollment. Mice had free access to food (ssniff M-Z autoclavable Soest, Germany) and sterile water and were housed on 12 hours light/dark cycle at 22° C.±2° C. with a relative humidity of 55%±10%. CT26 cells were obtained from the ATCC® (Cat No. CRL-2638™) and cultured in Roswell Park Memorial Institute medium (RPMI) 1640 Medium, GlutaMAX™ (Life technologies, Cat No. 61870-044) supplemented with 10% Fetal Bovine Serum (FBS) (Biochrom, Cat No. S 0115) in 5% $CO_2$ at 37° C. The cells were harvested using StemPro® Accutase® Cell Dissociation Reagent (Life technologies, Cat No. A1110501), resuspended in DPBS (Life technologies, Cat No. 14190-169), and $0.5\times10^6$ cells/100 μl per mouse subcutaneously (SC) implanted into the right shaven flank of female BALB/c Rj mice. Tumor volume was assessed by caliper measurements every 2-3 days and is expressed as the product of the perpendicular diameters using the following formula: $a^2 \times b/2$ where b is the longer of the two diameters (a<b). Animals were stratified into four groups when a mean tumor volume of 30 mm$^3$ was reached. Treatment started the next day with intraperitoneal injection of 20 μg bispecific antibody binding to mPD-L1 and mCD137 (mCD137-3H3× mPD-L1-MPDL3280A), with the monovalent mCD137- or mPD-L1-control antibodies having one irrelevant binding-arm (mCD137-3H3×b12 and mPD-L1-MPDL3280A×b12), or PBS as negative control. Dosing schedule was every 2-3 days for the first eight injections, followed by an injection every 7 days until the end of the experiment. At day 29 post tumor cell inoculation, 100 μL blood was drawn via the retro-orbital route and analyzed for gp70-specific CD8$^+$ T cells (gp70 is an envelope protein expressed on CT26 tumor cells) on a BD FACSCanto II cytometer (Becton Dickinson GmbH) using V500 rat anti-mouse CD45 (Becton Dickinson GmbH, Cat No. 561487), FITC rat anti-mouse CD8a (Life technologies, Cat No. MCDO801) antibodies and T-Select H-2Ld MuLV gp70 tetramer-SPSYVYHQF-APC (MBL Ltd. Corp., Cat No. TS-M521-2).

FIG. 12A shows the tumor growth curves for all four treatment groups with individual lines being representative of a single tumor/mouse. Progression-free survival (PFS) frequencies for the respective treatment groups are given at the bottom of each plot. FIG. 12B displays the corresponding Kaplan-Meier survival curves until the end of the experiment at day 71 post tumor cell inoculation. FIG. 12C shows the analysis of gp70 tetramer$^+$ CD8$^+$ T-cell frequencies as determined by flow cytometry. For each treatment modality, all mice that were still alive at day 29 post tumor cell implantation were analyzed. In summary, the bispecific antibody binding to mPD-L1 and mCD137 (mCD137-3H3× mPD-L1-MPDL3280A) provided most efficient tumor control with 5 out of 10 (i.e. 50%) animals going into complete tumor regression. In comparison, a slightly weaker but still prominent anti-tumor effect was observed for the mCD137-3H3×b12 control; treatment led to 3 out of 11 (i.e. 27%) animals being able to reject tumors. In both cases, all mice that went into full remission remained tumor-free until the end of the experiment. In striking contrast, both the mPD-L1-MPDL3280A×b12-treated cohort as well as the PBS control were not able to control tumor burden, with mPD-L1-MPDL3280A×b12-treatment leading at least to some intermittent tumor growth inhibition in 2 out of 11 (i.e. 18%) animals between day 15 and 30 post tumor cell inoculation. When looking at the frequency of CD8$^+$ T cells that were able to bind gp70 tetramers, highest gp70-specific CD8$^+$ T-cell frequencies were detectable in mCD137-3H3×mPD-L1-MPDL3280A treated animals (2.14%±1.52%). In comparison, gp70 tetramer$^+$ CD8-T-cell frequencies in mCD137-3H3×b12 (0.90%±0.46%), mPD-L1-MPDL3280A×b12 (0.94%±1.06%) and PBS-treated control animals (0.66%±0.49%) were considerably lower with only minimal differences between those three treatment modalities.

Example 12: Binding of PD-L1 Antibodies or b12×PD-L1 Bispecific Antibodies to Tumor Cells Binding of PD-L1 antibodies and b12×PD-L1 bispecific antibodies to human tumor cell lines MDA-MB-231 (breast adenocarcinoma; ATCC; Cat. no. HTB-26), PC-3 (prostate adenocarcinoma; ATCC; Cat. no. CRL-1435) and SK-MES-1 (lung squamous cell carcinoma; ATCC; Cat. no. HTB-58) was analyzed by flow cytometry.

Cells ($3-5\times10^4$ cells/well) were incubated in polystyrene 96-well round-bottom plates (Greiner bio-one, cat. no. 650101) with serial dilutions of antibodies (range 0.0001 to 10 μg/mL in 5-fold dilution steps) in 50 μL PBS/0.1% BSA/0.02% azide (FACS buffer) at 4° C. for 30 min. After washing twice in FACS buffer, cells were incubated with secondary antibody at 4° C. for 30 min. As a secondary antibody, R-Phycoerythrin (PE)-conjugated goat-anti-human IgG F(ab')$_2$ (Cat. no. 109-116-098, Jackson ImmunoResearch Laboratories, Inc., West Grove, Pa.) diluted 1:500 in 50 μL FACS buffer, was used for all experiments. Next, cells were washed twice in FACS buffer, re-suspended in 20 μL FACS buffer and analyzed on an iQue screener (Intellicyt Corporation, USA). Binding curves were analyzed using non-linear regression (sigmoidal dose-response with variable slope) using GraphPad Prism V75.04 software (GraphPad Software, San Diego, Calif., USA).

Figure 13A:
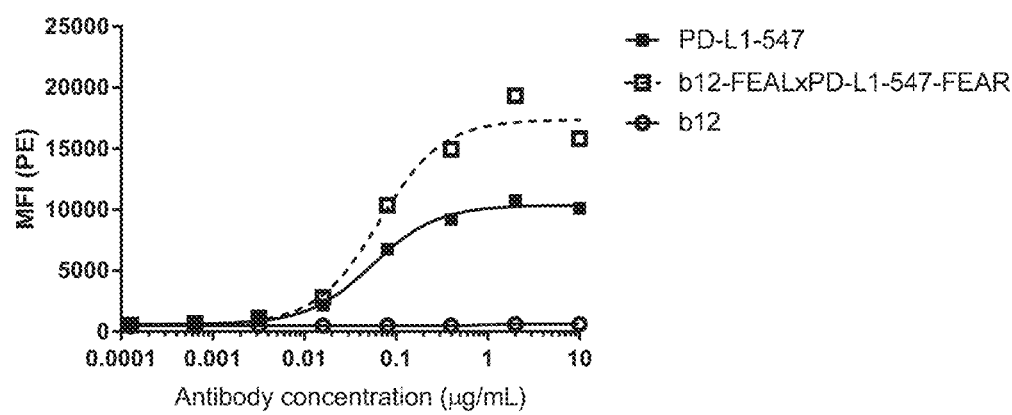
FIGS. 13A-13C: Binding of monospecific, bivalent PD-L1 antibodies and monovalent b12×PD-L1 antibodies to tumor cells. Binding of PD-L1-547 and b12-FEAL×PD-L1-547-FEAR to MDA-MB-231 (FIG. 13A), PC-3 (FIG. 13B) and SK-MES-1 (FIG. 13C) cells. Data shown are mean fluorescence intensities (MFI) as determined by flow cytometry. Monospecific, bivalent b12 antibodies were included as negative control.

Quantitative flow cytometry (QIFIKIT®, Dako; cat. no K0078) was performed as described (oncelet and Carayon, 1985, J. Immunol. Meth. 85: 65-74) using M DL3280A (heavy and light chain variable sequences set forth in SEQ ID NOs: 57 and 58, respectively), to quantify antigen density on the plasma membrane of MDA-MB-231, C-3 and SK-MES-1 cells. It was determined that the cells lines have the following D-L1 antigen density (ABC, antibody binding capacity):
MDA-MB-231: appr. 21,000 ABC/cell
C-3: appr. 6,000 ABC/cell
SK-MES-1: appr. 30,000 ABC/cell Binding to MDA-MB-231 Cells FIG. 13A shows dose-dependent binding of b12-FEAL×PD-L1-547-FEAR to MDA-MB-231 cells, with higher maximum binding than monospecific, bivalent PD-L1-547-FEAR.

Binding to PC-3 Cells

Figure 13B:
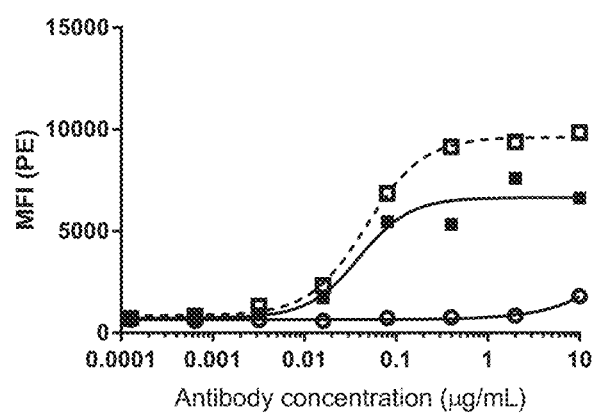

FIG. 13B shows dose-dependent binding of b12-FEAL×PD-L1-547-FEAR to PC3 cells, with higher maximum binding than monospecific, bivalent PD-L1-547-FEAR.

Binding to SK-MES-1 Cells

Figure 13C:
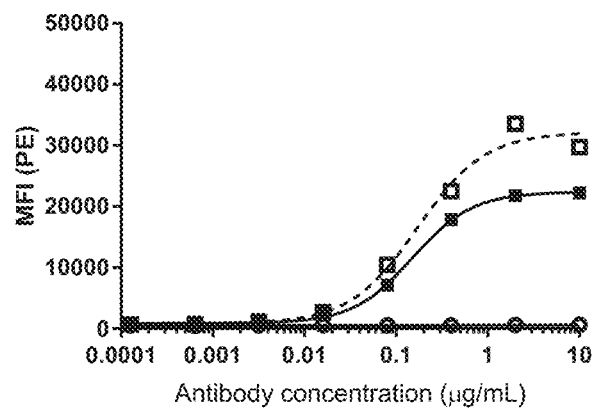

FIG. 13C shows dose-dependent binding of b12-FEAL×PD-L1-547-FEAR to SK-MES-1 cells, with higher maximum binding than monospecific, bivalent PD-L1-547-FEAR.

Example 13. Determination of the Contribution of CD137 Amino Acid Residues to Antibody Binding Using Alanine Scanning Library Design A CD137 (Uniprot Q07011) single residue alanine library was synthesized (Geneart) in which all amino acid residues in the extracellular domain of human CD137 were individually mutated to alanines, except for positions already containing alanines or cysteines. To minimize the chance of structural disruption of the antigen, cysteines were not mutated. Positions with alanines were mutated to glycines. The library was cloned in the pMAC expression vector containing a CMV/TK-polyA expression cassette, an Amp resistance gene and a pBR322 replication origin.

Library Production and Screening

The wild type CD137 and alanine mutants were expressed individually in FreeStyle HEK293 cells according to the manufacturer's instructions (Thermo Scientific). One day post transfection, the cells were harvested. Approximately 100,000 cells were incubated with 20 µL Alexa Fluor® 488-(A488-) conjugated antibody of interest in FACS buffer (Table 3). Cells were incubated at room temperature for 30 min. Subsequently, cells were washed twice by centrifugation using 150-200 µL FACS buffer. Cells were suspended in 30 µL FACS buffer and stored at 4° C. until analysis by flow cytometry using an iQue screener.

The entire experiment was performed in triplicate.

TABLE 3

Antibodies used in determination of the contribution of CD137 amino acid residues in antibody binding using alanine scanning. Antibodies were labeled with Alexa488 (Invitrogen, cat. no. A20000) according to the manufacturer's instructions, prior to performing the experiment. CD137-MOR7480-FEAR is a surrogate MOR7480 antibody that was cloned into the human IgG1 backbone containing the FEAR mutations.

| Antibody | Final concentration | Conjugate |
|---|---|---|
| b12-FEALxCD137-009-FEAR-A488 | 3 µg/mL | Alexa488 |
| CD137-005-FEAR-A488 | | |
| CD137-MOR7480-FEAR-A488 | | |

Data Analysis

For every sample, the average amount of antibody bound per cell was determined as the geometric mean of the fluorescence intensity (gMFI) for the viable, single cell population. The gMFI is influenced by the affinity of the antibody for the CD137 mutant and the expression level of the CD137 mutant per cell. Since specific alanine mutations can impact the surface expression level of the mutant CD137, and to correct for expression differences for each CD137 mutant in general, data were normalized against the binding intensity of a non-cross blocking CD137 specific control antibody, using the following equation:

$$\text{Normalized } gMFI_{aa\ position} = \text{Log}_{10}\left(\frac{gMFI_{Test\ Ab}}{gMFI_{Control\ Ab}}\right)$$

In which 'aa position' refers to the position that was mutated into an alanine or a glycine. To express loss or gain of binding of the antibodies, the zscore was calculated according to the following calculation:

$$zscore(\text{fold change}) = \frac{\text{Normalized } gMFI_{aa\ position} - \mu}{\sigma}$$

Where µ and σ are the mean and standard deviation of the Normalized gMFI calculated from all mutants.

A zscore of 0 indicates that there is no loss or gain of binding by a particular antibody, as compared to binding of the reference antibody; a zscore >0 indicates gain of binding, as compared to binding of the reference antibody; a zscore of <0 indicates a loss of binding, as compared to binding of the reference antibody. In most cases, gain of binding, as determined by zscore, is caused by loss of binding of the reference antibody to specific alanine or glycine mutants. To correct for sample variation, only CD137 amino acid residues where the zscore in binding was lower than −1.5 were considered 'loss of binding mutants'.

If the gMFI of the control antibody for a particular CD137 mutant was lower than the mean gMFI$_{aa\ position}$−2.5× SD of the mean gMFI$_{control\ Ab}$, data were excluded from analysis (it was assumed that expression levels for those CD137 mutants were not sufficient to draw conclusions).

Figure 14A:
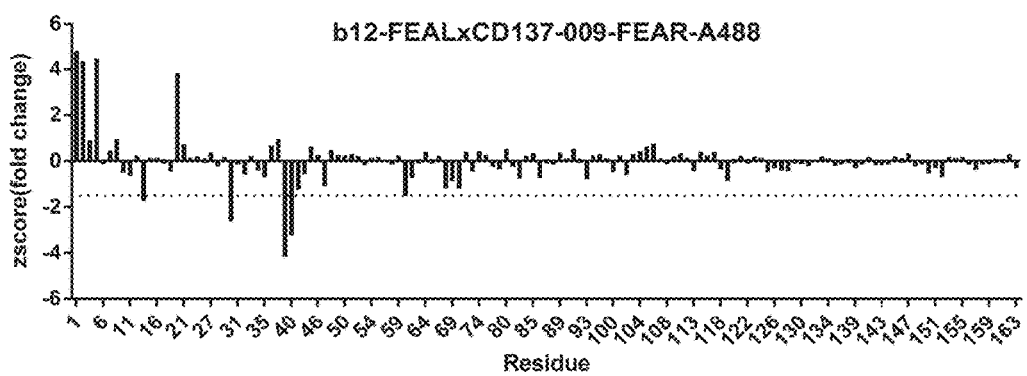
FIGS. 14A-14C: Binding of CD137 antibodies to CD137 variants with alanine mutations at positions 1 to 163. Binding was expressed as zscore (fold change), as a measure for change in binding compared to control antibody. Zscore (fold change) was defined as (Normalized gMFI$_{aa\ position}$−μ)/σ, where μ and σ are the mean and standard deviation of the Normalized gMFI over all mutants. Residues where the zscore in binding was lower than −1.5 (indicated by the dotted line) were considered 'loss of binding mutants'. Residues with a positive zscore in binding are loss of binding residues for the non-cross blocking CD137 specific control antibody. The number on the x-axis refers to the amino acid positions.
Figure 14B:
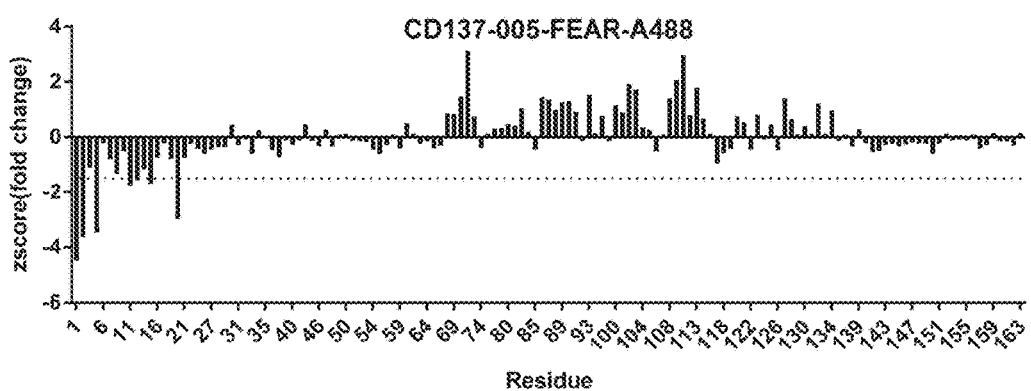
Figure 14C:
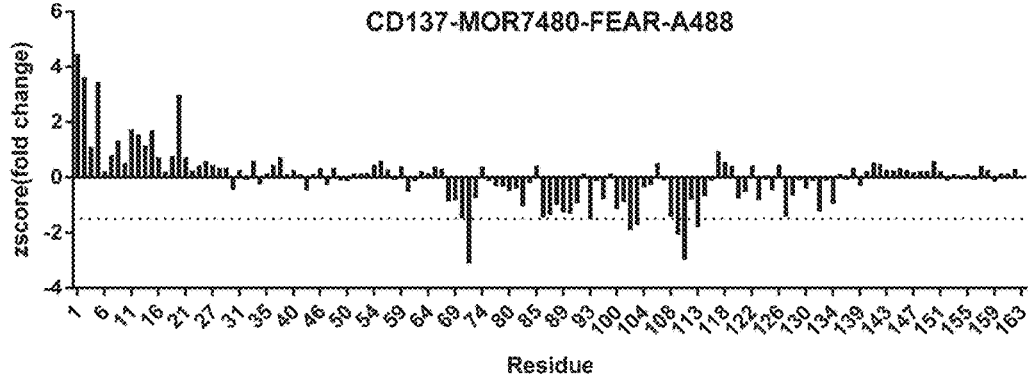

FIGS. 14A-14C show the loss of binding of the CD137 antibodies to CD137 variants with alanine or glycine mutations at positions 1 to 163 (according to SEQ ID 41). The results indicate that antibody CD137-005-FEAR showed loss of binding when aa L1, Q2, P4, G11, T12, D15, or Q20 were mutated to an alanine. This suggests that binding of antibody CD137-005-FEAR is at least dependent on aa L1, Q2, P4, G11, T12, D15, Q20 of human CD137, antibody b12-FEALxCD137-009-FEAR showed loss of binding when aa F13, F30, T38, D40, or N60 were mutated to an alanine. This suggests that binding of antibody b12-FEALxCD137-009-FEAR is at least dependent on aa F13, F30, T38, D40, and N60 of human CD137. Since F13 and F30 are most likely structurally impacting the epitope interaction, antibody b12-FEALxCD137-009-FEAR is at least dependent on aa T38, D40, and N60, antibody CD137-MOR7048-FEAR showed loss of binding when aa L72, G93, F102, N103, I109, R111, or W113 were mutated to an alanine. This suggests that binding of antibody MOR7048 is at least dependent on aa L72, G93, F102, N103, I109, R111, and W113 of human CD137.

Example 14: Non-Antigen-Specific T-Cell Proliferation Assay to Measure Effects of Bispecific Antibodies Binding to PD-L1 and CD137

A schematic representation of the anticipated mode of action of PD-L1xCD137 bispecific antibodies is shown in FIGS. 6A-6B.

To measure induction of T-cell proliferation in polyclonally activated T cells, PBMCs were incubated with a sub-optimal concentration of anti-CD3 antibody (clone UCHT1), to activate T cells, combined with PD-L1-547-FEALxCD137-009-HC7LC2-FEAR bispecific antibody or control antibodies. Within the PBMC population, cells expressing PD-L1 can be bound by the PD-L1-specific arm of the bispecific antibody, whereas the T cells in the population can be bound by the CD137-specific arm. In this assay, T-cell proliferation is a measure for trans-activation of the T cells via the CD137-specific arm, induced by cross-linking with the PD-L1-expressing cells via the bispecific antibody and by blockade of PD-L1:PD-1 interaction, is measured as T-cell proliferation.

PBMCs were obtained from buffy coats of healthy donors (Transfusionszentrale, University Hospital, Mainz, Germany) using a Ficoll gradient (VWR, cat. no. 17-5446-02). PBMCs were labeled using 1.6 µM carboxyfluorescein succinimidyl ester (CFSE) (Thermo Fisher, cat. no. C34564) in PBS, according to the manufacturer's instructions. 75,000 CFSE-labeled PBMCs were seeded per well in a 96-well round-bottom plate (Sigma Aldrich, CLS3799-50EA) and incubated with a sub-optimal concentration of anti-CD3 antibody (R&D Systems, clone UCHT1, cat. no. MAB100; 0.03-0.1 µg/mL final concentration) that was pre-determined for each donor to induce sub-optimal T cell proliferation, and bispecific or control antibodies, in 150 µL IMDM GlutaMAX supplemented with 5% human AB serum, at 37° C., 5% $CO_2$, for four days. Proliferation of $CD4^+$ and $CD8^+$ T cells was analyzed by flow cytometry, essentially as described supra. 30 µL containing PE-labeled CD4 antibody (BD Biosciences, cat. no. 555347; 1:80 final dilution), PE-Cy7-labeled CD8a antibody (clone RPA-T8, eBioscience, cat. no. 25-0088-41; 1:80 final dilution), APC-labeled CD56 antibody (eBiosciences, cat. no. 17-0567; 1:80 final dilution) and 7-AAD (Beckman Coulter, cat. no. A07704; 1:80 final dilution) in FACS buffer was used to stain the cells and exclude $CD56^+$ natural killer (NK) cells and $7-AAD^+$ dead cells from the analysis. Samples were measured on a BD FACSCanto II flow cytometer (BD Biosciences) as proliferation read-out. Detailed analyses of T-cell proliferation based on CFSE-peaks indicating cell divisions were made by FlowJo 10.4 software and exported expansion index values were used to plot dose-response curves in GraphPad Prism version 6.04 (GraphPad Software, Inc). The expansion index determines the fold-expansion of the overall culture; an expansion index of 2.0 represents a doubling of the cell count, whereas an expansion index of 1.0 represents no change of the overall cell count.

Figure 15A:
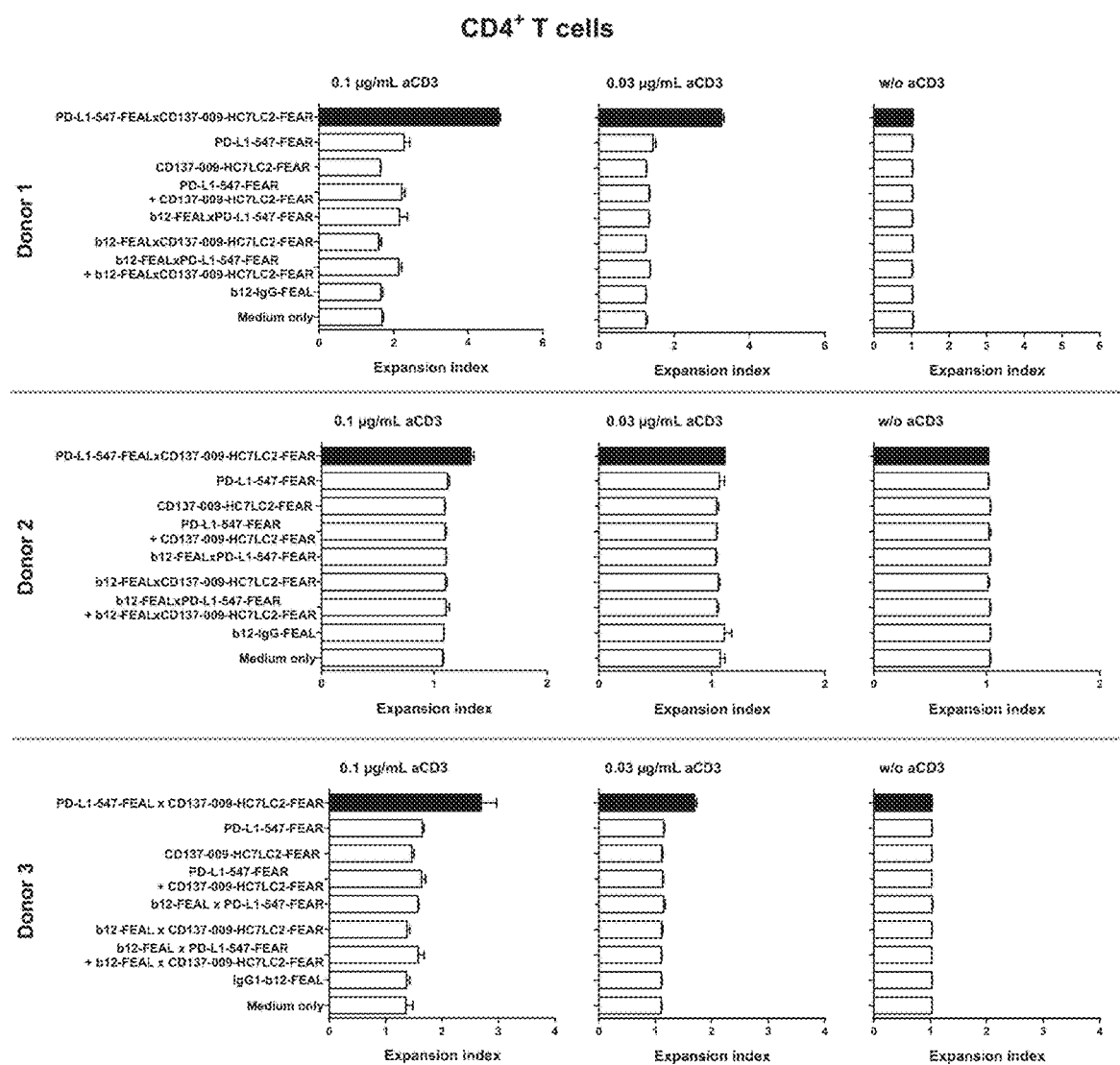
FIGS. 15A-15B: Comparison of PD-L1-547-FEAL×CD137-009-HC7LC2-FEAR with a combination of the two monovalent controls (b12-FEAL×CD137-009-HC7LC2-FEAR+b12-FEAL×PD-L1-547-FEAR) or the two parental antibodies (CD137-009-HC7LC2-FEAR+PD-L1-547-FEAR) in a non-antigen-specific T-cell proliferation assay. CFSE-labeled PBMCs were incubated with sub-optimal concentration of anti-CD3 antibody (0.03 µg/mL and 0.1 µg/mL), or without (w/o) anti-CD3 antibody (as negative control for T-cell activation), and cultured in the presence of 0.2 µg/mL i) PD-L1-547-FEAL×CD137-009-HC7LC2-FEAR, ii) b12-FEAL×CD137-009-HC7LC2-FEAR+b12-FEAL×PD-L1-547-FEAR each, iii) b12-FEAL×CD137-009-HC7LC2-FEAR, iv) b12-FEAL×PD-L1-547-FEAR, v) CD137-009-HC7LC2-FEAR+PD-L1-547-FEAR each, vi) CD137-009-HC7LC2-FEAR, vii) PD-L1-547-FEAR, or viii) b12-IgG-FEAL control antibody for four days. CD4$^+$ (FIG. 15A) and CD8$^+$ (FIG. 15B) T-cell proliferation was measured by flow cytometry. Data are shown from three donors as the mean expansion index of three replicates, as calculated using FlowJo v10.4 software. Error bars (SD) indicate the variation within the experiment (three replicates, using cells from one donor).
Figure 15B:
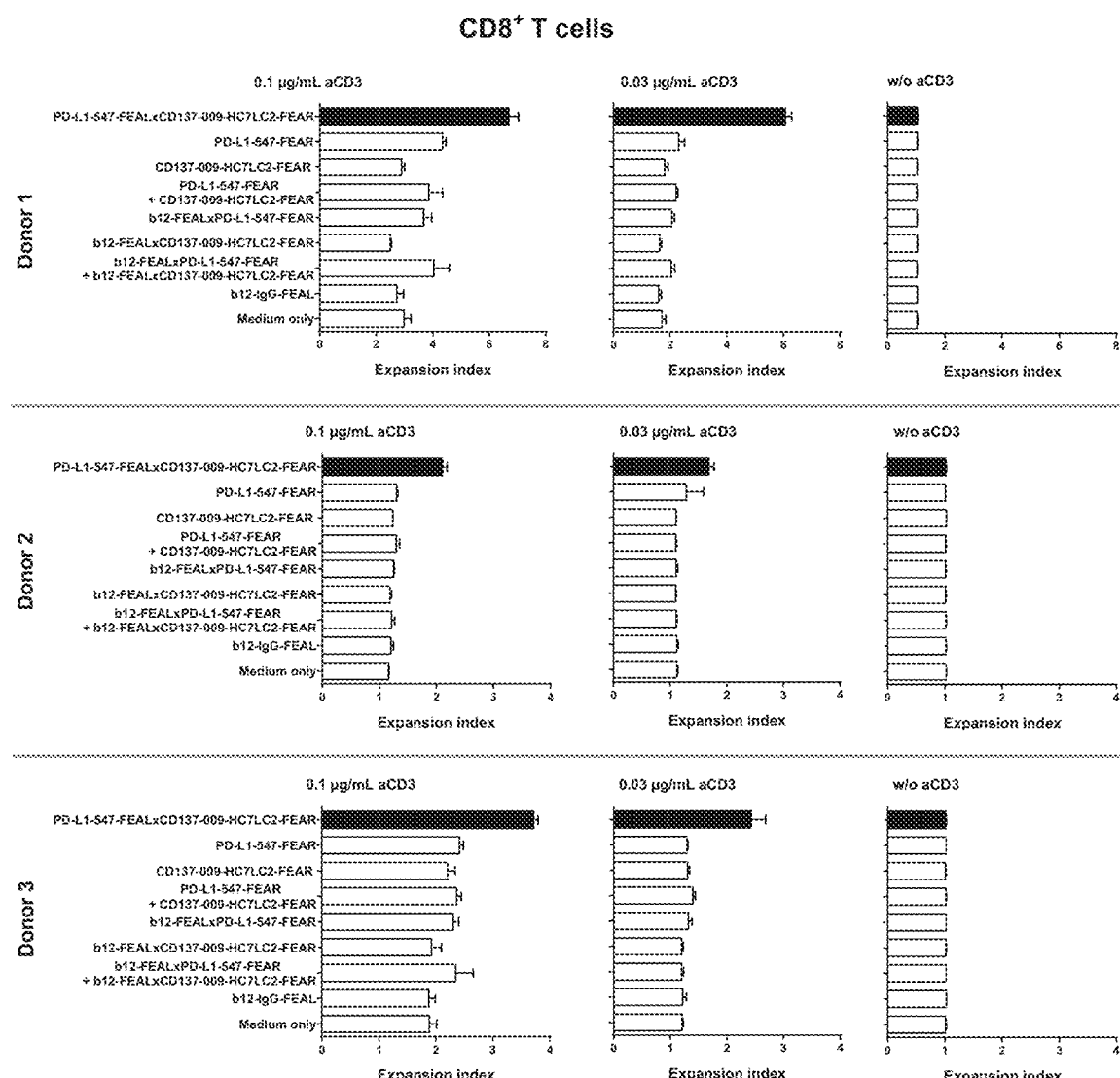
Figure 16A:
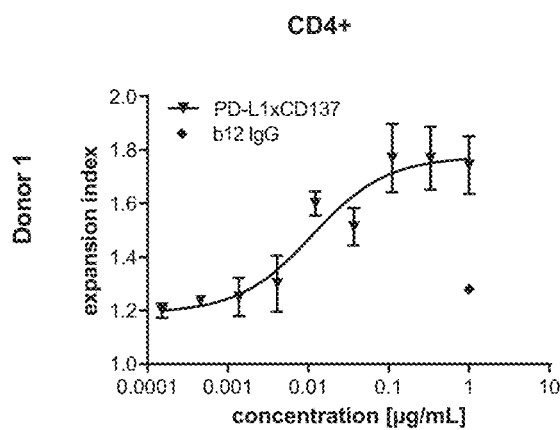
FIGS. 16A-16D: Determination of EC$_{50}$ values for induction of T-cell proliferation by PD-L1-547-FEAL×CD137-009-HC7LC2-FEAR× in a non-antigen-specific T-cell proliferation assay. CFSE-labeled PBMCs were incubated for four days with a sub-optimal concentration of anti-CD3 antibody and serial dilutions of PD-L1-547-FEAL×CD137-009-HC7LC2-FEAR (1-0.00015 µg/mL) or 1 µg/mL b12 IgG as control antibody. Data from two representative donors are shown; PBMCs from donor 1 were stimulated with 0.03 µg/mL anti-CD3 (FIGS. 16A, 16B) and PBMCs from donor 2 with 0.09 µg/mL anti-CD3 (C, D). CD4$^+$ (FIGS. 16A and 16C) and CD8$^+$ (FIGS. 16B and 16D) T-cell proliferation was measured by flow cytometry. Data shown are mean expansion index values of three replicates, as calculated using FlowJo v10.4 software and fitted with a four parameter logarithmic fit. Error bars (SD) indicate the variation within the experiment (three replicates, using cells from one donor).
Figure 16B:
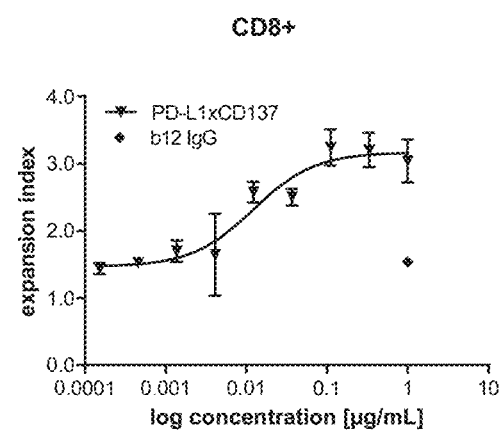
Figure 16C:
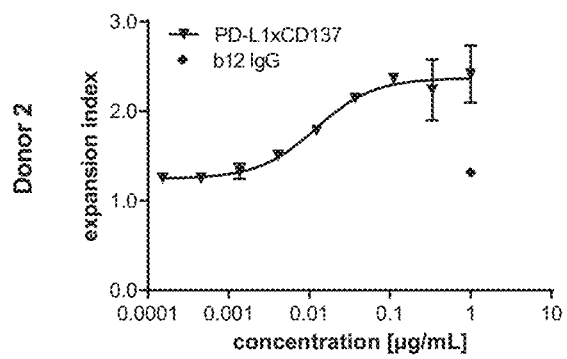
Figure 16D:
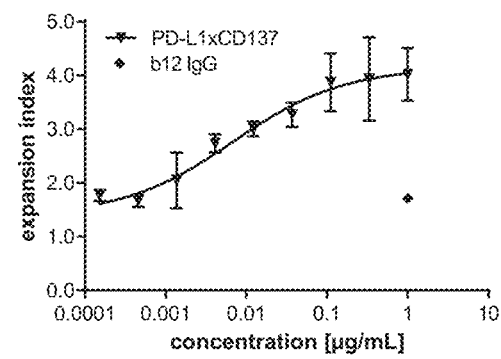

PBMCs from three different donors were analyzed testing two different anti-CD3 concentrations for stimulation and as control without anti-CD3. FIGS. 15A-15B show that the bispecific antibody PD-L1-547-FEALxCD137-009-HC7LC2-FEAR induced a strong expansion of both $CD4^+$ and $CD8^+$ T cells. The monovalent CD137-control antibody, b12-FEALxCD137-009-HC7LC2-FEAR, having one irrelevant arm and the corresponding bivalent parental antibody CD137-009-HC7LC2-FEAR did not affect $CD4^+$ (FIG. 6A) or CD8 (FIG. 6B) T-cell proliferation when compared to incubation with the isotype control antibody b12 IgG. The monovalent PD-L1-control antibody as well as the bivalent parental antibody (b12-FEALxPD-L1-547-FEAR and PD-L1-547-FEAR, respectively) slightly enhanced T-cell proliferation compared to b12 IgG, only when the PBMC stimulation by anti-CD3 already resulted in a strong T cell activation (as observed by a higher expansion index in the medium only control group [see donor 1 at 0.1 µg/ml anti-CD3 stimulation]). A level of T-cell proliferation comparable to the monovalent and bivalent PD-L1 control antibodies was also detectable for the combined monovalent control antibodies (b12-FEALxCD137-009-HC7LC2-FEAR+b12-FEALxPD-L1-547-FEAR) and the combined corresponding parental antibodies (CD137-009-HC7LC2-FEAR+PD-L1-547-FEAR). However, the enhancement of proliferation induced by the bispecific PD-L1-547-FEALx CD137-009-HC7LC2-FEAR antibody was superior to both combined controls (monovalent and bivalent) (FIGS. 15A-15B).

In another independent study $EC_{50}$ values for PD-L1-547-FEALxCD137-009-HC7LC2-FEAR were determined using PBMCs obtained from two donors, which were suboptimally stimulated with 0.03 and 0.09 µg/mL anti-CD3. PD-L1-547-FEAL xCD137-009-HC7LC2-FEAR was assayed using serial dilutions starting at 1 µg/mL and ending at 0.15 ng/mL and b12-IgG-FEAL at 1 µg/mL was included as an isotype control antibody. For proliferation of CD4 and $CD8^+$ T-cells dose-response curves were generated (FIGS. 16A-16D) and for $CD8^+$ T-cell proliferation, $EC_{20}$, $EC_{50}$ and $EC_{90}$ values were determined as well, as shown in table 4.

TABLE 4

Determination of $EC_{20}$, $EC_{50}$ and $EC_{90}$-values of PD-L1-547-FEALxCD137-009-HC7LC2-FEAR based on $CD8^+$ T-cell expansion data as measured by a non-antigen-specific T-cell proliferation assay. Data shown are the values calculated based on the four parameter logarithmic fits (FIGS. 16A-16D).

| Donor | anti-CD3 [µg/ml] | $EC_{50}$ value [µg/ml] | Hill-Slope | Calc. $EC_{20}$ [µg/ml] | Calc. $EC_{90}$ [µg/ml] |
|---|---|---|---|---|---|
| 1 | 0.03 | 0.01218 | 1.134 | 0.00359 | 0.08455 |
| 2 | 0.09 | 0.00689 | 0.635 | 0.00078 | 0.21917 |

Example 15: Antigen-Specific $CD8^+$ T-Cell Proliferation Assay to Measure Cytokine Release Induced by Bispecific Antibodies Binding to PD-L1 and CD137

The induction of cytokine release by bispecific antibody PD-L1-547-FEALxCD137-009-HC7LC2-FEAR targeting PD-L1 and CD137 was measured in an antigen-specific assay, performed essentially as described in Example 7.

T cells were electroporated with 10 µg TCR α chain- and 10 µg β chain-encoding RNA, with or without 2 µg PD-1-encoding IVT RNA. Electroporated T cells were not CFSE-labeled (as described supra), but transferred into fresh IMDM medium (Life Technologies GmbH, cat. no. 12440-061) supplemented with 5% human AB serum, immediately after electroporation. iDCs were electroporated with 5 µg claudin-6 (CLDN6)-encoding RNA, as described supra. After O/N incubation, DCs were stained with Alexa647-conjugated CLDN6-specific antibody and T cells with anti-mouse TCR β chain antibody and with anti-human CD279 antibody, as described supra.

5,000 electroporated DCs were incubated with 50,000 electroporated T cells in the presence of different concentrations of PD-L1-547-FEALxCD137-009-HC7LC2-FEAR bispecific antibody or control antibody b12xIgG-FEAL in IMDM GlutaMAX supplemented with 5% human AB serum in a 96-well round-bottom plate. Following a 48-hour incubation period, the plates were centrifuged at 500×g for 5 min and the supernatant was carefully transferred from each well to a fresh 96-well round bottom plate and stored at −80° C. until cytokine analysis on the MSD® platform. The collected supernatants from the antigen-specific proliferation assay were analyzed for cytokine levels of 10 different cytokines by an MSD V-Plex Human Proinflammatory panel 1 (10-Plex) kit (Meso Scale Diagnostics, LLC., cat. no. K15049D-2) on a MESO QuickPlex SQ 120 instrument (Meso Scale Diagnostics, LLC., cat. no. R31QQ-3), according to the manufacturer's instructions.

Figure 17:
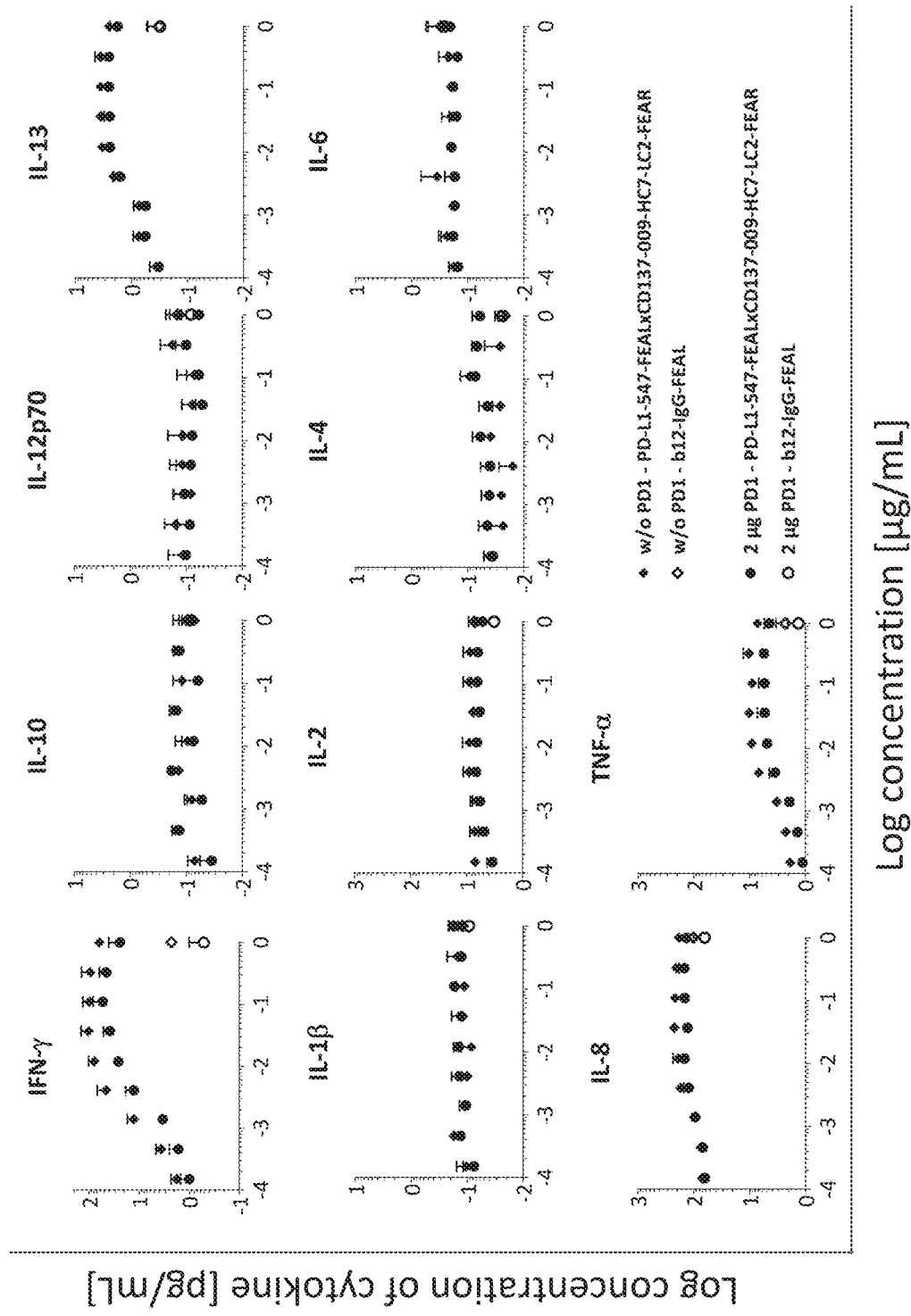
FIG. 17: Effect of PD-L1-547-FEAL×CD137-009-HC7LC2-FEAR on secretion of 10 pro-inflammatory cytokines in an antigen-specific T-cell assay with or without PD-1 electroporation into T cells. T cells electroporated with a CLDN6-specific TCR- and with or without 2 µg PD1-IVT-RNA were incubated with CLDN6-IVT-RNA-electroporated iDCs in the presence of different concentrations of CD137-009-HC7LC2-FEAL×PD-L1-547-FEAR (threefold serial dilutions; ranging from 1 µg/mL to 0.00015 µg/mL) or b12 control antibody b12-IgG-FEAL. Cytokine levels of supernatants were determined 48 hours after antibody addition by multiplex sandwich immunoassay using the MSD V-Plex Human Proinflammatory panel 1 (10-Plex) kit. Each data point represents mean±SD of three individual wells.

The addition of PD-L1-547-FEALxCD137-009-HC7LC2-FEAR led to a concentration-dependent increase in secretion of primarily IFN-γ, TNF-α, IL-13 and IL-8 (FIG. 17). Cytokine levels of all other cytokines (IL-10, IL-12p70, IL-1β, IL-2, IL-4, IL-6) were not elevated above those levels detected for co-cultures treated with control antibody b12-IgG-FEAL. When comparing T cell:DC co-cultures where T cells were not electroporated with PD-1 RNA to those where T cells were electroporated with 2 µg PD-1 RNA, slightly higher cytokine levels were detectable for co-cultures without PD-1 RNA electroporation. This was observed for both the PD-L1-547-FEALxCD137-009-FEAR dose response curve as well as for the b12-IgG-FEAL control antibody values.

Example 16: Antigen-Unspecific In Vitro T-Cell Proliferation Assay to Measure Cytokine Release Induced by Bispecific Antibodies Binding to PD-L1 and CD137

Induction of cytokine release by the bispecific antibody PD-L1-547-FEALxCD137-009-HC7LC2-FEAR targeting PD-L1 and CD137 was measured in an antigen-unspecific in vitro T-cell proliferation assay, performed essentially as described supra (Example 14). The effect of trans-binding, i.e. simultaneous binding of both arms to its respective targets, on cytokine release of ten pro-inflammatory cytokines (IFN-γ, TNF-α, IL-13, IL-8, IL-10, IL-12p70, IL-13, IL-2, IL-4, IL-6) was analyzed by a multiplex sandwich immunoassay of supernatants collected at 48 hours after antibody addition.

PBMCs were not CSFE labeled (as described supra), but were seeded immediately after isolation and only one concentration of anti-CD3 antibody (0.03 µg/mL final concentration) was used.

Following a 48-hour incubation period, the cells were collected by centrifugation at 500×g for 5 minutes and the supernatant was carefully transferred from each well to a fresh 96-well round bottom plate and stored at −80° C. until cytokine analysis on the MSD® platform. The collected supernatants were analyzed for cytokine levels of 10 different cytokines by an MSD V-Plex Human Proinflammatory panel 1 (10-Plex) kit (Meso Scale Diagnostics, LLC., cat. no. K15049D-2) on a MESO QuickPlex SQ 120 instrument (Meso Scale Diagnostics, LLC., cat. no. R31QQ-3), according to the manufacturer's instructions.

Figure 18:
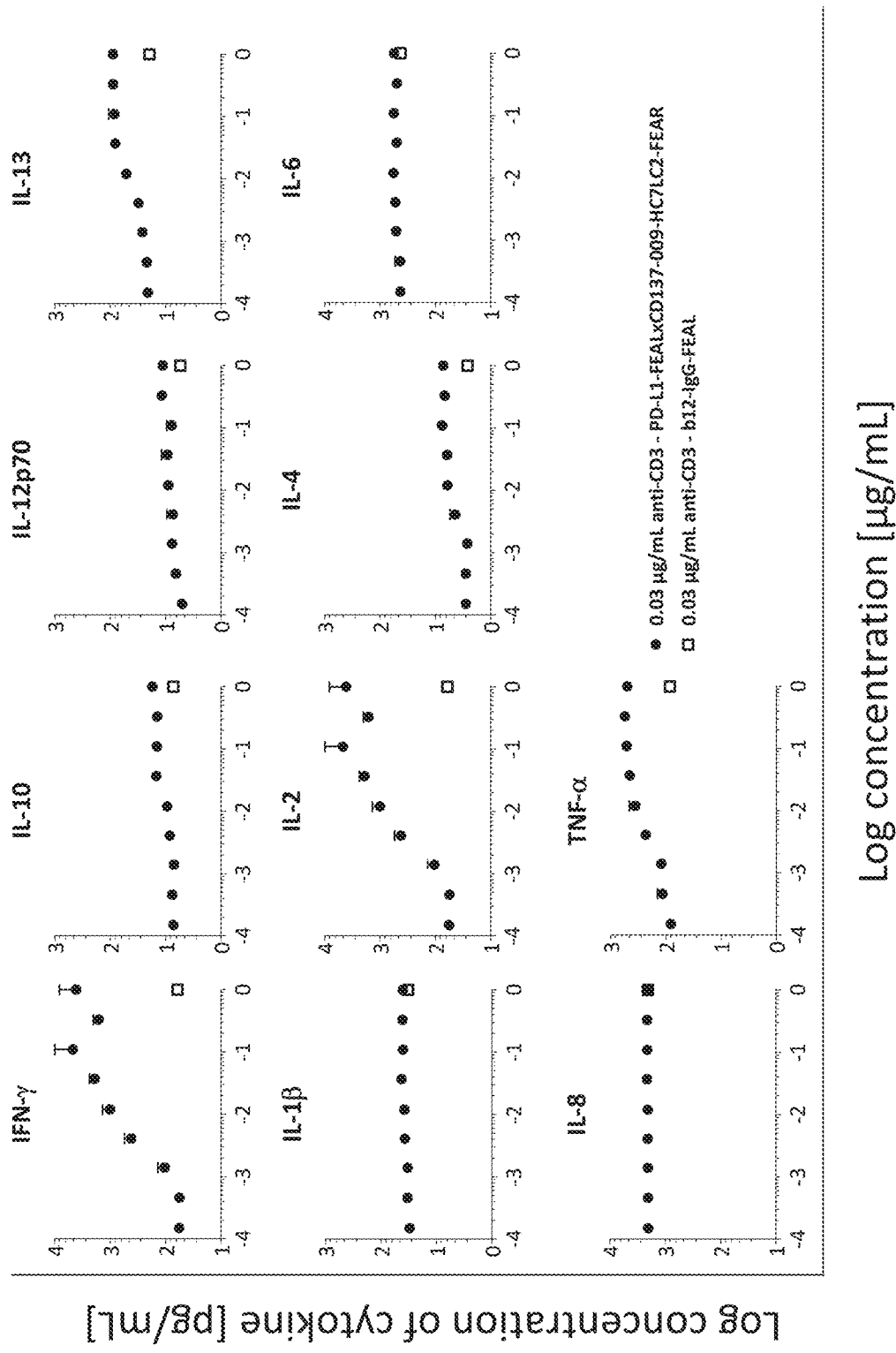
FIG. 18: Effect of PD-L1-547-FEAL×CD137-009-HC7LC2-FEAR on secretion of 10 pro-inflammatory cytokines in an antigen-unspecific T-cell assay. Human PBMCs were sub-optimally stimulated with anti-CD3 antibody in the presence of different concentrations of PD-L1-547-FEAL×CD137-009-HC7LC2-FEAR (three-fold serial dilutions; ranging from 1 µg/mL to 0.00015 µg/mL) or b12 control antibody b12-IgG-FEAL. Cytokine levels in supernatants were determined at 48 hours after antibody addition by multiplex sandwich immunoassay using the MSD V-Plex Human Proinflammatory panel 1 (10-Plex) kit. Each data point represents mean±SD of three individual wells.

The addition of PD-L1-547-FEALxCD137-009-HC7LC2-FEAR induced a concentration-dependent increase in secretion of primarily IFN-γ, TNF-α, IL-2 and IL-13 (FIG. 18). A dose-response curve with only slightly elevated levels was also detectable for IL-10, IL-12p70 as well as IL-4. Cytokine levels of IL-113, IL-6 and IL-8 remained at baseline levels and hence were comparable to those levels detected for co-cultures treated with control antibody b12-IgG-FEAL.

The invention claimed is:
1. A multispecific antibody comprising a first antigen-binding region capable of binding to human CD137 and a second antigen-binding region capable of binding to human PD-L1, wherein the second antigen-binding region inhibits the binding of human PD-L1 to human PD-L1, wherein
(i) the first antigen-binding region comprises
a first heavy chain variable region (VH) and a first light chain variable region (VL), wherein the first VH comprises the amino acid sequence as set forth in SEQ ID NO: 15, and
wherein the first VH comprises a first HCDR1 sequence, a first HCDR2 sequence, and a first HCDR3 sequence, wherein the first HCDR1 sequence comprises an amino acid sequence as set forth in SEQ ID NO: 9, wherein the first HCDR2 sequence comprises an amino acid sequence as set forth in SEQ ID NO: 10, and wherein the first HCDR3 sequence comprises an amino acid sequence as set forth in SEQ ID NO: 11, and wherein the first VL comprises a first LCDR1 sequence, a first LCDR2 sequence, and a first LCDR3 sequence, wherein the first LCDR1 sequence comprises an amino acid sequence as set forth in SEQ ID NO: 13, wherein the first LCDR2 sequence comprises the amino acid sequence GAS, and wherein the first LCDR3 sequence comprises an amino acid sequence as set forth in SEQ ID NO: 14; and
(ii) the second antigen-binding region comprises a second heavy chain variable region (VH) and a second light chain variable region (VL), wherein the second VH comprises the amino acid sequence as set forth in SEQ ID NO: 17, and
wherein the second VH comprises a second HCDR1 sequence, a second HCDR2 sequence, and a second HCDR3 sequence, wherein the second HCDR1 sequence comprises an amino acid sequence as set forth in SEQ ID NO: 18, wherein the second HCDR2 sequence comprises an amino acid sequence as set forth in SEQ ID NO: 19, and wherein the second HCDR3 sequence comprises an amino acid sequence as set forth in SEQ ID NO: 20, and wherein the second VL comprises a second LCDR1 sequence, a second LCDR2 sequence, and a second LCDR3 sequence, wherein the second LCDR1 sequence comprises an amino acid sequence as set forth in SEQ ID NO: 22, wherein the second LCDR2 sequence comprises the amino acid sequence DDN, and wherein the second LCDR3 sequence comprises an amino acid sequence as set forth in SEQ ID NO: 23.

2. The multispecific antibody of claim 1, wherein
(i) the first VL comprises the amino acid sequence as set forth in SEQ ID NO: 16; and
(ii) the second VL comprises the amino acid sequence as set forth in SEQ ID NO: 21.

3. The multispecific antibody of claim 1, wherein the first antigen binding region further comprises a first heavy chain constant region (CH) which comprises at least one amino acid substitution in a position corresponding to positions T366, L368, K370, D399, F405, Y407, or K409 in a human IgG1 heavy chain according to EU numbering, and
wherein the second antigen binding region further comprises a second CH which comprises at least one amino acid substitution in a position corresponding to positions T366, L368, K370, D399, F405, Y407, or K409 in a human IgG1 heavy chain according to EU numbering, and
wherein the first CH and the second CH are not substituted in the same positions.

4. The multispecific antibody of claim 3, wherein
(i) the amino acid in the position corresponding to F405 in a human IgG1 heavy chain according to EU numbering is L in the first CH and the amino acid in the position corresponding to K409 in a human IgG1 heavy chain according to EU numbering is R in the second CH; or
(ii) the amino acid in the position corresponding to K409 in a human IgG1 heavy chain according to EU numbering is R in the said first CH heavy chain, and the amino acid in the position corresponding to F405 in a human IgG1 heavy chain according to EU numbering is L in the second CH.

5. The multispecific antibody of claim 3, wherein in at least one of the first CH and the second CH one or more amino acids in the positions corresponding to positions L234, L235, D265, N297, and P331 in a human IgG1 heavy chain according to EU numbering, are not L, L, D, N, and P, respectively.

6. The multispecific antibody of claim 5, wherein the positions corresponding to positions L234, L235, and D265 in a human IgG1 heavy chain according to EU numbering are F, E, and A, respectively, in the first CH and the second CH.

7. The multispecific antibody of claim 4, wherein the first CH comprises the amino acid sequence as set forth in SEQ ID NO: 24, and the second CH comprises the amino acid sequence as set forth in SEQ ID NO: 25.

8. The multispecific antibody of claim 4, wherein the first CH comprises the amino acid sequence as set forth in SEQ ID NO: 25, and the second CH comprises the amino acid sequence as set forth in SEQ ID NO: 24.

9. A multispecific antibody comprising a first antigen-binding region capable of binding to human CD137 and a second antigen-binding region capable of binding to human PD-L1, wherein the second antigen-binding region inhibits the binding of human PD-L1 to human PD-1, wherein:
(i) the first antigen-binding region comprises a first heavy chain variable region (VH) and a first light chain variable region (VL),
wherein the first VH comprises the amino acid sequence as set forth in SEQ ID NO: 15, and
wherein the first VH comprises a first HCDR1 sequence, a first HCDR2 sequence, and a first HCDR3 sequence, wherein the first HCDR1 sequence comprises an amino acid sequence as set forth in SEQ ID NO: 9, wherein the first HCDR2 sequence comprises an amino acid sequence as set forth in SEQ ID NO: 10, and wherein the first HCDR3 sequence comprises an amino acid sequence as set forth in SEQ ID NO: 11;
wherein the first VL comprises the amino acid sequence as set forth in SEQ ID NO: 16, and
wherein the first VL comprises a first LCDR1 sequence, a first LCDR2 sequence, and a first LCDR3 sequence, wherein the first LCDR1 sequence comprises an amino acid sequence as set forth in SEQ ID NO: 13, wherein the first LCDR2 sequence comprises the amino acid sequence GAS, and wherein the first LCDR3 sequence comprises an amino acid sequence as set forth in SEQ ID NO: 14;
(ii) the second antigen-binding region comprises a second heavy chain variable region (VH) and a second light chain variable region (VL), wherein the second VH comprises the amino acid sequence as set forth in SEQ ID NO: 17, and wherein the second VH comprises a second HCDR1 sequence, a second HCDR2 sequence, and a second HCDR3 sequence, wherein the second HCDR1 sequence comprises an amino acid sequence as set forth in SEQ ID NO: 18, wherein the second HCDR2 sequence comprises an amino acid sequence as set forth in SEQ ID NO: 19, and wherein the second HCDR3 sequence comprises an amino acid sequence as set forth in SEQ ID NO: 20;

wherein the second VL comprises the amino acid sequence as set forth in SEQ ID NO: 21, wherein the second VL comprises a second LCDR1 sequence, a second LCDR2 sequence, and a second LCDR3 sequence, wherein the second LCDR1 sequence comprises an amino acid sequence as set forth in SEQ ID NO: 22, wherein the second LCDR2 sequence comprises the amino acid sequence DDN, and wherein the second LCDR3 sequence comprises an amino acid sequence as set forth in SEQ ID NO: 23;

wherein the first antigen binding region comprises a first heavy chain constant region (CH) and the second antigen binding region comprises a second CH, wherein positions L234, L235, and D265 in a human IgG1 heavy chain according to EU numbering are F, E, and A, respectively, in the first CH and the second CH, and wherein the amino acid in the position corresponding to F405 in a human IgG1 heavy chain according to EU numbering is L in the first CH and the amino acid in the position corresponding to K409 in a human IgG1 heavy chain according to EU numbering is R in the second CH.

10. The multispecific antibody of claim 9, wherein the first CH comprises the amino acid sequence as set forth in SEQ ID NO: 25 and the second CH comprises the amino acid sequence as set forth in SEQ ID NO: 24.

11. A multispecific antibody comprising a first antigen-binding region capable of binding to human CD137 and a second antigen-binding region capable of binding to human PD-L1, wherein the second antigen-binding region inhibits the binding of human PD-L1 to human PD-1, wherein:

(i) the first antigen-binding region comprises a first heavy chain variable region (VH) and a first light chain variable region (VL), wherein the first VH comprises the amino acid sequence as set forth in SEQ ID NO: 15, and wherein the first VH comprises a first HCDR1 sequence, a first HCDR2 sequence, and a first HCDR3 sequence, wherein the first HCDR1 sequence comprises an amino acid sequence as set forth in SEQ ID NO: 9, wherein the first HCDR2 sequence comprises an amino acid sequence as set forth in SEQ ID NO: 10, and wherein the first HCDR3 sequence comprises an amino acid sequence as set forth in SEQ ID NO: 11;

wherein the first VL comprises the amino acid sequence as set forth in SEQ ID NO: 16, and wherein the first VL comprises a first LCDR1 sequence, a first LCDR2 sequence, and a first LCDR3 sequence, wherein the first LCDR1 sequence comprises an amino acid sequence as set forth in SEQ ID NO: 13, wherein the first LCDR2 sequence comprises the amino acid sequence GAS, and wherein the first LCDR3 sequence comprises an amino acid sequence as set forth in SEQ ID NO: 14;

(ii) the second antigen-binding region comprises a second heavy chain variable region (VH) and a second light chain variable region (VL), wherein the second VH comprises the amino acid sequence as set forth in SEQ ID NO: 17, and wherein the second VH comprises a second HCDR1 sequence, a second HCDR2 sequence, and a second HCDR3 sequence, wherein the second HCDR1 sequence comprises an amino acid sequence as set forth in SEQ ID NO: 18, wherein the second HCDR2 sequence comprises an amino acid sequence as set forth in SEQ ID NO: 19, and wherein the second HCDR3 sequence comprises an amino acid sequence as set forth in SEQ ID NO: 20;

wherein the second VL comprises the amino acid sequence as set forth in SEQ ID NO: 21, wherein the second VL comprises a second LCDR1 sequence, a second LCDR2 sequence, and a second LCDR3 sequence, wherein the second LCDR1 sequence comprises an amino acid sequence as set forth in SEQ ID NO: 22, wherein the second LCDR2 sequence comprises the amino acid sequence DDN, and wherein the second LCDR3 sequence comprises an amino acid sequence as set forth in SEQ ID NO: 23;

wherein the first antigen binding region comprises a first heavy chain constant region (CH) and the second antigen binding region comprises a second CH, wherein positions L234, L235, and D265 in a human IgG1 heavy chain according to EU numbering are F, E, and A, respectively, in the first CH and the second CH, and wherein the amino acid in the position corresponding to K409 in a human IgG1 heavy chain according to EU numbering is R in the first CH and the amino acid in the position corresponding to F405 in a human IgG1 heavy chain according to EU numbering is L in the second CH.

12. The multispecific antibody of claim 9, wherein the first CH comprises the amino acid sequence as set forth in SEQ ID NO: 24 and the second CH comprises the amino acid sequence as set forth in SEQ ID NO: 25.

\* \* \* \* \*

UNITED STATES PATENT AND TRADEMARK OFFICE
CERTIFICATE OF CORRECTION

| | | |
|---|---|---|
| PATENT NO. | : 10,968,280 B2 | Page 1 of 1 |
| APPLICATION NO. | : 16/779011 | |
| DATED | : April 6, 2021 | |
| INVENTOR(S) | : Isil Altintas et al. | |

It is certified that error appears in the above-identified patent and that said Letters Patent is hereby corrected as shown below:

On the Title Page

At item (72), please add inventor --Edward van den Brink, Utrecht (NL); Dennis Verzijl, Utrecht (NL)--

Signed and Sealed this
Twenty-fifth Day of March, 2025

Coke Morgan Stewart
*Acting Director of the United States Patent and Trademark Office*